US010093991B2

(12) United States Patent
Kramer

(10) Patent No.: US 10,093,991 B2
(45) Date of Patent: Oct. 9, 2018

(54) COMPOSITIONS AND METHODS FOR THE DETECTION OF THE SHRUNKEN2-R MUTATION IN MAIZE

(71) Applicant: Syngenta Participations AG, Basel (CH)

(72) Inventor: Vance Cary Kramer, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/617,105

(22) Filed: Jun. 8, 2017

(65) Prior Publication Data

US 2017/0275709 A1 Sep. 28, 2017

Related U.S. Application Data

(62) Division of application No. 14/271,489, filed on May 7, 2014, now Pat. No. 9,702,014.

(60) Provisional application No. 61/820,427, filed on May 7, 2013.

(51) Int. Cl.
*C12Q 1/68* (2018.01)
*C12Q 1/6895* (2018.01)

(52) U.S. Cl.
CPC .................................. *C12Q 1/6895* (2013.01)

(58) Field of Classification Search
CPC .................................................... C12Q 1/6895
See application file for complete search history.

(56) References Cited

U.S. PATENT DOCUMENTS

| | | | |
|---|---|---|---|
| 6,184,438 | B1 | 2/2001 | Hannah |
| 2012/0054896 | A1 | 3/2012 | Long |

OTHER PUBLICATIONS

Bhave et al., Identification and molecular characterization of Shrunken-2 cDNA clones of maize, The Plant Cell, 1990, 2:581-588.
Civardi et al., The relationship between genetic and physical distances in the cloned a1-sh2 interval of the *Zea mays* L. genome, Proc. Natl. Acad. Scie, 1994, 91:8268-8272.
Hannah and Nelson, Characterization of ADP-glucose pyrophosphorylase from Shrunken-2 and Brittle-2 mutants of maize, Biochemical Genetics, 14(7/8):547-560.
Hannah et al., A shrunken-2 transgene increases maize yield by acting in maternal tissues to increase the frequency of seed development, The Plant Cell, 2012, 24:2352-2363.
Yao et al., Molecular characterization of meiotic recombination across the 140-kb multigenic a1-sh2 interval of maize, PNAS, 2002, 99(9):6157-6162.

*Primary Examiner* — David C Thomas
(74) *Attorney, Agent, or Firm* — Karen A. Magri

(57) ABSTRACT

The present invention relates to compositions and methods for detecting the shrunken2-R (sh2-R) mutation and identifying maize plants, maize plant parts and/or maize germplasm having the sh2-R mutation.

12 Claims, 2 Drawing Sheets

Specification includes a Sequence Listing.

5' Side Insertion Clone Map

3' Side Insertion Clone Map

3' insertion ends 69.686 kb

COMPOSITIONS AND METHODS FOR THE DETECTION OF THE SHRUNKEN2-R MUTATION IN MAIZE

RELATED APPLICATION INFORMATION

This application is a divisional of U.S. patent application Ser. No. 14/271,489 filed May 7, 2014 (allowed), which claims the benefit of U.S. Provisional Patent Application No. 61/820,427 filed May 7, 2013, the contents of which are incorporated herein by reference.

STATEMENT REGARDING ELECTRONIC SUBMISSION OF A SEQUENCE LISTING

A Sequence Listing in ASCII text format, submitted under 37 C.F.R. § 1.821, entitled "80234-US-REG-ORG-NAT-1_Sequence_Listing_ST25" bytes in size, generated on May 1, 2014 and filed via EFS-Web is provided in lieu of a paper copy. This Sequence Listing is hereby incorporated by reference into the specification for its disclosures.

FIELD OF THE INVENTION

The present invention relates to compositions and methods for identifying the shrunken2-R (sh2-R) mutation and maize plants and/or maize germplasm having the sh2-R mutation.

BACKGROUND

Maize (corn) is one of the most diverse grain crops present in nature, comprising a number of different types, which are generally classified by characteristics of their kernel endosperm. The most common types of corn include flint, flour, dent, pop, sweet, waxy and pod. The physical appearance of each kernel type is determined by its endosperm pattern, quality and quantity.

Sweet corn is a corn plant classified as *Zea mays*, var. *rugosa*, and has white, yellow or bi-colored kernels that are sweet when they are in the immature milky stage as a result of having a high sugar content (i.e., sucrose content). Higher levels of sugar or sucrose in the sweet corn kernels result in a lower osmotic potential, causing greater water uptake into the kernels. Sweet corn is typically eaten by human beings as a vegetable, either directly from the maize cob, or by having the sweet kernels removed from the cob, and is a major vegetable crop grown all over the world primarily for fresh consumption, rather than as animal feed or for flour production.

Sweet corn occurs as a spontaneous mutation in field corn and can be the result of naturally-occurring mutations in one or more genes that control conversion of sucrose to starch inside the endosperm of the corn kernel. Unlike field corn varieties, which are intended for livestock and are typically harvested when the kernels are dry and fully mature (at the dent stage), sweet corn is typically picked when it is immature (at the milk stage), and eaten as a vegetable, rather than as a grain. Because the process of maturation involves converting sucrose into starch, sweet corn typically stores poorly and must be eaten in a fresh, canned or frozen manner before the kernels become tough and/or starchy. Following harvest, or if left on the stalk too long, sucrose in standard sweet corn becomes rapidly converted to starch. Kernels can lose as much as 50% of their sucrose at room temperature at around 24 hours after harvest.

Open pollinated (non-hybrid) varieties of white sweet corn started to become widely available in the United States in the 19th century. Two of the most enduring varieties, which are still available today, are Country Gentleman (a Shoepeg corn with small, white kernels in irregular rows) and Stowell's Evergreen. Sweet corn production in the 20th century was influenced by the following key developments: (i) hybridization, which allowed for more uniform maturity, improved quality and disease resistance; and (ii) identification of separate gene mutations responsible for sweetness in corn, and the ability to breed varieties based on these characteristics, for example: su1 (sugary); se1 (sugary enhanced); and sh2 (shrunken-2). There are currently hundreds of varieties of sweet corn, with more varieties continuously being developed.

The sh2 gene encodes the ADP-glucose pyrophosphorylase (AGPase) large subunit, gene ID GRMZM2G429899 located on Chr3 map position 216,414,684. The small subunit of AGPase is encoded by Brittle2 (Bt2). AGPase catalyzes the reversible synthesis of ADP-glucose and pyrophosphate from ATP and glucose-1-phosphate and is one of the main regulatory steps in the biosynthesis of starch in plants. A mutation in the sh2 gene called sh2-R results in maize kernels that have greatly reduced starch levels and increased sugar resulting from reduced levels of the enzyme. In addition, sh2-R mutants exhibit reduced seed germination and seedling vigor, as well as reduced yield. Thus, in some settings there is a need in the art for methods for rapid identification of the sh2-R mutation in germplasm so that the mutation can be reduced or eliminated from a breeding population. The present invention provides methods and compositions that address this need.

SUMMARY OF THE INVENTION

Compositions and methods for identifying the shrunken2-R (sh2-R) mutation and plants and/or germplasm having the sh2-R mutation, which is associated with higher kernel sucrose levels, shrunken kernels, reduced germination and seedling vigor, and reduced yield are provided. Methods for reducing the presence of the mutation in breeding population are also provided.

Thus, one aspect of the present invention provides a pair oligonucleotide primers, comprising a first oligonucleotide, being about 10-50 nucleotides in length and comprising at least 10 contiguous nucleotides of a nucleotide sequence of any one of the nucleotide sequences of SEQ ID NO:1, the full complement of SEQ ID NO:1, SEQ ID NO:32, or the full complement of SEQ ID NO:32; and a second oligonucleotide, being about 10-50 nucleotides in length and comprising at least 10 contiguous nucleotides of a nucleotide sequence of any one of the nucleotide sequences of SEQ ID NO:1, the full complement of SEQ ID NO:1, SEQ ID NO:32, or the full complement of SEQ ID NO:32.

In another aspect, the present invention provides a pair of oligonucleotide primers, comprising a first oligonucleotide, being about 10-50 nucleotides in length and comprising at least 10 contiguous nucleotides of a nucleotide sequence of any one of the nucleotide sequences of SEQ ID NO:2-16, or the full complement of a nucleotide sequence of SEQ ID NOs:2-16; and a second oligonucleotide, being about 10-50 nucleotides in length and comprising at least 10 contiguous nucleotides of a nucleotide sequence of any one of the nucleotide sequences of SEQ ID NOs:2-16, or the full complement of a nucleotide sequence of SEQ ID NOs:2-16.

In other aspects, the present invention provides a pair of oligonucleotide primers, comprising a first oligonucleotide, being about 10-50 nucleotides in length and comprising at least 10 contiguous nucleotides of a nucleotide sequence of any one of the nucleotide sequences of SEQ ID NOs:17-24, or the full complement of a nucleotide sequence of SEQ ID NOs:17-24; and a second oligonucleotide, being about 10-50 nucleotides in length and comprising at least 10 contiguous nucleotides of a nucleotide sequence of any one of the nucleotide sequences of SEQ ID NOs:25-31, or the full complement of a nucleotide sequence of SEQ ID NOs:25-31.

In still other aspects, the present invention provides a pair of oligonucleotide primers, comprising a first oligonucleotide, being about 10-50 nucleotides in length and comprising at least 10 contiguous nucleotides of a nucleotide sequence of SEQ ID NO:56, or the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57.

In an additional aspect, the present invention provides a pair of oligonucleotide primers, comprising a first oligonucleotide, being about 10-50 nucleotides in length and comprising at least 10 contiguous nucleotides of a nucleotide sequence of SEQ ID NO:58, or the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59.

In a further aspect, the present invention provides a pair of oligonucleotide primers, comprising a first oligonucleotide, being about 10-50 nucleotides in length and comprising at least 10 contiguous nucleotides of a nucleotide sequence of any one of the nucleotide sequences of SEQ ID NOs:33-42, or the full complement of a nucleotide sequence of SEQ ID NOs:33-42; and a second oligonucleotide, being about 10-50 nucleotides in length and comprising at least 10 contiguous nucleotides of a nucleotide sequence of any one of the nucleotide sequences of SEQ ID NOs:33-42, or the full complement of a nucleotide sequence of SEQ ID NOs:33-42.

In other aspects, the present invention provides a pair of oligonucleotide primers, comprising a first oligonucleotide, being about 10-50 nucleotides in length and comprising at least 10 contiguous nucleotides of a nucleotide sequence of any one of the nucleotide sequences of SEQ ID NOs:43-50, or the full complement of a nucleotide sequence of SEQ ID NOs:43-50; and a second oligonucleotide, being about 10-50 nucleotides in length and comprising at least 10 contiguous nucleotides of a nucleotide sequence of any one of the nucleotide sequences of SEQ ID NOs:51-55, or the full complement of a nucleotide sequence of SEQ ID NOs:51-55.

In representative embodiments, a primer pair of the present invention, as described herein, can be used to amplify the region of the sh2-R allele that encompasses the junction of the sh2 gene and the insertion at either the 5' end of the insertion or the 3' end of the insertion (e.g., nucleotides 765-766 of SEQ ID NO:1 or nucleotides 69686-69687 of SEQ ID NO:32). Thus, a primer pair of the present invention can be any primer pair that amplifies the region of the sh2-R allele encompassing the junction of the sh2 gene and the insertion at either the 5' end of the insertion or the 3' end of the insertion (e.g., nucleotides 765-766 of SEQ ID NO:1 or nucleotides 69686-69687 of SEQ ID NO:32).

In other aspects, the present invention provides a method of identifying a maize plant, plant part and/or plant cell having a sh2-R mutation, comprising amplifying in a nucleic acid sample from said maize plant, plant part and/or plant cell a region of at least 60 consecutive nucleotides of a nucleotide sequence of any one of the nucleotide sequences of SEQ ID NO:1-16 or 32-42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation.

In particular aspects, the present invention provides a method of identifying a maize plant, plant part and/or plant cell having a sh2-R mutation, comprising amplifying in a nucleic acid sample from said maize plant, plant part and/or plant cell a region of at least 60 consecutive nucleotides of a nucleotide sequence of SEQ ID NO:11, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation. In some aspects, the pair of oligonucleotide primers comprises a first oligonucleotide, being about 10-50 nucleotides in length and comprising at least 10 contiguous nucleotides of a nucleotide sequence of SEQ ID NO:58, or the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59.

In particular aspects, the present invention provides a method of identifying a maize plant, plant part and/or plant cell having a sh2-R mutation, comprising amplifying in a nucleic acid sample from said maize plant, plant part and/or plant cell a region of at least 60 consecutive nucleotides of a nucleotide sequence of SEQ ID NO:42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation. In some aspects, the pair of oligonucleotide primers comprises a first oligonucleotide, being about 10-50 nucleotides in length and comprising at least 10 contiguous nucleotides of a nucleotide sequence of SEQ ID NO:56, or the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57.

In a further aspect, a method of reducing the presence of, or eliminating, the sh2-R mutation from a maize population is provided, comprising amplifying in a nucleic acid sample from said maize plant, plant part and/or plant cell a region of at least 60 consecutive nucleotides of a nucleotide sequence of any one of the nucleotide sequences of SEQ ID NO:1-16 or 32-42, or the full complement thereof, in an amplification reaction under conditions whereby amplification can occur to produce an amplification product; analyzing the amplification reaction for the presence of the amplification product, thereby identifying a maize plant, plant part and/or plant cell in the population having a sh2-R mutation; and removing said one or more maize plants and parts thereof, from the population thereby reducing the presence of, or eliminating, the sh2-R mutation from the maize population.

These and other aspects of the invention are set forth in more detail in the description of the invention below.

DETAILED DESCRIPTION

Figure 1:
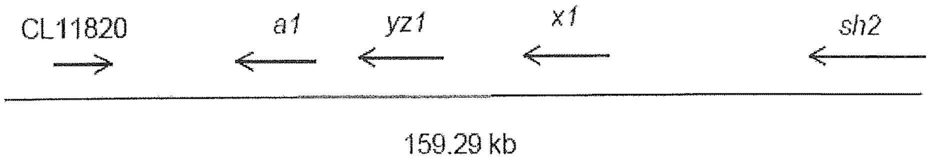
FIG. 1 shows the interval in the maize genome from GRMZM2G316635 (CL11820) to sh2.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

The present invention provides compositions and methods for identifying plants, plant parts, and/or germplasm having the sh2-R mutation as well as methods for reducing the presence of the mutation in breeding population.

Thus, one embodiment of the present invention provides a pair oligonucleotide primers for the amplification of a portion of a nucleotide sequence encoding the sh2-R mutation, comprising, consisting essentially of or consisting of a first oligonucleotide, being about 10-50 nucleotides in length and comprising at least 10 contiguous nucleotides of a nucleotide sequence of any one of the nucleotide sequences of SEQ ID NO:1, the full complement of SEQ ID NO:1, SEQ ID NO:32, or the full complement of SEQ ID NO:32; and a second oligonucleotide, being about 10-50 nucleotides in length and comprising at least 10 contiguous nucleotides of a nucleotide sequence of any one of the nucleotide sequences of SEQ ID NO:1, the full complement of SEQ ID NO:1, SEQ ID NO:32, or the full complement of SEQ ID NO:32.

In another embodiment, the present invention provides a pair of oligonucleotide primers for the amplification of a portion of a nucleotide sequence encoding the sh2-R mutation, comprising, consisting essentially of or consisting of a first oligonucleotide, being about 10-50 nucleotides in length and comprising at least 10 contiguous nucleotides of a nucleotide sequence of any one of the nucleotide sequences of SEQ ID NOs:2-16, or of the full complement of a nucleotide sequence of SEQ ID NOs:2-16; and a second oligonucleotide, being about 10-50 nucleotides in length and comprising at least 10 contiguous nucleotides of a nucleotide sequence of any one of the nucleotide sequences of SEQ ID NOs:2-16, or the full complement of a nucleotide sequence of SEQ ID NOs:2-16.

In additional embodiments, the present invention provides a pair of oligonucleotide primers for the amplification of a portion of a nucleotide sequence encoding the sh2-R mutation, comprising, consisting essentially of or consisting of a first oligonucleotide, being about 10-50 nucleotides in length and comprising at least 10 contiguous nucleotides of a nucleotide sequence of any one of the nucleotide sequences of SEQ ID NOs:17-24, or the full complement of a nucleotide sequence of any one of the nucleotide sequences of SEQ ID NOs:17-24; and a second oligonucleotide, being about 10-50 nucleotides in length and comprising at least 10 contiguous nucleotides of a nucleotide sequence of SEQ ID NOs:25-31, or the full complement of a nucleotide sequence of SEQ ID NOs:25-31.

In an additional aspect, the present invention provides a pair of oligonucleotide primers for the amplification of a portion of a nucleotide sequence encoding the sh2-R mutation, comprising, consisting essentially of or consisting of a first oligonucleotide, being 10-50 nucleotides in length and comprising at least 10 contiguous nucleotides of a nucleotide sequence of SEQ ID NO:56, or the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57.

In an further aspect, the present invention provides a pair of oligonucleotide primers for the amplification of a portion of a nucleotide sequence encoding the sh2-R mutation, comprising, consisting essentially of or consisting of a first oligonucleotide, being 10-50 nucleotides in length and comprising at least 10 contiguous nucleotides of a nucleotide sequence of SEQ ID NO:58, or the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59.

In a further embodiment, the present invention provides a pair of oligonucleotide primers for the amplification of a portion of a nucleotide sequence encoding the sh2-R mutation, comprising, consisting essentially of or consisting of a first oligonucleotide, being about 10-50 nucleotides in length and comprising at least 10 contiguous nucleotides of a nucleotide sequence of any one of the nucleotide sequences of SEQ ID NOs:33-42, or the full complement of a nucleotide sequence of SEQ ID NOs:33-42; and a second oligonucleotide, being about 10-50 nucleotides in length and comprising at least 10 contiguous nucleotides of a nucleotide sequence of any one of the nucleotide sequences of SEQ ID NOs:33-42, or the full complement of a nucleotide sequence of SEQ ID NOs:33-42.

In an additional embodiment, the present invention provides a pair of oligonucleotide primers for the amplification of a portion of a nucleotide sequence encoding the sh2-R mutation, comprising, consisting essentially of or consisting of a first oligonucleotide, being about 10-50 nucleotides in length and comprising at least 10 contiguous nucleotides of a nucleotide sequence any one of the nucleotide sequences of SEQ ID NOs:43-50, or of the full complement of a nucleotide sequence of SEQ ID NOs: 43-50; and a second oligonucleotide, being about 10-50 nucleotides in length and comprising at least 10 contiguous nucleotides of a nucleotide sequence any one of the nucleotide sequences of SEQ ID NOs:51-55, or of the full complement of a nucleotide sequence of SEQ ID NOs:51-55.

The effects of the sh2-R gene mutation include reduced starch and elevated sugars in the corn kernel, reduced germination and seedling vigor, as well as reduced yield. The sh2-R phenotype was first identified by E. B. Mains (*J. Heredity* 40:21-24 (1949)). Northern data showed that this mutation does not produce a transcript (Giroux and Hannah, *Mol. Gen. Genet.* 243:400-408 (1994)). The present inventors have determined that the sh2-R mutation comprises a very large insertion in the sh2 gene (MaizeSequence Accession No. GRMZM2G429899 (maizesequence.org/).

Figure 2:
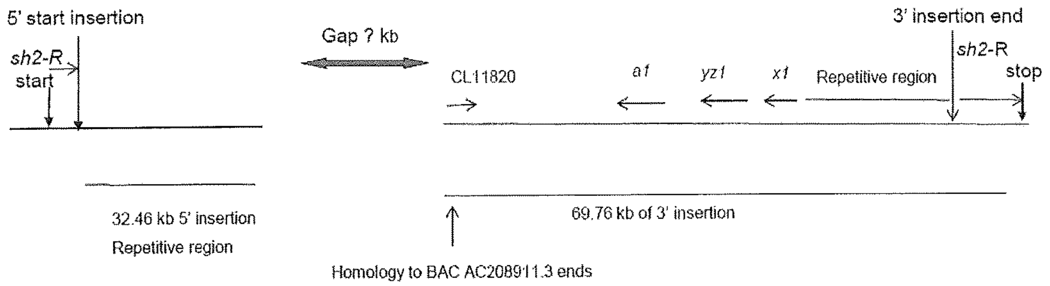
FIG. 2 shows the sh2-R mutation.

The interval in the maize genome from GRMZM2G316635 (CL11820) to sh2 is 159 kb and contains in order the five genes GRMZM2G316635 (CL11820), a1, yz1, x1 and sh2 (See, FIG. 1). The sh2-R allele is a complex re-arrangement whereby the genes from GRMZM2G316635 (CL11820) to x1, and possibly others upstream, have been inserted 3 bp upstream of the 3' end of exon 3 of sh2 (See, FIG. 2). The four genes in the insertion are in the opposite orientation in the sh2-R allele compared with maize cultivar B73. Approximately 32.46 kb of the 5' end of the insertion and 69.76 kb of the insertion on the 3' end have been cloned. The insertion is at least 102.22 kb in length.

Thus, the 5' side of the sh2-R allele comprises the 5' end of sh2 gene followed by an insertion comprising a repetitive region of DNA about 32 kb (e.g., SEQ ID NO:1) and the 3' side of the sh2-R allele comprises the 3' end of the sh2 gene and about a 70 kb insertion (that is 5' of the 3' end of the sh2 gene) comprising at least the genes from GRMZM2G316635 (CL11820) to x1 (e.g., SEQ ID NO:32).

In representative embodiments, the oligonucleotide primer pairs of the present invention comprise, consist essentially of or consist of a pair of oligonucleotide sequences that can hybridize to and amplify a portion of a nucleotide sequence encoding the sh2-R mutation, for example, a portion of a nucleotide sequence of SEQ ID NO:1 or SEQ ID NO:32, which encode the 5'-side of the sh2-R mutation and the 3'-side of the sh2-R mutation, respectively. Thus, non-limiting examples of a nucleotide sequence that encodes a portion of the sh2-R mutant gene include a nucleotide sequence of any one of the nucleotide sequences of SEQ ID NOs:1-56. The nucleotide sequences of SEQ ID NOs:2-31, 58 and 59 encode portions of the 5'-side of the sh2-R mutation (e.g., SEQ ID NO:1) and the nucleotide sequences of SEQ ID NOs:33-57 encode portions of the 3'-side of the sh2-R mutation (e.g., SEQ ID NO:32).

As one of skill in the art would appreciate, to detect the presence of the sh2-R mutation, the amplified product must be "anchored" in a portion of both the sh2 gene and the insertion sequence (comprising the repetitive DNA and upstream genes). Therefore, to detect the presence of the sh2-R mutation from the 5'-side of the sh2-R allele (e.g., SEQ ID NO:1), the forward primer of a pair of oligonucleotide primers can be designed to hybridize to consecutive nucleotides of the sh2 region of the 5'-side sh2-R nucleotide sequence (e.g., nucleotides 1 to 765 of SEQ ID NO:1) and the reverse primer of the pair of oligonucleotide primers can be designed to hybridize to consecutive nucleotides of the repetitive DNA insertion region of the 5'-side sh2-R nucleotide sequence (e.g., nucleotides 766 to 33,224 of SEQ ID NO:1). Thus, as a non-limiting example, an oligonucleotide primer pair for the 5'-side of the sh2-R mutation includes SEQ ID NO:58 and SEQ ID NO:59.

Similarly, to detect the presence of the sh2-R mutation from the 3'-side of the sh2-R allele (e.g., SEQ ID NO:32), the forward primer of a pair of oligonucleotide primers can be designed to hybridize to consecutive nucleotides of the insertion region (e.g., the region including the genes from GRMZM2G316635 (CL11820) to x1) of the 3'-side sh2-R nucleotide sequence (e.g., nucleotides 1 to 69686 of SEQ ID NO:32) and a reverse primer of the pair of oligonucleotide primers can be designed to hybridize to consecutive nucleotides of the sh2 region of the 3'-side sh2-R nucleotide sequence (e.g., nucleotides 69687 to 74428 of SEQ ID NO:32). Thus, as a non-limiting example, a pair of oligonucleotide primers for the 5'-side of the sh2-R mutation includes SEQ ID NO:56 and SEQ ID NO:57.

Thus, in particular embodiments, a primer pair of the invention amplifies a region of the sh2-R allele that encompasses a junction of the sh2 allele and the insertion within the sh2 allele at the 5'end (beginning) of the insertion mutation (e.g., nucleotides 765-766 of SEQ ID NO:1) or the 3' end of the insertion mutation (nucleotides 69686-69687 of SEQ ID NO:32). Accordingly, in some embodiments, detecting the sh2-R mutation can comprise amplifying a region of the maize genome with a primer pair comprising a first oligonucleotide that hybridizes to a nucleotide sequence of SEQ ID NO:1, or the full complement thereof, at a site 5' to the location of the beginning/start of the insertion (e.g., 5' end of the insertion) in the sh2 gene as described herein (e.g., nucleotide 766 of SEQ ID NO:1) and a second oligonucleotide that hybridizes to a nucleotide sequence of SEQ ID NO:1, or the full complement thereof, at a site 3' to the location of the beginning/start of the insertion in the sh2 gene (e.g., nucleotide 766 of SEQ ID NO:1) to produce an amplification product, wherein detection of an amplification product that comprises the junction between the sh2-R gene and the insertion in the amplification reaction detects the sh2-R mutation.

In further embodiments of the invention, detecting the sh2-R mutation can comprise amplifying a region of the maize genome with a primer pair comprising a first oligonucleotide that hybridizes to a nucleotide sequence of SEQ ID NO:32, or the full complement thereof, at a site 5' to the location of the 3'end of the insertion within the sh2 gene as described herein (e.g., nucleotide 69,686 of SEQ ID NO:32) and a second oligonucleotide that hybridizes to a nucleotide sequence of SEQ ID NO:32, or the full complement thereof, at a site 3' to the location of the 3'end of the insertion in the sh2 gene (e.g., nucleotide 69,687 of SEQ ID NO:32) to produce an amplification product that comprises the junction between the sh2-R gene and the insertion, wherein detection of an amplification product in the amplification reaction detects the sh2-R mutation.

In particular embodiments of this invention, detection of the insertion described herein can comprise amplifying a region of the maize genome with a primer pair comprising a first oligonucleotide comprising a nucleotide sequence of SEQ ID NO:56 (forward primer) and a second oligonucleotide comprising a nucleotide sequence of SEQ ID NO:57 (reverse primer) to produce an amplification product, wherein an amplification product of about 2150 base pairs detects the insertion. In a further embodiment of this invention, detection of the insertion described herein can comprise amplifying a region of the maize genome with a primer pair comprising a first oligonucleotide comprising a nucleotide sequence of SEQ ID NO:58 (forward primer) and a second oligonucleotide comprising a nucleotide sequence of SEQ ID NO:59 (reverse primer) to produce an amplification product, wherein an amplification product of about 1260 base pairs detects the insertion.

In representative embodiments of the invention, the length of the oligonucleotide primers can be about 10-50 nucleotides, about 15-50 nucleotides, about 20-50 nucleotides, about 30-50 nucleotides, about 40-50 nucleotides, about 10-40 nucleotides, about 10-30 nucleotides, about 10-20 nucleotides, about 15-30 nucleotides, about 15-20 nucleotides, about 20-30 nucleotides, about 20-40 nucleotides, and the like. Thus, the length of an oligonucleotide primer of the present invention can be about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 nucleotides, or the like, or any range therein.

In some embodiments, the oligonucleotide primer pair of this invention comprises, consists of, consists essentially of about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 contiguous nucleotides of a nucleotide sequence of any one of the nucleotide sequences of SEQ ID NO:1-59.

In some embodiments, the oligonucleotide primers of the invention can further comprise other nucleotide sequences. Thus for example, in some embodiments, at least one of the said oligonucleotide primers of the primer pair is operably linked to nucleotide acid sequence encoding a promoter (e.g., a 5'-region comprising the sequence of a promoter recognized by, for example, a DNA-dependent RNA polymerase).

In some additional embodiments, a pair of oligonucleotide primers of this invention can amplify a region of the sh2-R allele comprising, consisting essentially of or consisting of at least 60 consecutive nucleotides. In some embodiments, a pair of oligonucleotide primers of the present invention can amplify a region of the sh2-R allele comprising, consisting essentially of or consisting of about 60 consecutive nucleotides to about 15,000 consecutive nucleotides (e.g., 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, and the like nucleotides, and so on to about 15,000 nucleotides, and any range therein). Accordingly, in representative embodiments, an amplification product of the present invention can be about 60 nucleotides in length to about 15,000 nucleotides in length (e.g., 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, 400, 450, 500, 750, 1000, 1500, 2000, 2500, 3000, 3500, 4000, 4500, 5000, 5500, 6000, 6500, 7000, 7500, 8000, 8500, 9000, 9500, 10500, 11000, 11500, 12000, 12500, 13000, 13500, 14000, 14500, 15000 nucleotides in length, and the like, and any range therein).

The presently disclosed subject matter encompasses methods for identifying a maize plant, plant part and/or plant cell having the sh2-R mutation, comprising detecting in the plant the presence of an amplification product as defined herein. In an exemplary embodiment of the presently disclosed methods for identifying such a plant, plant part and/or plant cell, the method comprises amplifying in a nucleic acid sample from said maize plant, plant part and/or plant cell a region of at least 60 consecutive nucleotides of a nucleotide sequence as set forth herein (e.g., SEQ ID NOs:1-59, or full complement thereof) in an amplification reaction under conditions whereby amplification can occur to produce an amplification product; and analyzing the amplification reaction for the presence of the amplification product, thereby identifying a maize plant, plant part and/or plant cell having a sh2-R mutation Thus, in some embodiments, a method of identifying a maize plant, plant part and/or plant cell having the sh2-R mutation in is provided, comprising, consisting essentially of or consisting of detecting an amplification product in a nucleic acid sample from said maize plant, plant part and/or plant cell, the amplification product produced by an oligonucleotide primer pair of the present invention, wherein the primer pair amplifies at least 60 consecutive nucleotides of a nucleotide sequence of SEQ ID NO:1-16 or 32-42, or the full complement thereof, under conditions whereby amplification can occur; thereby identifying a maize plant, plant part and/or plant cell having the sh2-R mutation. In some aspects of the invention, the oligonucleotide primer pair is an oligonucleotide primer pair of the present invention (e.g., an oligonucleotide primer pair that comprises, consists essentially of or consists of a pair of oligonucleotide primers that comprise at least 10 contiguous nucleotide sequences of a nucleotide sequence selected from the group consisting of a nucleotide sequences of SEQ ID NOs:1-59, or the full complement thereof).

In still other embodiments, the present invention provides a method of identifying a maize plant, plant part and/or plant cell having a sh2-R mutation, comprising, consisting essentially of or consisting of amplifying in a nucleic acid sample from said maize plant, plant part and/or plant cell a region of at least 60 consecutive nucleotides of a nucleotide sequence of SEQ ID NOs:1-16 or 32-42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation. In some aspects of the invention, amplifying comprises hybridizing an oligonucleotide primer pair of the present invention to a nucleotide sequence of SEQ ID NOs:1-16 or 32-42, or the full complement thereof.

The subject matter disclosed herein also relates to methods for producing a population of maize plants having no or reduced levels of the sh2-R mutation comprising detecting an amplification product in a nucleic acid sample from one or more maize plants and/or plant parts thereof, in a population, the amplification product produced by an oligonucleotide primer pair of the present invention under conditions whereby amplification can occur, thereby identifying one or more maize plants and/or plant parts thereof, in the population having the sh2-R mutation; and removing said one or more maize plants, and parts thereof, from the population, thereby reducing the presence of, or eliminating, the sh2-R mutation from the maize population.

In particular embodiments, the present invention provides a method of identifying a maize plant, plant part and/or plant cell having a sh2-R mutation, comprising, consisting essentially of or consisting of amplifying in a nucleic acid sample from said maize plant, plant part and/or plant cell a region of at least 60 consecutive nucleotides of a nucleotide sequence of SEQ ID NO:11, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation. In some aspects, the pair of oligonucleotide primers comprises, consists essentially of or consists of a first oligonucleotide, being about 10-50 nucleotides in length and comprising at least 10 contiguous nucleotides of a nucleotide sequence of SEQ ID NO:58, or the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59.

In further embodiments, the present invention provides a method of identifying a maize plant, plant part and/or plant cell having a sh2-R mutation, comprising, consisting essentially of or consisting of amplifying in a nucleic acid sample from said maize plant, plant part and/or plant cell a region of at least 60 consecutive nucleotides of a nucleotide sequence of SEQ ID NO:42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation. In some aspects, the pair of oligonucleotide primers comprises, consists essentially of or consists of a first oligonucleotide, being about 10-50 nucleotides in length and comprising at least 10 contiguous nucleotides of a nucleotide sequence of SEQ ID NO:56, or the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57.

In an additional embodiment, a method of reducing the presence of or eliminating a sh2-R mutation from a maize population is provided, comprising, consisting essentially of or consisting of detecting an amplification product in a nucleic acid sample from one or more maize plants and/or plant parts thereof (i.e., germplasm) in a population, the amplification product produced by an oligonucleotide primer pair that hybridizes to and amplifies a region of at least 60 consecutive nucleotides of a nucleotide sequence of SEQ ID NOs:1-16 or 32-42, or the full complement thereof, under conditions whereby amplification can occur, thereby identifying one or more maize plants and/or plant parts thereof, in the population having the sh2-R mutation; and removing said one or more maize plants and parts thereof from the population thereby reducing the presence of, or eliminating, the sh2-R mutation from the maize population. In some embodiments, the population is a breeding population. In other aspects of the invention, the oligonucleotide primer pair is an oligonucleotide primer pair of the present invention (e.g., an oligonucleotide primer pair that comprises, consists essentially of or consists of a pair of oligonucleotide primers that comprise at least 10 contiguous nucleotide sequences of a nucleotide sequence selected from the group consisting of a nucleotide sequences of SEQ ID NOs:1-59, or the full complement thereof).

In an additional embodiment, a method of reducing the presence of or eliminating a sh2-R mutation from a maize population is provided, comprising, consisting essentially of or consisting of amplifying in a nucleic acid sample from said maize plant, plant part and/or plant cell a region of at least 60 consecutive nucleotides of a nucleotide sequence of any one of the nucleotide sequences of SEQ ID NO:1-16 or 32-42, or the full complement thereof, in an amplification reaction under conditions whereby amplification can occur to produce an amplification product; analyzing the amplification reaction for the presence of the amplification product, thereby identifying a maize plant, plant part and/or plant cell in the population having a sh2-R mutation; and removing said one or more maize plants and parts thereof, from the population thereby reducing the presence of, or eliminating, the sh2-R mutation from the maize population. In some embodiments, the population is a breeding population. In other aspects of the invention, the oligonucleotide primer pair is an oligonucleotide primer pair of the present invention (e.g., an oligonucleotide primer pair that comprises, consists essentially of or consists of a pair of oligonucleotide primers that comprise at least 10 contiguous nucleotide sequences of a nucleotide sequence selected from the group consisting of a nucleotide sequence of SEQ ID NOs:1-59, or the full complement thereof).

In another embodiment, a pair oligonucleotide primers, comprising a first oligonucleotide, being about 10-50 nucleotides in length and comprising at least 10 contiguous nucleotides of a nucleotide sequence selected from the group consisting of SEQ ID NO:1, the full complement of SEQ ID NO:1, SEQ ID NO:32, and the full complement of SEQ ID NO:32; and a second oligonucleotide, being about 10-50 nucleotides in length and comprising at least 10 contiguous nucleotides of a nucleotide sequence selected from the group consisting of SEQ ID NO:1, the full complement of SEQ ID NO:1, SEQ ID NO:32, and the full complement of SEQ ID NO:32.

In another embodiment, a pair of oligonucleotide primers, comprising a first oligonucleotide, being about 10-50 nucleotides in length and comprising at least 10 contiguous nucleotides of a nucleotide sequence selected from the group consisting of SEQ ID NOs:2-16, and the full complement of a nucleotide sequence of SEQ ID NOs:2-16; and a second oligonucleotide, being about 10-50 nucleotides in length and comprising at least 10 contiguous nucleotides of a nucleotide sequence selected from the group consisting of SEQ ID NOs:2-16, and the full complement of a nucleotide sequence of SEQ ID NOs:2-16.

In another embodiment, a pair of oligonucleotide primers, comprising a first oligonucleotide, being about 10-50 nucleotides in length and comprising at least 10 contiguous nucleotides of a nucleotide sequence selected from the group consisting of SEQ ID NOs:17-24, and the full complement of a nucleotide sequence of SEQ ID NOs:17-24; and a second oligonucleotide, being about 10-50 nucleotides in length and comprising at least 10 contiguous nucleotides of a nucleotide sequence selected from the group consisting of SEQ ID NOs:25-31, and the full complement of a nucleotide sequence of SEQ ID NOs:25-31.

In another embodiment, a pair of oligonucleotide primers, comprising a first oligonucleotide, being about 10-50 nucleotides in length and comprising at least 10 contiguous nucleotides of a nucleotide sequence of SEQ ID NO:56, or of the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57.

In another embodiment, a pair of oligonucleotide primers, comprising a first oligonucleotide, being about 10-50 nucleotides in length and comprising at least 10 contiguous nucleotides of a nucleotide sequence of SEQ ID NO:58, or of the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59.

In another embodiment, a pair of oligonucleotide primers, comprising a first oligonucleotide, being about 10-50 nucleotides in length and comprising at least 10 contiguous nucleotides of a nucleotide sequence selected from the group consisting of SEQ ID NOs:33-42, and the full complement of a nucleotide sequence of SEQ ID NOs:33-42; and a second oligonucleotide, being about 10-50 nucleotides in length and comprising at least 10 contiguous nucleotides of a nucleotide sequence selected from the group consisting of SEQ ID NOs:33-42, and the full complement of a nucleotide sequence of SEQ ID NOs:33-42.

In another embodiment, a pair of oligonucleotide primers, comprising a first oligonucleotide, being about 10-50 nucleotides in length and comprising at least 10 contiguous nucleotides of a nucleotide sequence selected from the group consisting of SEQ ID NOs:43-50, and the full complement of a nucleotide sequence of SEQ ID NOs:43-50; and a second oligonucleotide, being about 10-50 nucleotides in length and comprising at least 10 contiguous nucleotides of a nucleotide sequence selected from the group consisting of SEQ ID NOs:51-55, and the full complement of a nucleotide sequence of SEQ ID NOs:51-55.

In another embodiment, a method of identifying a maize plant, plant part and/or plant cell having a sh2-R mutation, comprising amplifying in a nucleic acid sample from said maize plant, plant part and/or plant cell a region of at least 60 consecutive nucleotides of a nucleotide sequence of SEQ ID NO:1-16 or 32-42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation.

In another embodiment, a method of identifying a maize plant, plant part and/or plant cell having a sh2-R mutation, comprising amplifying in a nucleic acid sample from said maize plant, plant part and/or plant cell a region of at least 60 consecutive nucleotides of a nucleotide sequence of SEQ ID NO:1-16 or 32-42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation wherein amplifying comprises hybridizing a pair of oligonucleotide primers to a nucleotide sequence of any one of the nucleotide sequences of SEQ ID NO:1-16 or 32-42 or the full complement thereof wherein the oligonucleotide primers are selected from the group consisting of: a) a first oligonucleotide, being about 10-50 nucleotides in length and comprising at least 10 contiguous nucleotides of a nucleotide sequence selected from the group consisting of SEQ ID NOs:2-16, and the full complement of a nucleotide sequence of SEQ ID NOs:2-16; and a second oligonucleotide, being about 10-50 nucleotides in length and comprising at least 10 contiguous nucleotides of a nucleotide sequence selected from the group consisting of SEQ ID NOs:2-16, and the full complement of a nucleotide sequence of SEQ ID NOs:2-16; b) a first oligonucleotide, being about 10-50 nucleotides in length and comprising at least 10 contiguous nucleotides of a nucleotide sequence selected from the group consisting of SEQ ID NOs:17-24, and the full complement of a nucleotide sequence of SEQ ID NOs:17-24; and a second oligonucleotide, being about 10-50 nucleotides in length and comprising at least 10 contiguous nucleotides of a nucleotide sequence selected from the group consisting of SEQ ID NOs:25-31, and the full complement of a nucleotide sequence of SEQ ID NOs:25-31; c) a first oligonucleotide, being about 10-50 nucleotides in length and comprising at least 10 contiguous nucleotides of a nucleotide sequence of SEQ ID NO:56, or of the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57; d) a first oligonucleotide, being about 10-50 nucleotides in length and comprising at least 10 contiguous nucleotides of a nucleotide sequence of SEQ ID NO:58, or of the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59; e) a first oligonucleotide, being about 10-50 nucleotides in length and comprising at least 10 contiguous nucleotides of a nucleotide sequence selected from the group consisting of SEQ ID NOs:33-42, and the full complement of a nucleotide sequence of SEQ ID NOs:33-42; and a second oligonucleotide, being about 10-50 nucleotides in length and comprising at least 10 contiguous nucleotides of a nucleotide sequence selected from the group consisting of SEQ ID NOs:33-42, and the full complement of a nucleotide sequence of SEQ ID NOs:33-42; and f) a first oligonucleotide, being about 10-50 nucleotides in length and comprising at least 10 contiguous nucleotides of a nucleotide sequence selected from the group consisting of SEQ ID NOs:43-50, and the full complement of a nucleotide sequence of SEQ ID NOs:43-50; and a second oligonucleotide, being about 10-50 nucleotides in length and comprising at least 10 contiguous nucleotides of a nucleotide sequence selected from the group consisting of SEQ ID NOs:51-55, and the full complement of a nucleotide sequence of SEQ ID NOs:51-55.

In some embodiments, a method of identifying a maize plant, plant part and/or plant cell having a sh2-R mutation, comprising amplifying in a nucleic acid sample from said maize plant, plant part and/or plant cell a region of at least 60 consecutive nucleotides of the nucleotide sequence of SEQ ID NO:11, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation.

In another embodiment, a method of identifying a maize plant, plant part and/or plant cell having a sh2-R mutation, comprising amplifying in a nucleic acid sample from said maize plant, plant part and/or plant cell a region of at least 60 consecutive nucleotides of the nucleotide sequence of SEQ ID NO:11, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation; wherein amplifying comprises hybridizing a pair of oligonucleotide primers to a nucleotide sequence of SEQ ID NO:11, or the full complement thereof wherein said oligonucleotide primers comprise: a first oligonucleotide, being about 10-50 nucleotides in length and comprising at least 10 contiguous nucleotides of a nucleotide sequence of SEQ ID NO:58, or of the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59.

In another embodiment, a method of identifying a maize plant, plant part and/or plant cell having a sh2-R mutation, comprising amplifying in a nucleic acid sample from said maize plant, plant part and/or plant cell a region of at least 60 consecutive nucleotides of the nucleotide sequence of SEQ ID NO:42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation.

In another embodiment, a method of identifying a maize plant, plant part and/or plant cell having a sh2-R mutation, comprising amplifying in a nucleic acid sample from said maize plant, plant part and/or plant cell a region of at least 60 consecutive nucleotides of the nucleotide sequence of SEQ ID NO:42, or the full complement thereof, in an amplification reaction under conditions whereby amplification can occur to produce an amplification product; and analyzing the amplification reaction for the presence of the amplification product, thereby identifying a maize plant, plant part and/or plant cell having a sh2-R mutation; wherein amplifying comprises hybridizing a pair of oligonucleotide primers to the nucleotide sequence of SEQ ID NO:42, or the full complement thereof wherein said oligonucleotide primers compirse: a first oligonucleotide, being about 10-50 nucleotides in length and comprising at least 10 contiguous nucleotides of a nucleotide sequence of SEQ ID NO:56, or of the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57.

In another embodiment, a method of reducing the presence of, or eliminating, the sh2-R mutation from a maize population, comprising amplifying in a nucleic acid sample from one or more maize plants, plant parts and/or plant cells from said population a region of at least 60 consecutive nucleotides of a nucleotide sequence of SEQ ID NO:1-16 or 32-42, or the full complement thereof, in an amplification reaction under conditions whereby amplification can occur to produce an amplification product; analyzing the amplification reaction for the presence of the amplification product, thereby identifying one or more maize plants, plant parts and/or plant cells in the population having a sh2-R mutation; and removing said one or more maize plants and parts thereof, from the population thereby reducing the presence of, or eliminating, the sh2-R mutation from the maize population.

In another embodiment, a method of reducing the presence of, or eliminating, the sh2-R mutation from a maize population, comprising amplifying in a nucleic acid sample from one or more maize plants, plant parts and/or plant cells from said population a region of at least 60 consecutive nucleotides of a nucleotide sequence of SEQ ID NO:1-16 or 32-42, or the full complement thereof, in an amplification reaction under conditions whereby amplification can occur to produce an amplification product; analyzing the amplification reaction for the presence of the amplification product, thereby identifying one or more maize plants, plant parts and/or plant cells in the population having a sh2-R mutation; and removing said one or more maize plants and parts thereof, from the population thereby reducing the presence of, or eliminating, the sh2-R mutation from the maize population, wherein amplifying comprises hybridizing a pair of oligonucleotide primers to a nucleotide sequence of any one of the nucleotide sequences of SEQ ID NO:1-16 or 32-42 or the full complement thereof wherein said pair of oligonucleotide primers is selected from the group consisting of; a) a first oligonucleotide, being about 10-50 nucleotides in length and comprising at least 10 contiguous nucleotides of a nucleotide sequence selected from the group consisting of SEQ ID NOs:2-16, and the full complement of a nucleotide sequence of SEQ ID NOs:2-16; and a second oligonucleotide, being about 10-50 nucleotides in length and comprising at least 10 contiguous nucleotides of a nucleotide sequence selected from the group consisting of SEQ ID NOs:2-16, and the full complement of a nucleotide sequence of SEQ ID NOs:2-16; b) a first oligonucleotide, being about 10-50 nucleotides in length and comprising at least 10 contiguous nucleotides of a nucleotide sequence selected from the group consisting of SEQ ID NOs:17-24, and the full complement of a nucleotide sequence of SEQ ID NOs:17-24; and a second oligonucleotide, being about 10-50 nucleotides in length and comprising at least 10 contiguous nucleotides of a nucleotide sequence selected from the group consisting of SEQ ID NOs:25-31, and the full complement of a nucleotide sequence of SEQ ID NOs:25-31; c) a first oligonucleotide, being about 10-50 nucleotides in length and comprising at least 10 contiguous nucleotides of a nucleotide sequence of SEQ ID NO:56, or of the full complement of SEQ ID NO:56; and a second oligonucleotide, being about 10-50 nucleotides in length and comprising at least 10 contiguous nucleotides of a nucleotide sequence of SEQ ID NO:57, or the full complement of SEQ ID NO:57; d) a first oligonucleotide, being about 10-50 nucleotides in length and comprising at least 10 contiguous nucleotides of a nucleotide sequence of SEQ ID NO:58, or of the full complement of SEQ ID NO:58; and a second oligonucleotide, being about 10-50 nucleotides in length and comprising at least 10 contiguous nucleotides of a nucleotide sequence of SEQ ID NO:59, or the full complement of SEQ ID NO:59; e) a first oligonucleotide, being about 10-50 nucleotides in length and comprising at least 10 contiguous nucleotides of a nucleotide sequence selected from the group consisting of SEQ ID NOs:33-42, and the full complement of a nucleotide sequence of SEQ ID NOs:33-42; and a second oligonucleotide, being about 10-50 nucleotides in length and comprising at least 10 contiguous nucleotides of a nucleotide sequence selected from the group consisting of SEQ ID NOs:33-42, and the full complement of a nucleotide sequence of SEQ ID NOs:33-42; and f) a first oligonucleotide, being about 10-50 nucleotides in length and comprising at least 10 contiguous nucleotides of a nucleotide sequence selected from the group consisting of SEQ ID NOs:43-50, and the full complement of a nucleotide sequence of SEQ ID NOs:43-50; and a second oligonucleotide, being about 10-50 nucleotides in length and comprising at least 10 contiguous nucleotides of a nucleotide sequence selected from the group consisting of SEQ ID NOs:51-55, and the full complement of a nucleotide sequence of SEQ ID NOs:51-55.

A sample of genomic DNA from a corn plant can be provided by standard DNA isolation methods well known in the art.

Definitions

Although the following terms are believed to be well understood by one of ordinary skill in the art, the following definitions are set forth to facilitate understanding of the presently disclosed subject matter.

As used herein, the terms "a" or "an" or "the" may refer to one or more than one. For example, a cell can mean a single cell or a multiplicity of cells (e.g., 2, 3, 4, 5, 6, 7, 8, 9, 10 and the like).

As used herein, the term "and/or" refers to and encompasses any and all possible combinations of one or more of the associated listed items, as well as the lack of combinations when interpreted in the alternative ("or").

As used herein, the term "about," when used in reference to a measurable value such as length of a nucleotide sequence, number of nucleotides, an amount of mass, dose, time, temperature, and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the phrase "reducing the presence of the sh2-R mutation from a maize population" means reducing the number of maize plants and parts thereof, (i.e., germplasm) in a maize population that have the mutation as compared to a sh2 and sh2-1 population. Thus, in some embodiments, the presence of the sh2-R mutation can be reduced by about 1%, 5%, 10%, 15%, 20%, 25%, 30%, 35%, 40%, 45%, 50%, 55%, 60%, 65%, 70%, 75%, 80%, 85%, 90%, 95%, or 100%, and the like, or any range therein, as compared to a sh2 and sh2-1 population.

As used herein, the phrase "eliminating the presence of the sh2-R mutation from a maize population" means identifying and removing from a population most or all of the plants and/or parts thereof having the sh2-R mutation, thereby eliminating the sh2-R mutation from the population. Thus, in some embodiments, eliminating the sh2-R mutation results in about 0.01%, 0.1%, 0.5%, 1%, 2%, 3%, 4%, 5%, 6%, 7%, 8%, 9%, or 10%, or any range therein, of the plants and/or parts thereof in a population having the sh2-R mutation as compared to a sh2 and sh2-1 population.

As used herein, the term "allele" refers to one of two or more different nucleotides or nucleotide sequences that occur at a specific locus.

A "locus" is a position on a chromosome where a gene or marker or allele is located. In some embodiments, a locus may encompass one or more nucleotides.

A marker is "associated with" a trait when it is linked to it and/or statistically correlated with the trait and when the presence of the marker is an indicator of whether and/or to what extent the desired trait or trait form will occur in a plant/germplasm comprising the marker.

As used herein, the terms "cultivar" and "variety" refer to a group of similar plants that by structural or genetic features and/or performance can be distinguished from other cultivars/varieties within the same species.

A "genetic map" is a description of genetic linkage relationships among loci on one or more chromosomes within a given species, generally depicted in a diagrammatic or tabular form. For each genetic map, distances between loci are measured by the recombination frequencies between them. Recombination between loci can be detected using a variety of markers. A genetic map is a product of the mapping population, types of markers used, and the polymorphic potential of each marker between different populations. The order and genetic distances between loci can differ from one genetic map to another.

As used herein, the term "genotype" refers to the genetic constitution of an individual (or group of individuals) at one or more genetic loci, as contrasted with the observable and/or detectable and/or manifested trait (the phenotype). Genotype is defined by the allele(s) of one or more known loci that the individual has inherited from its parents. The term genotype can be used to refer to an individual's genetic constitution at a single locus, at multiple loci, or more generally, the term genotype can be used to refer to an individual's genetic make-up for all the genes in its genome. Genotypes can be indirectly characterized, e.g., using markers and/or directly characterized by nucleic acid sequencing.

As used herein, the term "germplasm" refers to genetic material of or from an individual (e.g., a plant), a group of individuals (e.g., a plant line, variety or family), or a clone derived from a line, variety, species, or culture. The germplasm can be part of an organism or cell, or can be separate from the organism or cell. In general, germplasm provides genetic material with a specific molecular makeup that provides a physical foundation for some or all of the hereditary qualities of an organism or cell culture. As used herein, the term "germplasm" includes but is not limited to cells, seed or tissues from which new plants may be grown, as well as plants and plant parts, such as leaves, stems, pollen, or cells that can be cultured into a whole plant.

As used herein, the term "heterozygous" refers to a genetic status wherein different alleles reside at corresponding loci on homologous chromosomes.

As used herein, the term "homozygous" refers to a genetic status wherein identical alleles reside at corresponding loci on homologous chromosomes.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous plant or variety. The term may refer to a plant or plant variety that is substantially homozygous throughout the entire genome or that is substantially homozygous with respect to a portion of the genome that is of particular interest.

As used herein, the term "linkage" refers to the degree with which one marker locus is associated with another marker locus. The linkage relationship between a molecular marker and a phenotype may be given as a "probability" or "adjusted probability." Linkage can be expressed as a desired limit or range. For example, in some embodiments, any marker is linked (genetically and physically) to any other marker when the markers segregate from each other in the next generation less than 50% of the time, less than 25% of the time, less than 20% of the time, less than 15% of the time, less than 10% of the time, less than 5% of the time, less than 4% of the time, less than 3% of the time, less than 2% of the time, or less than 1% of the time. Thus, in some embodiments, two loci are linked when they are separated by less than about 50, 40, 30, 25, 20, 15, 10, 5, 4, 3, 2, 1, or 0.5 map units or centiMorgans (cM).

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, the term "linkage group" is synonymous with the physical entity of a chromosome, although one of ordinary skill in the art will understand that a linkage group can also be defined as corresponding to a region (i.e., less than the entirety) of a given chromosome.

As used herein, the term "linkage disequilibrium" refers to a non-random segregation of genetic loci or traits (or both). In either case, linkage disequilibrium implies that the relevant loci are within sufficient physical proximity along a length of a chromosome so that they segregate together with greater than random (i.e., non-random) frequency (in the case of co-segregating traits, the loci that underlie the traits are in sufficient proximity to each other). Markers that show linkage disequilibrium are considered linked. Linked loci co-segregate more than 50% of the time, e.g., from about 51% to about 100% of the time. In other words, two markers that co-segregate have a recombination frequency of less than 50% (and, by definition, are separated by less than 50 cM on the same chromosome). As used herein, linkage can be between two markers, or alternatively between a marker and a phenotype/trait. The degree of linkage of a genetic marker to a phenotypic trait is measured, e.g., as a statistical probability of co-segregation of that genetic marker with the phenotype.

Linkage disequilibrium is most commonly assessed using the measure $r^2$, which is calculated using the formula described by Hill and Robertson (*Theor. Appl. Genet.* 38:226 (1968)). When $r^2=1$, complete linkage disequilibrium exists between the two marker loci, meaning that the markers have not been separated by recombination and have the same allele frequency. Values for $r^2$ above ⅓ indicate sufficiently strong linkage disequilibrium to be useful for mapping. Ardlie et al. (*Nature Reviews Genetics* 3:299 (2002)). Hence, alleles are in linkage disequilibrium when $r^2$ values between pairwise marker loci are greater than or equal to about 0.33, 0.4, 0.5, 0.6, 0.7, 0.8, 0.9, or 1.0.

As used herein, the term "linkage equilibrium" describes a situation where two markers independently segregate, i.e., sort among progeny randomly. Markers that show linkage equilibrium are considered unlinked (whether or not they lie on the same chromosome).

As used herein, the terms "marker" and "genetic marker" are used interchangeably to refer to a nucleotide and/or a nucleotide sequence that has been associated with a phenotype and/or trait. A marker may be, but is not limited to, a deletion, an insertion, a SNP allele and/or combination of SNP alleles (haplotype) (Brookes, Gene 234:177 (1993)), a gene, a chromosome interval, a restriction fragment length polymorphism (RFLP), a simple sequence repeat (SSR), a random amplified polymorphic DNA (RAPD), a cleaved amplified polymorphic sequence (CAPS) (Rafalski and Tingey, *Trends in Genetics* 9:275 (1993)), an amplified fragment length polymorphism (AFLP) (Vos et al., *Nucleic Acids Res.* 23:4407 (1995)), a sequence-characterized amplified region (SCAR) (Paran and Michelmore, *Theor. Appl. Genet.* 85:985 (1993)), a sequence-tagged site (STS) (Onozaki et al., *Euphytica* 138:255 (2004)), a single-stranded conformation polymorphism (SSCP) (Orita et al., *Proc. Natl. Acad. Sci. USA* 86:2766 (1989)), an inter-simple sequence repeat (ISSR) (Blair et al., *Theor. Appl. Genet.* 98:780 (1999)), an inter-retrotransposon amplified polymorphism (IRAP), a retrotransposon-microsatellite amplified polymorphism (REMAP) (Kalendar et al., *Theor. Appl. Genet.* 98:704 (1999)), an isozyme marker, an RNA cleavage product (such as a Lynx tag) or any combination of the markers described herein. A marker may be present in genomic or expressed nucleic acids (e.g., ESTs).

Markers corresponding to genetic polymorphisms between members of a population can be detected by methods well-established in the art. These include, e.g., nucleic acid sequencing, hybridization methods, amplification methods (e.g., PCR-based sequence specific amplification methods and other methods by which amplification of a target nucleotide sequence can occur), detection of a deletion, detection of an insertion, detection of restriction fragment length polymorphisms (RFLP), detection of isozyme markers, detection of polynucleotide polymorphisms by allele specific hybridization (ASH), detection of amplified variable sequences of the plant genome, detection of self-sustained sequence replication, detection of simple sequence repeats (SSRs), detection of single nucleotide polymorphisms (SNPs), and/or detection of amplified fragment length polymorphisms (AFLPs). Well established methods are also known for detecting expressed sequence tags (ESTs) and SSR markers derived from EST sequences and randomly amplified polymorphic DNA (RAPD).

Accordingly, in some embodiments of this invention, a marker corresponds to an amplification product generated by amplifying a corn genomic nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying corn genomic DNA with a particular set of primers. In some embodiments, the amplifying is by PCR, and the primers are PCR primers that are designed to hybridize to opposite strands of the maize genomic DNA in order to amplify a maize genomic DNA sequence present between the sequences to which the PCR primers hybridize in the maize genomic DNA. In other embodiments, a marker that "corresponds to" an amplified fragment is a marker that has the same sequence of one of the strands of the amplified fragment.

A "marker allele," also described as an "allele of a marker locus," can refer to one of a plurality of polymorphic nucleotide sequences found at a marker locus in a population that is polymorphic for the marker locus.

"Marker-assisted selection" (MAS) is a process by which phenotypes are selected based on marker genotypes. Marker assisted selection includes the use of marker genotypes for identifying plants for inclusion in and/or removal from a breeding program or planting.

As used herein, the terms "marker locus" and "marker loci" refer to a specific chromosome location or locations in the genome of an organism where a specific marker or markers can be found. A marker locus can be used to track the presence of a second linked locus, e.g., a linked locus that encodes or contributes to expression of a phenotypic trait. For example, a marker locus can be used to monitor segregation of alleles at a locus, such as a QTL or single gene, that are genetically or physically linked to the marker locus.

As used herein, the terms "marker probe" and "probe" refer to a nucleotide sequence or nucleic acid molecule that can be used to detect the presence of one or more particular alleles within a marker locus (e.g., a nucleic acid probe that is complementary to all of or a portion of the marker or marker locus, through nucleic acid hybridization). Marker probes comprising about 8, 10, 15, 20, 30, 40, 50, 60, 70, 80, 90, 100 or more contiguous nucleotides may be used for nucleic acid hybridization. Alternatively, in some aspects, a marker probe refers to a probe of any type that is able to distinguish (i.e., genotype) the particular allele that is present at a marker locus. In some embodiments, the term "probe" refers to a single-stranded oligonucleotide sequence that will form a hydrogen-bonded duplex with a complementary sequence in a target nucleic acid sequence analyte or its cDNA derivative.

As used herein, the term "molecular marker" may be used to refer to a genetic marker, as defined above, or an encoded product thereof (e.g., a protein) used as a point of reference when identifying a linked locus. A molecular marker can be derived from genomic nucleotide sequences or from expressed nucleotide sequences (e.g., from a spliced RNA, a cDNA, etc.). The term also refers to nucleotide sequences complementary to or flanking the marker sequences, such as nucleotide sequences used as probes and/or primers capable of amplifying the marker sequence. Nucleotide sequences are "complementary" when they specifically hybridize in solution, e.g., according to Watson-Crick base pairing rules. Some of markers can also be referred to as hybridization markers when located on an indel region. This is because the insertion or deletion region is, by definition, a polymorphism vis-ã-vis a plant without the insertion or deletion. Thus, the marker need only indicate whether the indel region is present or absent. Any suitable marker detection technology may be used to identify such a hybridization marker.

As used herein, an "amplification reaction" refers to the reaction mixture in which the amplification of a target nucleotide sequence can occur thereby increasing the number of copies of the target nucleic acid sequence by enzymatic means. Amplification procedures are well-known in the art and include, but are not limited to, polymerase chain reaction (PCR), TMA, rolling circle amplification, nucleic acid sequence based amplification (NASBA), strand displacement amplification (SDA) and Q-beta replicase amplification. One skilled in the art will understand that for use in certain amplification techniques the primers described herein may need to be modified, for example, SDA primers comprise additional nucleotides near the 5' end that constitute a recognition site for a restriction endonuclease. Similarly, NASBA primers comprise additional nucleotides near the 5' end that are not complementary to the target sequence but which constitute an RNA polymerase promoter. Polynucleotides thus modified are considered to be within the scope of the present invention. Further, the term "PCR" as used herein refers to the various forms of PCR known in the art including, but not limited to, quantitative PCR, reverse-transcriptase PCR, real-time PCR, hot start PCR, long PCR, LAPCR, multiplex PCR, touchdown PCR, and the like. "Real-time PCR" refers to a PCR reaction in which the amplification of a target sequence is monitored in real time by, for example, the detection of fluorescence emitted by the binding of a labelled probe to the amplified target sequence. See, U.S. Pat. No. 8,088,572.

As used herein, the term "primer" refers to an oligonucleotide which is capable of annealing to a nucleic acid target and serving as a point of initiation of DNA synthesis when placed under conditions in which synthesis of a primer extension product is induced (e.g., in the presence of nucleotides and an agent for polymerization such as DNA polymerase and at a suitable temperature and pH). A primer (in some embodiments an extension primer and in some embodiments an amplification primer) is in some embodiments single stranded for maximum efficiency in extension and/or amplification. In some embodiments, the primer is an oligodeoxyribonucleotide. A primer is typically sufficiently long to prime the synthesis of extension and/or amplification products in the presence of the agent for polymerization. The minimum length of a primer can depend on many factors, including, but not limited to temperature and composition (A/T vs. G/C content) of the primer.

In the context of amplification primers, these are typically provided as a pair of bi-directional primers (i.e., a primer pair) consisting of one forward and one reverse primer or provided as a pair of forward primers as commonly used in the art of DNA amplification such as in PCR amplification.

As such, it will be understood that the term "primer," as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

The PCR method is well described in handbooks and known to the skilled person. After amplification by PCR, target polynucleotides can be detected by hybridization with a probe polynucleotide which forms a stable hybrid with that of the target sequence under stringent to moderately stringent hybridization and wash conditions. If it is expected that the probes are essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell (2001). *Molecular Cloning: A Laboratory Manual*, Third Edition, Cold Spring Harbor Laboratory Press, Cold Spring Harbor, N.Y., United States of America. Generally, lower salt concentration and higher temperature hybridization and/or washes increase the stringency of hybridization conditions.

Different nucleotide sequences or polypeptide sequences having homology are referred to herein as "homologues." The term homologue includes homologous sequences from the same and other species and orthologous sequences from the same and other species. "Homology" refers to the level of similarity between two or more nucleotide sequences and/or amino acid sequences in terms of percent of positional identity (i.e., sequence similarity or identity). Homology also refers to the concept of similar functional properties among different nucleic acids, amino acids, and/or proteins.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. The "percentage of sequence homology" for polynucleotides, such as 50, 55, 60, 65, 70, 75, 80, 85, 90, 95, 96, 97, 98, 99 or 100 percent sequence homology, can be determined by comparing two optimally aligned sequences over a comparison window (e.g., about 20-200 contiguous nucleotides), wherein the portion of the polynucleotide sequence in the comparison window can include additions or deletions (i.e., gaps) as compared to a reference sequence for optimal alignment of the two sequences. Optimal alignment of sequences for comparison can be conducted by computerized implementations of known algorithms, or by visual inspection. Readily available sequence comparison and multiple sequence alignment algorithms are, respectively, the Basic Local Alignment Search Tool (BLAST; Altschul et al. (1990) *J Mol Biol* 215:403-10; Altschul et al. (1997) *Nucleic Acids Res* 25:3389-3402) and ClustalX (Chenna et al. (2003) *Nucleic Acids Res* 31:3497-3500) programs, both available on the Internet. Other suitable programs include, but are not limited to, GAP, BestFit, PlotSimilarity, and FASTA, which are part of the Accelrys GCG Package available from Accelrys Software, Inc. of San Diego, Calif., United States of America.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "substantially identical" or "corresponding to" means that two nucleotide sequences have at least 50%, 60%, 70%, 75%, 80%, 85%, 90% or 95% sequence identity. In some embodiments, the two nucleotide sequences (e.g., an oligonucleotide primer) can have at least 85%, 90%, 95%, 96%, 97%, 98%, 99% or 100% sequence identity.

An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned (with appropriate nucleotide insertions, deletions, or gaps totaling less than 20 percent of the reference sequence over the window of comparison). In some embodiments, "percent identity" can refer to the percentage of identical amino acids in an amino acid sequence.

Optimal alignment of sequences for aligning a comparison window is well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., Burlington, Mass.). The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

The percent of sequence identity can be determined using the "Best Fit" or "Gap" program of the Sequence Analysis Software Package™ (Version 10; Genetics Computer Group, Inc., Madison, Wis.). "Gap" utilizes the algorithm of Needleman and Wunsch (Needleman and Wunsch, *J Mol. Biol.* 48:443-453, 1970) to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman (*Adv. Appl. Math.,* 2:482-489, 1981, Smith et al., *Nucleic Acids Res.* 11:2205-2220, 1983).

Useful methods for determining sequence identity are also disclosed in *Guide to Huge Computers* (Martin J. Bishop, ed., Academic Press, San Diego (1994)), and Carillo et al. (*Applied Math* 48:1073(1988)). More particularly, preferred computer programs for determining sequence identity include but are not limited to the Basic Local Alignment Search Tool (BLAST) programs which are publicly available from National Center Biotechnology Information (NCBI) at the National Library of Medicine, National Institutes of Health, Bethesda, Md. 20894; see BLAST Manual, Altschul et al., NCBI, NLM, NIH; (Altschul et al., *J. Mol. Biol.* 215:403-410 (1990)); version 2.0 or higher of BLAST programs allows the introduction of gaps (deletions and insertions) into alignments; for peptide sequence BLASTX can be used to determine sequence identity; and for polynucleotide sequence BLASTN can be used to determine sequence identity.

As used herein, the terms "phenotype," "phenotypic trait" or "trait" refer to one or more traits of an organism. The phenotype can be observable to the naked eye, or by any other means of evaluation known in the art, e.g., microscopy, biochemical analysis, and/or an electromechanical assay. In some cases, a phenotype is directly controlled by a single gene or genetic locus, i.e., a "single gene trait." In other cases, a phenotype is the result of several genes.

As used herein, the term "polymorphism" refers to a variation in a nucleotide sequence at a locus, where the variation is too common to be due merely to a spontaneous mutation. A polymorphism can be a single nucleotide polymorphism (SNP), or an insertion/deletion polymorphism, also referred to herein as an "indel." Additionally, the variation can be in a transcriptional profile or a methylation pattern. The polymorphic site or sites of a nucleotide sequence can be determined by comparing a nucleotide sequences at one or more loci in two or more germplasm entries.

As used herein, the term "plant" can refer to a whole plant, any part thereof, or a cell or tissue culture derived from a plant. Thus, the term "plant" can refer to a whole plant, a plant component or a plant organ (e.g., leaves, stems, roots, etc.), a plant tissue, a seed and/or a plant cell. A plant cell is a cell of a plant, taken from a plant, or derived through culture from a cell taken from a plant.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); and specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs plant cell tissue cultures, plant calli, plant clumps, and the like. As used herein, "shoot" refers to the above ground parts including the leaves and stems.

The term "tissue culture" encompasses cultures of tissue, cells, protoplasts and callus. Thus, a plant part can include a maize tissue culture from which maize plants can be regenerated.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ.

The following examples are included to demonstrate various embodiments of the invention and are not intended to be a detailed catalog of all the different ways in which the present invention may be implemented or of all the features that may be added to the present invention. Persons skilled in the art will appreciate that numerous variations and additions to the various embodiments may be made without departing from the present invention. Hence, the following descriptions are intended to illustrate some particular embodiments of the invention, and not to exhaustively specify all permutations, combinations and variations thereof.

EXAMPLES

Example 1. Plant Materials

Maize sweet corn line W1065A was grown under 16 hr day/8 hr night light conditions. Plants were harvested at 12 days and frozen at −80° C.

Example 2. Genomic DNA Isolation

Leaf genomic DNA was isolation from young shoots using the CTAB method from the CIMMYT Applied Molecular Genetics Laboratory (based on method of Saghai-Maroof et al. *Proc. Nall. Acad. Sci*. vol. 81:8014-8018 (1984)).

Example 3. Lambda Genomic Library Construction

W1065A DNA was digested with 1U EcoRI (New England BioLabs®, NEB), samples were taken out at 5 min intervals for 30 min at 37° C. as described by the supplier. The digested DNA was pooled and fractionated on a 1% SeaPlaque® agarose (Lonza) Tris-Acetate-EDTA (TBE) gel run 16 hrs at 40 volts. The gel was stained with ethidium bromide, 3 to 8 kb and 8 to 20 kb fractions were cutout using a 1 to 10 kb DNA ladder (NEB) as reference. The gel slice was heated to 65° C. to melt the agarose and placed in a 37° C. heating block to equilibrate. The agarose was digested with Gelase™ (Epicentre®), 1U/200 μl agarose for 2 hrs. Sample was centrifuged for 2 min at 10K in a microfuge. The supernate was removed, 2 vol isopropanol and 0.1 vol NaAcetate pH 4.8 were added and centrifuged for 15 min at 12K in a microfuge. The pellet was washed 2× with 70% ethanol and air dried. The DNA was resuspended at 50 ng/μl inTE buffer. Lambda ZapExpress (0-12 kb insert size) and Lambda DASHII (9-20 kb insert size) vectors pre-digested with EcoRI was used in the ligations as described by the supplier (Stratagene). Ligations were packaged using Max-Plaque (Epicentre®) packing extract as described by the supplier.

Example 4. Fosmid Genomic Library Construction

The CopyControl Fosmid library production kit (Epicentre®) was used to generate fosmid libraries for screening. The libraries were constructed as described by the supplier (Epicentre®).

Example 5. DNA Hybridization Probes

PCR was used to generate probes from 5' and 3' side of the sh2-R insertion in W1065A DNA. The 3'insertion primers were (5'-GATAACACTGAACATCCAACGT-3') (SEQ ID NO:59) and (5'-GATCCATCAGCAAAGTTGATCCCGCC-3')(SEQ ID NO:60), 442 bp amplicon. The 5' primers were (5'-GGGAGTTCTATACTTCTGTTGGACTGG-3') (SEQ ID NO:61) and (5'-CGTAGCTCTTGTGCTTGTCAGA-3') (SEQ ID NO:62), 506 bp amplicon. The x1 probe 5' and 3' primers were (5'-CAGGTGGTGGGAAAAAAAGC-3') (SEQ ID NO:63) and (5'-CACTACTACTTACAGTAGACA-3') (SEQ ID NO:64). The yx1 5' and 3' primers were (5'-CATGTACATCTTCCTCACTG-3') (SEQ ID NO:65) and (5'-CAGGTTTGCAAATGTGAGG-3') (SEQ ID NO:66), 690 bp amplicon. The a1 5' and 3' primers were (5'-TTTTTGCATACATCCACTCAG-3') (SEQ ID NO:67) and (5'-TAATTACTAACAAAACACTCGG-3') (SEQ ID NO:68), 600 bp amplicon and the CL11820 5' and 3' primers were (5'-TTGGAATAAGTACAATTCT-3') (SEQ ID NO:69) and (5'-ACAAATTCTCCGTGAGCATAT-3') (SEQ ID NO:70), 410 bp amplicon. PCR was completed with the following conditions [94° C., 4 min], 35 cycles [94° C., 30 s, x° C., 30 s, 72° C., 1 min] with the annealing temperate varying with primer pair Tm. The reaction contained 1× Expand buffer, 1U Expand DNA polymerase (Roche), 200 uM dNTP, 50 ng DNA, 50 ng primers, and nuclease free water to 50 ul. PCR products were fractionated in 1% SeaPlaque-TAE agarose gel and isolated gel slice treated with Gelase™ as described above. Probes were labeled with EasyTide (ά-32P) dCTP 3000 Ci/mmol (Perkin Elmer) using Rediprime II random prime labeling system (GE Amersham). Unincorporated nucleotides were removed using BioRad Micro Bio-Spin 30 columns Probes were heated at 95° C. for 5 min before addition to hybridization solution.

Example 6. Lambda Phage Screen

The phage library was plated a density of 50,000 pfu per 150×25 mm L-agar plate as described by supplier (Stratagene), a total of 10 plates, 500,000 pfu were plated per library screened with the 5' and 3' sh2 probes. Plates were incubated overnight at 37° C. Plates were placed at 4° C. for 1 hr prior to filter lifts. BioRad C/P or Hybond NX (GE Amersham) 137 mm filter circles and filters were treated as described by the supplier. Lifts were completed as follows: filters placed on plates for 1 min, using forceps, lift membrane from agar surface and place membrane phage/colony side up on Whatman paper soaked with 0.5 M NaOH for 5 minutes. Place on Whatman paper soaked in 2×SSC for 5 min. then Stratalink at 2000×100 uJ (Stratgene) to fix the DNA to the membrane. Air dried on Whatman paper. Filters were pre-hybridized for 4 hrs and hybridized in 250 mM $NaPO_4$, pH 7.0, 7% SDS, 1% BSA at 65° C. as described by the supplier. Hybridization Filters were washed in 2×SSC, 0.5% SDS for 30 min at 65° C., followed by 0.2×SSC, 0.2% SDS for 30 min at 65° C. Filters were exposed to Kodak® BIOMAX® XAR film overnight with intensifying screens at −80° C.

Example 7. Colony Hybridization Screen

The fosmid library was plated at a density of 5,000 cfu per 150×25 mm L-agar plus 15 ug/ml chloramphenicol plate. A 100,000 cfu or 20 plates were screened for the x1, yx1, a1 and CL1180 probes. Hybond™ NX (GE Amersham) 137 mm filter circles were used in lifts. Lifts were completed as follows: filters placed on plates for 5 min, using forceps, lift membrane from agar surface and place membrane colony side up on Whatman filter paper soaked with 0.5 M NaOH for 5 minutes. Place on Whatman filter paper soaked in 2×SSC for 5 min. and then Stratalink at 2000×100 uJ (Stratgene) to fix the DNA to the membrane. Air dried on Whatman filter paper. Filters were pre-hybridized and hybridized in 250 min NaPO4, pH 7.0, 7% SDS, 1% BSA at 65° C. as described by the supplier. Hybridization filters were washed in 2×SSC, 0.5% SDS for 30 min at 65° C., followed by 0.2×SSC, 0.2% SDS for 30 min at 65° C. Filters were exposed to Kodak® BIOMAX® XAR film overnight with intensifying screens at −80° C.

Example 8. Isolation of Phage DNA and Fosmid DNA for Sequencing

Lambda DASHII phage DNA was isolated using the Qiagen Lambda Mini Kit. The isolated lambda DNA was amplified using the GE GenomPhi Whole Genome Amplification kit for sequencing. Lambda Zap Express phage were converted to plasmid using the In Vivo Excision Protocol described in the Lambda Zap Express manual (Stratagene). Fosmid DNA was isolated using the Sigma PhasePrep BAC DNA kit.

Example 9. Sequencing

DNA isolated as described in Example 8 is used as follows. DNA is subjected to sequencing analysis using the BIGDYE™ Terminator Kit according to manufacturer's instructions (Applied Biosystems, Foster City, Calif.) Sequencing makes use of primers designed to both strands of the predicted nucleotide sequence of interest. DNA sequencing is performed using standard dye-terminator sequencing procedures and automated sequencers (models 373 and 377; Applied Biosystems, Foster City, Calif.). All sequencing data are analyzed and assembled using the Sequencher 4.9 program (GeneCodes, Ann Arbor, Mich.) to an error ratio equal to or less than $10^{-4}$ at the consensus sequence level.

Fosmid DNA was treated with the EZ-Tn5 insertion kit (Epicentre) to generate random insertions for rapid sequencing of the 35-40 kb fosmid inserts Lambda DNA was sequenced by primer walking. Fosmid clones were digested with restriction enzymes, fragments isolated and ligated into BlueScript (Stratagene) and sequenced. This allowed the assembly of repetitive regions that transposon mutagensis or primer walked failed to complete alone. Alignment with gene prediction and BLAST analysis programs are used to ascertain that this is in fact the right gene for the non-repetitive sequences in the assembly.

Example 10. PCR Confirmation of 3' Lambda DASH Clone 6

Figure 4:
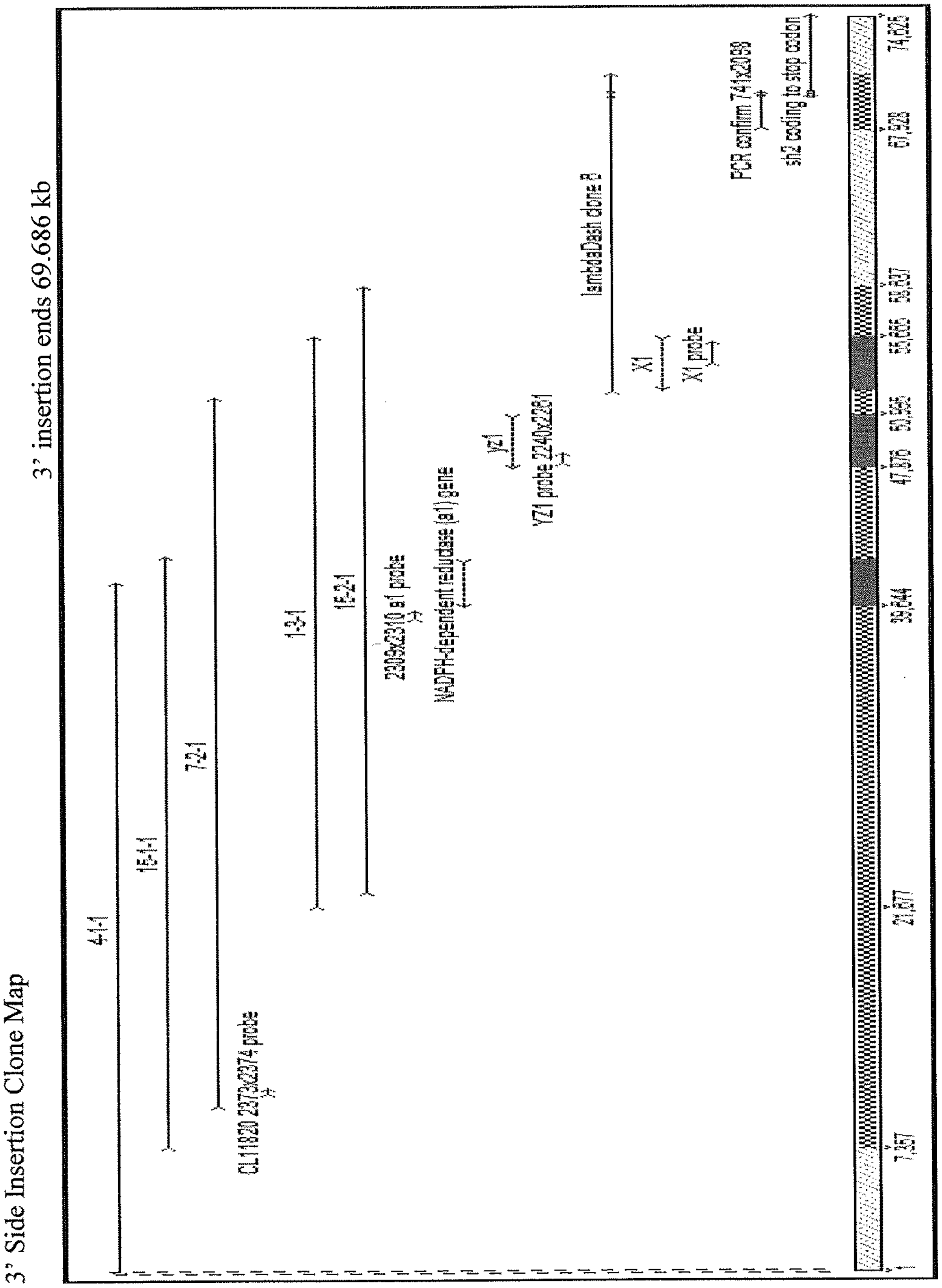
FIG. 4 shows the 3' side insertion clone map.

PCR was used to confirm that clone 6 was not chimeric. Primers were designed to amplify from clone 6 into the coding sequence of the sh2 gene. The primers were 2098f (5'-GCACTGTGCTCATCATCCCTT-3') (SEQ ID NO:56) and 741r (5'-AGAAAATTTGACTGGAAGTCTC-3') (SEQ ID NO:57), 2.1 kb amplicon (FIG. 4). The following cycle condition were used: [94° C., 4 min], 35 cycles [94° C., 30 s, 52° C., 30 s, 72° C., 2 min]. The reaction contained 1× Expand buffer, 1U Expand DNA polymerase (Roche), 200 uM dNTP, 50 ng DNA, 50 ng primers, and nuclease free water to 50 ul. The positive result indicates that the internal EcoRI at 68,160 is not a chimeric fragment but part of the sh2-R insertion. Thus, Table 1, below, shows the gene content of the isolated clones and overlap between the clones and Table 2, below, provides the insertion length for the 5' and 3' sides of the insertion and the total length of the insertion.

TABLE 1 sh2-R Clone Insertion Size and Gene Content

| Clone | 5' or 3' side clone | Size | x1 gene | yz1 gene | a1 gene | CL11820 gene |
|---|---|---|---|---|---|---|
| Lambda Zap clone 8 | 5' | 4.85 kb | | | | |
| Fosmid clone 11-1 | 5' | 37.456 kb | | | | |
| Lambda DASH clone 6 | 3' | 18.879 kb | yes | | | |
| Fosmid clone 1-3-1 | 3' | 33.865 kb | yes | yes | | |
| Fosmid clone 15-2-1 | 3' | 39.902 kb | yes | yes | yes | |
| Fosmid clone 7-2-1 | 3' | 42.099 kb | | yes | yes | yes |
| Fosmid clone 15-1-1 | 3' | 35.145 kb | | yes | yes | yes |
| Fosmid clone 4-1-1 | 3' | 41.020 kb | | yes | yes | yes |

TABLE 2

5' and 3' Insertion Size and Total Known Length

| | |
|---|---|
| 5' side insertion sequence | 32.459 kb |
| 3' side insertion sequence | 69.762 kb |
| Total insertion sequence excluding the gap | 102.221 kb |

Figure 3:
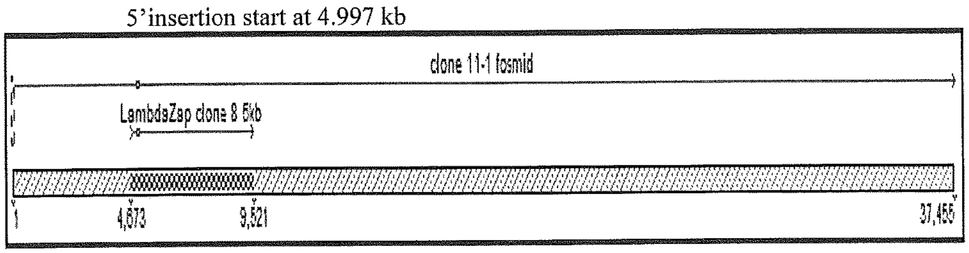
FIG. 3 shows the 5' side insertion clone map.

FIG. 3 and FIG. 4 provide the 5'-side insertion clone map and the 3'-side insertion clone map, respectively of the sh2-R allele.

Example 11. PCR Assay to Identify Sh2-R Mutation in W1056A Sh2-R

Nucleic acid samples taken from W1056A sh2-R (having the sh2-R mutant allele) and corn cultivar B73 sh2 (wild-type sh2 allele) and sweet corn cultivar 765 sh2-I (having the sh2-I allele, which contains 3 bp insertion in sh2 with reduced gene function) were subjected to a PCR assay using the oligonucleotide primer pair GATTATCACAAATCATT-GCTACGA (SEQ ID NO:58) and CCCACAAGACT-TATAGCTCC (SEQ ID NO:59).

The following conditions were used:

(95 C, 4 min)

12 cycles at (95 C, 30 s, 62 C, 30 s to 56 C, 30 s, 68 C 4 min)

25 cycles at (95 C, 30 s, 56 C 30 s, 68 C 4 min), then (68 C, 10 min)

Only the W1065A sh2-R cultivar provided positive results, producing an amplification fragment of about 1200 bp in length. The 765 sh2-I and B73 sh2 were negative (no amplification product).

The above examples clearly illustrate the advantages of the invention. Although the present invention has been described with reference to specific details of certain embodiments thereof, it is not intended that such details should be regarded as limitations upon the scope of the invention except as and to the extent that they are included in the accompanying claims.

Throughout this application, various patents, patent publications and non-patent publications are referenced. The disclosures of these patents, patent publications and non-patent publications in their entireties are incorporated by reference herein into this application in order to more fully describe the state of the art to which this invention pertains.

That which is claimed:

1. A method of identifying a maize plant, plant part or plant cell having a sh2-R mutation, the method comprising:

(a) isolating a nucleic acid from a maize plant, plant part or plant cell;

(b) amplifying in said nucleic acid a region of a sh2-R nucleotide sequence, wherein said region comprises a junction between a sh2 gene and an insertion of the 3' end of the sh2-R nucleotide sequence, wherein said junction corresponds to nucleotides 69686-69687 of SEQ ID NO: 32; and c) analyzing the amplification reaction for the presence of an amplification product, thereby identifying a maize plant, plant part or plant cell having a sh2-R mutation.

2. The method of claim 1, wherein amplifying in step b) comprises hybridizing a pair of oligonucleotide primers, wherein amplification of said region by said primers results in an amplicon comprising said junction corresponding to nucleotides 69686-69687 of SEQ ID NO: 32.

3. The method of claim 2, wherein a first primer hybridizes to the sh2 gene and a second primer hybridizes to the 3' end of the sh2-R nucleotide sequence.

4. The method of claim 3, wherein the first primer hybridizes to consecutive nucleotides within a nucleotide sequence corresponding to nucleotides 1-69686 of SEQ ID NO:32 and the second primer hybridizes to consecutive nucleotides within a nucleotide sequence corresponding to nucleotides 69687-74428 of SEQ ID NO: 32.

5. The method of claim 4, wherein the first primer comprises SEQ ID NO: 56 or the second primer comprises SEQ ID NO:57.

6. The method of claim 4, wherein the first primer comprises SEQ ID No: 56 and the second primer comprises SEQ ID NO: 57.

7. A method of reducing the presence of, or eliminating, the sh2-R mutation from a maize population, the method comprising:

(a) isolating a nucleic acid from a maize plant or a plant part or plant cell thereof;

(b) amplifying in said nucleic acid a region of a sh2-R nucleotide sequence, wherein said region comprises a junction between a sh2 gene and an insertion of the 3' end of the sh2-R nucleotide sequence, wherein said junction corresponds to nucleotides 69686-69687 of SEQ ID NO: 32;

c) analyzing the amplification reaction for the presence of an amplification product, thereby identifying a maize plant having a sh2-R mutation; and (d) removing said maize plant from the population, thereby reducing the presence of, or eliminating, the sh2-R mutation from the maize population.

8. The method of claim 7, wherein amplifying in step b) comprises hybridizing a pair of oligonucleotide primers, wherein amplification of said region by said primers results in an amplicon comprising said junction corresponding to nucleotides 69686-69687 of SEQ ID NO: 32.

9. The method of claim 8, wherein a first primer hybridizes to the sh2 gene and a second primer hybridizes to the 3' end of the sh2-R nucleotide sequence.

10. The method of claim 9, wherein the first primer hybridizes to consecutive nucleotides within a nucleotide sequence corresponding to nucleotides 1-69686 of SEQ ID NO:32 and the second primer hybridizes to consecutive nucleotides within a nucleotide sequence corresponding to nucleotides 69687-74428 of SEQ ID NO: 32.

11. The method of claim 10, wherein the first primer comprises SEQ ID NO: 56 or the second primer comprises SEQ ID NO:57.

12. The method of claim 10, wherein the first primer comprises SEQ ID No: 56 and the second primer comprises SEQ ID NO: 57.

* * * * *

SEQUENCE LISTING

<160> NUMBER OF SEQ ID NOS: 59

<210> SEQ ID NO 1
<211> LENGTH: 33224
<212> TYPE: DNA
<213> ORGANISM: Zea mays

<400> SEQUENCE: 1

```
atgcagtttg cacttgcatt ggacacgaac tcaggtcctc accagataag atcttgtgag     60
ggtgatggga ttgacaggtt ggaaaaatta agtattgggg gcagaaagca ggagaaagct    120
ttgagaaata ggtgctttgg tggtagagtt gctacaacta cacaatgtat tcttacctca    180
gatgcttgtc ctgaaactct tgtaagtatc cacctcaatt attactctta catgttggtt    240
tactttacgt ttgtcttttc aagggaaatt tactgtattt tttgtgtttt gtgggagttc    300
tatacttctg ttggactggt tattgtaaag atttgttcaa atagggtcat cttataattg    360
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
catgaggacg aggactccct catcaaacgc agatgggaac ccagggtcgg gacctagccc   1080
tacggcaagt accaaaccaa gaagggctct gcaactctcc cctagctggg aaggaccctt   1140
caaggtgatg ggaatacgcc gacccggggg tgactgtcta gctatgactg aaggagtacc   1200
tttggagcac ctctgtaagt tctatccata ggagcaagcc tgaggggtcg aatttttctc   1260
cctttttgta gctaggtaac gcatacatgt acgccaaccc ggtgaggtcc gccctcataa   1320
gcccggcatg ttggtctgca cccatacatg acaagttata aagaacagaa ttacccccctc   1380
agatgtgtct ctaagtttta tcctactgct ccatggtctt gccttgcagt ttttcagaga   1440
ttattttatc taacccaccc aaacagttcc ctttccatca gacataacga cattcgaatt   1500
gaacagccag gcttgcagtt taggacctat ttacgaaagc gggagggccc gacagcctgg   1560
gggtggttct agagaacgga agcccgttcc atggggtggt ctagagcctg tgtggccgct   1620
tagcctggtc ctatacccga aagtctgcac actccaccac tccgtgacgg gtaccctagt   1680
atttggagct ataagtcctg tgggtccggc aacctggggt ccggaactag agaatggaca   1740
cttgtctcct ggggtggtcc ggagcccgtg tagccgctca gcttggttcc gtaccgtggg   1800
cgtgcacgct ccaccactct gcgacgggtg tcctagtacc tagaaccacc atctaggggg   1860
tccagacgca caacttggcc tcccagacta aaccctgcag gtcccgagca tgtatcaaag   1920
```

-continued

```
gatgactaat gtcagatggc gggtcctgtg ggtgtactac taatgctccc tagccaaagc   1980
tgtgtgcagg ctcaggtccc agtcgaggct gcctcctggg ggccattgcc aactcttcct   2040
taggtatgct ggtttgcagc ctcgacaaat cgagcctaca tcccgggggc caggtaccaa   2100
ggaggaatca gttacaccac acacaacagg gacaagtggt atacaaataa gtgctaatac   2160
tgcttgataa atagtactca aaagtacctt acaaaaagca aaaatattac atccgccttc   2220
aagcggagtt ctagctccat ctctactcta cagatatgaa ctgcctccac accactaggg   2280
tcgcgtgggt agctagctcc gagcggctcg ccagcgaagg cgaccacctc tgcaccgacg   2340
gatcgacagc ggcgacgact acctcggctc caagcggctc gccagcagag gcaaccacct   2400
ctgcaacggg cagcctcacc agcgatggcg accacctctg cgccaggcag cctccccagt   2460
cgtggcgacc acctcagcat gcgcgccatg gtgaagaggt cctcgccttc gtccccctac   2520
gggggtgagg acaagaccat ccaagccttg gagctgggag catggtggaa ggcggtgctt   2580
gcggtctggc tgggaccgcg tagccgaagt tcgcctcctt cacaaggctg gtgatcatcc   2640
ttttcctccg aatgctggag gaagagatgg gcaccaaccc atgtgggagg cgaaaccgcg   2700
gctcagctcg ttccccgcca ccgcgaggct catgaacatc cttgaagcca agaatcggtg   2760
gaagagcgcc gctcccacaa gaccgcgcat ctccagcaga ggaaaaacaa gaccggtagc   2820
accagcccgc tagggaggag aaaaggcaaa aactctctag cggcaagctc atcggagtgg   2880
ataacgccgg cgcaaatcct tccgctgagc gccagcgcat tccatccaag caagtggtat   2940
accatttcga gcactcactc agtttgggtg tgctcgggat tgagagcacc tagagggggg   3000
gtgaataggt gatcctgtaa aaacttgaaa cttaattcgc aaaacttgat taggagttag   3060
cacgaataag ctaagtggct agagaggaga acttgcacaa cacgataacc acaaagagat   3120
caacacagag atggcacagt ggtttatccc gtggttcggc caagtccaac acttgcctac   3180
tccacgttgt ggcgtcccaa tggacgaggg ttgcaatcaa ccccttcaa gcggtccaaa   3240
gacccacttg aataccacgg tgttttgctt tcactttact atatctcgct tgtgaggaat   3300
ctccacaact tggagcctct cgcccttaca ctttgatgtt cacaaagaag cacggagtaa   3360
gggagggatg agcaacgcac acaagacatg aaatcagagt accaacacgc acacaaatca   3420
caacaagagc tcacaacaca acccggcgag ttcactacta aaatggagct ctagttgcta   3480
tcacaaagag tcaaatgcgc agaatcgaag tcttggtgct taggaatgct tagagaatgc   3540
ttggtgcact cctccatgcg cctaggggtc ccttttatag ccccaaggca gctaggagcc   3600
gttgagagca attcaagaag gcaattcttg ccttctgtcg cctggcgcac cggacagttc   3660
ggtgcaccac cggacactgt ccggtgcgga tctctttcct tatttggcga agccgaccgt   3720
tgcagattgc tagccgttgg cacaccggac actgtccggt gcacaccgga caatccgatg   3780
ccccctctg accgttggct ctgccacgcg tcgcgcgcgg attccacggc cgaccgttgg   3840
cccggccgac tgttggctca ccagacagtc cggtgcacca ccggacagtc cggtgaattt   3900
tagccgtacg ccgccaacga tttcccgaga gcaacaagtt cgcgtgagtc agcctggtgc   3960
accggacact gtccggtgca ccaccgggca gtccggtgca ccaccggaca gtccggtgca   4020
cccagactgc gcagagtctt cgctactcag ccaagtcttt tccaatttgg tcttttcctg   4080
tttctagcac ttagacacaa tacattagtc ttcaaaacaa tgtactaagt cttagaaaca   4140
tacctttaga cttgatttgc actttgtcca tcaattggca tagattatca tttaagcact   4200
tgtgttggca ctcaatcacc aaaatactta gaaatggccc aagggcacat ttccctttca   4260
atctccccct ttttggtgat ttatgccaac acaacaaaaa gcaacttaaa gaagtgcaac   4320
```

-continued

```
atcaatgcaa atgagaccac aaatttgttt tgatcaagtt tgacatattt ggatcattct   4380
ttgccaccac ttggtttgtt tttgcaaacc aaactcaatt tcctatctct aagtcaaaca   4440
cacttgttga aacataaaga gagatatttc acgagaaatt gatcaaagat tcaacaactc   4500
cccctttcc cataaatcca gccttctccc cacaagagat caatgttttg acaataagag   4560
acaaacaaga gtatttagac aaacaaaaac tctaactcta ctattttcaa aattcctaag   4620
tggtagctga tccatttctt gctttggcct tattttctcc ccctttggca tcaagcacca   4680
aaacaggatc aattttggcc ctttaacccc attgcctcac caaaattttc aactaagagt   4740
aaaaaggcaa taagagtaca aagatgaact tgaaattagt tactctttca tcggagtgta   4800
gtggaagtct tgcatggtcc aagtccacct tttccctttc aaacctcctt tgagactaaa   4860
ttaagcagac tcaagcaaac aattagtctc aaagggtcaa gttgtagctc atctcccccct   4920
agatgtgtgc atcacttgca aaggacttgt gaggtccggg gtgtgcttgt acaacttgag   4980
caccataaat aaacaacaaa atgcattaag gaacatgatc aaaggcataa acacatgtat   5040
gctataaatc aacccaagtt ccgcgaatct aagacattta gctcactacg caacttgcaa   5100
aaggtctgct catctaaagg cttggtaaag atatcggcta gctggttctc ggagctaaca   5160
tgaaacactt cgatatctcc cttttgctgg tggtgtaacg ccccgaattt tgcagttgaa   5220
tttttttct tttctttact cgccaaattc gggcgttacc ttttcttttt ctttttgccc   5280
tcgctagacc ttgacttttt ccaaagctag cgggattcgg tttggaattc ccgtgtaaag   5340
aaaaactcta aaaaaatact ttatgtggtt tgatgcacca tgccgagcta tgcattcttt   5400
gattgtttga aagtgcaaat gcattcatct aggaagatcg gatttcgaaa gcagggaaat   5460
aatcttttct ttttctttct ctttctttct ctctccctct tcccctttcc ctctctcccg   5520
cgccatgggc tccttggccg gcccagccgc cccttggccg gcccaagccc cctgcgcgcc   5580
ccccctcttg ggccttggca ggcccagccg cccccccacc tcccctttt ttccccaatt   5640
ccctctccct ctctctctct ccctctcatt ttccctctct ctccctaagc cgccgcccct   5700
acccctctgc cctaaccgcc gccgcccct gctcggccgc cgccctcgcc gtcggccgcc   5760
catcgccggt gagcccccccc ctttccctct cctccctccc tctcccctct cccctcctcc   5820
ctcccccttgg cagcccagcc gcacggccac ccctggccgc gcccctggcc gcccccagcc   5880
cagccgccgg ccgcgccctg gccccagccg cgcctggcca gcctcggccg cgccctggcc   5940
ggccccggcc gcgcccagcc gcgcccccgg cccgccctgg ccgcgccctc ggccgcccct   6000
ggcccctggc cgcccgccag ccgccccctg cccgctggtt cggccgcgcc cctggccggc   6060
ccagccgctc gcccagccgg gcggttcccc ctttttttta ttttttttta ttttatttta   6120
tttactttct gtgatcataa ttaccttatt ttgggtagac taatcatggt tcatgctatg   6180
gaaatgagaa gtttaattta gaatttcgtt gcgctagttg attcattcag ttaattgttt   6240
atcccgtgca atgttaatca acttaaaatg attaggttcc cactagtgca tataacagaa   6300
ttcttttgtt aggaacctat tgaaactaga gtgcataatt taactaatca ttagtgcata   6360
aactttaacc cccctgcgag acccttttcc cgtttctttc taaccataac aaatgcaatg   6420
tcaaatgtca tacttgatgc atattcgctt tatttgttcc cttgtatggt gtactgttct   6480
tttgtattaa atatgtggat ggatgtatgt atgtttgcgc tcgcatagag aacgatccgg   6540
tcaaagagcc cgaggaattc gcaggagaag cccctgagca gcagtcggtt ggtggaggca   6600
agtgtccttt gacctatctc tgtcctaatc attctttaat tcacctcccg catcacacat   6660
```

-continued

```
ttatacctaa ggattgacta gctttttgtt atccatgtcc ttatttacct atttgggtcg   6720
gattattact gcttagtttg atgctattgc tcaactttaa tcaatgaaca tgatgtggtt   6780
atctatgata cgctgttttc ccgttctcat ttatgattat acttgtggca tttaagggga   6840
ctcgagcggt ttctcgagtg cctctccgta aggacctgtt caatggatga ccgcccggga   6900
aaacaatgca accatgaggg tggaatgggg tgcccttagc tgaataatta gaggatccgg   6960
ggtgtagttc gcttcgccgt cgtgccgtca atggggctcg gtgtatgcgg ctcgctctgc   7020
caaggttgat ttgtcccttg gggaggagtg cggtacattt aggaaaccta acgggtggct   7080
acagccccgg ggaatctttg taaaggcttc gtagtgaatc cttggccatt cacctcggga   7140
gtgaataagg gtcttgcaag cccgggccag agagggaatc acggcttgtg ggtaaagtgc   7200
acaacctctg cagagtgtta tgaaactgat atatcagccg tgctcgcggt tatgagcggc   7260
caagggagct ccagagatta gtgatacttg atcagagata ctttggtaca ggtgacaatg   7320
agattgatgg ttctgattac gattatggta ttggtaagtg gtattctttc cgtttggaaa   7380
ggatacattg ggctaataac ttgggttaat gttaaaacct ggctttctac tagtaagtaa   7440
taacctgacc aactaaaagc aactgcttga cttatcccca cataaagcta gtccactaca   7500
gccaaacagg atacttgctg agtatgttga tgtgtactca cccttgctct acacaccaaa   7560
ccccccccca ggttgtcagc attgcaacca ctgctcaggc gaagatgaag ctgtggaagg   7620
agacttccgg gagttccaag actacgacga gttctaggtg tgggttagcg gcaacccccc   7680
agtcggctgc ctgtgaaggc cgtgttatct acgtttcttt tccgcacttt gatttattgt   7740
aagaactata tggacgtctc agacgtatga tgtaatcgac tatttccctt attaatacta   7800
ttttgagcac tgtgtgatga tgtccatatt atgtaactgc tgtgtatgtg aataactgat   7860
cctggcacgt acatggttcg cattcggttt gccttctaaa accgggtgtg tcataagtgg   7920
tatcaaagcc gtgctgactg taggaccgct aacctagagt agaatggtcg ttctaaggat   7980
tatagacctc tgtccctacc ttgactttga tatctcttca aaagttggtc ctaccgacca   8040
aacctatgtt ctactatata ttataccttg ctaaaaaatt gtgtttcatt ctgatccttc   8100
atttacttat gattcattat ttgctggtca tattaattct gttctcaccc ttttgcttgc   8160
gatgtctttt gtagatggct cgacttagac acactgcacg aaagtccgtc atccccttct   8220
taccctcccg ccttgctgag cgtccgcttc gccgtcccgt ggccggacag tccagccact   8280
tggagagact acaccaccgc ctgcgtgagg agcaggaacg tcgacgacag gagcaacagg   8340
gctcttcttt ctcgctccac caggagatag agtctgtgag gagctgctct cctgtgcttc   8400
ctctggaggt gccccctgca ccaccactgg gcgccccagc ttctggagta gctgctggag   8460
gagacccaga cgacggagat ggcgacgaca gctcgagcca cgacaccgac ttctctgcta   8520
accctgagcc ggaaggatgg gttgctcgac ccatcactcg cgacgctgct cgcgggtgtc   8580
acttccacga tgcgctcgac accctgctac gtcgggcatt tgaccggcat acttggtccg   8640
tcgagtatcg ctgtgtggtc taccagcata gtcgcggggt ctacccggac cgctgggaga   8700
cgacttgctt ggtgcgctgc ccggaggaca gtctccaggg tgcagaggcc tgctcagagc   8760
actattctat ctctgaacgg gactcagctg aggcagccat gcaagatgct gcacggcgtg   8820
cgctttcgca ctactgctcg gttttcggtg gggcagctga cggtcttgac ctgaagtatt   8880
acccccgccg tccatctggc agcacaggag gcgtgattgt ctcacctgtc ggtgagggca   8940
atcctaggtt gagcagcaca gtcaacctag ccgccgtgct aaacacggag ctggaccatg   9000
cattagacga gctgagtagg gctcgtgctg agatcgccca gctgcgggct gagcgcgcgg   9060
```

-continued

```
aacgtcgtca tctggatggt ggttcccccg ctcccgtcgg gactcagcac ccgtaccgct   9120
cacctcagcg tggacaccag ccttatggca atcccgactg caagaccaag ataaatctag   9180
aaccatagat cgctagagtt ggatcttgta attaatacga aatatatgca tagaagcttc   9240
agtcttagcg ttaatctcgg tcttagttag tcttagttag acagggtagt ttgctatatc   9300
ctgtgcattt atgtttgtca tgatgaactt tgtttggttt ggatctttgt aatgattgtc   9360
accagagtgt gggtatcccc tgcattttgg ttcacctatt atgttaataa agttagttat   9420
atagttggga aacctttttat tccactttcc tcttgatctg agaagttgtg tggtctgtgt   9480
tggagatcag tgaagatgct cacctgctca gtgctgttga agaattctat actcttttct   9540
tatgctgcaa gatttgccag atcagttctg atgtgtggtt gcattctgca gatgtcagag   9600
aacaggcgca gaggaggaag gcgtgctcag caggagcaag ccggtcaaca agatgaggcg   9660
ccccagcagc agcagctgcc acccccgccc ccgatgtcga tcgagcagat gtttctgatg   9720
cagactcagg cagttcaggc catcggtcag actctggccg ccattcagca gcagcagcag   9780
cagcaacagc agcaagcacc accccagcct cagatgcctc agatgcccag agacaagcgt   9840
gctgaattca tgagaggtca tcccccaacg ttcgctcact cttctgaccc catggatgct   9900
gaagattggc tgcgcactgt ggagcgggag ttgcataccg ctcagtgtga tgacagggag   9960
aaagtcttgt atggtccccg tctgttgaga ggagcagccc aatcatggtg ggagtcttac  10020
ctcgccaccc atgccaaccc cgacaccatc acctgggaag aattcagagg tagctttcgt  10080
cagtaccacg tgcctgcagg tctgatgaca gtgaagaagg aggagttcct ggcccttaag  10140
caagggtcat catctgtcag tgagtatcga gacaggtttc tgcaattgtc tcgctatgct  10200
cctgaggatg tcaacactga cgccaagcga caataccgtt ttctaagagg cttggtcgac  10260
cccctgcagt atcaactgat gaatcacacc ttcccgacat tccagcacct gattgataga  10320
gcgatcatga cagaaaggaa gcgttaggag atggaagatc gtaagcgcaa gatcagtgga  10380
ccccagcctg gaagcagcag ccgccctcgt tttcaggca atcaacctca gcagttcagg  10440
cagaaccagc gtccacctca gcagcgtcag cagcatcagc agttccaaag gcagtatcct  10500
cagcatcagt accagaaccg tcagagcaat cagtcaggag gtcagtttca aaggcagaat  10560
cagcaagcac cccgtcttcc tgccccagca aaccagcaga acagtcaggc agcaccagct  10620
caggttggaa acagggcatg tttccactgt ggagagcagg gccattgggt gatgcaatgt  10680
ccgaagaagg cagcccagca gcagtcaggc cccaatgccc cagcaaagca gaatgtgtct  10740
cagcctggag caggcaaccg ctctcaacag cgctataatc atggaagatt gaatcacttg  10800
gaggctgaag cagttcagga gacccccggc atgatagtag gtatgttccc agtcgactcc  10860
catattgcag aagtgttatt ggatactgga gcaacgcatt ctttcattac tgcatcatgg  10920
gtagaagcac ataatcttcc aactactacc atgtcaaccc ccattcaaat tgactcagct  10980
ggtggtagaa ttcgagctga tagcatttgt ttaaatataa gtgtggaaat aagggggata  11040
gcgtttcccg ccaaccttat agtaatgggt actcagggaa tagatgtcat cctagggatg  11100
aattggttag ataagtatca ggcagttatc agttgtgata aaaggacaat aaagttggtg  11160
tccccactag gagaggaagt ggtgaccgag ttagtcccgc ctgagccaaa gaaaggaagt  11220
tgttatcaga tagctgttga tagcagtgaa gcagactcga tcgagagcat caaggttgtg  11280
tccgagttcc tagatgtgtt tccaaaggac ttaccgggta tgccaccaga gcggaaagtt  11340
gagtttgcca tagagcttct tcctggaacc gcccccatct ttaagagagc ttacagaata  11400
```

-continued

```
tccggaccag agttggttga gcttaagaag cagattgatg agctgtcaga gaaaggttac  11460
attcggccaa gcacctcgcc ttgggccgcc cctgtcttat ttgtggaaaa gaaagatggc  11520
accaagagga tgtgcatcga ttatcgagct ttgaatgagg tcacgatcaa gaacaagtat  11580
cccttgccca gaatagagga tctgttcgac cagttgagag gagccagcgt gttctccaag  11640
attgatctga ggtcaggtta tcatcagctc aggatccgac cttcggacat tccgaagacg  11700
gcattcattt ccaagtatgg tttgtatgag ttcacagtga tgtcttttgg tttgaccaat  11760
gcaccagcgt tctttatgaa tctgatgaac agtgtattca tggattacct tgataagttt  11820
gtggtggtat tcattgatga cattctgatt tattcccaaa gcgaagaaga gcacgcagat  11880
catttgagga tggtattgca gagattgcga gagcaccagt tgtatgcaaa gttgagtaag  11940
tgtgagttct ggatcagtga agtcctgttt ttgggtcaca taatcaacaa ggaaggattg  12000
gctgtggatc cgaagaaagt ggcagacatt ctgaactgga aagcgccaac agatgctcga  12060
ggaatcaaga gtttcattgg aatggccgga tactatcggc gattcattga agggttttcg  12120
aagattgcaa aaccaatgac agcattgcta ggcaacaagg ttgagttcaa gtggacccag  12180
aaatgtcaag aggcctttga agcgctgaaa gggaagttga ctacagcgcc tgtcctagtc  12240
ttgcctgatg tgcacaagcc cttctcggtg tattgcgatg cttgttacac aggtttggga  12300
tgcgtattga tgcaagaggg aagagttgtg gcttactcgt cccgacagtt gaaggttcat  12360
gagaagaact acccaatcca tgatctagag ttggcagaag tggttcacgc actgaagaca  12420
tggaggcact atctgtatgg acagaaatgc gatgtttaca cagatcacaa gagtctgaag  12480
tacatattca ctcagacaga gttgaacatg aggcaacgaa gatggttaga gctgatcaaa  12540
gactatgagt tggagattca ttaccatcca ggcaaagcaa acgtagtggc agatgctttg  12600
agcagaaaga gtcaagtcaa tctgatggtc gctcgcccga tgccttatga gttggccaag  12660
gagttcgaca ggttgagtct cgggcttctg aacaattcgc gaggagtcac agttgaattg  12720
gaacctacct tggagcgaga aatcaaagaa gcgcagaaga atgatgaaaa gatcagtgag  12780
attcggcgat tgattctaga tggcagaggc aaagattttc gagaagatgc tgaaggcgtg  12840
atatggttca aagaccgctt atgtgttccc aatgtccagt ctattcggga gttgattctc  12900
aaggaagctc atgagacagc ctattcgatt caccctggta gtgagaagat gtatcaggat  12960
ctgaggaaga aattctggtg gtacggaatg aagaggaaaa tcgcagagca tgtggctaag  13020
tgcgatagtt gtcgaagaat taaggcagag caccagagac cagctggatt gttgcaaccg  13080
ttgcagatcc ctcagtggaa atgggatgaa attggtatgg atttcatagt cggattgcct  13140
cgcactcgag ccggctacga ttctatttgg gtagtggtgg accgtttgac caagtcagcc  13200
cacttcatac ctgtcaagac cagctacaac agtgcagtat tggcagagtt gtatatgtct  13260
cggatcgttt gtcttcatgg tgtgccaaag aagatagtgt cagacagagg aacgcagttc  13320
acttctcatt tctggcagca gttgcatgaa gccttgggca cacatttgaa tttcagttca  13380
gcttatcacc cgcagacaga tggccagact gaaaggacca atcaaattct cgaagatatg  13440
ttgagagcct gtgcgttgca agatcagtcc ggatgggaca agcgattgcc ttatgcagag  13500
ttttcctata acaacagtta ccaggccagt ttgaagatgt caccgtttca ggcgctttat  13560
ggaaggagtt gtagaactcc gttgcaatgg gatcagcctg gagaaaagca agtgtttggg  13620
ccagacattc tgcttgaagc cgaagagaac atcaagatgg tccgagagaa tctgaagata  13680
gcgcaatcga ggcagcgaag ctatgcagac acaagaagaa gagagctgag ttttgaagtc  13740
ggagactttg tctatctaaa gtgtcaccga tcagaggagt cagaagattc ggagtgaaag  13800
```

```
gcaagctagc accccgctac attggtccgt accagatcct ctcatagcgt ggagaagtgg  13860
cttatcagct cagcctgcca gagaatttgt ctgctgtgca tgatgtcttt catgtgtctc  13920
agttgaagaa gtgcttgcgt gtgccagaag agcagttgcc agtggaaggt cttgaggtcc  13980
aggaggactt gacctatgtt gagaagccag ctcagatcct tgagattgca gacagagtca  14040
cccgaaggaa gaccatcaga atgtgcaaag tcagatggaa tcaccactct gaggaagaag  14100
caacctggga gcgtgaagat gatctagtgg ccaagtaccc agagctcttt gctagccagc  14160
cctgaatctc gagggcgaga ttcttttaag gggataggt  ttgtaacgcc ccgaattttg  14220
cagttgaatt tttttctttt tctttactcg ccaaattcgg gcgttacctt ttctttttct  14280
ttttgccctc gctagacctt gactttttcc aaagctagcg ggattcggtt tggaattccc  14340
gtgtaaagaa aaactctaaa aaaatacttt atgtggtttg atgcaccatg ccgagctatg  14400
cattctttga ttgtttgaaa gtgcaaatgc attcatctag gaagatcgga tttcgaaagc  14460
agggaaataa tcttttcttt ttctttctct ttctttctct ctccctcttc ccctttccct  14520
ctctcccgcg ccatgggctc cttggccggc ccagccgccc cttggccggc ccaagccccc  14580
tgcgcgcccc ccctcttggg ccttggcagg cccagccgcc cccccacctc cccttttttt  14640
ccccaattcc ctctccctct ctctctctcc ctctcatttt ccctctctct ccctaagccg  14700
ccgcccctac ccctctgccc taaccgccgc cgccccctgc tcggccgccg ccctcgccgt  14760
cggccgccca tcgccggtga gcccccccct ttccctctcc tccctccctc tcccctctcc  14820
cctcctccct ccccttggca gcccagccgc acggccaccc ctggccgcgc ccctggccgc  14880
ccccagccca gccgccggcc gcgccctggc cccagccgcg cctggccagc ctcggccgcg  14940
ccctggccgg ccccggccgc gcccagccgc gcccccggcc cgccctggcc gcgccctcgg  15000
ccgcccctgg cccctggccg cccgccagcc ggcccctgcc cgctggttcg gccgcgcccc  15060
tggccggccc agccgctcgc ccagccggcc ggttccccct tttttttatt tttttttatt  15120
ttattttatt tactttctgt gatcataatt accttatttt gggtagacta atcatggttc  15180
atgctatgga aatgagaagt ttaatttaga atttcgttgc gctagttgat tcattcagtt  15240
aattgtttat cccgtgcaat gttaatcaac ttaaaatgat taggttccca ctagtgcata  15300
taacagaatt cttttgttag gaacctattg aaactagagt gcataattta actaatcatt  15360
agtgcataaa ctttaacccc cctgcgagac ccttttcccg tttctttcta accataacaa  15420
atgcaatgtc aaatgtcata cttgatgcat attcgcttta tttgttccct tgtatggtgt  15480
actgttcttt tgtattaaat atgtggatgg atgtatgtat gtttgcgctc gcatagagaa  15540
cgatccggtc aaagagcccg aggaattcgc aggagaagcc cctgagcagc agtcggttgg  15600
tggaggcaag tgtcctttga cctatctctg tcctaatcat tctttaattc acctcccgca  15660
tcacacattt atacctaagg attgactagc tttttgttat ccatgtcctt atttacctat  15720
ttgggtcgga ttattactgc ttagtttgat gctattgctc aactttaatc aatgaacatg  15780
atgtggttat ctatgatacg ctgttttccc gttctcattt atgattatac ttgtggcatt  15840
taaggggact cgagcggttt ctcgagtgcc tctccgtaag gacctgttca atggatgacc  15900
gcccgggaaa acaatgcaac catgagggtg gaatggggtg cccttagctg aataattaga  15960
ggatccgggg tgtagttcgc ttcgccgtcg tgccgtcaat ggggctcggt gtatgcggct  16020
cgctctgcca aggttgattt gtcccttggg gaggagtgcg gtacatttag gaaacctaac  16080
gggtggctac agccccgggg aatctttgta aaggcttcgt agtgaatcct tggccattca  16140
```

cctcgggagt gaataagggt cttgcaagcc cgggccagag agggaatcac ggcttgtggg 16200
taaagtgcac aacctctgca gagtgttatg aaactgatat atcagccgtg ctcgcggtta 16260
tgagcggcca agggagctcc agagattagt gatacttgat cagagatact ttggtacagg 16320
tgacaatgag attgatggtt ctgattacga ttatggtatt ggtaagtggt attctttccg 16380
tttggaaagg atacattggg ctaataactt gggttaatgt taaaacctgg ctttctacta 16440
gtaagtaata acctgaccaa ctaaaagcaa ctgcttgact tatccccaca taaagctagt 16500
ccactacagc caaacaggat acttgctgag tatgttgatg tgtactcacc cttgctctac 16560
acaccaaacc cccccccccc aggttgtcag cattgcaacc actgctcagg cgaagatgaa 16620
gctgtggaag gagacttccg ggagttccaa gactacgacg agttctaggt gtgggttagc 16680
ggcaaccccc cagtcggctg cctgtgaagg ccgcgttatc tacgtttctt ttccgcactt 16740
tgatttattg taagaactat atggacgtct cagacgtatg atgtaatcga ctatttccct 16800
tattaatact attttgagca ctgtgtgatg atgtccatat tatgtaactg ctgtgtatgt 16860
gaataactga tcctggcacg tacatggttc gcattcggtt tgccttctaa aaccgggtgt 16920
gtcaggtggt ctctcaaaaa gtgatgtcgg atgtctatgt gctttgtgcg gctgtgttca 16980
acaggattat ccgccatgca gatagcactc tcattatcac acaggagtgg gactttgctc 17040
aaattgtagc caaagtccct gagggtttgc ctcatccaaa gtagttgcgc gcaacactgt 17100
cctgcggcaa cgcactcgga ctcagcggtg gatagggcaa cagaagtttg tttcttagaa 17160
ctccatgaca ccagggacct tcctaagaat tggcacgtcc ccgatgtact cttcctatcg 17220
accttacatc cagcatagtc ggagtctgaa tatccaatca agtcaatggt agaccccttt 17280
ggataccaga tcccgaagca aggcgtagcg actaaatatc taagaattcg cttcacagcc 17340
actaagtgac actcccttgg atcggattga aatctagcac acatgcatac actaagcata 17400
atatccggtc tactagcaca taaataaagt aaagacccta tcatagactg gtatgccttt 17460
tgatcaacgg acttacctcc tttgttgagg tcggtgtgtc cgtcggttcc cattggagtc 17520
tttgcgggct tggcgtcctt catcccaaac cgcttgatca agtcttgcgt gtacttcgtt 17580
taggagatga aggtcccatc cttgagttgc ctcacttgga acccaaggaa atagcttaac 17640
tcgcccatca tcgacatctc aaacttttga gtcatcaccc tgctaaactc ttcacaagac 17700
ttttggttag tagaaccaaa tattatgtca tcgacataaa tttggcacac aaaaagatca 17760
ccatcacatg tcttagtaaa aagagttgga tcggctttcc caaccttgaa agcattagca 17820
attaaaaagt ctctaaggca ttcataccat tctcttgggg cttgcttaag tccatagagc 17880
gccttagaga gcttacagac gtggtcgggg taccgttcat cctcgaagcc agggggttgc 17940
tccacgtaca cctcctcctt gattggcccg ttgaggaaag cgctcttcac atccatttgg 18000
aacaacctga aagaatggtg agcggcatat gctagcaaaa tacgaatgga ctctagccta 18060
tccacaggag caaaagtctc ctcaaagtcc aaacctacga cttgggcata accttttgcc 18120
acaagtcgtg ccttgttcct tgtcaccacc ccgtgcttgt cctgtttgtt gcggaacacc 18180
cacttggttc ccacaacatt ttgcttggga caaggcacca gtgtccaaac ttcatttctc 18240
ttgaagttgt tgagctcctc ctgcatggcc aacacccagt ctggatctag caaggcctcc 18300
tctaccctga aaggctcaat agaagagaca aaagagtaat gctgacaaaa attaactaat 18360
cgagaccgag tagttactcc cttgctaatg tcacccaaaa tctggtcgac aggatgatac 18420
ctttgaatca tcgctcggac ttgagttgga ggtgccggtt gtgcttcttc ctccattaca 18480
tgatcagctt ttgctcccct tgatcatacg cctcctcttg atgaacctgt tcatcgtctt 18540

```
gagttggggg atgcaccatt gttgaggaag aaggttgatc tcgctcattt tgttcctgtg  18600
gccgcacatc tccaatcgcc atggtgcgta ttggccgttg gaacgtcttc ttcatctaca  18660
tcatcaagat caacaacttg ctctcttgga gagccattag tctcatcaaa tacaacgtcg  18720
ctagagactt caaccaaacc cgatgatttg ttgaagaccc tatacgcttt tgtatttgag  18780
tcataaccta acaaaaaccc ttctacggct ttgggagcaa atttggaatt cctacccttc  18840
ttcactagaa tgtagcattt actcccaaaa actcggaata cgaaacattg ggtttgttac  18900
cggttagtag ctcatacgaa gtcttcttga ggaggcgatg aaggtagacc cgccagttga  18960
tggcgtggca agccatgttc acggctttcg accaaaaacg ctcgggggtc ttgaactctc  19020
caagcatcgt tctcaccatg tctataagta tcctgttctt cctctctacc acaccatttt  19080
gttgtggtgt gtagggagcg gagaactcgt gcttgattcc ttcctcctca agatactcct  19140
ccacttgaag gttcttgaat tcggacccat tgtcgatcct tatcttcttc accttgagct  19200
caaactcgtt ttgagctctc cttaggaagc gcttgagggt cccttgggtt tcagatttat  19260
cctgcaaaaa gaatacccaa gtgaagcggg aaaaatcatc aactataaca ataccatact  19320
tacttcctcc tatgcttaga taggcgatgg gtccgaagag gtccatatga agtaactcca  19380
ggggtcttga tgttgtcatc acatttttgg catgatgaga gcttcctacc tgtttccctg  19440
cttgacaagc tgcacaaggt ctatcttttt tcgaaagtaa cattagttag acctattaca  19500
tgttctccct ttagaagctt gtgaaggttc ttcatcccca catgtgctaa gcgacgacgc  19560
tacagctagc ccatgctagt cttagcaatt aagcatgcat ctagaccggc ctcctctttt  19620
gcaaaatcaa ctaaatagag tttgccgtct aatacaccct taaaagctaa tgaaccatca  19680
cttctccaaa agacaaacac atctacattt gtgaatagac aattatatcc catattacat  19740
aattgactta cagataacaa attatatcca agcgactcaa ctaagaatac attagaaata  19800
gagtgctcat ttgagattgc aatcttgcct aagcctttaa ccttgccttg attcccgtca  19860
ccgaatatga ttgaatcttg ggaatcttta ttcttgacgt aagaggtgaa catcttcttc  19920
tcccccgtca tgtggtttgt gcatccgctg tcgataatcc agcttgatcc cccggatgca  19980
taaaccagca aggcaaattt aggcttgggt cttaggtacc caactcttgt tgggtcctac  20040
aaggttagtg acaatatcct tagggaccca aatgcaagtt ttatctccct tgcattttgc  20100
ccctagtttc ctagcaatca ctttcctatc ctttctacaa atcgcaaatg aagcattgca  20160
agcatgataa attgtagaag gttcatttat tattttccta gaaacatgaa caacatttct  20220
tctaggcatg tgattaataa catttctcct agctaaattt ctatcatgca taatagaaga  20280
actagaagca accatggcat gagaatcaaa agcatcataa cttctataac catttctaga  20340
atgtctccta tcatgataca tgaaggcatg gttcttttga gcactactag ccataggggc  20400
cttccctttc tccttggtgg agatggaagc cttatggctt gttaagttct tgacttccct  20460
cttgaagcca agaccatcct taattgaggg gtgtctacca atcgtgtagg catcccttgc  20520
aaattttagc ttgtcaaatt cattcttgct agtcttaagt tgggcattaa gctagccact  20580
tcatcattta atttagaaat gcaaactagg tgttcactac aagcatcaac attaaaatct  20640
ttgcacctat tgcaaatcat aacatgttct acacaagagt tagatttact tgctacttct  20700
agtttagcat ttaaatcatc attaacactt tttaaagtag aaatggtttc atgacaagta  20760
gattgttcac aagaaagcat ttcattcctt ttaacttcta gaacaagaga attttgtgca  20820
ctaacaaatt tatcatgctc ttcatataaa aggtcctctt gtttttctag taatctattc  20880
```

```
ttatcattca aagcatcaat caattcatta atcttatcaa tcttagttct atctaatccc  20940
ttgaataagc atgaatagtc tatttcatca tcatcactag actcatcctc gcttgaagaa  21000
gcataagtag tattatttca agtacatacc ttcttctcct ttgccatgag gcatgtgtga  21060
tgctcgttgg ggaagaggga tgacttgttg aaggcggtgg cgacgagtcc ttcgttgtcg  21120
gagtcggacg aggagcaatc cgaatcccac tcctttccaa gatgtgcctc acccttcgcc  21180
ttcttgtagt tcttcttttc ccactttcca ctcttctttt cctggtcact atcattatcg  21240
ggacaattag cgataaaatg accaatctta ccacatttga agcaggagcg cttccccttc  21300
gtcttgttct tgttggggtg ctccttgcga ccctttagcg ccgtcttgaa ccgcttgatg  21360
ataagggcca tttcttcctc attaagcccg gccgcctcaa cttgcgccac cttgctaggt  21420
agtgcctcct tgctccttgt cgctttgaga gcaacggttt gaggctcgtg gattgggcca  21480
ttcaatgcat catccacgta tctcgcctcc ttgatcatca tccgcccgct tacaaatttc  21540
ccaagaattt cttcgggtga catcttggtg tacctaggat tttcacgaat attgtttacc  21600
agatgtggat caagtacagt aaaggagcct tagcattagg cggacgacgt cgtgatccgt  21660
ccatcgcgtg cttccatagc tccttatctt gttgacaagg gtcttgagcc tgttgtacgt  21720
ctgggttggc tcctcccctc ttatcatcgc gaatctcccg agttcgcctt ccaccaactc  21780
catcttggtg agcatggtga cgtcgttccc ctcatgtgag atcttgaggg tgtcccagat  21840
ctgcttggca ttgtccaagc cgctcacctt atcgtactcg tccctgcata atgaggctaa  21900
caacacagta gtagcttgtg catttttatg aatctgttca ttgataaaca aaggactatc  21960
cgagctatca aatttcattc cactctctac tatctcccat atactaggat ggagagagaa  22020
caagtgacta cgcattttgt gactccaaaa ttcgtagtcc tctccatcaa aatgaggagg  22080
tttaccaagt ggaatggaga gtaaatgagc attggtactt tgaggaatac gagaataatc  22140
aaaagagaag tttgaattaa ccgtcttctt tttctcatag tcgttgtcgt cgtccttttg  22200
ggaagaagag gattcgtcgc tgtcgtagta gactatctct ttgatgcgcc ttgttttctt  22260
cttcctccca tcttttcttt tgtggctcca gcccgagtca gtaggcttgt cctcctttgg  22320
atcattgaca aaggactcct tctccttatc gttgaccacc atccccttgc ccttaggatc  22380
catctcttcg ggcgattagt ccctttcttg aagagaacga ctccgatacc aattgagagc  22440
acctagaggg ggggtgaata cgtgatcctg taaaaacttg aaacttaatc cgcaaaactt  22500
gattaggagt tagcacgaat aagctaagtg gctagagagg agaacttgca caacacgata  22560
accacaaaga gatcaacaca gagatggcac agtggtttat cccgtggttc ggccaagtcc  22620
aacacttgcc tactccacat tgtggtgtcc caacggacga gggttgcaat caacccc ttt  22680
caagcggtcc aaagacccac ttgaatacca tggtgttttg ctttcacttt actatatccc  22740
gcttgcgagg aatctccaca acttggagca tctcgccctt acactttgat gttcacaaag  22800
aagcacggag taagggaggg atgagcaatg cacacaagac acgaaatcag agtaccaaca  22860
cgcacacaag tcacaacaag agctcacaac acaacccggc gagttcacta ctcaaatgga  22920
gctctagttg ctatcacaaa gattcaaatg cgcggaatcg aagtcttggt gcttaggaat  22980
gcttagagaa tgcttggtgt actcctccat gtgcctaggg gtccctttta tagccccaag  23040
gcagctagga gccgttgaga gcaattcaag aaggcaattc ttgccttctg tcgcctggca  23100
caccggacag tccggtgcag atctctttcc ttatttggcg aagccgaccg ttgtagattg  23160
ctagccgttg gcgtaccgga cactgtccgg tgcacactgg acagtccggt gcccccttct  23220
gaccgttggc tctgccacgc gtcgcgcgtg gattccacgg ccgaccgttg gcccgaccga  23280
```

```
ctgttggctc accggacagt ccggtgcacc accggacagt ccggtgaatt ttagccgtac  23340
gccgccgacg atttcccgag agcagcaatt tcgcctgagt cagcctggtg caccaccgga  23400
cagtccggtg cacccagact gtgtagagtc ttcgctgctc agccaagtct tttccaattt  23460
ggtcttttcc tgtttctagc acttagacac aatacattag tcttcaaaac aatatactaa  23520
gtcttagaaa catacccttta gacttgattt gcactttgtc catcaattgg catagattat  23580
catttaagca cttgtgttgg cactcaatca ccaaaatact tagaaatggc ccaagggcac  23640
atttcccttt catggatgaa gtcacaaggc catggcaaac tacggcaacg caaagcagaa  23700
acttgaaggc aaaggggcac agagagctcg aagatgaaag ggcaccgcga gtgggagaga  23760
agcaagacat ggctgctacc tgaggggtga acccctttt aaaggcagat ttccccactc  23820
gcgccccgaa gcgtcatggc aagatctccc ccgatgcgca ccagggttcc catcctatga  23880
cacgggggg caggcctcac atgtcataca agctggcctg aagcgcgaag aaggcaaatc  23940
gtcgcacaag gagcgtgcaa ccgccctgcg gttatacgcc tttgcatctt cgccgcaacc  24000
agcggtcaaa aaggcgaacc gccgcacaag gtgcgtgcaa ccgccctacg gttatacgcc  24060
ctttcatctt cgccgcaacc agcggtcaag aaggcgaacc gccgcacaag gagcgtgcaa  24120
ccgccccgca gttgtgcgcc ccctcggctt cgctgcagcc agcggtccaa cctctggcat  24180
ggggccccag gcccacatgt cacgcacctg gcgcaccggt ttctgcatac agagaagtcg  24240
caccatcact cacgccagta ctgcgcctcc tcggggccac cgtagaagat ggagaagtta  24300
agttttcaaa aatgcagcga ctcgaggcac cccgtgcatg gcccaacaaa gccattaagt  24360
gcggaggtca tgggccagtc agccgcgggg acatgcatgg cagtcggtgc gaccatgggc  24420
ggaccgacag ttattgcatc aacgggcacg cggggacaac aagccaatca gactttggcc  24480
ccacctgcaa gctcgtatcc tcccctgagg cgggcccgag gccactgtcg gtaccctgaa  24540
ccaggggtac cccctactac agtataagga agcggtgccc gtatggcgtt ccctagccac  24600
acggtgagca gcacccgacc ccaccacgtg ggtggctcaa ggggtaccac gtggcgagaa  24660
acgatgacac atcccgagat atatcagttg aaccggacca ccacgaagga gcaccggacc  24720
cctgtacgca caacccggac ccccgattac gtctcgggac tcccaagtaa gcatgccgag  24780
ccccttggat ggggtccaga tccctttgag taaggtccgg accacaacga ggtcccggga  24840
caggggagac cctggcataa gcaagggtct ggtactgaca tgtgttaggg ccttatccta  24900
tgcgcttgcg ctacccgctc aggcggagac ccgctgctgc cacgtggctt gttgcccgtg  24960
acataagcca acgggcggag cctgatgtaa ggcctctagg ccgtgcggtc tctgcattta  25020
ttgcggagga gacgcgccgc ctatccacct tgcggcttcg ctttggcgga cgctctcgta  25080
gaggcgagtc cgaaccctct agggtatcgt atgcggtcac cctgggaccg gctgacggac  25140
gtctcgacct acgggccctc ggggtccgag gaagatgacg agcccgactt ctgttgggac  25200
ttctccggac ttggtaaccc cagtgccatg cgggacttca tgaccgcatg cgactactgc  25260
ctttccgact gttccgacgg tagccgcagc ctcggcgacg aggactacgg cccaagtcgt  25320
gaatgtttcc acgtcgatct agggggtccc tccgaaggca accatcttgg tatgccggag  25380
aacggtgatc tccctaggcc tgtgcctcgc gttgacatcc tacgggagct agctgtggtc  25440
cccgttccgg cggggggtca tgacccacag ctcgagcaaa tctatggggt gccggccagg  25500
ctcgacgagg gagtaggagc acttgagccg atccgccggg acgtcgggca ggaatgggca  25560
ggccaacctc cggccggaga aatgcgtcat ctaccccagg gcttccagca ccgcatcacc  25620
```

-continued

```
gatgatgtca gggtaaggcc gccacccgct tccagtgggg tcggccagaa cctggctgca  25680
gcggcaatgc ttctccgcgc gatgccggag ccatcaacca ccgaggggcg gtgaatccag  25740
ggagagctca agaatctcct ggagggcgcc gcagttcggc gggccgaaag ctccgcctcc  25800
cgaaggcagg ggtacccctc ggaacatcgc gccgcgactt cccgattcat gcgggaagcc  25860
tcggtccaca ccgggcgcac gcgcaacaca gcgcctgcgg ccccaggtcg cctcagcaac  25920
gagcaccatc accgcgaccg tcgggcccac ctcgacgaga gggtgcgccg aggctaccac  25980
cccaggcgtg ggggatgcta cgacagcggg gaggatcgga gtccctcgcc cgaaccaccc  26040
ggtccgcagg ctttcagccg cgccatacga cgggcgccgt tcccgacccg gttctgaccc  26100
ctgactacta tcgcaaagta ctcgagcgag acgagaccag aactgtggct cgcggactac  26160
cggctggcct gccaactggg tggaacggac gatgacaacc tcatcatccg caacctcccc  26220
ctgtttcctc tccgacaccg ctcgcgcctg gttggagcac ctgcctccgg ggcagatctc  26280
caactgggac gacctggtcc aagccttcgc cggcaatttc cagggcacgt acgtgcgccc  26340
tggaaactcc tgggacctcc gaagctgccg acagcagtcg agagagtctc tccgggacta  26400
catccggcga ttctcgaagc agcgcaccga gctgcccaac atcaccgatt cggatgtcat  26460
cgacgcgttc ctcaccggca ccacctgccg cgacctgggc agcaagctgg gtcgaaagac  26520
ccccaccagg gtgagcgagc tgatggacat cgccaccaag ttcgcctctg gccaggaggc  26580
ggtcgaggct atcttccgga aggacaagca gccccagggc cgcccaccgg aagatgcccc  26640
cgaggcgtca actcagcgcg gcgccaagaa gaagggcaag aagaagtcgc aagcgaaacg  26700
cgacgccgcc gacgcggacc ttgtcgccgc cgccgagtac aagaaccctc ggaaacctcc  26760
cggaggtgcc aacctcttcg acaagatgct caaggagacg tgcccctatc atcaggggcc  26820
cgtcaagcac acccttgagg agtgcgccat gcttcggcgc cacttccaca gggccgggcc  26880
acccgcggag ggtggcaggg ctcacgacga cgacaagaag gaagatcacc aggcaggaga  26940
gttccccgag gtccgcgact gctttatgat ctacggtgga caagcggcaa atgcctcggc  27000
tcggcaccgc aagcaagagc gtcgggaggt ctgttcggtg aaggtggcgg caccagtcta  27060
cctagactgc tccgacaagc ccatcacctt cgacacaggc cgaccacccc gaccacgtgc  27120
cgagcccggg gaaatacccg ctcgttgtcg accccatcat cggcgacgtc aagctcacca  27180
aggtcctcat ggacggaggc agcagcctca acatcatcta cgccgagacc ctcgggctcc  27240
tgcgtgttga tctgtcctcg gtccgggcag gcgctatgcc tttccacggg atcatccccg  27300
ggaagcgcgt ccagcccctc ggacaactcg accttcccgt ctgcttcgga gcaccctcca  27360
acttccgaag ggagaccctc acgttcgagg tggtcgggtt ccgaggaacc taccacgcag  27420
tattggggag gccatgctac gcgaagttca tggccgtccc caactacacc tacctcaagc  27480
tcaagatgtc gggccccaac agggtcatca ccgtcggccc cacgtaccga cacacattcg  27540
aatgcgatgt cgagtgcgtg gagtacgccg aggccctcgc cgaatccgag gccctcatcg  27600
ccgacctgga gagcctctcg aaggaggtgt cagacgtgaa gcgccacacc ggcaacttcg  27660
agccagcgga gacggttaag tccgtccccc ttgaccccag cagcgatgtc tccaagcaga  27720
tccggatcgg ctacgagctt gaccccaaat aggaagcagt gctcgtcgac tttctccgcg  27780
caaacgccga tgttttcgcg tggagtctct cggacatgcc cggcataccg agggatgtcg  27840
ccgagcactc gctggacatc cgagccgggg cccgacccgt caagcagcct atgcgccgat  27900
tcgatgaaga aaagcacaga gccataggcg aggagatcca caagctaatg gcggcagggt  27960
tcatcaaaga ggtattccat cccgaatggc ttgccaaccc tgtgcttgtg agaaagaaag  28020
```

gagggaaatg gcggatgtgt gtagactaca ctggtctaaa caaagcatgt ccgaaggttc 28080
cctaccctct gcctcgcatc gatcaaatcg tggattccac tgctgggtgc tgaaagggaa 28140
ttaggcttac acctagttcc taaataattt ttggtggttg aattgcccaa cacaaatctt 28200
tggactaact agtttgccca agtgtataga ttatacaggt gtaaaaggtt cacactcagc 28260
caataaaaag accaagtttt ggattcaaca aaggagcaaa ggggcaaccg aaggcacccc 28320
tggtctggcg caccggactg tccggtgcgc caccggacat gtccggtgca ccagggagac 28380
tcagactcaa actcgccacc ttcgggaatt tccagaggca ctcgcgctat aattcaccgg 28440
actgtccggt gtacaccgga cagtgtctgg tgcgccaagg gaggtcggcc tcaggaactc 28500
gccagcttcg ggaaactcca acggctagtc cactataatt caccggactg tccggtgtgc 28560
accggactgt ccggtgcgac tccggagcaa cggctaactc cgcgccaacg gctctctgcc 28620
gcgcatttaa tgcgcgctct gcgcgcgcag agggcaggct cgcccatgct ggcacaccgg 28680
acagcaaaca gtacatgtcc gatgtgcacc ggacacccag gcgggcccac aagtcagaag 28740
ctccaacggt cagaatccaa cggcagtgat gacgtggcag gggcaccgg actgtccggt 28800
gtgcaccgga ctgtccggtg cgccatcgag cagacagcct cccaacgacc actttggtg 28860
gttgggggta taaataccc aaccacccca ccattcattg catccaagtt ttccacttcc 28920
caactactac aagagctcta gcattcaatt ctagacacac caaagagatc aaatcctctc 28980
caattccaca cacaaaaccc tagtgactag agagagtgat ttgcttgtgt tctttcgagc 29040
tcttgcgctt ggattgcttt cttctttctt gaatctttct tgtgatcaaa cactcacatt 29100
gtaattgagg caagaggcac caattgtgtg gtggcccttg cgggaagttt gattcccaag 29160
tgatttgaga agagaagctc actcggtccg agggaccgtt tgagagaggg aagggttgaa 29220
agagacccgg cctttgtggc ctcctcaacg gggagtaggt ttgcaagaac caaacctcgg 29280
taaaacaaat ccgtgtgtct cacttcatta tttgcttgcg atttgttttg cgccctctct 29340
cgcggactca tttatatttc taacgctaac tcggcttgta gttgtgttta tatttgtaaa 29400
tttcagtttc gccctattca cccccccccc ctctaggcga ctatcaattt gtatcagagc 29460
cggtgcttca ttagagccta accgctcgaa gtgatgtcgg gagatcacgc caagaaggag 29520
atggaaactg gcgaaaagcc cactacaagc cacgggagca cctcatcgga agagtcccgc 29580
accaagagga aggagaagaa gaaggactcc tccaaacgga aggagaaaag gtcttcctct 29640
tctcaccaca aagagaagaa ggaaaaatct tcttcccaca agccgcatcg gaaaggccga 29700
caagcacaag aggatgagga aggtggtcta ctacgagacc gacacttcat caacgtctac 29760
ctccgactcc gatacaccgt ccgtcacttc caagcgccaa gagcgcaaga agtatagtaa 29820
gatcccccta cgctaccctc gcatttccaa acatacacct ttactttccg tcccattagg 29880
caaaccacca acttttgatg gtgaagatta cgctaggtgg agcgatttaa tgcgatttca 29940
tctaacctcg ctccacaaaa gcatatggga tgttgttgag tttggtgcac aggtaccatc 30000
cgtaggggat gagaactatg atgaggatga ggtggcccaa atcgagcact tcaactctca 30060
agcaacaaca atactcctcg cctctctaag tagagaggag tataacaaag tacaagggtt 30120
gaagagcgcc aaggagattt gggatgtgct caaaaccgcg cacgagggag acgagctcac 30180
caagatcacc aagcgggaaa cgatcgaggg ggagctcggt cggtttcggc ttcgcaaagg 30240
ggaggagcca caacacatgt acaaccggct caagacattg gtgaatcaag tgcgcaacct 30300
cgggagcgta aagtgggatg accacgagat ggttaaggtt attctaagat ctcttatttt 30360

-continued

```
ccttaacccc actcaagttc aattaatccg tggtaatcct agatatacta aaatgacccc  30420
cgaggaagtt atcgggaatt ttgttagttt tgagtgcatg atcgaaggct cgaggaagat  30480
caacgagctt gatgatgcca ccacatccga agctcaaccc gttgcattca aggcaacgga  30540
ggagaagaag gagtctacac cgagtagaca accgatagac gcctccaagc tcgacaatga  30600
ggaaatggcg ctcgttatca agagcttccg ccaaatcctc aagcaaagga gggggaagga  30660
ttacaaatcc cgctccaaga aggtttgcta caagtgtggt aagcccggtc attttattgc  30720
taaatgccct atatctagtg acagtgaccg aggtgacgac aagaagggga ggcgaaagga  30780
gaagaagagg tactacaaga agaagggcgg tgatgcccat gtttgtcggg agtgggactc  30840
cgacgaaagc tcaagcgact cctccgacga cgaggacgcc gccaacatcg ccgtcaccaa  30900
gggactcctc ttccccaacg tcggccacaa gtgcctcatg gcaaaggacg gcaaacggaa  30960
gaaggttaaa tctaactcct ccactaaata tgagtcttct agtgatgata ataatagtga  31020
tgaggaggat aatttgcgtg ttctctttgc caatcttaac atggagcaaa aagaaaaatt  31080
aaatgaatta gttagtgcta ttcatgaaaa ggatgacctt ttggactccc aagaggattg  31140
tctaattaaa gaaaacaaga gacatgttaa ggttaaaaag gcttatgctc tagaagtaga  31200
aaaatgtgaa aaattatcta gtgagctaag cacttgccgt gagatgattg acaaccttag  31260
gaatgaaaat gctagtttaa atgctaaggt tgattctcat gtttgcattg tttcaacttc  31320
caatcctaaa gataataatg atgatttgct tgctaggatt gaagaattaa acatttctct  31380
tgctagcctt agattagaga atgaaaattt aattgctaag gctaaagatt ttgatgtttg  31440
caattctatt atttccgacc ttagaactaa gaatgatatg ttacatgcta aggttgttga  31500
attaaaatct tgcaaaccct ctacatctat tgttgagcat gtatctattt gtactagatg  31560
tagaaatgtt gatattgatg ctattcatga tcatatggct ttaattaaac aacaaaatga  31620
tcatatagca aaactagatg ctaaaattgc cgagcacaac ctagagaatg agaaattcaa  31680
atttgctcgt agcatgcttt ataatgggag acgccctggc attaaggatg gcattggcta  31740
ccaaagggga gacaatgtca aacttagtgc ccctcctaaa agattgtcaa attttgttaa  31800
gggcaaggct cccatgcctc aggataacga gggttacatt ttataccctg tcggttatcc  31860
cgaggacaaa attaggaaaa ttcattctag gaagtctcac tctggcccta atcatgcttt  31920
tatgtataag ggtgagacat ctagttctag gcaatcaact cgtactaagt tgcctaagaa  31980
gaaaatttct aatgcatcaa atgatcatgc tatttcattt aaaacttttg atgcttctta  32040
tgtgttgact aacaaatccg gcaaagtagt tgccaaatat gttgggggca agcacaaggg  32100
gtcaaggact tgtgtttggg tacccaaaaa tcttgtgcct aatgccaaag gacccaaaac  32160
catttgggta cctaaagtca agaactaaaa ttgttttgta ggtttatgca tccgggggct  32220
caagttggat actcgacagc gggtgcacaa accacatgac tggggagaaa aggatgttct  32280
cctcctacga gaaaaaccaa gatccccaac gagctatcac attcggggat ggaaatcaag  32340
gtttggtcaa aggtcttggt aaaattgcta tatcttctga ccattctatt tccaatgttt  32400
ttcttgtaga ttctttagat tacaatttgc tttccgtttc ccaattatgt caaatgggct  32460
acaactgtct ttttactgat ataggtgtca ctgtctttag aagaagtgat gattcaatag  32520
catttaaggg tgtgttagag ggtcagctat acttagtaga ttttgataga gctgaactcg  32580
acacatgctt aatcgctaag actaacatgg gttggctttg gcaccgccga ctagcccatg  32640
ttgggatgaa gaatcttcac aagcttctaa agggagaaca cattttagga ttaacaaatg  32700
ttcattttga gaaagacagg gtttgtagcg catgccaggc gggaaagcaa gttggagtcc  32760
```

-continued

```
atcatccaca caagaacatc atgacgaccg acaggccgct tgagctactc cacatggatc  32820

tattcggccc gattgcttac ataagcatcg gcgggagtaa gtattgtctt gtaattgtgg  32880

atgattattc tcgcttcact tgggtattct ttttacagga aaaatctcaa acccaagaga  32940

ccttaaaggg attcttgaga cgggctcaaa atgagttcgg cttaaggatc aagaaaataa  33000

gaagcgacaa cgggacggag ttcaagaact ctcaaatcga aggcttcctt gaggaggagg  33060

gcatcaagca tgagttctcc tctccctaca cgccacaaca aaatggtgta gtcgagagga  33120

agaatcgaac tctattggac atggcaagaa ccatgcttga tgagtacaag acaccggacc  33180

ggttttgggc cgaagcggtc aacaccgcct gctacgccat caac                    33224
```

```
<210> SEQ ID NO 2
<211> LENGTH: 1000
<212> TYPE: DNA
<213> ORGANISM: Zea mays

<400> SEQUENCE: 2

atgcagtttg cacttgcatt ggacacgaac tcaggtcctc accagataag atcttgtgag     60

ggtgatggga ttgacaggtt ggaaaaatta agtattgggg gcagaaagca ggagaaagct    120

ttgagaaata ggtgctttgg tggtagagtt gctacaacta cacaatgtat tcttacctca    180

gatgcttgtc ctgaaactct tgtaagtatc cacctcaatt attactctta catgttggtt    240

tactttacgt ttgtcttttc aagggaaatt tactgtattt tttgtgtttt gtgggagttc    300

tatacttctg ttggactggt tattgtaaag atttgttcaa atagggtcat cttataattg    360

tttgaaatct gggaactgtg gtttcactgc gttcaggaaa aagtgaattc ttggttactg    420

catgaataac ttatgaaaat agaccttaga gttgctgcat gattatcaca aatcattgct    480

acgatatctt ataatagttc tttcgacctc gcattacata tataactgca actcgtagtt    540

gcgttcaaaa aaaatgcaac tcttagaacg ctcaccagtg taatctttcc tgaattgtta    600

tttaatggca tgtatgcact acttgtatac ttatctagga ttaagtaatc taactctagg    660

ccccatattt gcagcattct caaacacagt cctctaggaa aaattatgct gatgcaaacc    720

gtgtatctgc tatcattttg ggcggaggca ctggatctca gctctttcct ctgacaagca    780

caagagctac gcctggcgag gtggccgcgg ctgaacggga cctcgggtat cagtcacccg    840

agggggacct gaaggatgtc ttcgtcggag gatcctactc cggtggagac aactagatgg    900

actcccgggg ggaccccgtg ctccccgttc tacggggccg aaacctgcct tcccccagaa    960

acccctctgg actccccacg ggtccagact tctaacaaat                         1000
```

```
<210> SEQ ID NO 3
<211> LENGTH: 1500
<212> TYPE: DNA
<213> ORGANISM: Zea mays

<400> SEQUENCE: 3

atgcagtttg cacttgcatt ggacacgaac tcaggtcctc accagataag atcttgtgag     60

ggtgatggga ttgacaggtt ggaaaaatta agtattgggg gcagaaagca ggagaaagct    120

ttgagaaata ggtgctttgg tggtagagtt gctacaacta cacaatgtat tcttacctca    180

gatgcttgtc ctgaaactct tgtaagtatc cacctcaatt attactctta catgttggtt    240

tactttacgt ttgtcttttc aagggaaatt tactgtattt tttgtgtttt gtgggagttc    300

tatacttctg ttggactggt tattgtaaag atttgttcaa atagggtcat cttataattg    360
```

```
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
catgaggacg aggactccct catcaaacgc agatgggaac ccagggtcgg gacctagccc   1080
tacggcaagt accaaaccaa gaagggctct gcaactctcc cctagctggg aaggaccctt   1140
caaggtgatg ggaatacgcc gacccggggg tgactgtcta gctatgactg aaggagtacc   1200
tttggagcac ctctgtaagt tctatccata ggagcaagcc tgaggggtcg aatttttctc   1260
ccttttttgta gctaggtaac gcatacatgt acgccaaccc ggtgaggtcc gccctcataa   1320
gcccggcatg ttggtctgca cccatacatg acaagttata aagaacagaa ttaccccctc   1380
agatgtgtct ctaagtttta tcctactgct ccatggtctt gccttgcagt tttcagaga    1440
ttattttatc taacccaccc aaacagttcc ctttccatca gacataacga cattcgaatt   1500
```

<210> SEQ ID NO 4
<211> LENGTH: 2000
<212> TYPE: DNA
<213> ORGANISM: Zea mays

<400> SEQUENCE: 4

```
atgcagtttg cacttgcatt ggacacgaac tcaggtcctc accagataag atcttgtgag     60
ggtgatggga ttgacaggtt ggaaaaatta agtattgggg gcagaaagca ggagaaagct    120
ttgagaaata ggtgctttgg tggtagagtt gctacaacta cacaatgtat tcttacctca    180
gatgcttgtc ctgaaactct tgtaagtatc cacctcaatt attactctta catgttggtt    240
tactttacgt ttgtcttttc aagggaaatt tactgtattt tttgtgtttt gtgggagttc    300
tatacttctg ttggactggt tattgtaaag atttgttcaa atagggtcat cttataattg    360
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
```

catgaggacg aggactccct catcaaacgc agatgggaac ccagggtcgg gacctagccc 1080
tacggcaagt accaaaccaa gaagggctct gcaactctcc cctagctggg aaggaccctt 1140
caaggtgatg ggaatacgcc gacccggggg tgactgtcta gctatgactg aaggagtacc 1200
tttggagcac ctctgtaagt tctatccata ggagcaagcc tgaggggtcg aatttttctc 1260
cctttttgta gctaggtaac gcatacatgt acgccaaccc ggtgaggtcc gccctcataa 1320
gcccggcatg ttggtctgca cccatacatg acaagttata aagaacagaa ttacccccctc 1380 agatgtgtct ctaagtttta tcctactgct ccatggtctt gccttgcagt ttttcagaga 1440
ttattttatc taacccaccc aaacagttcc ctttccatca gacataacga cattcgaatt 1500
gaacagccag gcttgcagtt taggacctat ttacgaaagc gggagggccc gacagcctgg 1560
gggtggttct agagaacgga agcccgttcc atggggtggt ctagagcctg tgtggccgct 1620
tagcctggtc ctatacccga aagtctgcac actccaccac tccgtgacgg gtaccctagt 1680
atttggagct ataagtcctg tgggtccggc aacctggggt ccggaactag agaatggaca 1740
cttgtctcct ggggtggtcc ggagcccgtg tagccgctca gcttggttcc gtaccgtggg 1800
cgtgcacgct ccaccactct gcgacgggtg tcctagtacc tagaaccacc atctaggggg 1860
tccagacgca caacttggcc tcccagacta aaccctgcag gtcccgagca tgtatcaaag 1920
gatgactaat gtcagatggc gggtcctgtg ggtgtactac taatgctccc tagccaaagc 1980
tgtgtgcagg ctcaggtccc 2000

<210> SEQ ID NO 5
<211> LENGTH: 2500
<212> TYPE: DNA
<213> ORGANISM: Zea mays

<400> SEQUENCE: 5
atgcagtttg cacttgcatt ggacacgaac tcaggtcctc accagataag atcttgtgag 60
ggtgatggga ttgacaggtt ggaaaaatta agtattgggg gcagaaagca ggagaaagct 120
ttgagaaata ggtgctttgg tggtagagtt gctacaacta cacaatgtat tcttacctca 180
gatgcttgtc ctgaaactct tgtaagtatc cacctcaatt attactctta catgttggtt 240
tactttacgt ttgtcttttc aagggaaatt tactgtattt tttgtgtttt gtgggagttc 300
tatacttctg ttggactggt tattgtaaag atttgttcaa atagggtcat cttataattg 360
tttgaaatct gggaactgtg gtttcactgc gttcaggaaa aagtgaattc ttggttactg 420
catgaataac ttatgaaaat agaccttaga gttgctgcat gattatcaca aatcattgct 480
acgatatctt ataatagttc tttcgacctc gcattacata tataactgca actcgtagtt 540
gcgttcaaaa aaaatgcaac tcttagaacg ctcaccagtg taatctttcc tgaattgtta 600
tttaatggca tgtatgcact acttgtatac ttatctagga ttaagtaatc taactctagg 660
ccccatattt gcagcattct caaacacagt cctctaggaa aaattatgct gatgcaaacc 720
gtgtatctgc tatcattttg ggcggaggca ctggatctca gctctttcct ctgacaagca 780
caagagctac gcctggcgag gtggccgcgg ctgaacggga cctcgggtat cagtcacccg 840
agggggacct gaaggatgtc ttcgtcggag gatcctactc cggtggagac aactagatgg 900
actcccgggg ggaccccgtg ctccccgttc tacggggccg aaacctgcct tcccccagaa 960
acccctctgg actccccacg ggtccagact tctaacaaat ccatgcagaa atggctacat 1020
catgaggacg aggactccct catcaaacgc agatgggaac ccagggtcgg gacctagccc 1080
tacggcaagt accaaaccaa gaagggctct gcaactctcc cctagctggg aaggaccctt 1140
caaggtgatg ggaatacgcc gacccggggg tgactgtcta gctatgactg aaggagtacc 1200
tttggagcac ctctgtaagt tctatccata ggagcaagcc tgaggggtcg aatttttctc 1260 ccttttttgta gctaggtaac gcatacatgt acgccaaccc ggtgaggtcc gccctcataa 1320
gcccggcatg ttggtctgca cccatacatg acaagttata aagaacagaa ttaccccctc 1380
agatgtgtct ctaagtttta tcctactgct ccatggtctt gccttgcagt ttttcagaga 1440
ttattttatc taacccaccc aaacagttcc ctttccatca gacataacga cattcgaatt 1500
gaacagccag gcttgcagtt taggacctat ttacgaaagc gggagggccc gacagcctgg 1560
gggtggttct agagaacgga agcccgttcc atggggtggt ctagagcctg tgtggccgct 1620
tagcctggtc ctatacccga aagtctgcac actccaccac tccgtgacgg gtaccctagt 1680
atttggagct ataagtcctg tgggtccggc aacctggggt ccggaactag agaatggaca 1740
cttgtctcct ggggtggtcc ggagcccgtg tagccgctca gcttggttcc gtaccgtggg 1800
cgtgcacgct ccaccactct gcgacgggtg tcctagtacc tagaaccacc atctaggggg 1860
tccagacgca caacttggcc tcccagacta aaccctgcag gtcccgagca tgtatcaaag 1920
gatgactaat gtcagatggc gggtcctgtg ggtgtactac taatgctccc tagccaaagc 1980
tgtgtgcagg ctcaggtccc agtcgaggct gcctcctggg ggccattgcc aactcttcct 2040
taggtatgct ggtttgcagc ctcgacaaat cgagcctaca tcccgggggc caggtaccaa 2100
ggaggaatca gttacaccac acacaacagg gacaagtggt atacaaataa gtgctaatac 2160
tgcttgataa atagtactca aaagtacctt acaaaaagca aaaatattac atccgccttc 2220
aagcggagtt ctagctccat ctctactcta cagatatgaa ctgcctccac accactaggg 2280
tcgcgtgggt agctagctcc gagcggctcg ccagcgaagg cgaccacctc tgcaccgacg 2340
gatcgacagc ggcgacgact acctcggctc caagcggctc gccagcagag gcaaccacct 2400
ctgcaacggg cagcctcacc agcgatggcg accacctctg cgccaggcag cctccccagt 2460
sgtggcgacc acctcagcat gcgcgccatg gtgaagaggt 2500

<210> SEQ ID NO 6
<211> LENGTH: 3000
<212> TYPE: DNA
<213> ORGANISM: Zea mays

<400> SEQUENCE: 6
atgcagtttg cacttgcatt ggacacgaac tcaggtcctc accagataag atcttgtgag 60
ggtgatggga ttgacaggtt ggaaaaatta agtattgggg gcagaaagca ggagaaagct 120
ttgagaaata ggtgctttgg tggtagagtt gctacaacta cacaatgtat tcttacctca 180
gatgcttgtc ctgaaactct tgtaagtatc cacctcaatt attactctta catgttggtt 240
tactttacgt ttgtcttttc aagggaaatt tactgtattt tttgtgtttt gtgggagttc 300
tatacttctg ttggactggt tattgtaaag atttgttcaa atagggtcat cttataattg 360
tttgaaatct gggaactgtg gtttcactgc gttcaggaaa aagtgaattc ttggttactg 420
catgaataac ttatgaaaat agaccttaga gttgctgcat gattatcaca aatcattgct 480
acgatatctt ataatagttc tttcgacctc gcattacata tataactgca actcgtagtt 540
gcgttcaaaa aaaatgcaac tcttagaacg ctcaccagtg taatctttcc tgaattgtta 600
tttaatggca tgtatgcact acttgtatac ttatctagga ttaagtaatc taactctagg 660
ccccatattt gcagcattct caaacacagt cctctaggaa aaattatgct gatgcaaacc 720

```
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
catgaggacg aggactccct catcaaacgc agatgggaac ccagggtcgg gacctagccc   1080
tacggcaagt accaaaccaa gaagggctct gcaactctcc cctagctggg aaggaccctt   1140
caaggtgatg ggaatacgcc gacccggggg tgactgtcta gctatgactg aaggagtacc   1200
tttggagcac ctctgtaagt tctatccata ggagcaagcc tgaggggtcg aatttttctc   1260
ccttttgta gctaggtaac gcatacatgt acgccaaccc ggtgaggtcc gccctcataa   1320
gcccggcatg ttggtctgca cccatacatg acaagttata aagaacagaa ttaccccctc   1380
agatgtgtct ctaagtttta tcctactgct ccatggtctt gccttgcagt ttttcagaga   1440
ttattttatc taacccaccc aaacagttcc ctttccatca gacataacga cattcgaatt   1500
gaacagccag gcttgcagtt taggacctat ttacgaaagc gggagggccc gacagcctgg   1560
gggtggttct agagaacgga agcccgttcc atggggtggt ctagagcctg tgtggccgct   1620
tagcctggtc ctatacccga aagtctgcac actccaccac tccgtgacgg gtaccctagt   1680
atttggagct ataagtcctg tgggtccggc aacctggggt ccggaactag agaatggaca   1740
cttgtctcct ggggtggtcc ggagcccgtg tagccgctca gcttggttcc gtaccgtggg   1800
cgtgcacgct ccaccactct gcgacgggtg tcctagtacc tagaaccacc atctaggggg   1860
tccagacgca caacttggcc tcccagacta aaccctgcag gtcccgagca tgtatcaaag   1920
gatgactaat gtcagatggc gggtcctgtg ggtgtactac taatgctccc tagccaaagc   1980
tgtgtgcagg ctcaggtccc agtcgaggct gcctcctggg ggccattgcc aactcttcct   2040
taggtatgct ggtttgcagc ctcgacaaat cgagcctaca tcccgggggc caggtaccaa   2100
ggaggaatca gttacaccac acacaacagg gacaagtggt atacaaataa gtgctaatac   2160
tgcttgataa atagtactca aaagtacctt acaaaaagca aaaatattac atccgccttc   2220
aagcggagtt ctagctccat ctctactcta cagatatgaa ctgcctccac accactaggg   2280
tcgcgtgggt agctagctcc gagcggctcg ccagcgaagg cgaccacctc tgcaccgacg   2340
gatcgacagc ggcgacgact acctcggctc caagcggctc gccagcagag gcaaccacct   2400
ctgcaacggg cagcctcacc agcgatggcg accacctctg cgccaggcag cctccccagt   2460
sgtggcgacc acctcagcat gcgcgccatg gtgaagaggt cctcgccttc gtccccctac   2520
gggggtgagg acaagaccat ccaagccttg gagctgggag catggtggaa ggcggtgctt   2580
gcggtctggc tgggaccgcg tagccgaagt tcgcctcctt cacaaggctg gtgatcatcc   2640
ttttcctccg aatgctggag gaagagatgg gcaccaaccc atgtgggagg cgaaaccgcg   2700
gctcagctcg ttccccgcca ccgcgaggct catgaacatc cttgaagcca agaatcggtg   2760
gaagagcgcc gctcccacaa gaccgcgcat ctccagcaga ggaaaaacaa gaccggtagc   2820
accagcccgc tagggaggag aaaaggcaaa aactctctag cggcaagctc atcggagtgg   2880
ataacgccgg cgcaaatcct tccgctgagc gccagcgcat tccatccaag caagtggtat   2940
accatttcga gcactcactc agtttgggtg tgctcgggat tgagagcacc tagagggggg   3000
```

<210> SEQ ID NO 7

<211> LENGTH: 5000
<212> TYPE: DNA
<213> ORGANISM: Zea mays

<400> SEQUENCE: 7

```
atgcagtttg cacttgcatt ggacacgaac tcaggtcctc accagataag atcttgtgag     60
ggtgatggga ttgacaggtt ggaaaaatta agtattgggg gcagaaagca ggagaaagct    120
ttgagaaata ggtgctttgg tggtagagtt gctacaacta cacaatgtat tcttacctca    180
gatgcttgtc ctgaaactct tgtaagtatc cacctcaatt attactctta catgttggtt    240
tactttacgt ttgtcttttc aagggaaatt tactgtattt tttgtgtttt gtgggagttc    300
tatacttctg ttggactggt tattgtaaag atttgttcaa atagggtcat cttataattg    360
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
catgaggacg aggactccct catcaaacgc agatgggaac ccagggtcgg gacctagccc   1080
tacggcaagt accaaaccaa gaagggctct gcaactctcc cctagctggg aaggaccctt   1140
caaggtgatg ggaatacgcc gacccggggg tgactgtcta gctatgactg aaggagtacc   1200
tttggagcac ctctgtaagt tctatccata ggagcaagcc tgaggggtcg aatttttctc   1260
cctttttgta gctaggtaac gcatacatgt acgccaaccc ggtgaggtcc gccctcataa   1320
gcccggcatg ttggtctgca cccatacatg acaagttata aagaacagaa ttacccccctc   1380
agatgtgtct ctaagtttta tcctactgct ccatggtctt gccttgcagt ttttcagaga   1440
ttattttatc taacccaccc aaacagttcc ctttccatca gacataacga cattcgaatt   1500
gaacagccag gcttgcagtt taggacctat ttacgaaagc gggagggccc gacagcctgg   1560
gggtggttct agagaacgga agcccgttcc atggggtggt ctagagcctg tgtggccgct   1620
tagcctggtc ctatacccga aagtctgcac actccaccac tccgtgacgg gtaccctagt   1680
atttggagct ataagtcctg tgggtccggc aacctggggt ccggaactag agaatggaca   1740
cttgtctcct ggggtggtcc ggagcccgtg tagccgctca gcttggttcc gtaccgtggg   1800
cgtgcacgct ccaccactct gcgacgggtg tcctagtacc tagaaccacc atctaggggg   1860
tccagacgca caacttggcc tcccagacta aaccctgcag gtcccgagca tgtatcaaag   1920
gatgactaat gtcagatggc gggtcctgtg ggtgtactac taatgctccc tagccaaagc   1980
tgtgtgcagg ctcaggtccc agtcgaggct gcctcctggg ggccattgcc aactcttcct   2040
taggtatgct ggtttgcagc ctcgacaaat cgagcctaca tcccgggggc caggtaccaa   2100
ggaggaatca gttacaccac acacaacagg gacaagtggt atacaaataa gtgctaatac   2160
tgcttgataa atagtactca aaagtacctt acaaaaagca aaaatattac atccgccttc   2220
```

aagcggagtt ctagctccat ctctactcta cagatatgaa ctgcctccac accactaggg 2280
tcgcgtgggt agctagctcc gagcggctcg ccagcgaagg cgaccacctc tgcaccgacg 2340
gatcgacagc ggcgacgact acctcggctc caagcggctc gccagcagag gcaaccacct 2400
ctgcaacggg cagcctcacc agcgatggcg accacctctg cgccaggcag cctccccagt 2460
sgtggcgacc acctcagcat gcgcgccatg gtgaagaggt cctcgccttc gtccccctac 2520
gggggtgagg acaagaccat ccaagccttg gagctgggag catggtggaa ggcggtgctt 2580
gcggtctggc tgggaccgcg tagccgaagt tcgcctcctt cacaaggctg gtgatcatcc 2640
ttttcctccg aatgctggag gaagagatgg gcaccaaccc atgtgggagg cgaaaccgcg 2700
gctcagctcg ttccccgcca ccgcgaggct catgaacatc cttgaagcca agaatcggtg 2760
gaagagcgcc gctcccacaa gaccgcgcat ctccagcaga ggaaaaacaa gaccggtagc 2820
accagcccgc tagggaggag aaaaggcaaa aactctctag cggcaagctc atcggagtgg 2880
ataacgccgg cgcaaatcct tccgctgagc gccagcgcat tccatccaag caagtggtat 2940
accatttcga gcactcactc agtttgggtg tgctcgggat tgagagcacc tagagggggg 3000
gtgaataggt gatcctgtaa aaacttgaaa cttaattcgc aaaacttgat taggagttag 3060
cacgaataag ctaagtggct agagaggaga acttgcacaa cacgataacc acaaagagat 3120
caacacagag atggcacagt ggtttatccc gtggttcggc caagtccaac acttgcctac 3180
tccacgttgt ggcgtcccaa tggacgaggg ttgcaatcaa ccccttttcaa gcggtccaaa 3240 gacccacttg aataccacgg tgttttgctt tcactttact atatctcgct tgtgaggaat 3300
ctccacaact tggagcctct cgcccttaca ctttgatgtt cacaaagaag cacggagtaa 3360
gggagggatg agcaacgcac acaagacatg aaatcagagt accaacacgc acacaaatca 3420
caacaagagc tcacaacaca acccggcgag ttcactacta aaatggagct ctagttgcta 3480
tcacaaagag tcaaatgcgc agaatcgaag tcttggtgct taggaatgct tagagaatgc 3540
ttggtgcact cctccatgcg cctaggggtc ccttttatag ccccaaggca gctaggagcc 3600
gttgagagca attcaagaag gcaattcttg ccttctgtcg cctggcgcac cggacagttc 3660
ggtgcaccac cggacactgt ccggtgcgga tctctttcct tatttggcga agccgaccgt 3720
tgcagattgc tagccgttgg cacaccggac actgtccggt gcacaccgga caatccgatg 3780 ccccccttctg accgttggct ctgccacgcg tcgcgcgcgg attccacggc cgaccgttgg 3840
cccggccgac tgttggctca ccagacagtc cggtgcacca ccggacagtc cggtgaattt 3900
tagccgtacg ccgccaacga tttcccgaga gcaacaagtt cgcgtgagtc agcctggtgc 3960
accggacact gtccggtgca ccaccgggca gtccggtgca ccaccggaca gtccggtgca 4020
cccagactgc gcagagtctt cgctactcag ccaagtcttt tccaatttgg tcttttcctg 4080
tttctagcac ttagacacaa tacattagtc ttcaaaacaa tgtactaagt cttagaaaca 4140
tacctttaga cttgatttgc actttgtcca tcaattggca tagattatca tttaagcact 4200
tgtgttggca ctcaatcacc aaaatactta gaaatggccc aagggcacat ttccctttca 4260
atctccccct ttttggtgat ttatgccaac acaacaaaaa gcaacttaaa gaagtgcaac 4320
atcaatgcaa atgagaccac aaatttgttt tgatcaagtt tgacatattt ggatcattct 4380
ttgccaccac ttggtttgtt tttgcaaacc aaactcaatt tcctatctct aagtcaaaca 4440
cacttgttga aacataaaga gagatatttc acgagaaatt gatcaaagat tcaacaactc 4500 cccctttttcc cataaatcca gccttctccc cacaagagat caatgttttg acaataagag 4560

-continued

```
acaaacaaga gtatttagac aaacaaaaac tctaactcta ctattttcaa aattcctaag   4620
tggtagctga tccatttctt gctttggcct tattttctcc ccctttggca tcaagcacca   4680
aaacaggatc aattttggcc ctttaacccc attgcctcac caaaatttc aactaagagt    4740
aaaaaggcaa taagagtaca aagatgaact tgaaattagt tactctttca tcggagtgta   4800
gtggaagtct tgcatggtcc aagtccacct tttccctttc aaacctcctt tgagactaaa   4860
ttaagcagac tcaagcaaac aattagtctc aaagggtcaa gttgtagctc atctccccct   4920
agatgtgtgc atcacttgca aaggacttgt gaggtccggg gwgtgcttgt acaacttgag   4980
caccataaat aaacaacaaa                                               5000
```

<210> SEQ ID NO 8
<211> LENGTH: 7000
<212> TYPE: DNA
<213> ORGANISM: Zea mays

<400> SEQUENCE: 8

```
atgcagtttg cacttgcatt ggacacgaac tcaggtcctc accagataag atcttgtgag     60
ggtgatggga ttgacaggtt ggaaaaatta agtattgggg gcagaaagca ggagaaagct    120
ttgagaaata ggtgctttgg tggtagagtt gctacaacta cacaatgtat tcttacctca    180
gatgcttgtc ctgaaactct tgtaagtatc cacctcaatt attactctta catgttggtt    240
tactttacgt ttgtcttttc aagggaaatt tactgtattt tttgtgtttt gtgggagttc    300
tatacttctg ttggactggt tattgtaaag atttgttcaa atagggtcat cttataattg    360
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
catgaggacg aggactccct catcaaacgc agatgggaac ccagggtcgg gacctagccc   1080
tacggcaagt accaaaccaa gaagggctct gcaactctcc cctagctggg aaggaccctt   1140
caaggtgatg ggaatacgcc gacccggggg tgactgtcta gctatgactg aaggagtacc   1200
tttggagcac ctctgtaagt tctatccata ggagcaagcc tgaggggtcg aatttttctc   1260
ccttttgta gctaggtaac gcatacatgt acgccaaccc ggtgaggtcc gccctcataa    1320
gcccggcatg ttggtctgca cccatacatg acaagttata aagaacagaa ttaccccctc   1380
agatgtgtct ctaagtttta tcctactgct ccatggtctt gccttgcagt ttttcagaga   1440
ttattttatc taacccaccc aaacagttcc ctttccatca gacataacga cattcgaatt   1500
gaacagccag gcttgcagtt taggacctat ttacgaaagc gggagggccc gacagcctgg   1560
gggtggttct agagaacgga agcccgttcc atggggtggt ctagagcctg tgtggccgct   1620
tagcctggtc ctatacccga aagtctgcac actccaccac tccgtgacgg gtaccctagt   1680
```

```
atttggagct ataagtcctg tgggtccggc aacctggggt ccggaactag agaatggaca   1740
cttgtctcct ggggtggtcc ggagcccgtg tagccgctca gcttggttcc gtaccgtggg   1800
cgtgcacgct ccaccactct gcgacgggtg tcctagtacc tagaaccacc atctaggggg   1860
tccagacgca caacttggcc tcccagacta aaccctgcag gtcccgagca tgtatcaaag   1920
gatgactaat gtcagatggc gggtcctgtg ggtgtactac taatgctccc tagccaaagc   1980
tgtgtgcagg ctcaggtccc agtcgaggct gcctcctggg ggccattgcc aactcttcct   2040
taggtatgct ggtttgcagc ctcgacaaat cgagcctaca tcccgggggc caggtaccaa   2100
ggaggaatca gttacaccac acacaacagg gacaagtggt atacaaataa gtgctaatac   2160
tgcttgataa atagtactca aaagtacctt acaaaaagca aaaatattac atccgccttc   2220
aagcggagtt ctagctccat ctctactcta cagatatgaa ctgcctccac accactaggg   2280
tcgcgtgggt agctagctcc gagcggctcg ccagcgaagg cgaccacctc tgcaccgacg   2340
gatcgacagc ggcgacgact acctcggctc caagcggctc gccagcagag gcaaccacct   2400
ctgcaacggg cagcctcacc agcgatggcg accacctctg cgccaggcag cctccccagt   2460
sgtggcgacc acctcagcat gcgcgccatg gtgaagaggt cctcgccttc gtccccctac   2520
gggggtgagg acaagaccat ccaagccttg gagctgggag catggtggaa ggcggtgctt   2580
gcggtctggc tgggaccgcg tagccgaagt tcgcctcctt cacaaggctg gtgatcatcc   2640
ttttcctccg aatgctggag gaagagatgg gcaccaaccc atgtgggagg cgaaaccgcg   2700
gctcagctcg ttccccgcca ccgcgaggct catgaacatc cttgaagcca agaatcggtg   2760
gaagagcgcc gctcccacaa gaccgcgcat ctccagcaga ggaaaaacaa gaccggtagc   2820
accagcccgc tagggaggag aaaaggcaaa aactctctag cggcaagctc atcggagtgg   2880
ataacgccgg cgcaaatcct tccgctgagc gccagcgcat tccatccaag caagtggtat   2940
accatttcga gcactcactc agtttgggtg tgctcgggat tgagagcacc tagagggggg   3000
gtgaataggt gatcctgtaa aaacttgaaa cttaattcgc aaaacttgat taggagttag   3060
cacgaataag ctaagtggct agagaggaga acttgcacaa cacgataacc acaaagagat   3120
caacacagag atggcacagt ggtttatccc gtggttcggc caagtccaac acttgcctac   3180
tccacgttgt ggcgtcccaa tggacgaggg ttgcaatcaa ccccttttcaa gcggtccaaa   3240
gacccacttg aataccacgg tgttttgctt tcactttact atatctcgct tgtgaggaat   3300
ctccacaact tggagcctct cgcccttaca ctttgatgtt cacaaagaag cacggagtaa   3360
gggagggatg agcaacgcac acaagacatg aaatcagagt accaacacgc acacaaatca   3420
caacaagagc tcacaacaca acccggcgag ttcactacta aaatggagct ctagttgcta   3480
tcacaaagag tcaaatgcgc agaatcgaag tcttggtgct taggaatgct tagagaatgc   3540
ttggtgcact cctccatgcg cctaggggtc ccttttatag ccccaaggca gctaggagcc   3600
gttgagagca attcaagaag gcaattcttg ccttctgtcg cctggcgcac cggacagttc   3660
ggtgcaccac cggacactgt ccggtgcgga tctctttcct tatttggcga agccgaccgt   3720
tgcagattgc tagccgttgg cacaccggac actgtccggt gcacaccgga caatccgatg   3780
ccccccttctg accgttggct ctgccacgcg tcgcgcgcgg attccacggc cgaccgttgg   3840
cccggccgac tgttggctca ccagacagtc cggtgcacca ccggacagtc cggtgaattt   3900
tagccgtacg ccgccaacga tttcccgaga gcaacaagtt cgcgtgagtc agcctggtgc   3960
accggacact gtccggtgca ccaccgggca gtccggtgca ccaccggaca gtccggtgca   4020
```

-continued cccagactgc gcagagtctt cgctactcag ccaagtcttt tccaatttgg tcttttcctg 4080
tttctagcac ttagacacaa tacattagtc ttcaaaacaa tgtactaagt cttagaaaca 4140
tacctttaga cttgatttgc actttgtcca tcaattggca tagattatca tttaagcact 4200
tgtgttggca ctcaatcacc aaaatactta gaaatggccc aagggcacat ttccctttca 4260
atctccccct ttttggtgat ttatgccaac acaacaaaaa gcaacttaaa gaagtgcaac 4320
atcaatgcaa atgagaccac aaatttgttt tgatcaagtt tgacatattt ggatcattct 4380
ttgccaccac ttggtttgtt tttgcaaacc aaactcaatt tcctatctct aagtcaaaca 4440
cacttgttga aacataaaga gagatatttc acgagaaatt gatcaaagat tcaacaactc 4500 cccctttcc cataaatcca gccttctccc cacaagagat caatgttttg acaataagag 4560
acaaacaaga gtatttagac aaacaaaaac tctaactcta ctattttcaa aattcctaag 4620
tggtagctga tccatttctt gctttggcct tattttctcc ccctttggca tcaagcacca 4680
aaacaggatc aattttggcc ctttaacccc attgcctcac caaaattttc aactaagagt 4740
aaaaaggcaa taagagtaca aagatgaact tgaaattagt tactctttca tcggagtgta 4800
gtggaagtct tgcatggtcc aagtccacct tttccctttc aaacctcctt tgagactaaa 4860
ttaagcagac tcaagcaaac aattagtctc aaagggtcaa gttgtagctc atctccccct 4920
agatgtgtgc atcacttgca aaggacttgt gaggtccggg gwgtgcttgt acaacttgag 4980
caccataaat aaacaacaaa atgcattaag gaacatgatc aaaggcataa acacatgtat 5040
gctataaatc aacccaagtt ccgcgaatct aagacattta gctcactacg caacttgcaa 5100
aaggtctgct catctaaagg cttggtaaag atatcggcta gctggttctc ggagctaaca 5160
tgaaacactt cgatatctcc cttttgctgg tggtgtaacg ccccgaattt tgcagttgaa 5220 tttttttct tttctttact cgccaaattc gggcgttacc ttttcttttt ctttttgccc 5280
tcgctagayc ttgacttttt ccaaagctag cgggattcgg tttggaattc ccgtgtaaag 5340
aaaaactcta aaaaaatact ttatgtggtt tgatgcacca tgccgagcta tgcattcttt 5400
gattgtttga aagtgcaaat gcattcatct aggaagatcg gatttcgaaa gcagggaaat 5460
aatcttttct ttttctttct ctttctttct ctctccctct tcccctttcc ctctctcccg 5520
cgccatgggc tccttggccg gcccagccgc cccttggccg gcccaagccc cctgcgcgcc 5580
ccccctcttg ggccttggca ggcccagccg cccccccacc tccccttttt ttccccaatt 5640
ccctctccct ctctctctct ccctctcatt ttccctctct ctccctaagc cgccgcccct 5700
acccctctgc cctaaccgcc gccgcccct gctcggccgc cgccctcgcc gtcggccgcc 5760
catcgccggt gagccccccc ctttccctct cctccctccc tctcccctct cccctcctcc 5820
ctccccttgg cagcccagcc gcacggccac ccctggccgc gcccctggcc gcccccagcc 5880
cagccgccgg ccgcgccctg gccccagccg cgcctggcca gcctcggccg cgccctggcc 5940
ggccccggcc gcgcccagcc gcgcccccgg cccgccctgg ccgcgccctc ggccgcccct 6000
ggcccctggc cgcccgccag ccgcccccctg cccgctggtt cggccgcgcc cctggccggc 6060
ccagccgctc gcccagccgg gcggttcccc cttttttta ttttttttta ttttatttta 6120
tttactttct gtgatcataa ttaccttatt ttgggtagac taatcatggt tcatgctatg 6180
gaaatgagaa gtttaattta gaatttcgtt gcgctagttg attcattcag ttaattgttt 6240
atcccgtgca atgttaatca acttaaaatg attaggttcc cactagtgca tataacagaa 6300
ttcttttgtt aggaacctat tgaaactaga gtgcataatt taactaatca ttagtgcata 6360
aactttaacc cccctgcgag accctttcc cgtttctttc taaccataac aaatgcaatg 6420

```
tcaaatgtca tacttgatgc atattcgctt tatttgttcc cttgtatggt gtactgttct   6480
tttgtattaa atatgtggat ggatgtatgt atgtttgcgc tcgcatagag aacgatccgg   6540
tcaaagagcc cgaggaattc gcaggagaag cccctgagca gcagtcggtt ggtggaggca   6600
agtgtccttt gacctatctc tgtcctaatc attctttaat tcacctcccg catcacacat   6660
ttatacctaa ggattgacta gctttttgtt atccatgtcc ttatttacct atttgggtcg   6720
gattattact gcttagtttg atgctattgc tcaactttaa tcaatgaaca tgatgtggtt   6780
atctatgata cgctgttttc ccgttctcat ttatgattat acttgtggca tttaagggga   6840
ctcgagcggt ttctcgagtg cctctccgta aggacctgtt caatggatga ccgcccggga   6900
aaacaatgca accatgaggg tggaatgggg tgcccttagc tgaataatta gaggatccgg   6960
ggtgtagttc gcttcgccgt cgtgccgtca atggggctcg                         7000
```

```
<210> SEQ ID NO 9
<211> LENGTH: 10000
<212> TYPE: DNA
<213> ORGANISM: Zea mays

<400> SEQUENCE: 9

atgcagtttg cacttgcatt ggacacgaac tcaggtcctc accagataag atcttgtgag     60
ggtgatggga ttgacaggtt ggaaaaatta agtattgggg gcagaaagca ggagaaagct    120
ttgagaaata ggtgctttgg tggtagagtt gctacaacta cacaatgtat tcttacctca    180
gatgcttgtc ctgaaactct tgtaagtatc cacctcaatt attactctta catgttggtt    240
tactttacgt ttgtcttttc aagggaaatt tactgtattt tttgtgtttt gtgggagttc    300
tatacttctg ttggactggt tattgtaaag atttgttcaa atagggtcat cttataattg    360
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctctttcct ctgacaagca    780
caagagctac gcctggcgag gtggccgcgg ctgaacggga cctcgggtat cagtcacccg    840
agggggacct gaaggatgtc ttcgtcggag gatcctactc cggtggagac aactagatgg    900
actcccgggg ggaccccgtg ctccccgttc tacggggccg aaacctgcct tcccccagaa    960
acccctctgg actccccacg ggtccagact tctaacaaat ccatgcagaa atggctacat   1020
catgaggacg aggactccct catcaaacgc agatgggaac ccagggtcgg gacctagccc   1080
tacggcaagt accaaaccaa gaagggctct gcaactctcc cctagctggg aaggaccctt   1140
caaggtgatg ggaatacgcc gacccggggg tgactgtcta gctatgactg aaggagtacc   1200
tttggagcac ctctgtaagt tctatccata ggagcaagcc tgaggggtcg aatttttctc   1260
cctttttgta gctaggtaac gcatacatgt acgccaaccc ggtgaggtcc gccctcataa   1320
gcccggcatg ttggtctgca cccatacatg acaagttata aagaacagaa ttacccccctc   1380
agatgtgtct ctaagtttta tcctactgct ccatggtctt gccttgcagt tttcagaga    1440
ttattttatc taacccaccc aaacagttcc ctttccatca gacataacga cattcgaatt   1500
```

-continued

```
gaacagccag gcttgcagtt taggacctat ttacgaaagc gggagggccc gacagcctgg   1560
gggtggttct agagaacgga agcccgttcc atggggtggt ctagagcctg tgtggccgct   1620
tagcctggtc ctatacccga aagtctgcac actccaccac tccgtgacgg gtaccctagt   1680
atttggagct ataagtcctg tgggtccggc aacctggggt ccggaactag agaatggaca   1740
cttgtctcct ggggtggtcc ggagcccgtg tagccgctca gcttggttcc gtaccgtggg   1800
cgtgcacgct ccaccactct gcgacgggtg tcctagtacc tagaaccacc atctaggggg   1860
tccagacgca caacttggcc tcccagacta aaccctgcag gtcccgagca tgtatcaaag   1920
gatgactaat gtcagatggc gggtcctgtg ggtgtactac taatgctccc tagccaaagc   1980
tgtgtgcagg ctcaggtccc agtcgaggct gcctcctggg ggccattgcc aactcttcct   2040
taggtatgct ggtttgcagc ctcgacaaat cgagcctaca tcccgggggc caggtaccaa   2100
ggaggaatca gttacaccac acacaacagg gacaagtggt atacaaataa gtgctaatac   2160
tgcttgataa atagtactca aaagtacctt acaaaaagca aaaatattac atccgccttc   2220
aagcggagtt ctagctccat ctctactcta cagatatgaa ctgcctccac accactaggg   2280
tcgcgtgggt agctagctcc gagcggctcg ccagcgaagg cgaccacctc tgcaccgacg   2340
gatcgacagc ggcgacgact acctcggctc caagcggctc gccagcagag gcaaccacct   2400
ctgcaacggg cagcctcacc agcgatggcg accacctctg cgccaggcag cctccccagt   2460
sgtggcgacc acctcagcat gcgcgccatg gtgaagaggt cctcgccttc gtccccctac   2520
gggggtgagg acaagaccat ccaagccttg gagctgggag catggtggaa ggcggtgctt   2580
gcggtctggc tgggaccgcg tagccgaagt tcgcctcctt cacaaggctg gtgatcatcc   2640
ttttcctccg aatgctggag gaagagatgg gcaccaaccc atgtgggagg cgaaaccgcg   2700
gctcagctcg ttccccgcca ccgcgaggct catgaacatc cttgaagcca agaatcggtg   2760
gaagagcgcc gctcccacaa gaccgcgcat ctccagcaga ggaaaaacaa gaccggtagc   2820
accagcccgc tagggaggag aaaaggcaaa aactctctag cggcaagctc atcggagtgg   2880
ataacgccgg cgcaaatcct tccgctgagc gccagcgcat tccatccaag caagtggtat   2940
accatttcga gcactcactc agtttgggtg tgctcgggat tgagagcacc tagagggggg   3000
gtgaataggt gatcctgtaa aaacttgaaa cttaattcgc aaaacttgat taggagttag   3060
cacgaataag ctaagtggct agagaggaga acttgcacaa cacgataacc acaaagagat   3120
caacacagag atggcacagt ggtttatccc gtggttcggc caagtccaac acttgcctac   3180
tccacgttgt ggcgtcccaa tggacgaggg ttgcaatcaa cccctttcaa gcggtccaaa   3240
gacccacttg aataccacgg tgttttgctt tcactttact atatctcgct tgtgaggaat   3300
ctccacaact tggagcctct cgcccttaca ctttgatgtt cacaaagaag cacggagtaa   3360
gggagggatg agcaacgcac acaagacatg aaatcagagt accaacacgc acacaaatca   3420
caacaagagc tcacaacaca acccggcgag ttcactacta aaatggagct ctagttgcta   3480
tcacaaagag tcaaatgcgc agaatcgaag tcttggtgct taggaatgct tagagaatgc   3540
ttggtgcact cctccatgcg cctaggggtc ccttttatag ccccaaggca gctaggagcc   3600
gttgagagca attcaagaag gcaattcttg ccttctgtcg cctggcgcac cggacagttc   3660
ggtgcaccac cggacactgt ccggtgcgga tctctttcct tatttggcga agccgaccgt   3720
tgcagattgc tagccgttgg cacaccggac actgtccggt gcacaccgga caatccgatg   3780
ccccttctg accgttggct ctgccacgcg tcgcgcgcgg attccacggc cgaccgttgg   3840
cccggccgac tgttggctca ccagacagtc cggtgcacca ccggacagtc cggtgaattt   3900
```

-continued tagccgtacg ccgccaacga tttcccgaga gcaacaagtt cgcgtgagtc agcctggtgc 3960
accggacact gtccggtgca ccaccgggca gtccggtgca ccaccggaca gtccggtgca 4020
cccagactgc gcagagtctt cgctactcag ccaagtcttt tccaatttgg tcttttcctg 4080
tttctagcac ttagacacaa tacattagtc ttcaaaacaa tgtactaagt cttagaaaca 4140
tacctttaga cttgatttgc actttgtcca tcaattggca tagattatca tttaagcact 4200
tgtgttggca ctcaatcacc aaaatactta gaaatggccc aagggcacat ttccctttca 4260
atctccccct ttttggtgat ttatgccaac acaacaaaaa gcaacttaaa gaagtgcaac 4320
atcaatgcaa atgagaccac aaatttgttt tgatcaagtt tgacatattt ggatcattct 4380
ttgccaccac ttggtttgtt tttgcaaacc aaactcaatt tcctatctct aagtcaaaca 4440
cacttgttga aacataaaga gagatatttc acgagaaatt gatcaaagat tcaacaactc 4500 cccctttcc cataaatcca gccttctccc cacaagagat caatgttttg acaataagag 4560
acaaacaaga gtatttagac aaacaaaaac tctaactcta ctattttcaa aattcctaag 4620
tggtagctga tccatttctt gctttggcct tattttctcc ccctttggca tcaagcacca 4680
aaacaggatc aattttggcc ctttaacccc attgcctcac caaaattttc aactaagagt 4740
aaaaaggcaa taagagtaca aagatgaact tgaaattagt tactctttca tcggagtgta 4800
gtggaagtct tgcatggtcc aagtccacct tttccctttc aaacctcctt tgagactaaa 4860
ttaagcagac tcaagcaaac aattagtctc aaagggtcaa gttgtagctc atctccccct 4920
agatgtgtgc atcacttgca aaggacttgt gaggtccggg gwgtgcttgt acaacttgag 4980
caccataaat aaacaacaaa atgcattaag gaacatgatc aaaggcataa acacatgtat 5040
gctataaatc aacccaagtt ccgcgaatct aagacattta gctcactacg caacttgcaa 5100
aaggtctgct catctaaagg cttggtaaag atatcggcta gctggttctc ggagctaaca 5160
tgaaacactt cgatatctcc cttttgctgg tggtgtaacg ccccgaattt tgcagttgaa 5220
ttttttttct tttctttact cgccaaattc gggcgttacc ttttcttttt ctttttgccc 5280
tcgctagayc ttgacttttt ccaaagctag cgggattcgg tttggaattc ccgtgtaaag 5340
aaaaactcta aaaaaatact ttatgtggtt tgatgcacca tgccgagcta tgcattcttt 5400
gattgtttga aagtgcaaat gcattcatct aggaagatcg gatttcgaaa gcagggaaat 5460
aatcttttct ttttctttct ctttctttct ctctccctct tccccttcc ctctctcccg 5520 cgccatgggc tccttggccg gcccagccgc cccttggccg gcccaagccc cctgcgcgcc 5580
ccccctcttg ggccttggca ggcccagccg cccccccacc tcccctttt ttccccaatt 5640 ccctctccct ctctctctct ccctctcatt ttccctctct ctccctaagc cgccgcccct 5700
acccctctgc cctaaccgcc gccgcccct gctcggccgc cgccctcgcc gtcggccgcc 5760
catcgccggt gagcccccc ctttccctct cctccctccc tctcccctct cccctcctcc 5820
ctccccttgg cagcccagcc gcacggccac ccctggccgc gcccctggcc gcccccagcc 5880
cagccgccgg ccgcgccctg gccccagccg cgcctggcca gcctcggccg cgccctggcc 5940
ggccccggcc gcgcccagcc gcgcccccgg cccgccctgg ccgcgccctc ggccgcccct 6000
ggcccctggc cgcccgccag ccgccccctg cccgctggtt cggccgcgcc cctggccggc 6060
ccagccgctc gcccagccgg gcggttcccc cttttttta tttttttta ttttatttta 6120 tttactttct gtgatcataa ttaccttatt ttgggtagac taatcatggt tcatgctatg 6180
gaaatgagaa gtttaattta gaatttcgtt gcgctagttg attcattcag ttaattgttt 6240

```
atcccgtgca atgttaatca acttaaaatg attaggttcc cactagtgca tataacagaa   6300
ttcttttgtt aggaacctat tgaaactaga gtgcataatt taactaatca ttagtgcata   6360
aactttaacc cccctgcgag accctttcc  cgtttctttc taaccataac aaatgcaatg   6420
tcaaatgtca tacttgatgc atattcgctt tatttgttcc cttgtatggt gtactgttct   6480
tttgtattaa atatgtggat ggatgtatgt atgtttgcgc tcgcatagag aacgatccgg   6540
tcaaagagcc cgaggaattc gcaggagaag cccctgagca gcagtcggtt ggtggaggca   6600
agtgtccttt gacctatctc tgtcctaatc attctttaat tcacctcccg catcacacat   6660
ttatacctaa ggattgacta gctttttgtt atccatgtcc ttatttacct atttgggtcg   6720
gattattact gcttagtttg atgctattgc tcaactttaa tcaatgaaca tgatgtggtt   6780
atctatgata cgctgttttc ccgttctcat ttatgattat acttgtggca tttaaggggga  6840
ctcgagcggt ttctcgagtg cctctccgta aggacctgtt caatggatga ccgcccggga   6900
aaacaatgca accatgaggg tggaatgggg tgcccttagc tgaataatta gaggatccgg   6960
ggtgtagttc gcttcgccgt cgtgccgtca atggggctcg gtgtatgcgg ctcgctctgc   7020
caaggttgat ttgtcccttg gggaggagtg cggtacattt aggaaaccta acgggtggct   7080
acagccccgg ggaatctttg taaaggcttc gtagtgaatc cttggccatt cacctcggga   7140
gtgaataagg gtcttgcaag cccgggccag agagggaatc acggcttgtg ggtaaagtgc   7200
acaacctctg cagagtgtta tgaaactgat atatcagccg tgctcgcggt tatgagcggc   7260
caagggagct ccagagatta gtgatacttg atcagagata ctttggtaca ggtgacaatg   7320
agattgatgg ttctgattac gattatggta ttggtaagtg gtattctttc cgtttggaaa   7380
ggatacattg ggctaataac ttgggttaat gttaaaacct ggctttctac tagtaagtaa   7440
taacctgacc aactaaaagc aactgcttga cttatcccca cataaagcta gtccactaca   7500
gccaaacagg atacttgctg agtatgttga tgtgtactca cccttgctct acacaccaaa   7560
ccccccccca ggttgtcagc attgcaacca ctgctcaggc gaagatgaag ctgtggaagg   7620
agacttccgg gagttccaag actacgacga gttctaggtg tgggttagcg gcaaccccc    7680
agtcggctgc ctgtgaaggc cgtgttatct acgtttcttt tccgcacttt gatttattgt   7740
aagaactata tggacgtctc agacgtatga tgtaatcgac tatttccctt attaatacta   7800
ttttgagcac tgtgtgatga tgtccatatt atgtaactgc tgtgtatgtg aataactgat   7860
cctggcacgt acatggttcg cattcggttt gccttctaaa accgggtgtg tcataagtgg   7920
tatcaaagcc gtgctgactg taggaccgct aacctagagt agaatggtcg ttctaaggat   7980
tatagacctc tgtccctacc ttgactttga tatctcttca aaagttggtc ctaccgacca   8040
aacctatgtt ctactatata ttatacttg  ctaaaaaatt gtgtttcatt ctgatccttc   8100
atttacttat gattcattat ttgctggtca tattaattct gttctcaccc ttttgcttgc   8160
gatgtctttt gtagatggct cgacttagac acactgcacg aaagtccgtc atccccttct   8220
taccctcccg ccttgctgag cgtccgcttc gccgtcccgt ggccggacag tccagccact   8280
tggagagact acaccaccgc ctgcgtgagg agcaggaacg tcgacgacag gagcaacagg   8340
gctcttcttt ctcgctccac caggagatag agtctgtgag gagctgctct cctgtgcttc   8400
ctctggaggt gccccctgca ccaccactgg gcgccccagc ttctggagta gctgctggag   8460
gagacccaga cgacggagat ggcgacgaca gctcgagcca cgacaccgac ttctctgcta   8520
accctgagcc ggaaggatgg gttgctcgac ccatcactcg cgacgctgct cgcgggtgtc   8580
acttccacga tgcgctcgac accctgctac gtcgggcatt tgaccggcat acttggtccg   8640
```

tcgagtatcg ctgtgtggtc taccagcata gtcgcggggt ctacccggac cgctgggaga 8700
cgacttgctt ggtgcgctgc ccggaggaca gtctccaggg tgcagaggcc tgctcagagc 8760
actattctat ctctgaacgg gactcagctg aggcagccat gcaagatgct gcacggcgtg 8820
cgctttcgca ctactgctcg gttttcggtg gggcagctga cggtcttgac ctgaagtatt 8880
acccccgccg tccatctggc agcacaggag gcgtgattgt ctcacctgtc ggtgagggca 8940
atcctaggtt gagcagcaca gtcaacctag ccgccgtgct aaacacggag ctggaccatg 9000
cattagacga gctgagtagg gctcgtgctg agatcgccca gctgcgggct gagcgcgcgg 9060
aacgtcgtca tctggatggt ggttccccccg ctcccgtcgg gactcagcac ccgtaccgct 9120
cacctcagcg tggacaccag ccttatggca atcccgactg caagaccaag ataaatctag 9180
aaccatagat cgctagagtt ggatcttgta attaatacga aatatatgca tagaagcttc 9240
agtcttagcg ttaatctcgg tcttagttag tcttagttag acagggtagt ttgctatatc 9300
ctgtgcattt atgtttgtca tgatgaactt tgtttggttt ggatctttgt aatgattgtc 9360
accagagtgt gggtatcccc tgcattttgg ttcacctatt atgttaataa agttagttat 9420
atagttggga aacctttat tccactttcc tcttgatctg agaagttgtg tggtctgtgt 9480
tggagatcag tgaagatgct cacctgctca gtgctgttga agaattctat actcttttct 9540
tatgctgcaa gatttgccag atcagttctg atgtgtggtt gcattctgca gatgtcagag 9600
aacaggcgca gaggaggaag gcgtgctcag caggagcaag ccggtcaaca agatgaggcg 9660
ccccagcagc agcagctgcc accccccgccc ccgatgtcga tcgagcagat gtttctgatg 9720
cagactcagg cagttcaggc catcggtcag actctggccg ccattcagca gcagcagcag 9780
cagcaacagc agcaagcacc accccagcct cagatgcctc agatgcccag agacaagcgt 9840
gctgaattca tgagaggtca tcccccaacg ttcgctcact cttctgaccc catggatgct 9900
gaagattggc tgcgcactgt ggagcgggag ttgcataccg ctcagtgtga tgacagggag 9960
aaagtcttgt atggtccccg tctgttgaga ggagcagccc 10000

<210> SEQ ID NO 10
<211> LENGTH: 2401
<212> TYPE: DNA
<213> ORGANISM: Zea mays

<400> SEQUENCE: 10
ggcagaaagc aggagaaagc tttgagaaat aggtgctttg gtggtagagt tgctacaact 60
acacaatgta ttcttacctc agatgcttgt cctgaaactc ttgtaagtat ccacctcaat 120
tattactctt acatgttggt ttactttacg tttgtctttt caagggaaat ttactgtatt 180
ttttgtgttt tgtgggagtt ctatacttct gttggactgg ttattgtaaa gatttgttca 240
aatagggtca tcttataatt gtttgaaatc tgggaactgt ggtttcactg cgttcaggaa 300
aaagtgaatt cttggttact gcatgaataa cttatgaaaa tagaccttag agttgctgca 360
tgattatcac aaatcattgc tacgatatct tataatagtt ctttcgacct cgcattacat 420
atataactgc aactcgtagt tgcgttcaaa aaaaatgcaa ctcttagaac gctcaccagt 480
gtaatctttc ctgaattgtt atttaatggc atgtatgcac tacttgtata cttatctagg 540
attaagtaat ctaactctag gccccatatt tgcagcattc tcaaacacag tcctctagga 600
aaaattatgc tgatgcaaac cgtgtatctg ctatcatttt gggcggaggc actggatctc 660
agctctttcc tctgacaagc acaagagcta cgcctggcga ggtggccgcg gctgaacggg 720

```
acctcgggta tcagtcaccc gagggggacc tgaaggatgt cttcgtcgga ggatcctact    780
ccggtggaga caactagatg gactcccggg gggaccccgt gctccccgtt ctacggggcc    840
gaaacctgcc ttcccccaga aacccctctg gactccccac gggtccagac ttctaacaaa    900
tccatgcaga aatggctaca tcatgaggac gaggactccc tcatcaaacg cagatgggaa    960
cccagggtcg ggacctagcc ctacggcaag taccaaacca agaagggctc tgcaactctc   1020
ccctagctgg gaaggaccct tcaaggtgat gggaatacgc cgacccgggg gtgactgtct   1080
agctatgact gaaggagtac ctttggagca cctctgtaag ttctatccat aggagcaagc   1140
ctgaggggtc gaatttttct cccttttttgt agctaggtaa cgcatacatg tacgccaacc  1200
cggtgaggtc cgccctcata agcccggcat gttggtctgc acccatacat gacaagttat   1260
aaagaacaga attacccct cagatgtgtc tctaagtttt atcctactgc tccatggtct    1320
tgccttgcag tttttcagag attattttat ctaacccacc caaacagttc cctttccatc   1380
agacataacg acattcgaat tgaacagcca ggcttgcagt ttaggaccta tttacgaaag   1440
cgggagggcc cgacagcctg gggtggttc tagagaacgg aagcccgttc catggggtgg    1500
tctagagcct gtgtggccgc ttagcctggt cctatacccg aaagtctgca cactccacca   1560
ctccgtgacg ggtaccctag tatttggagc tataagtcct gtgggtccgg caacctgggg   1620
tccggaacta gagaatggac acttgtctcc tggggtggtc cggagcccgt gtagccgctc   1680
agcttggttc cgtaccgtgg gcgtgcacgc tccaccactc tgcgacgggt gtcctagtac   1740
ctagaaccac catctagggg gtccagacgc acaacttggc ctcccagact aaaccctgca   1800
ggtcccgagc atgtatcaaa ggatgactaa tgtcagatgg cgggtcctgt gggtgtacta   1860
ctaatgctcc ctagccaaag ctgtgtgcag gctcaggtcc cagtcgaggc tgcctcctgg   1920
gggccattgc caactcttcc ttaggtatgc tggtttgcag cctcgacaaa tcgagcctac   1980
atcccggggg ccaggtacca aggaggaatc agttacacca cacacaacag ggacaagtgg   2040
tatacaaata agtgctaata ctgcttgata aatagtactc aaaagtacct tacaaaaagc   2100
aaaaatatta catccgcctt caagcggagt tctagctcca tctctactct acagatatga   2160
actgcctcca caccactagg gtcgcgtggg tagctagctc cgagcggctc gccagcgaag   2220
gcgaccacct ctgcaccgac ggatcgacag cggcgacgac tacctcggct ccaagcggct   2280
cgccagcaga ggcaaccacc tctgcaacgg gcagcctcac cagcgatggc gaccacctct   2340
gcgccaggca gcctccccag tsgtggcgac cacctcagca tgcgcgccat ggtgaagagg   2400
t                                                                   2401
```

<210> SEQ ID NO 11
<211> LENGTH: 1901
<212> TYPE: DNA
<213> ORGANISM: Zea mays

<400> SEQUENCE: 11

```
ggcagaaagc aggagaaagc tttgagaaat aggtgctttg gtggtagagt tgctacaact     60
acacaatgta ttcttacctc agatgcttgt cctgaaactc ttgtaagtat ccacctcaat    120
tattactctt acatgttggt ttactttacg tttgtctttt caagggaaat ttactgtatt    180
ttttgtgttt tgtgggagtt ctatacttct gttggactgg ttattgtaaa gatttgttca    240
aatagggtca tcttataatt gtttgaaatc tgggaactgt ggtttcactg cgttcaggaa    300
aaagtgaatt cttggttact gcatgaataa cttatgaaaa tagaccttag agttgctgca    360
tgattatcac aaatcattgc tacgatatct tataatagtt ctttcgacct cgcattacat    420
```

atataactgc aactcgtagt tgcgttcaaa aaaaatgcaa ctcttagaac gctcaccagt 480
gtaatctttc ctgaattgtt atttaatggc atgtatgcac tacttgtata cttatctagg 540
attaagtaat ctaactctag gccccatatt tgcagcattc tcaaacacag tcctctagga 600
aaaattatgc tgatgcaaac cgtgtatctg ctatcatttt gggcggaggc actggatctc 660
agctctttcc tctgacaagc acaagagcta cgcctggcga ggtggccgcg gctgaacggg 720
acctcgggta tcagtcaccc gagggggacc tgaaggatgt cttcgtcgga ggatcctact 780
ccggtggaga caactagatg gactcccggg gggaccccgt gctccccgtt ctacggggcc 840
gaaacctgcc ttcccccaga aacccctctg gactccccac gggtccagac ttctaacaaa 900
tccatgcaga aatggctaca tcatgaggac gaggactccc tcatcaaacg cagatgggaa 960
cccagggtcg ggacctagcc ctacggcaag taccaaacca agaagggctc tgcaactctc 1020
ccctagctgg gaaggaccct tcaaggtgat gggaatacgc cgacccgggg gtgactgtct 1080
agctatgact gaaggagtac ctttggagca cctctgtaag ttctatccat aggagcaagc 1140
ctgaggggtc gaatttttct cccttttgt agctaggtaa cgcatacatg tacgccaacc 1200
cggtgaggtc cgccctcata agcccggcat gttggtctgc acccatacat gacaagttat 1260
aaagaacaga attacccct cagatgtgtc tctaagtttt atcctactgc tccatggtct 1320
tgccttgcag tttttcagag attattttat ctaacccacc caaacagttc cctttccatc 1380
agacataacg acattcgaat tgaacagcca ggcttgcagt ttaggaccta tttacgaaag 1440
cgggagggcc cgacagcctg ggggtggttc tagagaacgg aagcccgttc catggggtgg 1500
tctagagcct gtgtggccgc ttagcctggt cctatacccg aaagtctgca cactccacca 1560
ctccgtgacg ggtaccctag tatttggagc tataagtcct gtgggtccgg caacctgggg 1620
tccggaacta gagaatggac acttgtctcc tggggtggtc cggagcccgt gtagccgctc 1680
agcttggttc cgtaccgtgg gcgtgcacgc tccaccactc tgcgacgggt gtcctagtac 1740
ctagaaccac catctagggg gtccagacgc acaacttggc ctcccagact aaaccctgca 1800
ggtcccgagc atgtatcaaa ggatgactaa tgtcagatgg cgggtcctgt gggtgtacta 1860
ctaatgctcc ctagccaaag ctgtgtgcag gctcaggtcc c 1901

<210> SEQ ID NO 12
<211> LENGTH: 1401
<212> TYPE: DNA
<213> ORGANISM: Zea mays

<400> SEQUENCE: 12
ggcagaaagc aggagaaagc tttgagaaat aggtgctttg gtggtagagt tgctacaact 60
acacaatgta ttcttacctc agatgcttgt cctgaaactc ttgtaagtat ccacctcaat 120
tattactctt acatgttggt ttactttacg tttgtctttt caagggaaat ttactgtatt 180
ttttgtgttt tgtgggagtt ctatacttct gttggactgg ttattgtaaa gatttgttca 240
aatagggtca tcttataatt gtttgaaatc tgggaactgt ggtttcactg cgttcaggaa 300
aaagtgaatt cttggttact gcatgaataa cttatgaaaa tagaccttag agttgctgca 360
tgattatcac aaatcattgc tacgatatct tataatagtt ctttcgacct cgcattacat 420
atataactgc aactcgtagt tgcgttcaaa aaaaatgcaa ctcttagaac gctcaccagt 480
gtaatctttc ctgaattgtt atttaatggc atgtatgcac tacttgtata cttatctagg 540
attaagtaat ctaactctag gccccatatt tgcagcattc tcaaacacag tcctctagga 600

```
aaaattatgc tgatgcaaac cgtgtatctg ctatcatttt gggcggaggc actggatctc    660
agctctttcc tctgacaagc acaagagcta cgcctggcga ggtggccgcg gctgaacggg    720
acctcgggta tcagtcaccc gagggggacc tgaaggatgt cttcgtcgga ggatcctact    780
ccggtggaga caactagatg gactcccggg gggaccccgt gctccccgtt ctacggggcc    840
gaaacctgcc ttcccccaga aacccctctg gactccccac gggtccagac ttctaacaaa    900
tccatgcaga aatggctaca tcatgaggac gaggactccc tcatcaaacg cagatgggaa    960
cccagggtcg ggacctagcc ctacggcaag taccaaacca agaagggctc tgcaactctc   1020
ccctagctgg gaaggaccct tcaaggtgat gggaatacgc cgacccgggg gtgactgtct   1080
agctatgact gaaggagtac ctttggagca cctctgtaag ttctatccat aggagcaagc   1140
ctgaggggtc gaatttttct cccttttttgt agctaggtaa cgcatacatg tacgccaacc   1200
cggtgaggtc cgccctcata agcccggcat gttggtctgc acccatacat gacaagttat   1260
aaagaacaga attacccccct cagatgtgtc tctaagtttt atcctactgc tccatggtct   1320
tgccttgcag tttttcagag attattttat ctaacccacc caaacagttc cctttccatc   1380
agacataacg acattcgaat t                                             1401
```

<210> SEQ ID NO 13
<211> LENGTH: 1301
<212> TYPE: DNA
<213> ORGANISM: Zea mays

<400> SEQUENCE: 13

```
ttgtaagtat ccacctcaat tattactctt acatgttggt ttactttacg tttgtctttt     60
caagggaaat ttactgtatt ttttgtgttt tgtgggagtt ctatacttct gttggactgg    120
ttattgtaaa gatttgttca aatagggtca tcttataatt gtttgaaatc tgggaactgt    180
ggtttcactg cgttcaggaa aaagtgaatt cttggttact gcatgaataa cttatgaaaa    240
tagaccttag agttgctgca tgattatcac aaatcattgc tacgatatct tataatagtt    300
ctttcgacct cgcattacat atataactgc aactcgtagt tgcgttcaaa aaaaatgcaa    360
ctcttagaac gctcaccagt gtaatctttc ctgaattgtt atttaatggc atgtatgcac    420
tacttgtata cttatctagg attaagtaat ctaactctag gccccatatt tgcagcattc    480
tcaaacacag tcctctagga aaaattatgc tgatgcaaac cgtgtatctg ctatcatttt    540
gggcggaggc actggatctc agctctttcc tctgacaagc acaagagcta cgcctggcga    600
ggtggccgcg gctgaacggg acctcgggta tcagtcaccc gagggggacc tgaaggatgt    660
cttcgtcgga ggatcctact ccggtggaga caactagatg gactcccggg gggaccccgt    720
gctccccgtt ctacggggcc gaaacctgcc ttcccccaga aacccctctg gactccccac    780
gggtccagac ttctaacaaa tccatgcaga aatggctaca tcatgaggac gaggactccc    840
tcatcaaacg cagatgggaa cccagggtcg ggacctagcc ctacggcaag taccaaacca    900
agaagggctc tgcaactctc ccctagctgg gaaggaccct tcaaggtgat gggaatacgc    960
cgacccgggg gtgactgtct agctatgact gaaggagtac ctttggagca cctctgtaag   1020
ttctatccat aggagcaagc ctgaggggtc gaatttttct cccttttttgt agctaggtaa   1080
cgcatacatg tacgccaacc cggtgaggtc cgccctcata agcccggcat gttggtctgc   1140
acccatacat gacaagttat aaagaacaga attacccccct cagatgtgtc tctaagtttt   1200
atcctactgc tccatggtct tgccttgcag tttttcagag attattttat ctaacccacc   1260
caaacagttc cctttccatc agacataacg acattcgaat t                       1301
```

<210> SEQ ID NO 14
<211> LENGTH: 901
<212> TYPE: DNA
<213> ORGANISM: Zea mays

<400> SEQUENCE: 14
ctatacttct gttggactgg ttattgtaaa gatttgttca aatagggtca tcttataatt 60
gtttgaaatc tgggaactgt ggtttcactg cgttcaggaa aaagtgaatt cttggttact 120
gcatgaataa cttatgaaaa tagaccttag agttgctgca tgattatcac aaatcattgc 180
tacgatatct tataatagtt ctttcgacct cgcattacat atataactgc aactcgtagt 240
tgcgttcaaa aaaaatgcaa ctcttagaac gctcaccagt gtaatctttc ctgaattgtt 300
atttaatggc atgtatgcac tacttgtata cttatctagg attaagtaat ctaactctag 360
gccccatatt tgcagcattc tcaaacacag tcctctagga aaaattatgc tgatgcaaac 420
cgtgtatctg ctatcatttt gggcggaggc actggatctc agctctttcc tctgacaagc 480
acaagagcta cgcctggcga ggtggccgcg gctgaacggg acctcgggta tcagtcaccc 540
gagggggacc tgaaggatgt cttcgtcgga ggatcctact ccggtggaga caactagatg 600
gactcccggg gggaccccgt gctccccgtt ctacggggcc gaaacctgcc ttcccccaga 660
aacccctctg gactccccac gggtccagac ttctaacaaa tccatgcaga aatggctaca 720
tcatgaggac gaggactccc tcatcaaacg cagatgggaa cccagggtcg ggacctagcc 780
ctacggcaag taccaaacca agaagggctc tgcaactctc ccctagctgg gaaggaccct 840
tcaaggtgat gggaatacgc cgacccgggg gtgactgtct agctatgact gaaggagtac 900
c 901

<210> SEQ ID NO 15
<211> LENGTH: 801
<212> TYPE: DNA
<213> ORGANISM: Zea mays

<400> SEQUENCE: 15
aaagtgaatt cttggttact gcatgaataa cttatgaaaa tagaccttag agttgctgca 60
tgattatcac aaatcattgc tacgatatct tataatagtt ctttcgacct cgcattacat 120
atataactgc aactcgtagt tgcgttcaaa aaaaatgcaa ctcttagaac gctcaccagt 180
gtaatctttc ctgaattgtt atttaatggc atgtatgcac tacttgtata cttatctagg 240
attaagtaat ctaactctag gccccatatt tgcagcattc tcaaacacag tcctctagga 300
aaaattatgc tgatgcaaac cgtgtatctg ctatcatttt gggcggaggc actggatctc 360
agctctttcc tctgacaagc acaagagcta cgcctggcga ggtggccgcg gctgaacggg 420
acctcgggta tcagtcaccc gagggggacc tgaaggatgt cttcgtcgga ggatcctact 480
ccggtggaga caactagatg gactcccggg gggaccccgt gctccccgtt ctacggggcc 540
gaaacctgcc ttcccccaga aacccctctg gactccccac gggtccagac ttctaacaaa 600
tccatgcaga aatggctaca tcatgaggac gaggactccc tcatcaaacg cagatgggaa 660
cccagggtcg ggacctagcc ctacggcaag taccaaacca agaagggctc tgcaactctc 720
ccctagctgg gaaggaccct tcaaggtgat gggaatacgc cgacccgggg gtgactgtct 780
agctatgact gaaggagtac c 801

<210> SEQ ID NO 16

<211> LENGTH: 641
<212> TYPE: DNA
<213> ORGANISM: Zea mays

<400> SEQUENCE: 16

```
ctttcgacct cgcattacat atataactgc aactcgtagt tgcgttcaaa aaaaatgcaa     60
ctcttagaac gctcaccagt gtaatctttc ctgaattgtt atttaatggc atgtatgcac    120
tacttgtata cttatctagg attaagtaat ctaactctag gccccatatt tgcagcattc    180
tcaaacacag tcctctagga aaaattatgc tgatgcaaac cgtgtatctg ctatcatttt    240
gggcggaggc actggatctc agctctttcc tctgacaagc acaagagcta cgcctggcga    300
ggtggccgcg gctgaacggg acctcgggta tcagtcaccc gagggggacc tgaaggatgt    360
cttcgtcgga ggatcctact ccggtggaga caactagatg gactcccggg gggaccccgt    420
gctccccgtt ctacggggcc gaaacctgcc ttcccccaga aacccctctg gactccccac    480
gggtccagac ttctaacaaa tccatgcaga aatggctaca tcatgaggac gaggactccc    540
tcatcaaacg cagatgggaa cccagggtcg ggacctagcc ctacggcaag taccaaacca    600
agaagggctc tgcaactctc ccctagctgg gaaggaccct t                        641
```

<210> SEQ ID NO 17
<211> LENGTH: 765
<212> TYPE: DNA
<213> ORGANISM: Zea mays

<400> SEQUENCE: 17

```
atgcagtttg cacttgcatt ggacacgaac tcaggtcctc accagataag atcttgtgag     60
ggtgatggga ttgacaggtt ggaaaaatta agtattgggg gcagaaagca ggagaaagct    120
ttgagaaata ggtgctttgg tggtagagtt gctacaacta cacaatgtat tcttacctca    180
gatgcttgtc ctgaaactct tgtaagtatc cacctcaatt attactctta catgttggtt    240
tactttacgt ttgtcttttc aagggaaatt tactgtattt tttgtgtttt gtgggagttc    300
tatacttctg ttggactggt tattgtaaag atttgttcaa atagggtcat cttataattg    360
tttgaaatct gggaactgtg gtttcactgc gttcaggaaa aagtgaattc ttggttactg    420
catgaataac ttatgaaaat agaccttaga gttgctgcat gattatcaca aatcattgct    480
acgatatctt ataatagttc tttcgacctc gcattacata tataactgca actcgtagtt    540
gcgttcaaaa aaaatgcaac tcttagaacg ctcaccagtg taatctttcc tgaattgtta    600
tttaatggca tgtatgcact acttgtatac ttatctagga ttaagtaatc taactctagg    660
ccccatattt gcagcattct caaacacagt cctctaggaa aaattatgct gatgcaaacc    720
gtgtatctgc tatcattttg ggcggaggca ctggatctca gctct                    765
```

<210> SEQ ID NO 18
<211> LENGTH: 666
<212> TYPE: DNA
<213> ORGANISM: Zea mays

<400> SEQUENCE: 18

```
ggcagaaagc aggagaaagc tttgagaaat aggtgctttg gtggtagagt tgctacaact     60
acacaatgta ttcttacctc agatgcttgt cctgaaactc ttgtaagtat ccacctcaat    120
tattactctt acatgttggt ttactttacg tttgtctttt caagggaaat ttactgtatt    180
ttttgtgttt tgtgggagtt ctatacttct gttggactgg ttattgtaaa gatttgttca    240
aatagggtca tcttataatt gtttgaaatc tgggaactgt ggtttcactg cgttcaggaa    300
```

```
aaagtgaatt cttggttact gcatgaataa cttatgaaaa tagaccttag agttgctgca    360

tgattatcac aaatcattgc tacgatatct tataatagtt ctttcgacct cgcattacat    420

atataactgc aactcgtagt tgcgttcaaa aaaaatgcaa ctcttagaac gctcaccagt    480

gtaatctttc ctgaattgtt atttaatggc atgtatgcac tacttgtata cttatctagg    540

attaagtaat ctaactctag gccccatatt tgcagcattc tcaaacacag tcctctagga    600

aaaattatgc tgatgcaaac cgtgtatctg ctatcatttt gggcggaggc actggatctc    660

agctct                                                               666

<210> SEQ ID NO 19
<211> LENGTH: 566
<212> TYPE: DNA
<213> ORGANISM: Zea mays

<400> SEQUENCE: 19

ttgtaagtat ccacctcaat tattactctt acatgttggt ttactttacg tttgtctttt     60

caagggaaat ttactgtatt ttttgtgttt tgtgggagtt ctatacttct gttggactgg    120

ttattgtaaa gatttgttca aatagggtca tcttataatt gtttgaaatc tgggaactgt    180

ggtttcactg cgttcaggaa aaagtgaatt cttggttact gcatgaataa cttatgaaaa    240

tagaccttag agttgctgca tgattatcac aaatcattgc tacgatatct tataatagtt    300

ctttcgacct cgcattacat atataactgc aactcgtagt tgcgttcaaa aaaaatgcaa    360

ctcttagaac gctcaccagt gtaatctttc ctgaattgtt atttaatggc atgtatgcac    420

tacttgtata cttatctagg attaagtaat ctaactctag gccccatatt tgcagcattc    480

tcaaacacag tcctctagga aaaattatgc tgatgcaaac cgtgtatctg ctatcatttt    540

gggcggaggc actggatctc agctct                                         566

<210> SEQ ID NO 20
<211> LENGTH: 466
<212> TYPE: DNA
<213> ORGANISM: Zea mays

<400> SEQUENCE: 20

ctatacttct gttggactgg ttattgtaaa gatttgttca aatagggtca tcttataatt     60

gtttgaaatc tgggaactgt ggtttcactg cgttcaggaa aaagtgaatt cttggttact    120

gcatgaataa cttatgaaaa tagaccttag agttgctgca tgattatcac aaatcattgc    180

tacgatatct tataatagtt ctttcgacct cgcattacat atataactgc aactcgtagt    240

tgcgttcaaa aaaaatgcaa ctcttagaac gctcaccagt gtaatctttc ctgaattgtt    300

atttaatggc atgtatgcac tacttgtata cttatctagg attaagtaat ctaactctag    360

gccccatatt tgcagcattc tcaaacacag tcctctagga aaaattatgc tgatgcaaac    420

cgtgtatctg ctatcatttt gggcggaggc actggatctc agctct                   466

<210> SEQ ID NO 21
<211> LENGTH: 366
<212> TYPE: DNA
<213> ORGANISM: Zea mays

<400> SEQUENCE: 21

aaagtgaatt cttggttact gcatgaataa cttatgaaaa tagaccttag agttgctgca     60

tgattatcac aaatcattgc tacgatatct tataatagtt ctttcgacct cgcattacat    120
```

atataactgc aactcgtagt tgcgttcaaa aaaaatgcaa ctcttagaac gctcaccagt 180
gtaatctttc ctgaattgtt atttaatggc atgtatgcac tacttgtata cttatctagg 240
attaagtaat ctaactctag gccccatatt tgcagcattc tcaaacacag tcctctagga 300
aaaattatgc tgatgcaaac cgtgtatctg ctatcatttt gggcggaggc actggatctc 360
agctct 366

<210> SEQ ID NO 22
<211> LENGTH: 266
<212> TYPE: DNA
<213> ORGANISM: Zea mays

<400> SEQUENCE: 22
ctttcgacct cgcattacat atataactgc aactcgtagt tgcgttcaaa aaaaatgcaa 60
ctcttagaac gctcaccagt gtaatctttc ctgaattgtt atttaatggc atgtatgcac 120
tacttgtata cttatctagg attaagtaat ctaactctag gccccatatt tgcagcattc 180
tcaaacacag tcctctagga aaaattatgc tgatgcaaac cgtgtatctg ctatcatttt 240
gggcggaggc actggatctc agctct 266

<210> SEQ ID NO 23
<211> LENGTH: 166
<212> TYPE: DNA
<213> ORGANISM: Zea mays

<400> SEQUENCE: 23
atttaatggc atgtatgcac tacttgtata cttatctagg attaagtaat ctaactctag 60
gccccatatt tgcagcattc tcaaacacag tcctctagga aaaattatgc tgatgcaaac 120
cgtgtatctg ctatcatttt gggcggaggc actggatctc agctct 166

<210> SEQ ID NO 24
<211> LENGTH: 151
<212> TYPE: DNA
<213> ORGANISM: Zea mays

<400> SEQUENCE: 24
atttaatggc atgtatgcac tacttgtata cttatctagg attaagtaat ctaactctag 60
gccccatatt tgcagcattc tcaaacacag tcctctagga aaaattatgc tgatgcaaac 120
cgtgtatctg ctatcatttt gggcggaggc a 151

<210> SEQ ID NO 25
<211> LENGTH: 235
<212> TYPE: DNA
<213> ORGANISM: Zea mays

<400> SEQUENCE: 25
ttcctctgac aagcacaaga gctacgcctg gcgaggtggc cgcggctgaa cgggacctcg 60
ggtatcagtc acccgagggg gacctgaagg atgtcttcgt cggaggatcc tactccggtg 120
gagacaacta gatggactcc cggggggacc ccgtgctccc cgttctacgg ggccgaaacc 180
tgccttcccc cagaaacccc tctggactcc ccacgggtcc agacttctaa caaat 235

<210> SEQ ID NO 26
<211> LENGTH: 1235
<212> TYPE: DNA
<213> ORGANISM: Zea mays

<400> SEQUENCE: 26

```
ttcctctgac aagcacaaga gctacgcctg gcgaggtggc cgcggctgaa cgggacctcg      60

ggtatcagtc acccgagggg gacctgaagg atgtcttcgt cggaggatcc tactccggtg     120

gagacaacta gatggactcc cggggggacc ccgtgctccc cgttctacgg ggccgaaacc     180

tgccttcccc cagaaacccc tctggactcc ccacgggtcc agacttctaa caaatccatg     240

cagaaatggc tacatcatga ggacgaggac tccctcatca aacgcagatg ggaacccagg     300

gtcgggacct agccctacgg caagtaccaa accaagaagg gctctgcaac tctcccctag     360

ctgggaagga cccttcaagg tgatgggaat acgccgaccc gggggtgact gtctagctat     420

gactgaagga gtacctttgg agcacctctg taagttctat ccataggagc aagcctgagg     480

ggtcgaattt ttctcccttt ttgtagctag gtaacgcata catgtacgcc aacccggtga     540

ggtccgccct cataagcccg gcatgttggt ctgcacccat acatgacaag ttataaagaa     600

cagaattacc ccctcagatg tgtctctaag ttttatccta ctgctccatg gtcttgcctt     660

gcagtttttc agagattatt ttatctaacc cacccaaaca gttccctttc catcagacat     720

aacgacattc gaattgaaca gccaggcttg cagtttagga cctatttacg aaagcgggag     780

ggcccgacag cctgggggtg gttctagaga acggaagccc gttccatggg gtggtctaga     840

gcctgtgtgg ccgcttagcc tggtcctata cccgaaagtc tgcacactcc accactccgt     900

gacgggtacc ctagtatttg gagctataag tcctgtgggt ccggcaacct ggggtccgga     960

actagagaat ggacacttgt ctcctggggt ggtccggagc ccgtgtagcc gctcagcttg    1020

gttccgtacc gtgggcgtgc acgctccacc actctgcgac gggtgtccta gtacctagaa    1080

ccaccatcta gggggtccag acgcacaact tggcctccca gactaaaccc tgcaggtccc    1140

gagcatgtat caaaggatga ctaatgtcag atggcgggtc ctgtgggtgt actactaatg    1200

ctccctagcc aaagctgtgt gcaggctcag gtccc                               1235
```

```
<210> SEQ ID NO 27
<211> LENGTH: 2235
<212> TYPE: DNA
<213> ORGANISM: Zea mays

<400> SEQUENCE: 27

ttcctctgac aagcacaaga gctacgcctg gcgaggtggc cgcggctgaa cgggacctcg      60

ggtatcagtc acccgagggg gacctgaagg atgtcttcgt cggaggatcc tactccggtg     120

gagacaacta gatggactcc cggggggacc ccgtgctccc cgttctacgg ggccgaaacc     180

tgccttcccc cagaaacccc tctggactcc ccacgggtcc agacttctaa caaatccatg     240

cagaaatggc tacatcatga ggacgaggac tccctcatca aacgcagatg ggaacccagg     300

gtcgggacct agccctacgg caagtaccaa accaagaagg gctctgcaac tctcccctag     360

ctgggaagga cccttcaagg tgatgggaat acgccgaccc gggggtgact gtctagctat     420

gactgaagga gtacctttgg agcacctctg taagttctat ccataggagc aagcctgagg     480

ggtcgaattt ttctcccttt ttgtagctag gtaacgcata catgtacgcc aacccggtga     540

ggtccgccct cataagcccg gcatgttggt ctgcacccat acatgacaag ttataaagaa     600

cagaattacc ccctcagatg tgtctctaag ttttatccta ctgctccatg gtcttgcctt     660

gcagtttttc agagattatt ttatctaacc cacccaaaca gttccctttc catcagacat     720

aacgacattc gaattgaaca gccaggcttg cagtttagga cctatttacg aaagcgggag     780

ggcccgacag cctgggggtg gttctagaga acggaagccc gttccatggg gtggtctaga     840
```

gcctgtgtgg ccgcttagcc tggtcctata cccgaaagtc tgcacactcc accactccgt 900
gacgggtacc ctagtatttg gagctataag tcctgtgggt ccggcaacct ggggtccgga 960
actagagaat ggacacttgt ctcctggggt ggtccggagc ccgtgtagcc gctcagcttg 1020
gttccgtacc gtgggcgtgc acgctccacc actctgcgac gggtgtccta gtacctagaa 1080
ccaccatcta gggggtccag acgcacaact tggcctccca gactaaaccc tgcaggtccc 1140
gagcatgtat caaaggatga ctaatgtcag atggcgggtc ctgtgggtgt actactaatg 1200
ctccctagcc aaagctgtgt gcaggctcag gtcccagtcg aggctgcctc ctgggggcca 1260
ttgccaactc ttccttaggt atgctggttt gcagcctcga caaatcgagc ctacatcccg 1320
ggggccaggt accaaggagg aatcagttac accacacaca acagggacaa gtggtataca 1380
aataagtgct aatactgctt gataaatagt actcaaaagt accttacaaa aagcaaaaat 1440
attacatccg ccttcaagcg gagttctagc tccatctcta ctctacagat atgaactgcc 1500
tccacaccac tagggtcgcg tgggtagcta gctccgagcg gctcgccagc gaaggcgacc 1560
acctctgcac cgacggatcg acagcggcga cgactacctc ggctccaagc ggctcgccag 1620
cagaggcaac cacctctgca acgggcagcc tcaccagcga tggcgaccac ctctgcgcca 1680
ggcagcctcc ccagtsgtgg cgaccacctc agcatgcgcg ccatggtgaa gaggtcctcg 1740
ccttcgtccc cctacggggg tgaggacaag accatccaag ccttggagct gggagcatgg 1800
tggaaggcgg tgcttgcggt ctggctggga ccgcgtagcc gaagttcgcc tccttcacaa 1860
ggctggtgat catccttttc ctccgaatgc tggaggaaga gatgggcacc aacccatgtg 1920
ggaggcgaaa ccgcggctca gctcgttccc cgccaccgcg aggctcatga acatccttga 1980
agccaagaat cggtggaaga gcgccgctcc cacaagaccg cgcatctcca gcagaggaaa 2040
aacaagaccg gtagcaccag cccgctaggg aggagaaaag gcaaaaactc tctagcggca 2100
agctcatcgg agtggataac gccggcgcaa atccttccgc tgagcgccag cgcattccat 2160
ccaagcaagt ggtataccat ttcgagcact cactcagttt gggtgtgctc gggattgaga 2220
gcacctagag ggggg 2235

<210> SEQ ID NO 28
<211> LENGTH: 3235
<212> TYPE: DNA
<213> ORGANISM: Zea mays

<400> SEQUENCE: 28
ttcctctgac aagcacaaga gctacgcctg gcgaggtggc cgcggctgaa cgggacctcg 60
ggtatcagtc acccgagggg gacctgaagg atgtcttcgt cggaggatcc tactccggtg 120
gagacaacta gatggactcc cggggggacc ccgtgctccc cgttctacgg ggccgaaacc 180
tgccttcccc cagaaacccc tctggactcc ccacgggtcc agacttctaa caaatccatg 240
cagaaatggc tacatcatga ggacgaggac tccctcatca aacgcagatg ggaacccagg 300
gtcgggacct agccctacgg caagtaccaa accaagaagg gctctgcaac tctcccctag 360
ctgggaagga cccttcaagg tgatgggaat acgccgaccc gggggtgact gtctagctat 420
gactgaagga gtacctttgg agcacctctg taagttctat ccataggagc aagcctgagg 480
ggtcgaattt ttctcccttt ttgtagctag gtaacgcata catgtacgcc aacccggtga 540
ggtccgccct cataagcccg gcatgttggt ctgcacccat acatgacaag ttataaagaa 600
cagaattacc ccctcagatg tgtctctaag ttttatccta ctgctccatg gtcttgcctt 660
gcagtttttc agagattatt ttatctaacc cacccaaaca gttccctttc catcagacat 720

-continued

```
aacgacattc gaattgaaca gccaggcttg cagtttagga cctatttacg aaagcgggag    780
ggcccgacag cctgggggtg gttctagaga acggaagccc gttccatggg gtggtctaga    840
gcctgtgtgg ccgcttagcc tggtcctata cccgaaagtc tgcacactcc accactccgt    900
gacgggtacc ctagtatttg gagctataag tcctgtgggt ccggcaacct ggggtccgga    960
actagagaat ggacacttgt ctcctggggt ggtccggagc ccgtgtagcc gctcagcttg   1020
gttccgtacc gtgggcgtgc acgctccacc actctgcgac gggtgtccta gtacctagaa   1080
ccaccatcta gggggtccag acgcacaact tggcctccca gactaaaccc tgcaggtccc   1140
gagcatgtat caaaggatga ctaatgtcag atggcgggtc ctgtgggtgt actactaatg   1200
ctccctagcc aaagctgtgt gcaggctcag gtcccagtcg aggctgcctc ctgggggcca   1260
ttgccaactc ttccttaggt atgctggttt gcagcctcga caaatcgagc ctacatcccg   1320
ggggccaggt accaaggagg aatcagttac accacacaca acagggacaa gtggtataca   1380
aataagtgct aatactgctt gataaatagt actcaaaagt accttacaaa aagcaaaaat   1440
attacatccg ccttcaagcg gagttctagc tccatctcta ctctacagat atgaactgcc   1500
tccacaccac tagggtcgcg tgggtagcta gctccgagcg gctcgccagc gaaggcgacc   1560
acctctgcac cgacggatcg acagcggcga cgactacctc ggctccaagc ggctcgccag   1620
cagaggcaac cacctctgca acgggcagcc tcaccagcga tggcgaccac ctctgcgcca   1680
ggcagcctcc ccagtsgtgg cgaccacctc agcatgcgcg ccatggtgaa gaggtcctcg   1740
ccttcgtccc cctacggggg tgaggacaag accatccaag ccttggagct gggagcatgg   1800
tggaaggcgg tgcttgcggt ctggctggga ccgcgtagcc gaagttcgcc tccttcacaa   1860
ggctggtgat catccttttc ctccgaatgc tggaggaaga gatgggcacc aacccatgtg   1920
ggaggcgaaa ccgcggctca gctcgttccc cgccaccgcg aggctcatga acatccttga   1980
agccaagaat cggtggaaga gcgccgctcc cacaagaccg cgcatctcca gcagaggaaa   2040
aacaagaccg gtagcaccag cccgctaggg aggagaaaag gcaaaaactc tctagcggca   2100
agctcatcgg agtggataac gccggcgcaa atccttccgc tgagcgccag cgcattccat   2160
ccaagcaagt ggtataccat ttcgagcact cactcagttt gggtgtgctc gggattgaga   2220
gcacctagag ggggggtgaa taggtgatcc tgtaaaaact tgaaacttaa ttcgcaaaac   2280
ttgattagga gttagcacga ataagctaag tggctagaga ggagaacttg cacaacacga   2340
taaccacaaa gagatcaaca cagagatggc acagtggttt atcccgtggt tcggccaagt   2400
ccaacacttg cctactccac gttgtggcgt cccaatggac gagggttgca atcaacccct   2460
ttcaagcggt ccaaagaccc acttgaatac cacggtgttt tgctttcact ttactatatc   2520
tcgcttgtga ggaatctcca caacttggag cctctcgccc ttacactttg atgttcacaa   2580
agaagcacgg agtaagggag ggatgagcaa cgcacacaag acatgaaatc agagtaccaa   2640
cacgcacaca aatcacaaca agagctcaca acacaacccg gcgagttcac tactaaaatg   2700
gagctctagt tgctatcaca aagagtcaaa tgcgcagaat cgaagtcttg gtgcttagga   2760
atgcttagag aatgcttggt gcactcctcc atgcgcctag gggtcccttt tatagcccca   2820
aggcagctag gagccgttga gagcaattca agaaggcaat tcttgccttc tgtcgcctgg   2880
cgcaccggac agttcggtgc accaccggac actgtccggt gcggatctct ttccttattt   2940
ggcgaagccg accgttgcag attgctagcc gttggcacac cggacactgt ccggtgcaca   3000
ccggacaatc cgatgccccc ttctgaccgt tggctctgcc acgcgtcgcg cgcggattcc   3060
```

-continued acggccgacc gttggcccgg ccgactgttg gctcaccaga cagtccggtg caccaccgga 3120
cagtccggtg aattttagcc gtacgccgcc aacgatttcc cgagagcaac aagttcgcgt 3180
gagtcagcct ggtgcaccgg acactgtccg gtgcaccacc gggcagtccg gtgca 3235

<210> SEQ ID NO 29
<211> LENGTH: 4235
<212> TYPE: DNA
<213> ORGANISM: Zea mays

<400> SEQUENCE: 29
ttcctctgac aagcacaaga gctacgcctg gcgaggtggc cgcggctgaa cgggacctcg 60
ggtatcagtc acccgagggg gacctgaagg atgtcttcgt cggaggatcc tactccggtg 120
gagacaacta gatggactcc cggggggacc ccgtgctccc cgttctacgg ggccgaaacc 180
tgccttcccc cagaaacccc tctggactcc ccacgggtcc agacttctaa caaatccatg 240
cagaaatggc tacatcatga ggacgaggac tccctcatca aacgcagatg ggaacccagg 300
gtcgggacct agccctacgg caagtaccaa accaagaagg gctctgcaac tctcccctag 360
ctgggaagga cccttcaagg tgatgggaat acgccgaccc gggggtgact gtctagctat 420
gactgaagga gtacctttgg agcacctctg taagttctat ccataggagc aagcctgagg 480
ggtcgaattt ttctcccttt ttgtagctag gtaacgcata catgtacgcc aacccggtga 540
ggtccgccct cataagcccg gcatgttggt ctgcacccat acatgacaag ttataaagaa 600
cagaattacc ccctcagatg tgtctctaag ttttatccta ctgctccatg gtcttgcctt 660
gcagtttttc agagattatt ttatctaacc cacccaaaca gttccctttc catcagacat 720
aacgacattc gaattgaaca gccaggcttg cagtttagga cctatttacg aaagcgggag 780
ggcccgacag cctgggggtg gttctagaga acggaagccc gttccatggg gtggtctaga 840
gcctgtgtgg ccgcttagcc tggtcctata cccgaaagtc tgcacactcc accactccgt 900
gacgggtacc ctagtatttg gagctataag tcctgtgggt ccggcaacct ggggtccgga 960
actagagaat ggacacttgt ctcctggggt ggtccggagc ccgtgtagcc gctcagcttg 1020
gttccgtacc gtgggcgtgc acgctccacc actctgcgac gggtgtccta gtacctagaa 1080
ccaccatcta gggggtccag acgcacaact tggcctccca gactaaaccc tgcaggtccc 1140
gagcatgtat caaaggatga ctaatgtcag atggcgggtc ctgtgggtgt actactaatg 1200
ctccctagcc aaagctgtgt gcaggctcag gtcccagtcg aggctgcctc ctgggggcca 1260
ttgccaactc ttccttaggt atgctggttt gcagcctcga caaatcgagc ctacatcccg 1320
ggggccaggt accaaggagg aatcagttac accacacaca acagggacaa gtggtataca 1380
aataagtgct aatactgctt gataaatagt actcaaaagt accttacaaa aagcaaaaat 1440
attacatccg ccttcaagcg gagttctagc tccatctcta ctctacagat atgaactgcc 1500
tccacaccac tagggtcgcg tgggtagcta gctccgagcg gctcgccagc gaaggcgacc 1560
acctctgcac cgacggatcg acagcggcga cgactacctc ggctccaagc ggctcgccag 1620
cagaggcaac cacctctgca acgggcagcc tcaccagcga tggcgaccac ctctgcgcca 1680
ggcagcctcc ccagtsgtgg cgaccacctc agcatgcgcg ccatggtgaa gaggtcctcg 1740
ccttcgtccc cctacggggg tgaggacaag accatccaag ccttggagct gggagcatgg 1800
tggaaggcgg tgcttgcggt ctggctggga ccgcgtagcc gaagttcgcc tccttcacaa 1860
ggctggtgat catccttttc ctccgaatgc tggaggaaga gatgggcacc aacccatgtg 1920
ggaggcgaaa ccgcggctca gctcgttccc cgccaccgcg aggctcatga acatccttga 1980

```
agccaagaat cggtggaaga gcgccgctcc cacaagaccg cgcatctcca gcagaggaaa   2040
aacaagaccg gtagcaccag cccgctaggg aggagaaaag gcaaaaactc tctagcggca   2100
agctcatcgg agtggataac gccggcgcaa atccttccgc tgagcgccag cgcattccat   2160
ccaagcaagt ggtataccat ttcgagcact cactcagttt gggtgtgctc gggattgaga   2220
gcacctagag ggggggtgaa taggtgatcc tgtaaaaact tgaaacttaa ttcgcaaaac   2280
ttgattagga gttagcacga ataagctaag tggctagaga ggagaacttg cacaacacga   2340
taaccacaaa gagatcaaca cagagatggc acagtggttt atcccgtggt tcggccaagt   2400
ccaacacttg cctactccac gttgtggcgt cccaatggac gagggttgca atcaacccct   2460
ttcaagcggt ccaaagaccc acttgaatac cacggtgttt tgctttcact ttactatatc   2520
tcgcttgtga ggaatctcca caacttggag cctctcgccc ttacactttg atgttcacaa   2580
agaagcacgg agtaagggag ggatgagcaa cgcacacaag acatgaaatc agagtaccaa   2640
cacgcacaca aatcacaaca agagctcaca acacaacccg gcgagttcac tactaaaatg   2700
gagctctagt tgctatcaca aagagtcaaa tgcgcagaat cgaagtcttg gtgcttagga   2760
atgcttagag aatgcttggt gcactcctcc atgcgcctag gggtcccttt tatagcccca   2820
aggcagctag gagccgttga gagcaattca agaaggcaat tcttgccttc tgtcgcctgg   2880
cgcaccggac agttcggtgc accaccggac actgtccggt gcggatctct ttccttattt   2940
ggcgaagccg accgttgcag attgctagcc gttggcacac cggacactgt ccggtgcaca   3000
ccggacaatc cgatgccccc ttctgaccgt tggctctgcc acgcgtcgcg cgcggattcc   3060
acggccgacc gttggcccgg ccgactgttg gctcaccaga cagtccggtg caccaccgga   3120
cagtccggtg aattttagcc gtacgccgcc aacgatttcc cgagagcaac aagttcgcgt   3180
gagtcagcct ggtgcaccgg acactgtccg gtgcaccacc gggcagtccg gtgcaccacc   3240
ggacagtccg gtgcacccag actgcgcaga gtcttcgcta ctcagccaag tcttttccaa   3300
tttggtcttt tcctgtttct agcacttaga cacaatacat tagtcttcaa aacaatgtac   3360
taagtcttag aaacatacct ttagacttga tttgcacttt gtccatcaat tggcatagat   3420
tatcatttaa gcacttgtgt tggcactcaa tcaccaaaat acttagaaat ggcccaaggg   3480
cacatttccc tttcaatctc cccctttttg gtgatttatg ccaacacaac aaaaagcaac   3540
ttaaagaagt gcaacatcaa tgcaaatgag accacaaatt tgttttgatc aagtttgaca   3600
tatttggatc attctttgcc accacttggt ttgtttttgc aaaccaaact caatttccta   3660
tctctaagtc aaacacactt gttgaaacat aaagagagat atttcacgag aaattgatca   3720
aagattcaac aactccccct tttcccataa atccagcctt ctccccacaa gagatcaatg   3780
ttttgacaat aagagacaaa caagagtatt tagacaaaca aaaactctaa ctctactatt   3840
ttcaaaattc ctaagtggta gctgatccat ttcttgcttt ggccttattt tctccccctt   3900
tggcatcaag caccaaaaca ggatcaattt tggcccttta accccattgc ctcaccaaaa   3960
ttttcaacta agagtaaaaa ggcaataaga gtacaaagat gaacttgaaa ttagttactc   4020
tttcatcgga gtgtagtgga agtcttgcat ggtccaagtc caccttttcc ctttcaaacc   4080
tcctttgaga ctaaattaag cagactcaag caaacaatta gtctcaaagg gtcaagttgt   4140
agctcatctc cccctagatg tgtgcatcac ttgcaaagga cttgtgaggt ccggggwgtg   4200
cttgtacaac ttgagcacca taaataaaca acaaa                              4235
```

<210> SEQ ID NO 30

<211> LENGTH: 6235
<212> TYPE: DNA
<213> ORGANISM: Zea mays

<400> SEQUENCE: 30
ttcctctgac aagcacaaga gctacgcctg gcgaggtggc cgcggctgaa cgggacctcg 60
ggtatcagtc acccgagggg gacctgaagg atgtcttcgt cggaggatcc tactccggtg 120
gagacaacta gatggactcc cggggggacc ccgtgctccc cgttctacgg ggccgaaacc 180
tgccttcccc cagaaacccc tctggactcc ccacgggtcc agacttctaa caaatccatg 240
cagaaatggc tacatcatga ggacgaggac tccctcatca aacgcagatg ggaacccagg 300
gtcgggacct agccctacgg caagtaccaa accaagaagg gctctgcaac tctcccctag 360
ctgggaagga cccttcaagg tgatgggaat acgccgaccc gggggtgact gtctagctat 420
gactgaagga gtacctttgg agcacctctg taagttctat ccataggagc aagcctgagg 480
ggtcgaattt ttctcccttt ttgtagctag gtaacgcata catgtacgcc aacccggtga 540
ggtccgccct cataagcccg gcatgttggt ctgcacccat acatgacaag ttataaagaa 600
cagaattacc ccctcagatg tgtctctaag ttttatccta ctgctccatg gtcttgcctt 660
gcagtttttc agagattatt ttatctaacc cacccaaaca gttccctttc catcagacat 720
aacgacattc gaattgaaca gccaggcttg cagtttagga cctatttacg aaagcgggag 780
ggcccgacag cctgggggtg gttctagaga acggaagccc gttccatggg gtggtctaga 840
gcctgtgtgg ccgcttagcc tggtcctata cccgaaagtc tgcacactcc accactccgt 900
gacgggtacc ctagtatttg gagctataag tcctgtgggt ccggcaacct ggggtccgga 960
actagagaat ggacacttgt ctcctggggt ggtccggagc ccgtgtagcc gctcagcttg 1020
gttccgtacc gtgggcgtgc acgctccacc actctgcgac gggtgtccta gtacctagaa 1080
ccaccatcta gggggtccag acgcacaact tggcctccca gactaaaccc tgcaggtccc 1140
gagcatgtat caaaggatga ctaatgtcag atggcgggtc ctgtgggtgt actactaatg 1200
ctccctagcc aaagctgtgt gcaggctcag gtcccagtcg aggctgcctc ctgggggcca 1260
ttgccaactc ttccttaggt atgctggttt gcagcctcga caaatcgagc ctacatcccg 1320
ggggccaggt accaaggagg aatcagttac accacacaca acagggacaa gtggtataca 1380
aataagtgct aatactgctt gataaatagt actcaaaagt accttacaaa aagcaaaaat 1440
attacatccg ccttcaagcg gagttctagc tccatctcta ctctacagat atgaactgcc 1500
tccacaccac tagggtcgcg tgggtagcta gctccgagcg gctcgccagc gaaggcgacc 1560
acctctgcac cgacggatcg acagcggcga cgactacctc ggctccaagc ggctcgccag 1620
cagaggcaac cacctctgca acgggcagcc tcaccagcga tggcgaccac ctctgcgcca 1680
ggcagcctcc ccagtsgtgg cgaccacctc agcatgcgcg ccatggtgaa gaggtcctcg 1740
ccttcgtccc cctacggggg tgaggacaag accatccaag ccttggagct gggagcatgg 1800
tggaaggcgg tgcttgcggt ctggctggga ccgcgtagcc gaagttcgcc tccttcacaa 1860
ggctggtgat catccttttc ctccgaatgc tggaggaaga gatgggcacc aacccatgtg 1920
ggaggcgaaa ccgcggctca gctcgttccc cgccaccgcg aggctcatga acatccttga 1980
agccaagaat cggtggaaga gcgccgctcc cacaagaccg cgcatctcca gcagaggaaa 2040
aacaagaccg gtagcaccag cccgctaggg aggagaaaag gcaaaaactc tctagcggca 2100
agctcatcgg agtggataac gccggcgcaa atccttccgc tgagcgccag cgcattccat 2160
ccaagcaagt ggtataccat ttcgagcact cactcagttt gggtgtgctc gggattgaga 2220
gcacctagag ggggggtgaa taggtgatcc tgtaaaaact tgaaacttaa ttcgcaaaac 2280
ttgattagga gttagcacga ataagctaag tggctagaga ggagaacttg cacaacacga 2340
taaccacaaa gagatcaaca cagagatggc acagtggttt atcccgtggt tcggccaagt 2400
ccaacacttg cctactccac gttgtggcgt cccaatggac gagggttgca atcaacccct 2460
ttcaagcggt ccaaagaccc acttgaatac cacggtgttt tgctttcact ttactatatc 2520
tcgcttgtga ggaatctcca caacttggag cctctcgccc ttacactttg atgttcacaa 2580
agaagcacgg agtaagggag ggatgagcaa cgcacacaag acatgaaatc agagtaccaa 2640
cacgcacaca aatcacaaca agagctcaca acacaacccg gcgagttcac tactaaaatg 2700
gagctctagt tgctatcaca aagagtcaaa tgcgcagaat cgaagtcttg gtgcttagga 2760
atgcttagag aatgcttggt gcactcctcc atgcgcctag ggtccctttt tatagcccca 2820
aggcagctag gagccgttga gagcaattca agaaggcaat tcttgccttc tgtcgcctgg 2880
cgcaccggac agttcggtgc accaccggac actgtccggt gcggatctct ttccttattt 2940
ggcgaagccg accgttgcag attgctagcc gttggcacac cggacactgt ccggtgcaca 3000
ccggacaatc cgatgccccc ttctgaccgt tggctctgcc acgcgtcgcg cgcggattcc 3060
acggccgacc gttggcccgg ccgactgttg gctcaccaga cagtccggtg caccaccgga 3120
cagtccggtg aattttagcc gtacgccgcc aacgatttcc cgagagcaac aagttcgcgt 3180
gagtcagcct ggtgcaccgg acactgtccg gtgcaccacc gggcagtccg gtgcaccacc 3240
ggacagtccg gtgcacccag actgcgcaga gtcttcgcta ctcagccaag tcttttccaa 3300
tttggtcttt tcctgtttct agcacttaga cacaatacat tagtcttcaa aacaatgtac 3360
taagtcttag aaacatacct ttagacttga tttgcacttt gtccatcaat tggcatagat 3420
tatcatttaa gcacttgtgt tggcactcaa tcaccaaaat acttagaaat ggcccaaggg 3480
cacatttccc tttcaatctc cccctttttg gtgatttatg ccaacacaac aaaaagcaac 3540
ttaaagaagt gcaacatcaa tgcaaatgag accacaaatt tgttttgatc aagtttgaca 3600
tatttggatc attctttgcc accacttggt ttgtttttgc aaaccaaact caatttccta 3660
tctctaagtc aaacacactt gttgaaacat aaagagagat atttcacgag aaattgatca 3720
aagattcaac aactccccct tttcccataa atccagcctt ctccccacaa gagatcaatg 3780
ttttgacaat aagagacaaa caagagtatt tagacaaaca aaaactctaa ctctactatt 3840
ttcaaaattc ctaagtggta gctgatccat ttcttgcttt ggccttattt tctccccctt 3900
tggcatcaag caccaaaaca ggatcaattt tggcccttta accccattgc ctcaccaaaa 3960
ttttcaacta agagtaaaaa ggcaataaga gtacaaagat gaacttgaaa ttagttactc 4020
tttcatcgga gtgtagtgga agtcttgcat ggtccaagtc cacctttcc ctttcaaacc 4080
tcctttgaga ctaaattaag cagactcaag caaacaatta gtctcaaagg gtcaagttgt 4140
agctcatctc cccctagatg tgtgcatcac ttgcaaagga cttgtgaggt ccggggwgtg 4200
cttgtacaac ttgagcacca taaataaaca acaaaatgca ttaaggaaca tgatcaaagg 4260
cataaacaca tgtatgctat aaatcaaccc aagttccgcg aatctaagac atttagctca 4320
ctacgcaact tgcaaaaggt ctgctcatct aaaggcttgg taaagatatc ggctagctgg 4380
ttctcggagc taacatgaaa cacttcgata tctccctttt gctggtggtg taacgccccg 4440
aattttgcag ttgaattttt tttcttttct ttactcgcca aattcgggcg ttaccttttc 4500
tttttctttt tgccctcgct agaycttgac tttttccaaa gctagcggga ttcggtttgg 4560

```
aattcccgtg taaagaaaaa ctctaaaaaa atactttatg tggtttgatg caccatgccg   4620
agctatgcat tctttgattg tttgaaagtg caaatgcatt catctaggaa gatcggattt   4680
cgaaagcagg gaaataatct tttctttttc tttctctttc tttctctctc cctcttcccc   4740
tttccctctc tcccgcgcca tgggctcctt ggccggccca gccgcccctt ggccggccca   4800
agccccctgc gcgccccccc tcttgggcct tggcaggccc agccgccccc ccacctcccc   4860
ttttttttccc caattccctc tccctctctc tctctccctc tcattttccc tctctctccc   4920
taagccgccg cccctacccc tctgccctaa ccgccgccgc cccctgctcg gccgccgccc   4980
tcgccgtcgg ccgcccatcg ccggtgagcc cccccctttc cctctcctcc ctccctctcc   5040
cctctcccct cctccctccc cttggcagcc cagccgcacg gccacccctg gccgcgcccc   5100
tggccgcccc cagcccagcc gccggccgcg ccctggcccc agccgcgcct ggccagcctc   5160
ggccgcgccc tggccggccc cggccgcgcc cagccgcgcc cccggcccgc cctggccgcg   5220
ccctcggccg cccctggccc ctggccgccc gccagccgcc ccctgcccgc tggttcggcc   5280
gcgcccctgg ccggcccagc cgctcgccca gccgggcggt tccccctttt ttttattttt   5340
ttttatttta ttttatttac tttctgtgat cataattacc ttattttggg tagactaatc   5400
atggttcatg ctatggaaat gagaagttta atttagaatt tcgttgcgct agttgattca   5460
ttcagttaat tgtttatccc gtgcaatgtt aatcaactta aaatgattag gttcccacta   5520
gtgcatataa cagaattctt ttgttaggaa cctattgaaa ctagagtgca taatttaact   5580
aatcattagt gcataaactt taaccccccct gcgagaccct tttcccgttt ctttctaacc   5640
ataacaaatg caatgtcaaa tgtcatactt gatgcatatt cgctttattt gttcccttgt   5700
atggtgtact gttcttttgt attaaatatg tggatggatg tatgtatgtt tgcgctcgca   5760
tagagaacga tccggtcaaa gagcccgagg aattcgcagg agaagcccct gagcagcagt   5820
cggttggtgg aggcaagtgt cctttgacct atctctgtcc taatcattct ttaattcacc   5880
tcccgcatca cacatttata cctaaggatt gactagcttt ttgttatcca tgtccttatt   5940
tacctatttg ggtcggatta ttactgctta gtttgatgct attgctcaac tttaatcaat   6000
gaacatgatg tggttatcta tgatacgctg ttttcccgtt ctcatttatg attatacttg   6060
tggcatttaa ggggactcga gcggtttctc gagtgcctct ccgtaaggac ctgttcaatg   6120
gatgaccgcc cgggaaaaca atgcaaccat gagggtggaa tggggtgccc ttagctgaat   6180
aattagagga tccggggtgt agttcgcttc gccgtcgtgc cgtcaatggg gctcg        6235
```

<210> SEQ ID NO 31
<211> LENGTH: 9235
<212> TYPE: DNA
<213> ORGANISM: Zea mays

<400> SEQUENCE: 31

```
ttcctctgac aagcacaaga gctacgcctg gcgaggtggc cgcggctgaa cgggacctcg     60
ggtatcagtc acccgagggg gacctgaagg atgtcttcgt cggaggatcc tactccggtg    120
gagacaacta gatggactcc cggggggacc ccgtgctccc cgttctacgg ggccgaaacc    180
tgccttcccc cagaaacccc tctggactcc ccacgggtcc agacttctaa caaatccatg    240
cagaaatggc tacatcatga ggacgaggac tccctcatca aacgcagatg ggaacccagg    300
gtcgggacct agccctacgg caagtaccaa accaagaagg gctctgcaac tctcccctag    360
ctgggaagga cccttcaagg tgatgggaat acgccgaccc gggggtgact gtctagctat    420
gactgaagga gtacctttgg agcacctctg taagttctat ccataggagc aagcctgagg    480
```

```
ggtcgaattt ttctcccttt ttgtagctag gtaacgcata catgtacgcc aacccggtga    540
ggtccgccct cataagcccg gcatgttggt ctgcacccat acatgacaag ttataaagaa    600
cagaattacc ccctcagatg tgtctctaag ttttatccta ctgctccatg gtcttgcctt    660
gcagtttttc agagattatt ttatctaacc cacccaaaca gttccctttc catcagacat    720
aacgacattc gaattgaaca gccaggcttg cagtttagga cctatttacg aaagcgggag    780
ggcccgacag cctgggggtg gttctagaga acggaagccc gttccatggg gtggtctaga    840
gcctgtgtgg ccgcttagcc tggtcctata cccgaaagtc tgcacactcc accactccgt    900
gacgggtacc ctagtatttg gagctataag tcctgtgggt ccggcaacct ggggtccgga    960
actagagaat ggacacttgt ctcctggggt ggtccggagc ccgtgtagcc gctcagcttg   1020
gttccgtacc gtgggcgtgc acgctccacc actctgcgac gggtgtccta gtacctagaa   1080
ccaccatcta gggggtccag acgcacaact tggcctccca gactaaaccc tgcaggtccc   1140
gagcatgtat caaaggatga ctaatgtcag atggcgggtc ctgtgggtgt actactaatg   1200
ctccctagcc aaagctgtgt gcaggctcag gtcccagtcg aggctgcctc ctgggggcca   1260
ttgccaactc ttccttaggt atgctggttt gcagcctcga caaatcgagc ctacatcccg   1320
ggggccaggt accaaggagg aatcagttac accacacaca acagggacaa gtggtataca   1380
aataagtgct aatactgctt gataaatagt actcaaaagt accttacaaa aagcaaaaat   1440
attacatccg ccttcaagcg gagttctagc tccatctcta ctctacagat atgaactgcc   1500
tccacaccac tagggtcgcg tgggtagcta gctccgagcg gctcgccagc gaaggcgacc   1560
acctctgcac cgacggatcg acagcggcga cgactacctc ggctccaagc ggctcgccag   1620
cagaggcaac cacctctgca acgggcagcc tcaccagcga tggcgaccac ctctgcgcca   1680
ggcagcctcc ccagtsgtgg cgaccacctc agcatgcgcg ccatggtgaa gaggtcctcg   1740
ccttcgtccc cctacggggg tgaggacaag accatccaag ccttggagct gggagcatgg   1800
tggaaggcgg tgcttgcggt ctggctggga ccgcgtagcc gaagttcgcc tccttcacaa   1860
ggctggtgat catccttttc ctccgaatgc tggaggaaga gatgggcacc aacccatgtg   1920
ggaggcgaaa ccgcggctca gctcgttccc cgccaccgcg aggctcatga acatccttga   1980
agccaagaat cggtggaaga gcgccgctcc cacaagaccg cgcatctcca gcagaggaaa   2040
aacaagaccg gtagcaccag cccgctaggg aggagaaaag gcaaaaactc tctagcggca   2100
agctcatcgg agtggataac gccggcgcaa atccttccgc tgagcgccag cgcattccat   2160
ccaagcaagt ggtataccat ttcgagcact cactcagttt gggtgtgctc gggattgaga   2220
gcacctagag ggggggtgaa taggtgatcc tgtaaaaact tgaaacttaa ttcgcaaaac   2280
ttgattagga gttagcacga ataagctaag tggctagaga ggagaacttg cacaacacga   2340
taaccacaaa gagatcaaca cagagatggc acagtggttt atcccgtggt tcggccaagt   2400
ccaacacttg cctactccac gttgtggcgt cccaatggac gagggttgca atcaacccct   2460
ttcaagcggt ccaaagaccc acttgaatac cacggtgttt tgctttcact ttactatatc   2520
tcgcttgtga ggaatctcca caacttggag cctctcgccc ttacactttg atgttcacaa   2580
agaagcacgg agtaagggag ggatgagcaa cgcacacaag acatgaaatc agagtaccaa   2640
cacgcacaca aatcacaaca agagctcaca acacaacccg gcgagttcac tactaaaatg   2700
gagctctagt tgctatcaca aagagtcaaa tgcgcagaat cgaagtcttg gtgcttagga   2760
atgcttagag aatgcttggt gcactcctcc atgcgcctag ggtccctttt tatagcccca   2820
```

-continued

```
aggcagctag gagccgttga gagcaattca agaaggcaat tcttgccttc tgtcgcctgg   2880
cgcaccggac agttcggtgc accaccggac actgtccggt gcggatctct ttccttattt   2940
ggcgaagccg accgttgcag attgctagcc gttggcacac cggacactgt ccggtgcaca   3000
ccggacaatc cgatgccccc ttctgaccgt tggctctgcc acgcgtcgcg cgcggattcc   3060
acggccgacc gttggcccgg ccgactgttg gctcaccaga cagtccggtg caccaccgga   3120
cagtccggtg aattttagcc gtacgccgcc aacgatttcc cgagagcaac aagttcgcgt   3180
gagtcagcct ggtgcaccgg acactgtccg gtgcaccacc gggcagtccg gtgcaccacc   3240
ggacagtccg gtgcacccag actgcgcaga gtcttcgcta ctcagccaag tcttttccaa   3300
tttggtcttt tcctgtttct agcacttaga cacaatacat tagtcttcaa aacaatgtac   3360
taagtcttag aaacatacct ttagacttga tttgcacttt gtccatcaat tggcatagat   3420
tatcatttaa gcacttgtgt tggcactcaa tcaccaaaat acttagaaat ggcccaaggg   3480
cacatttccc tttcaatctc cccctttttg gtgatttatg ccaacacaac aaaaagcaac   3540
ttaaagaagt gcaacatcaa tgcaaatgag accacaaatt tgttttgatc aagtttgaca   3600
tatttggatc attctttgcc accacttggt ttgtttttgc aaaccaaact caatttccta   3660
tctctaagtc aaacacactt gttgaaacat aaagagagat atttcacgag aaattgatca   3720
aagattcaac aactccccct tttcccataa atccagcctt ctccccacaa gagatcaatg   3780
ttttgacaat aagagacaaa caagagtatt tagacaaaca aaaactctaa ctctactatt   3840
ttcaaaattc ctaagtggta gctgatccat ttcttgcttt ggccttattt tctccccctt   3900
tggcatcaag caccaaaaca ggatcaattt tggcccttta accccattgc ctcaccaaaa   3960
ttttcaacta agagtaaaaa ggcaataaga gtacaaagat gaacttgaaa ttagttactc   4020
tttcatcgga gtgtagtgga agtcttgcat ggtccaagtc caccttttcc ctttcaaacc   4080
tcctttgaga ctaaattaag cagactcaag caaacaatta gtctcaaagg gtcaagttgt   4140
agctcatctc cccctagatg tgtgcatcac ttgcaaagga cttgtgaggt ccggggwgtg   4200
cttgtacaac ttgagcacca taaataaaca acaaaatgca ttaaggaaca tgatcaaagg   4260
cataaacaca tgtatgctat aaatcaaccc aagttccgcg aatctaagac atttagctca   4320
ctacgcaact tgcaaaaggt ctgctcatct aaaggcttgg taaagatatc ggctagctgg   4380
ttctcggagc taacatgaaa cacttcgata tctccctttt gctggtggtg taacgccccg   4440
aattttgcag ttgaattttt tttcttttct ttactcgcca aattcgggcg ttaccttttc   4500
tttttctttt tgccctcgct agaycttgac tttttccaaa gctagcggga ttcggtttgg   4560
aattcccgtg taaagaaaaa ctctaaaaaa atactttatg tggtttgatg caccatgccg   4620
agctatgcat tctttgattg tttgaaagtg caaatgcatt catctaggaa gatcggattt   4680
cgaaagcagg gaaataatct tttctttttc tttctctttc tttctctctc cctcttcccc   4740
tttccctctc tcccgcgcca tgggctcctt ggccggccca gccgcccctt ggccggccca   4800
agccccctgc gcgccccccc tcttgggcct tggcaggccc agccgccccc ccacctcccc   4860
ttttttttccc caattccctc tccctctctc tctctccctc tcattttccc tctctctccc   4920
taagccgccg cccctacccc tctgccctaa ccgccgccgc cccctgctcg gccgccgccc   4980
tcgccgtcgg ccgcccatcg ccggtgagcc ccccccttc cctctcctcc ctccctctcc   5040
cctctcccct cctccctccc cttggcagcc cagccgcacg gccacccctg gccgcgcccc   5100
tggccgcccc cagcccagcc gccggccgcg ccctggcccc agccgcgcct ggccagcctc   5160
ggccgcgccc tggccggccc cggccgcgcc cagccgcgcc cccggcccgc cctggccgcg   5220
```

```
ccctcggccg cccctggccc ctggccgccc gccagccgcc ccctgcccgc tggttcggcc   5280
gcgcccctgg ccggcccagc cgctcgccca gccgggcggt tccccctttt ttttattttt   5340
ttttatttta ttttatttac tttctgtgat cataattacc ttattttggg tagactaatc   5400
atggttcatg ctatggaaat gagaagttta atttagaatt tcgttgcgct agttgattca   5460
ttcagttaat tgtttatccc gtgcaatgtt aatcaactta aaatgattag gttcccacta   5520
gtgcatataa cagaattctt ttgttaggaa cctattgaaa ctagagtgca taatttaact   5580
aatcattagt gcataaactt taacccccct gcgagaccct tttcccgttt ctttctaacc   5640
ataacaaatg caatgtcaaa tgtcatactt gatgcatatt cgctttattt gttcccttgt   5700
atggtgtact gttcttttgt attaaatatg tggatggatg tatgtatgtt tgcgctcgca   5760
tagagaacga tccggtcaaa gagcccgagg aattcgcagg agaagcccct gagcagcagt   5820
cggttggtgg aggcaagtgt cctttgacct atctctgtcc taatcattct ttaattcacc   5880
tcccgcatca cacatttata cctaaggatt gactagcttt ttgttatcca tgtccttatt   5940
tacctatttg ggtcggatta ttactgctta gtttgatgct attgctcaac tttaatcaat   6000
gaacatgatg tggttatcta tgatacgctg ttttcccgtt ctcatttatg attatacttg   6060
tggcatttaa ggggactcga gcggtttctc gagtgcctct ccgtaaggac ctgttcaatg   6120
gatgaccgcc cgggaaaaca atgcaaccat gagggtggaa tggggtgccc ttagctgaat   6180
aattagagga tccggggtgt agttcgcttc gccgtcgtgc cgtcaatggg gctcggtgta   6240
tgcggctcgc tctgccaagg ttgatttgtc ccttggggag gagtgcggta catttaggaa   6300
acctaacggg tggctacagc cccggggaat ctttgtaaag gcttcgtagt gaatccttgg   6360
ccattcacct cgggagtgaa taagggtctt gcaagcccgg gccagagagg gaatcacggc   6420
ttgtgggtaa agtgcacaac ctctgcagag tgttatgaaa ctgatatatc agccgtgctc   6480
gcggttatga gcggccaagg gagctccaga gattagtgat acttgatcag agatactttg   6540
gtacaggtga caatgagatt gatggttctg attacgatta tggtattggt aagtggtatt   6600
ctttccgttt ggaaaggata cattgggcta ataacttggg ttaatgttaa aacctggctt   6660
tctactagta agtaataacc tgaccaacta aaagcaactg cttgacttat ccccacataa   6720
agctagtcca ctacagccaa acaggatact tgctgagtat gttgatgtgt actcaccctt   6780
gctctacaca ccaaaccccc ccccaggttg tcagcattgc aaccactgct caggcgaaga   6840
tgaagctgtg gaaggagact tccgggagtt ccaagactac gacgagttct aggtgtgggt   6900
tagcggcaac cccccagtcg gctgcctgtg aaggccgtgt tatctacgtt tcttttccgc   6960
actttgattt attgtaagaa ctatatggac gtctcagacg tatgatgtaa tcgactattt   7020
cccttattaa tactattttg agcactgtgt gatgatgtcc atattatgta actgctgtgt   7080
atgtgaataa ctgatcctgg cacgtacatg gttcgcattc ggtttgcctt ctaaaaccgg   7140
gtgtgtcata agtggtatca aagccgtgct gactgtagga ccgctaacct agagtagaat   7200
ggtcgttcta aggattatag acctctgtcc ctaccttgac tttgatatct cttcaaaagt   7260
tggtcctacc gaccaaacct atgttctact atatattata ccttgctaaa aaattgtgtt   7320
tcattctgat ccttcattta cttatgattc attatttgct ggtcatatta attctgttct   7380
caccctttttg cttgcgatgt cttttgtaga tggctcgact tagacacact gcacgaaagt   7440
ccgtcatccc cttcttaccc tcccgccttg ctgagcgtcc gcttcgccgt cccgtggccg   7500
gacagtccag ccacttggag agactacacc accgcctgcg tgaggagcag gaacgtcgac   7560
```

-continued

```
gacaggagca acagggctct tctttctcgc tccaccagga gatagagtct gtgaggagct   7620
gctctcctgt gcttcctctg gaggtgcccc ctgcaccacc actgggcgcc ccagcttctg   7680
gagtagctgc tggaggagac ccagacgacg gagatggcga cgacagctcg agccacgaca   7740
ccgacttctc tgctaaccct gagccggaag gatgggttgc tcgacccatc actcgcgacg   7800
ctgctcgcgg gtgtcacttc cacgatgcgc tcgacaccct gctacgtcgg gcatttgacc   7860
ggcatacttg gtccgtcgag tatcgctgtg tggtctacca gcatagtcgc ggggtctacc   7920
cggaccgctg ggagacgact tgcttggtgc gctgcccgga ggacagtctc cagggtgcag   7980
aggcctgctc agagcactat tctatctctg aacgggactc agctgaggca gccatgcaag   8040
atgctgcacg gcgtgcgctt tcgcactact gctcggtttt cggtggggca gctgacggtc   8100
ttgacctgaa gtattacccc cgccgtccat ctggcagcac aggaggcgtg attgtctcac   8160
ctgtcggtga gggcaatcct aggttgagca gcacagtcaa cctagccgcc gtgctaaaca   8220
cggagctgga ccatgcatta gacgagctga gtagggctcg tgctgagatc gcccagctgc   8280
gggctgagcg cgcggaacgt cgtcatctgg atggtggttc cccgctcccc gtcgggactc   8340
agcacccgta ccgctcacct cagcgtggac accagcctta tggcaatccc gactgcaaga   8400
ccaagataaa tctagaacca tagatcgcta gagttggatc ttgtaattaa tacgaaatat   8460
atgcatagaa gcttcagtct tagcgttaat ctcggtctta gttagtctta gttagacagg   8520
gtagtttgct atatcctgtg catttatgtt tgtcatgatg aactttgttt ggtttggatc   8580
tttgtaatga ttgtcaccag agtgtgggta tcccctgcat tttggttcac ctattatgtt   8640
aataaagtta gttatatagt tgggaaacct tttattccac tttcctcttg atctgagaag   8700
ttgtgtggtc tgtgttggag atcagtgaag atgctcacct gctcagtgct gttgaagaat   8760
tctatactct tttcttatgc tgcaagattt gccagatcag ttctgatgtg tggttgcatt   8820
ctgcagatgt cagagaacag gcgcagagga ggaaggcgtg ctcagcagga gcaagccggt   8880
caacaagatg aggcgcccca gcagcagcag ctgccacccc cgcccccgat gtcgatcgag   8940
cagatgtttc tgatgcagac tcaggcagtt caggccatcg gtcagactct ggccgccatt   9000
cagcagcagc agcagcagca acagcagcaa gcaccacccc agcctcagat gcctcagatg   9060
cccagagaca agcgtgctga attcatgaga ggtcatcccc caacgttcgc tcactcttct   9120
gaccccatgg atgctgaaga ttggctgcgc actgtggagc gggagttgca taccgctcag   9180
tgtgatgaca gggagaaagt cttgtatggt ccccgtctgt tgagaggagc agccc        9235
```

<210> SEQ ID NO 32
<211> LENGTH: 74400
<212> TYPE: DNA
<213> ORGANISM: Zea mays

<400> SEQUENCE: 32

```
atatatatat atatatatat atatatatat atatatatat atatatatat atatatatag     60
atagtattta gagccctggg ctctatttaa ctacaggaag ccctgaccag gtgcgcagac    120
cgcaccggac cctttttggt ttattgtacc taaatgtgct tacgctaaat tataatacga    180
gttatgctga tgtgtgtatc agtttatgca aatatagtct gcgcgtatta cgtgcatcag    240
gcccacgatc cggcccacgc gttcacaatt attcagtccc acgccgacac tataaaaaca    300
cccccacgcc gccagggatt aggttttagc ggcggcggcg gttccctcgg gcgtgcgagc    360
agcggtgatc ctgggggcca gcagcggtgt cgcctcgagg caggcgaccg acggtggcgc    420
tccaccagga acgagcgatg gtggcgctcc acagggagct cgcccgcctc gccgccagtt    480
```

-continued

```
ccgtcgcgcg cctgcctgct ggggctgggc tcggcgggag cggaaccgcc gaggaggccg    540
agatggccgc cgcgctcatg gacgtcgcgg ccgccagcgc cgccgcctcc gccgccgtgt    600
tctcggccgt cgcgtccgtg tctgccgccg cgtcgtcgtg ctcgaacaag aaggccccga    660
cggccttcgt ggctgctgcc ttcgccaaga agccggagac gccgacgacg accgatgtcg    720
cacaggagaa gcacgaggag cttgagcgat gcatcgacga gtgcgagagc ggcagcgagg    780
tggtgttcag gagcattgtt cggaataggg tttcgttgct caacatccat agtccggcga    840
tctagagaat cgatctctca tatcagtcgc catcacaatt tagttaacga ctattgtata    900
ctatgctaca tacgtatata tacagtgtaa atacacgttg aaacaataga gaataaaaat    960
atatatgtgc agttggaaat aacacagaaa ttcagtcagc atgtatagcc ccagggtaaa   1020
ttattaaaat tgtactactg taatcatcag gagggcatta tttaaatgtt gtatgattta   1080
cgctaaaatt cgcactcatt tacgctgttt tagctcacgt tttacgctgg aatccgcccg   1140
agcagaaccc gcgaactgcg gctataaatt aaaatttatt tccttctact aatgctcctc   1200
aaaccataac tgtcccttta tttacgcgat tatgcagcac gtctttcctt atatcaaacc   1260
ggtcaagatt tatataatgc atggtttatg ctatcatgtt acacatcgtt atgcagtcgt   1320
aaacgattta tttacgcatc gttatgcagt tgttaaccgc cgccaatatc acagatacga   1380
acgtggacga gcggctgtaa atgagaattt gtttcctccc gtaactgtgc ctttatttac   1440
gcgaacgtgg ggcacgtctt tctttatctc aaaccggtgg atatttaaat gttgcatggt   1500
ttacgctatc atgttacaca gcgttatgca gtcgtaagcg gtgcacacat ggtaatattc   1560
gttcccgtga ttcgtggcac aaaagattcc ttctatgcat gatttatgca catttctaca   1620
tatatttatg catgcgtata ttgcctgtca tatgcatggc tgacgcatgc tggcatacag   1680
tggcccaacc gcgacctggt tggcgtcctg gctggggctt cccccactaa cggaagccca   1740
gggcttccat tacctcttcc ctatatatat atatataaaa cgtaggtgac gtatattctt   1800
catatatata tttttattaa attgcagata cccgttattt aatatgcaga tagaatttga   1860
tacctatgct atgaatgaat aaatttatga atatctgaac ctcatgtatc tacgactacg   1920
aataaaattt taaatccgtg cctgcatcca acggctatga aacccgcgca tgtcgacgcc   1980
cgcgcgtggg aaagattatc accaccaagt accaacacac aacacgtttc acggctcgca   2040
ttggccgcgg tcggcggcat aggaagaaga aaaaactgcc ggctgctgct gcgcggccca   2100
cgtacgcggc atgcagtggc gcaccatgtg cccgtgtcac acacacgtta tgggtttgtc   2160
tgttgcggca aattaccgtg caggacggga cgggagccat ccgaatcgca tcgcactcgc   2220
acgggtgctc tccttaccga aaagacccgt tgtccggcgg cctgtgtgcg tcgcacgagt   2280
actagtattg ttgttcgcat gtacttgtcg ctaataatct ggggttttgg gaatttacag   2340
aagcgttact gtttaggagg agtaccctcg cctcggtgac cgcaagtcgc cggcggacaa   2400
gcgattctga caccgcgcgg acggcgagaa ggacagaggt gactggacga ccgacccccc   2460
tcggccccac cacgtcgacc caaataaaaa acgccacctg cacgcggctg gctccaccta   2520
ccactcgatt caccaccagt cgtccttcct tctcattccc ccagccaaac ccccggctcc   2580
atcgaaccaa acctatttga atcgccaaag ccggtggcgg tgggtctcac tctcacaggc   2640
agccctccgc tcctcgtcct cccccccccc cctgcttcgc ttgcctagcc ttccgtcccc   2700
tgctgtctgt ctccgaagcc ggcggcgccg ccggaaatgg aggaccccct cgccacggcg   2760
ccgccaccgc gccggcccca ccgggagcgg cggcaccggc ggaaggcgtc ggacgccgcc   2820
```

-continued

```
gcggccgcgc tggcggcgca ggcggcgtcc tcctacggcg acgtcttcgg cgggcccccg   2880
cggttcgcgc cgccgcctgc cgcgggggcg gggactgcgc cggcggacta cgccgaggtg   2940
ttcggcggag tcgcggcctc ctgctccatc ccctacctcg acctgccgcc cgccgttgcc   3000
agcggagtcg gcgctggcgg gtacggcgag atcttcggcc gcttcgactt cggggagttt   3060
gcggtgccgt acgaggacat gctttctggt gcagagtctc tggtggagga gatcgcgtca   3120
ccaagtggga gctcaaggta cgaactctgg ccccgtttca ggatttcgtt ttttttcttc   3180
ttcttcccag ccattgtgcc actgttgcct gaggctcatt gttcgggcca agaattctgc   3240
tccgctttta gccgaggcct taattttttt tggcgatttt agagataatg ggtttaatgg   3300
ggctaggttc tgcactgtag agagtttgct cgtctttacc gcacacaccg ttttggcgac   3360
gaaatgctgc ctttgcgtaa caatctgcgc gttggttccg ctctgctttt tactatttcg   3420
gctgatttgt tgtgagtagg atggtggaat gtcgtttcca agctacgtgt actgcatttt   3480
ttttctaatc cataaaggtt attgtgtttg gtgaagtgct atatttcgtc acgcgttcaa   3540
tactcacgat tgaaggagct atatctgtat atatatggag ttcttttagg aaatcctttt   3600
tcgcataaaa atattgcctt cgggttgaag tgctgtcttt tttcttctcc actttcgagt   3660
tgttttaaaa tcgaagaatt agcgaaatgc ctgtgaaatc ttgaatttta cttatgaaat   3720
ttatgtaatc gtgtgttttc atgactcttt atttctgtgt tgactagata tgtgtcatga   3780
tgacgacata taagggcatg tacagtggag agacaccaaa acggttctcc aagcacagga   3840
gacaactaag agactattgt acaatggagt gtctataaac gtagtctatt aataaataca   3900
gaattaaatg tatttgtata gcatcagatc gatagaacag acgacaaatt cgtacagtgg   3960
gaagtgaggc gtctgttgct acttgattta cgagccagag acgtctcttc acggagagac   4020
agctctaaga ttttttttgca aataaccccc ttaaacaact taagagactc cacattaaac   4080
accactgtac atgccctaat tatgaattct gatcctaggt ccccaaaaca tgtcgtagta   4140
acatactaac atttcaccta aaagtgtact cccgtaatgc aatggggcac tgactcaaac   4200
cctgcttccc tcctaagttc aactacataa tccctttagc tactttcata ttttttaatt   4260
cattgttttg tagttctttt ctgtgtcttt tcagggaatt cttagctgtg taaagtgggc   4320
tgaccttttg atgtcattga caagagtgaa tgcacatgcc atgttttatt gcttctgatt   4380
tatgctcatt acttccatat ctacagatca tcaactagaa aagaatcggt ccgattggat   4440
actgagccat ctgtacccta tcaacaagtt ccagatgctg gttctggcag gcactctgat   4500
gacgagcaat ttcatgcagt ctcctttcct ccagatggcg agcaaacgtt cactatgtca   4560
tataacaaga tcacccgggg aaggccagat gatcttgttg aaatgaccgc ttgcatagta   4620
gaaccttcaa ttagctatgt ggttgactct tgcaatttgt caaatgattt agaaatggat   4680
tatgtcccag taatggacag tggcacaaat gctaatgttg tgaaagaaaa gatgaaccta   4740
ccaaacattg cagattccgg cctggagtgt gctgatagtg cttatgtggt tgatcatcag   4800
caacatatcc caacatgccc tcccatctct gaaaatattt gccaggatga aaactacaac   4860
aagaggtcta gcacacattc agtgtcaagc gaggaagcac cttcccctga ctatccattc   4920
ttaagggtat ccaacatcaa ccttccagca gcacccatca aagtacaacc accaccgatg   4980
cccccatcta aattgcttaa taaaaaggga agcaacgaaa atggagattc tgatgtcaat   5040
cctaactcag ttgctgctgc tgctgctatg aaggaagcaa tgcaatttgc tgaagccaga   5100
ttaaaagctg caaaagaatt gatggagata aaaggtgtca gctctaaatt ccgtaagcgg   5160
ccagttcatc acaaaagcac aaaatcaact gaaattaagg aatacaatgc acctgaaaaa   5220
```

-continued gcacatctat ttgaagaaaa gctggatatg agaagattgg taaaagagga aaatcaaagc 5280
aatgatatag ctttgctgga taaaaacacg ggcagtgttg cacttgagca cagtgatcat 5340
gacaaaaaag ggattatatc accagggaag cctaaggaga tgatgcaaaa cgacagtgaa 5400
ctagaacaat taggagagtg gacatcagat gctgattttt atgaattggt tagcaatgat 5460
cagaaatgca gaactaatgg agctgaatgc agagacaatg gtctgatgac aaattcctta 5520
gccaagcttg accggtctga gaatgaaaaa ttaggaggct ttgcaggtga gtcaaaaagg 5580
tctaggaaat tgtgggattg taacaacaga acatgtctgc ggactgaaca tgtaaatcag 5640
ggaaaagatg gtataggttc attggaggtt gaacaaaaga atactaggtc tccagaagtt 5700
acagaacatg taaatcagca aaaagatgct atagattctg tggaaactga acaaaagact 5760
cctaggtcac ctgaagtttc tccttgtaat gaaagggtga cgtatgaaga gccaaccaaa 5820
ggaaataatg atctgatgac aaattcttcc accaagctcg accagtctgt gaaagtaaag 5880
gaagggggtt ttgcaggtga gccaaaaagg tttagaaaat tgtggggcag taacagtaca 5940
acagttctga gaacagtgca tgtaaatcag gaaaaagatg ctatagcttt cgtggaggct 6000
gaagaaaagg cacctaggtt ttcggaagtt cctccttgtg atgaaagggt ggcatcccaa 6060
gaggcaactg attcccgttt agaacaatgt ctaggggtgg ggaattctct aggtcacgaa 6120
aatggtgcac aatttgagac ttcatgcgtg aataatttac cttcagaggt ccatgcagac 6180
ccagaaatct ccagttcatt ttcggaatgt tgttcatcag gaagtcatgc caatggtaat 6240
gaaaatcatt ctgaaagcac agctcaggaa actgcatttg tagggaactc tagccaaaat 6300
gtcaacaata aagaggaact tgagcttccg tgcattgatg ggttgccttg tacttcagca 6360
aggaatcaga ttttgcagga acattttaat gttattaatg ctgatgaaaa caaggaaatt 6420
gaagtgaaaa tatcaaaatt agaagggtct tccaaatctt atttgaattt tgaggaagaa 6480
aagttaccca gttttgttga tgaatcatgc ctacagaaca aaaatgaaag agaaaatgaa 6540
gtaaattcag aatcacccat ccatgaaaag atgacaaagt tcgggtttga ggacaaaggt 6600
gatgcatatg aagattttca agagggagat atggatcagg ttgctggatc tgctgaagag 6660
gaaggttatg ttacttcagg aagtggtatt gctaatgaaa gcgaatatga agaagcagaa 6720
gatgatatat ttgtaggaga catggaatca aatgtaagaa acatgtggta gttttgacaa 6780
agatccatat cagcgccaag aatcacaagg atcatgggga ccccaagatt tggataatag 6840
aatggacaaa atcagtgata caatatctca tggaaaggaa agggagacta aagaatcctt 6900
gctggagaat gttgaaaaga cagcggcaga agaagtacta aaccatgact gcagggaagg 6960
gcagaaatcc atggaaaccg ttgactacat atggcccaaa tatgtatgtg cagaatttaa 7020
tgtaagtagt gacaaagatg gtaatgtgtt tgattctgct gatgaactta tcagcgacaa 7080
tggcagtgat tatgccatga acatgagcac aatgtcaaat aatctgcaag cttcgttttc 7140
agaagcatgc agtagcattc aacatctttc tcaaaaacct cagtctattt ctgctgagaa 7200
ggctgatgaa agcactcctg ttcttggaaa tcttgaagtg gactgcggag aagcaggtag 7260
aaaaattcca agtgaaaatt gtgaagtctc agaagaaggg caaaatattg gaatcgaaat 7320
ggaagaaaga aaaagagaag acaatatatc aaatataagg ttcatggatc agcaaccatt 7380
ttacttggac agtgacatta gacctaaggc tgcagaaggt actgcatcag aaactattct 7440
aaaatccaga gaagaggatc ttaatgttca gagaactaaa gtgaggaatg acataaaaga 7500
ggctgaagga gaactcgaga aggaggtaaa agttgttgaa gagaaagaaa aagaatgcaa 7560

```
aatgggaaaa gagaaggaac aagataaaga gagacaaaga agagagttgg aagaacagaa   7620
ggaacgggaa atggagcgag caaaagatag gcttgctgtt cagagagcta caagagaagc   7680
acatgaaagg gcattcgccg aggttcgagc taaggctgaa agaatagcat tagaaaggat   7740
cacctcagca cgtcaaagag catccgcaga agcccacgag aaagaagaga aggcaaccgc   7800
tcaagcagct ctggagcagg cttcaaggga agctagaatg aaagcagaac gtgcagccgt   7860
tgagagagca actgctgaag ctcgggagag ggcaattgaa aaggcaaaag ctgctgcaga   7920
tgcaaaggag cgaattggga agttcaggtc ctctttcaag gatagtttta aggcacctaa   7980
tcaggtagct gatgtcatta tgcatgcatt tttttgttgc atacacaaaa taaacactgt   8040
tctaatccgc attcttgaca caggacaatc aacatgaggc atcatctcag aagacggctt   8100
ataataagca tggaaaaagc atggattctt gtgttgaagg tattgctaga agtatatcct   8160
actgcaaaat agttcaagta tttgtctgtg caattttctg taatatttct atagtgttat   8220
cttatttgaa acatgggact tgacttgctc tggtcatgtt ccctatttat agtagtcgag   8280
gttgagtcag ctctacgaca taaagcaaaa ttggaaaggc accaacgcac agctgagcga   8340
gcggtatact tcaatgctat tgctatgttg cattctactt gtttgtttgc ctagcctgtg   8400
gcagtcctca tcattaccaa ttttcaggcg aaagcccttg ctgaaaagaa tatgcgggat   8460
atgctggtgc agagggagca tgctgagaaa catgtaagat agttggtcat caggaaagaa   8520
aaacatattc ctctgtttct aaataacatt tgttatccat gaacttttta cttttggata   8580
cagagactgg ctgaatttct tgatcctgaa gtcaagagat ggtcaaatgg aaaagaagga   8640
aatctgcgag cattgctgtc cacattgcaa tatgtacgtg ttttggctta tatgacttct   8700
atttgaacca tgtacatctt ggttactgta ggacttccac tggttcttat cagaaactta   8760
tgcccatcat tagattgcca ataaataata ctcctaatca tgggtgctcc agttaaaaaa   8820
tggatcgtat gtaaattcat ttcagacagc gcaagaaatg gttagctact atacaccagg   8880
tttaccacat tgtgtataat atatattttt tgttcatgtt aatatcgttc aagagtgtca   8940
agcataaaca taaatagttt gtaaggaaaa aaaaatcaag caccatgcgt taggtcatgt   9000
ctcccactaa tttattactt atgtttatgc catcttatct gttttgagaa ttttcttagc   9060
atgcatattt ttttatttca gtatgcatgc ataatccaat tcgttggagg ttcactcttg   9120
atatagtttt ggagaaaata actccatgag ctctttcttg agttcactta gctcaattct   9180
gcattatcat ttgactcgac ctgcgggggt aagaccgccc ccacggtatt atgttaagaa   9240
gaaaaccttc tcacgcaggt cgagaaaacc cccgaacccc tgccccaccc atacacagcg   9300
gcatcgtagc ccatgtgaga acgaccgcga ccggggctga gctttagacc tgtgctttgg   9360
cgtgggacag acgaggagat tttttaacca cagtctgaaa attcgctccc acagggagtc   9420
aaacctaaga cctgaggagt actacttaaa ccatctacca actctagagg ccctttctct   9480
gaatttgact tcgaatcaga caccagtcca atcatgcatt ttttcttctt ctgggcagat   9540
acttggttca gacagtggct ggcaggcagt tcccctcaca gaccttatca cagctgctgg   9600
tgtcaagaag gcatacagga aggcaaccct ttgtgtccat ccagataaag tgcagcaaag   9660
aggtgctaca atcagacaga aatacatttg tgagaaggtg tttgatcttc ttaaggtgtg   9720
ttctttggtc atcttgcttt ataaattagt tacttatcta cagttgctta agtttcaata   9780
tttttgttgg tatggctgct gctatactcc caagttctgt tagcctcagt cacctctggg   9840
agactgggac tatgttgatg tttctgcatt gctgtggtgc ttcacagatc cttattataa   9900
tgcaagcatt cgacttttcc tttcgaatgg agcaccatat tctgcattca tacccagcta   9960
```

-continued

```
tccatattct ctgttccaga catggatatc tgttagatgg acctatatat ggggaatatg  10020
cattacggtc tcattgctgg cctattgctg tttcattccc ttcatgttca tttctgaatg  10080
tgtaagatat gtgttcattt ggatataaca atacaactat catagtcaaa ttagtgtgaa  10140
taataagaca tgtcatacaa aggcttactt gccagcaggc tttcaaggac attcatttta  10200
tgattgacaa aaagcctact catgcaaagt gtatcatgtc ccaaaactgg ctgcatcaaa  10260
gaaaatacaa aaataacacc gaatcaatac tgaattagta atctgtacga acctggcatc  10320
cgtgagagac tggtaacaga tctagtaata ctgcgtttta aaatgcttgc tcattctaaa  10380
ttgtgagtac gtctctggcc acgcctttcg taaaatcttt ggaagtatgc ctgttgctaa  10440
tgactagcga aagcaagtct tgtgttgata atttgataac tgtctttccg aatatatcaa  10500
gttacttgtt gcgataaagg gaggctaact ttttcactcg tgatcgattg tgcaggaggc  10560
ttggaataag tacaattctg aagagcgcta gtgggatagg tggttcttta tcaattgttt  10620
acgggggaca ggatattggc taggtatctc tgtagcattt gccatactga ttattttta  10680
cattggtgaa aatatgcagc tgtagagggc atcttctggt catttttat ccatatcaat  10740
gcaatagtag agcatatgtt gtctcttatc tagcatcccc aagtttacct ttgctagact  10800
ttagttgtgc accttttgcg ttactttgac cattcctagc aaagtttgcc tacgtttggc  10860
gatcaacttg aagtagttga atttatattt tctttctgtg gctgagtgac tcgcagttgc  10920
gggggccttc tattcgaact agtagctgca atatgctcac ggagaatttg taccatttgt  10980
attaaagaat atcatgtgtt atgttactag ttggagctaa aaagaaactt aaattaacta  11040
cggttggtta gttagcttgg taataactag ttgaagattt gacaaaaaaa ataattcatt  11100
cgttagctct cctattttga tgtactagag ttaattttag ctattatttt tgctagctaa  11160
caattagctc ttgtatcaaa catgtccttt aggggttagt gttggaatct tctatataag  11220
gccttgttag gttattccaa ttctatgtgg attggagtgt attgggatga attgagatga  11280
attttgactt gttatggatt taaatcgact taatatcatt taatccacat ggattaacgg  11340
cgaaacgaac aagtccaacg tttgctctca atctatatgt attgggtggg attaaggcta  11400
gtttgtttcg ccgttaatcc atgtggatta ggtgatattg agtcggttta aatctataac  11460
aagttaaaat taatctcaat ccattccaat acagttcaat ccacatagaa ttggaataag  11520
cgaataaggg cttaagtggg ttttgatccc gaacaagtca aaaaaattta tatttttca  11580
atttcattta atccacacga gataagaata accgaacaag tcctaaatat aaataaatgg  11640
ggatatggga aaagataaac caaggcaagt tttctttcat aaatatgagg aaaggtgggt  11700
tcgaacccat gacctggtgg ctcagcgaga attcccacca ctgtatcaaa catattcttt  11760
acatagaaat tgtttcttag acaaatagtt attgtataag aagttttgtt tgatctagaa  11820
catcttttt gagttgccgc aaaaacgata acgaccatat caggtacaat cgcacatatt  11880
tagtataatc atgcaaccaa aacataaaca ttgaggtgtg atgacctatt ttaaaaatag  11940
ccttgagatg tgtaagtttt ttttaagtat ttttaaaaag tcctttgcac ctctatcttt  12000
gtgttttgat tgcagagtta cacaaatatg tacggttatg cctgatatgt ttgtaaaaca  12060
gtaattttt ggatatttgc atttgtatta ttatagttct ttaagttttg aaagctacca  12120
ttattatcca cctacttgaa accatgccat tacaattaca actcatagta aattgaatcc  12180
atgatatctt gtaggctagc aaagatgtta tgtccaatga agtgcattat atttttatag  12240
acaaagatac tccgacaacc tctgtctcct tccacctgtt gacgaatgga ccttgcaggc  12300
```

-continued

```
tagctgttga atttttacct agctccttca aactctctct aatgtagaca accctagcaa  12360
cccctctctc tatctccacc atacctacat agccccatat ctctctccaa tgccccccctc  12420
atcgatcgcc cgtgcacagc tagggctgga cgaaaaactc gtagctcgtt aactcgctcg  12480
gctcggctca actcgatagt ggctcgactc gactcgtttt ataatttgta acgagttgag  12540
cttgtatttc aactcgttac gttaacgagc cagctcgagc tggctcgcga gctgactcgc  12600
gagccaaacg agttggagta attagtcaaa tcacaataat ctccgatcca aaatagttaa  12660
tcttgtactc tcctatagtt aatcttgttc tttgttgagt gtggaacctt aagttgcaaa  12720
ctctattatt ttttctaaat agatctcctt ttctaaatag acatggtatt atcgagctgg  12780
ctcgcgagct aaacaagcca gctcgagttg gcaaacgagt cgaaccaagt tggatcttta  12840
gctcgttaac ataacgagtc gagccgagcc agctcattat cttaacgagc cagcttgagt  12900
cgagtcgaat cgagccgaac cagctcgata tccaaccctc agctcgatat ccacccctat  12960
gcatagctca ccgcaagctt ccgcgcattg ctaaaaattg atggagatcg gcctacagtg  13020
acttctcaat cccgtcgcct gcctcgtccg gttgccagca gagggcctgc aggtcggcgc  13080
cctcgacagg actgtccaag acaggctagg cgtctagtca gtcattaggg cacgatggct  13140
ctcctcgaag cccctcgcta caggggacag atgaaggttc ctctagtacc acgaccgccg  13200
ttggggtagg acctccactc cctccaacaa aggacgcggg ggcaagaata atggaggcct  13260
gagccgagtg agacaacccg tctgttcggc aaacctagat caaaggccag gaagccagcc  13320
agcctaggat cgagtggaac attcattctt ggccaggaat cgatccacgt gaggggacac  13380
ttggatttgt tctaggtgga gaagtgagaa tggggagtca aaatgagatg gatttgttct  13440
cgatccgggt caaaacgaac aactagatcg gattccaatc taggccaatt tgttcaacct  13500
ggaaggaggc tggaaacatg ccaattcgac cgatacgaac gcgccatggg tgccgacgga  13560
gttggcttcc gagcctgcta cgaaaaaggc taaccctcat ccgccttgtc caaattactt  13620
gcgggaaatg aaaaaatgaa ccggaaacac tagacccgac gacctcggtc gagggtggcg  13680
gggaaaaggt tcccgacgac ataatcgtgc tgcctctccc attgaaagca ggcaccaccc  13740
tcctcttttt caagatcacc tttctcagat acgccgtggg agccgcgagg cgaagagtgc  13800
ttccagaagg aaaaggagcc gactcaagaa ttgcaacaaa agggaggcaa acaatgggcc  13860
aacgatgctc gccgcccgcc gatcgcatag tgacaaacct acgcttctta tgcagtgccc  13920
cgctctccca tgacttcctg ttcctgatgg agtgccacac ccgccaccta cgacaggggc  13980
gaccagggga gcccctagag atacgacact cggggcctcc gacatgtctg ccacggcagg  14040
gacacctcca ctagccgccc caaacgaccc acaagaaaca agttcgacga gcgagggagc  14100
taacaccacc ggagccgctg gaccaggaga aaggacaggg agatccaaga aatcagcatc  14160
atccacggcg gagaaaatgt tagccgccct cctattataa gattagagat gtcaatgggc  14220
acccgatacc cactaacccg tggggaattc ctctattatg gtacggttat gggacaaaaa  14280
ttgtctccat atgtatggat atgggacaaa aatctccacc cattgggtaa acgggtatgg  14340
gtttggaaag caataatctg aacccgatta cccataggta tttcatacgt gtatatctgt  14400
cctgtttgta tgaatgagtt gaggccgagt cgaccaccaa gcccagcacg gcagcgcacc  14460
aggcctaggt cctagcccaa caaggcaaca cagcaagaca actagcagac tatcacaaaa  14520
caaaacccta aaataatcag ccatacgcta caccctgccg agctgcctga aagggaaata  14580
ggcttacacc ttttcctaaa tgattttggt ggttgaattg cccaacacaa ataattggac  14640
taactagttt gctctagatt ataagttcta caggtgctaa aggttcaacg caaaccaata  14700
```

gaaagtccaa gaaagggttc aaacaaaaag gagcaaagac aaccgaaggc tgccctggtc 14760
tggcgcaccg gactgttcgg tgcaccaggg tggattctct ccaactcgct agcttcggga 14820
atttgaggag ccactccgct ataattcacc ggactgtccg gtgtagcacc ggactgtccg 14880
gtgtgccagc gcagtaacag ctatacagcg ccaacggtcg tttgcaaagg aacagtgaaa 14940
cgctattgtg cgcgcctgcg cgcgcagaag tcagagcagg cgtcagatgc gcaccagaca 15000
gtgaacaaga cctgtccggt gcaccaccgg actgtccggt gcgccatacg acagcagact 15060
tccacaacga ccattttggt ggttggggct ataaataccc cctagccacc acacttcaat 15120
gcattcaagt ttttagccat caaacctcat acaagagcta tagacttcat tccaagacac 15180
aaacaaagag atcaaatcct ctcccaagtc cggaatcact ccaaacaaat tagtgactag 15240
agagagactt ttgtgttctt ttgagctctt acgcttggat tgcttttctt attcctctat 15300
tcttgttccc aagatcattg taatcaaagc aagagacacc aagttgtggt ggtccttgtg 15360
tggactaagt gtcccatttg attgagaaga gaagctcact cggtctaagt gatcgtttga 15420
gagagggaaa gggttgaaag agacccggtc tttgtaacca cctcaacggg gagtaggttt 15480
gcaagaaccg aacctcggta aaacaaatca ccgtgttcat ccgctttatt tctttgttga 15540
tttgttttcc ctctctttcg gactcgaatt taattctaat gctaaccccg gcttgtagtg 15600
tgcttaaact ttataaattt caggttccgc ctattcacct ccctctaggc gactttcacc 15660
acccaaccgc cgcacgccta gaaagttgcg ctgacactgc acactggcga ctttaccagc 15720
aacaaggagc accaccggct gctaggagcc taggatgacg gtgatggcca tggattttca 15780
agcgccaatg aactcggatg gtgaccaagg aaggtgagca gactccattt cttctattgg 15840
tcccgaagta ctgatttctt ttctgatgga tggatgaatg gatcatggtt catagatgag 15900
tgcttgacag gtggtgatgt ctgaaatctg gatagtttgt gctagttgtt agtacctagt 15960
tatctcttaa ttgcggatgg ggacccattg gggacccaaa acctgaatgg gaatgagtat 16020
gggatgagtt ttgcacccat gatgggtatg gggatggatg aaacatgatg gggataggtc 16080
tgagatgcta taactcggtg gggaattccc cattgacatc tctagccaag atggcatcag 16140
ccgccggtac atcaagggga gcgtcgccca cagggattac cgaaggtttc gagttcgcgc 16200
tcgcggcatc atcgtcctcc tcctcgtcgg ttgagttaat atcggcgcca cgatccccat 16260
gcatccgatg ctctaccctg cgacgtttct tctcgaccct ggctctcttt tccctcctcc 16320
gctgcaccgc ccttgggtgg gccacctcct tctcgatcac actttttggc aatcgaatgg 16380
gacgtcctat agcactggag aagaagactg gaaaaggatg aaggatggtc aagagacacg 16440
acaccgaagt cgaaagggga tcgaacaaac tcatgaattc aacgaaacct ggcttgggac 16500
gtatcagagg gtagccaaag aacgggaaga catacggatt agtggtcccg tctgcgccct 16560
tgcggacctc catggcttct ctaagcgaac gagcaatttc cgcatcgctg ggaggcaagg 16620
cgctcagttg tgtgccctct ggtaaagcat cggcggtctg cttgtacaga ggtagctgcc 16680
tggccataag gggagctacc ccatggtgga ggtagttccc aatcacccct tcaagcgtaa 16740
cccctcggtc acggagaatc gaaacgactg taataggtcc agtcgtcctc ttctctcatt 16800
cctttgggac accccacatc cagctctgag gagcctcagg ggtgctttgg gcaaaaatgg 16860
tggaaggctg cgaccggtgg caaggacccg tagccgtaga tgtataggta gaactactgg 16920
atgtgtcgac ccttattgga cgagcacaat cataactgga cgtacccctt gggttgagcc 16980
cctcagagat gatagccgcg caaccgatct atgccgcttt cgttggggtg tccgtcacca 17040
gtcgtataca aaacaattta gccgagaaaa aatggcacca ggggcaaaag tggggggcat 17100
cttgcggtat tcctcgcaca aagccacaaa agcggtcata tgttgaactc cattagggtt 17160
gaggtggtgt agtcggatct tgtaatagtg aagaagcccc accaggaacg ggcaccacga 17220
agccccactc gtggaaatgc atgaacgaaa ccacgcagct cgtcgacggt tttggaacgc 17280
cctcggagcc agggagtagg tggtctcctt catgtaggag gctacgagaa atgagcgcat 17340
ccaggtggct ttgatcaacc aaggagcggc tccagaatcc catgatcacc caagagcgaa 17400
tggcggtggt agggattcaa ggcgagaggc aggtagcggt gatggagtaa gagacacgcg 17460
acgccctata agatgaatag ggaaccaaag caaagtggcg cctcaacccc aaattgatag 17520
gagcgaccca ccacgacgtg accttcaaat tgaaggcacg acccagtaag caataaagaa 17580
tctaaactaa catgttgccg acaatggtga acaggcctgg tccaaacaag acgcccaccc 17640
ccgaggttcc gacccaggcg cctggcgaca accatgcggc gcaggtacga cgctgagtcc 17700
cgaagccgca cgaccatgct tggttatgat gactcatctc gccttgtcga ttcgtgatat 17760
tatctccccc aacaaggaag gaatcagtgg gcccacaccg accctcgaag ctcaaccaaa 17820
gtcttgaagc gcttgattac aagcgccatt tcttcctcat taaggtcatc tgtctcaaca 17880
tgtgccacct tgtttgggag cgcctccttg ttggttgttg ctttgagtgc aacgggttgc 17940
ggctcgtatt gaggaagagg tccgttggcg atgtcgtcga tgcacattgc ttcttttacc 18000
atcatgcacc cgcttacaaa cttaccaaga attacttcgg gtgacatttt ggtatacctg 18060
ggatcttcat gaataagatt aacaagatga ggattaataa cagtaaatga ccttaacatt 18120
aggcgcacga cgtcatgatc cgtccatctt gtacttccat agcttcggat tttgttcact 18180
agggtcttga gcctgttgta cattttagtt ggctcctcac tgaaagtcgc ctagaggggg 18240
ggggggtgg ataggcgaaa cctgaaaatt ataactttac accccaacta gatcccttga 18300
ttagtggtta gaacaagata cacatttgtc ggagtataaa aactaagtcc tttgcttgta 18360
aggagtattg ctttcaaata atgtggaatt gataaatcaa tactactaat aattctatga 18420
gaataaatca agagggctta gataagaaga gcaataacac aagttctttc ttgcaaggtg 18480
ttgcttcact aaatgagaat ttaacttaaa gcaacaccaa atattattag caaagaatag 18540
tgcaagaaaa acttataaag ggaaagaaca aacaaatcac aagcaataag cacacgagac 18600
acgagtgatt tgttttaccg aggttcgacc ctcgaaggtc tagtccccgt tgaggagtcc 18660
actaaggacg ggtctctttc aatcctttcc ctctctccac cgatcacaca agatcggcga 18720
gctcttcttc ttctcaagga tcacttaaga ccccgcaagg atcaccacac tctttggtgt 18780
ctcttgctag ctttacaacc ctccaaaact ttggaggaag ttcaatggga gtcaaaactc 18840
cacgcgcaaa tgaacacaaa gatgtagcac acactatctc tcaatgaatc tcacaaggca 18900
cacactatct ctcaatgagt agctctctct tgcttgctct ctttttgtg gcacttgtgt 18960
tggttgtagt ggtctaaatc ttgtgtatag gatggatcaa tgaatagagg tggttgggag 19020
ggcttgagta tgtcaactat atgacttgga atgttgcttg ggctccctca ccttgaagtg 19080
gccggttggg gtggtattta tagtcaccaa ccaaattgta gccgttagag aaggctgctg 19140
gcgatgggcg caccggacaa tgttcggtgc gccgccacgt catcctcccg ttagggcttg 19200
gagcttggtc gaccgttgga ggctttgtcc tcatgcggca ccggacagtc cggtgctaca 19260
ccggacagtc cggtgcccct ctgaccatct gctctgacat ctgaattgca ctgttcactt 19320
tgcagagtcg accgttacgc gcaggtagcc gttgcctcgc tggtgcaccg gacagtccga 19380
tgaattatag cggagctgcg cctgaagaaa ccggagctaa ggagtttgag ctgattcacc 19440
ctggtgcacc gaacactgtc cggtggcaca ccggacagtc cggtgagcca gaccagggca 19500
cactttggtt tcctttttgc tcctttcttt tgaagcctaa cttgttcttt tgattggttt 19560
gtgttgaacc tttggcacct atagaatgta tgatctagag caaactagtt agtccaatta 19620
tttgtgttgg acaattcaac caccaaaatt atttaggaaa atgtttgacc ctatttttcc 19680
ctttcaatct cccctttttg gtgattgatg ccaacacaaa ccaaagcaac tatataagtg 19740
cgaaaatgaa ctagtttgca taaggtaagt gcaaaggtta cttggaatta aactaatatt 19800
cttttcataa gatatgcatg gatgctttct tctgatttaa aattttggac catgtttgca 19860
ccacttgttt tgttttgcaa tgttttggaa attctttttt aaaatctttt gcaaatagtc 19920
aaaggtatat gaataagatt tcgagaagca ttttcaagat ttgaaatttt ctccccctgt 19980
ttcaaatgat tttcctttga ctaaacaaaa actcccccctt aatgaaattc tcctcttaga 20040
gttcaagagg attttagata ttaattttga agggggttat accaatttga atattttatc 20100
aaaaataaga taccaattga aaaatctttt cttaactcaa tttgaaagac tatatttttg 20160
aaattggtgg tggggcggtc cttttgcttt gggctaatac tttctccccc tttggcatga 20220
atcgccaaaa acggatactt gtgagtgaaa tataaaccct ttttacgttc tctccccctt 20280
gagcaaacaa tatatgagtg aagattatac caaattagag ggctggcgaa atatcggcaa 20340
agagtggata ataccaatgg agttgagtgg aagcaacgtc tttgccaaat actccatttc 20400
cctttcaatt ctatgactaa gcatgaaaat acacttgaaa gcacattagt catagacata 20460
tgatcaagag atatatcagt taaacataat catagttcta tgcaatatag attgttcccc 20520
ctaaatatgt gcatggagag caacacatat tttggcctta aatgccaatt gcacataatt 20580
aggttgatga gaacatatct atatcataca gaatgtgaag tgcattgtgt catagtataa 20640
gtgtgatgct catggcagtt tatgcactta tgaaagcatg ttagaaacat cttaagcatt 20700
ttacccttaa ggatttcaaa gaggcttaag gaccattcac ctttggaaca aaggcagctt 20760
atccttgtta caaagttaag ctttaagctc tttgacaata atattacttc actcagtttt 20820
aacaaagatg caagaatgaa tgtttgagaa gttaaactag gtatgaagca gggctaatgc 20880
atgaacatgc tttctcttcc tttttataca agatatgcaa agaaagtatg gacaaaggaa 20940
gatttaggta caagttagaa tgaaaggaag ttgttttacc cttttgtacc ttcacataga 21000
gacgctctct tcattgtgct ttgtccttag tcttagtcgc ttaagaccta tactcaagac 21060
aatatatgga aatattttgt acaagagaga gttctacaac tagtgatcct tttctaagtt 21120
attgtcagca tatatcaaat ggaccacaaa ttgcataata tatcatgaat tctcctttta 21180
acttagtgcg taccaagata gatgttgatt gagagaatat gcggcactaa gagacataag 21240
tgttaattga agttattcaa tgatcaaaca aataacagat gtgatcaaga gaacaacata 21300
tgcattaaat aaacttaaaa taggagaatc cattacatat gctactttag caatgaaagc 21360
aacaatcctt tataaaagcg atattatttt aacaagttgg attgatatgt agtagcatac 21420
ttcatgagaa acttattctc atacttgaga ctatgtgaga ttactaagat gaaggattag 21480
tttcaatata atcaagatat agaaataggc tccccctaaa aatatgcatc aagaaattga 21540
atgaattgga tagatgcact catttttaa agacaaatag ggagaagcat tattcatctt 21600
gatcaaggct tataagattt gcactaaaat aacttatgcc tagttattct cacaatgaaa 21660
aagatttaga atgcttacaa ccacaccatg attgttttga agatctcatt atccaagtag 21720
gttttgttgc tcttgatgtc ttcctttttc atttgagtgt cctccctttg tagttaactc 21780

-continued

```
tttttccttc caaacttatt gaaaatactc aagagagatg ttaatagcac aagggagtat  21840
atgatgaaga atgatttctt ttagataaga aatataaaca attcatcatt cacaagtcac  21900
acagacatga agtaaaatcc ttaacattag tgcacattat taagaaggag gaatgaacac  21960
tttttaaata tcttgatcaa tcataggaat tttacttctt catattgaat ttattatcat  22020
gatttaagag catatcaata tgagaacaga gatagcaaag gcatgaatta gattctaatg  22080
gacaagtgca ttttaagaga atgagattga atgcatatct agatgactta agtccactaa  22140
agaatctatt cttctcatag gtagaattta gagtaaataa ccattgatga gaactatatt  22200
tgattaagaa gatgagttcc catacctttg cttttacctt tcttcctttg ggtgaagagt  22260
agctcttgtg gcttgcggct tgcacttact ctcttgtaga ttttcataag taagctcaag  22320
agatatgtca ttagtaacac aagcactagt ttctcttttt gtaatcattt ttgacaagaa  22380
tggaaaatag attactaaag catggaaact ttataatatg aactagatta ttccatgatg  22440
tatgcttaat tttacacgca tagttaattc tttaagatta tgggaataaa tctaattcat  22500
aacatggaga gcaataaata tagaagaatc atatccaact taagcaaggg gcaaaccaac  22560
ataaatcatt ggattgactt ttcttttcat gatagattac gcatctccaa agagaaactt  22620
attctctaca tgtgagacta cttgggttac ttagataaaa gcattagtct cactcttcta  22680
gttatagaga gatttttcct tttataagtg tcctaaggat ttgaattcct tacatgacac  22740
cttattcttt taagaacatg gaatatctct ctatatctag aacatggcaa tgataggata  22800
aatagtgtaa agcatgccat gaggtactta caattactaa aagcatgtag attgccaaag  22860
taaagaaatg atgaatatgc aatgtaccat atgagaggaa tttcttcaaa gaatggtgaa  22920
ataatttaag atacttgcac ttaaaagcat aattgttatc atcctttggc tttcctccat  22980
gttgtaggcc ttgacttttc ggcataggat taattcttta tttcctacaa tatcaatatc  23040
ttctccgaga tgatatgagt tttagatata acaactcaaa ataactttgg gtcaatcttg  23100
aatatagatc attgaatatt gatagcttga gttaagaaaa attgaattaa ctctctcaag  23160
caccccaaag tttcatacca tctccttctc ctgcaaggct tgtcaagcat attttggtac  23220
ccatctcttg atgggtccat caaggttagt caacaaagat ctaggaaccc aaacgtcctt  23280
tgtgctagca ctaggtaaac tcattacctt tctagcataa gttgcaattt tggtgaagcg  23340
tcccgatcct ttgggactca aatgtgaaac aattactagt cccaggaggc tagtaaacac  23400
attccttcct tcaaatagta cagagtttag ataaaattat tacaataccg gggtacaagc  23460
tcgagagagc caaattagga aacgtagtag gaaaatacac tagcccaagc cacaggcaga  23520
actgggtgca gacacagccc tcttaatcaa gcatagcaga aaagaagtcc tcggcggctg  23580
aaaaacataa ataaatctgg gtgaatacac taggtattcc gcaagcccac cccgctcccg  23640
tagagagaaa gagacctatg atatacatgc tcaatttggt ggagttgtgg tcactcaaca  23700
tttttcttag agaaaggcag atacttgaag gtttttccca tagtcttata ctaaccaaaa  23760
actcaaccgc cattgagctt cccgctcccg tggccttagt ttctttccta acacctactt  23820
attcacacat tccccttttc ttgaaactca tagagaaagt tctaattgcc ataccatacc  23880
ggactcatcc ataccagtgg acacggacta ttcgaatagg tttcaaactc tgcgcagagg  23940
tgtacacttt acccactagc ccggtttctg cgatctcacc gtcgcgagac ccgaatgccg  24000
gatctctttc cttacccgta cgtcctaacc ttaatggtta tctggaagga gtcaggccac  24060
caccatgtcc aaaccggaca aatctttccc cctccttatc ctcccggtgc tccccagcct  24120
tcttaaccct ggggttggac cgcacgagtt cggattgagt gactgcccac acagtctcga  24180
```

-continued

```
gtggttgtac gataaaggag tacaggtagt gaaaatgaca agccggtcct tatatgaggg  24240
gataatcctt ctgctcacgc ctaaaccagc tgagccaaca ccttaggtcc tcccctaaac  24300
cagggagtcc ctgatcatcc cactcccagg gtgatgaggg tgagtaccct tcatcgcaaa  24360
acttttcaag aggagacttt atttgaagaa atcacatttc ctttcttccc aaaccacatt  24420
tcgtatccag aatgaatatg ttaatgcggg ccatctctca ctcacaatgc aatattcccc  24480
catagttccc ggcctaggca gtggtagaga gaatgggtaa tttatgcatc aagggaagga  24540
tggacttgcc ttctgttgaa gctctcttgg cacagaagat ctacttccgg aagttcgggc  24600
tccgaccctt cttccggagc tgcgggatcc ggatctgcgg tccccgcttc ttctaggaaa  24660
caggcagtaa aacaatacat caatagtgat ttatcaatca tagtgtgtca ttttctaaca  24720
acattattgt atgtaacctt ggaaatcctt tttgataatt tttggtgcat aaaatattga  24780
gaaaactatt taagtgggaa aactggtgga aaaagaaaaa gaaaagagaa atcctcatcc  24840
tgggctgggg gcacggcttt tggcccaccc cgggcgcgag cgcgtgcgct gaagcgcttt  24900
cggcccaggg gcggcccaag agcgaggggg agacggcgcg actgcgaggg tgacggcgct  24960
tctgtgggcc cacttgccag cgagaggggg ggaggaaacg gcatcgcggc cagacggcgg  25020
ggcgaaccgg ccgagcgagg gagaaaaggc cagccgccgg ggaagcttga cggcggcttg  25080
ccgccggtgg cccggttctt cgaccaaggg agggtggttt ggcacgggcg gaggctggcg  25140
attccaacgg taggctcaat ttggccggag agggttggga gggggctgcc cacggggagg  25200
gggcggagtt ccacggcggg gatcgccgcc ggtgggctct gggtggggga cgggggttgg  25260
aaggtggtgc ttcgggttcg tggctacgtg agggagctgc tcggcccact taatttcttg  25320
ccggaccaac ggagaaggag agggaggagg agaaagggac tcaccggaga ggagaacgac  25380
gccggcgctt cgcgaattgt gctcggggga ggggaggaga gggatggccg aggctggtgc  25440
gaggaaggag gggctcgggg cgagcctttt ataggcacgc gagggaaggg ggggcggtgg  25500
agcttctggg ctccggcgag cttcacagtg ccgccattaa tgctgcacag cgccgccgag  25560
gggacactac ggcggggcgg taccggcgag gacgctggtc aagggggggga cggagcggtg  25620
ccaaacttcc ctgtgcggcg agatggcaga ggggaggacg aaggcgatga ccagaggtga  25680
cttcggtgag gggacgggga aggacgacga agcaactgac cagcggggcc attctgccag  25740
agggagcgag cgcgcgagag agagggcggc tgacgggtgg ggacgccttg ccagcgagag  25800
ggatgcgggg tgtggagcgg gctggcgcgc gcgcgcggag gcaggccaga agatggagcc  25860
gagagaggag gagcgcgggc agcgtgggaa gggggatggt cgcgggtttg ggccgggatt  25920
cggtccagca gggagaggag aaagcttttc tctttttctt ttttactttc taattcctat  25980
ttcccatttt tccccttttc ttttgaacaa attattttgt ggatactcta agtgtttaga  26040
aaataggatc taagtgaggt gctttgtgat caaacaaaat gtatgcatat gaagaaagaa  26100
aaactagtgg aggtcttgga attagaggat gaaaggaggg gaaaagggta gattagggtt  26160
ccaaacctgg gttaggattt ttgggatgtt acaaacctac cccacttaaa ggaatctcac  26220
cctcgagatt cagacggggc tcgagaaaag gtaagggtat tccttcctca gagagtcctc  26280
actttccagg tggcttcctc ttctccatct ctgctccact aaatcttaca gagtttcact  26340
tctgaattgc gggtccttct gactgctgag tcgagaatct tcactggctt ttcccggtac  26400
tggagatcct tttgaatctg aattgcctct gcctcgatgc gggtttctgg tacttttagg  26460
catttgcgga gttgagacac atggaacaca ttgtgaatat ctgacatgga ttctggtagc  26520
```

-continued

```
tcaagacggt atgccacggg tcctattcgg gaaatgacag ggtagggacc gacgaaacgg  26580
ggtgccagtt ttcctttcat ctggaacctt ttgacaccat gcatcgggga aaccttgaga  26640
taaacaaaat ctccttcctc aaatctgagt tcccttcgcc tattgtctgc gtaactcttc  26700
tgtcgactct gagcttcaag taacctcctg cggattaaag cgactttttc ttcggcttct  26760
ttaacaaagt cgggtccttc tagtgtcctt tcccccacat tggaccacat taggggagtc  26820
tggcattttc ttccatacag tgcttcgaat ggtgacattt tgatgctggc ctgatggctg  26880
ttgttgtacg agaattcggc gtacggcaaa ctggactccc aatctctgtc gaaggctaac  26940
acgcaggctc tgagtaaatc ttcaaggacc ttgttgactc tttcggtttg accatctgac  27000
tggggatgat aagcagtgct gaaatctagc ttggtgccca ttgcttgctg aaggcccttc  27060
caaaattttg aagtgaactg cgttcctcta tctgatacta tcttccgtgg aatgccatgt  27120
agcctgacta tctctttaag gtatattcgg gcaatggctg ctcctccaaa agtggtcttt  27180
actggaacga agtgggccac cttggtgaga cgatcgatta tcacccatat ggaatcattt  27240
cctctctgtg atctgggcag tccggttacg aaatccatgc ctatttcttc ccacttccat  27300
tcgggtattg ggaggggttg aagtaggcct gcaggcttct gatgttcggc ctttgctcgc  27360
tgacaggtgt cacatcgggc cacatactgt gctatttcct tcttcatccc tttccaccaa  27420
tatctggcct taaggtctag gtacatcttg gtggtccctg ggtggataga gtaagccgag  27480
ttgtgggctt catcgagcag ggtttctcgt gcctctccca ctggcacgca caagcggttc  27540
ttgaaccaga ggactccttg cttatctgtc ctaaggtccg gaagttgctc cttgcgtgtt  27600
ctttccataa gcctggttgt ctctgcgtcc aggcgttggg ccttgcatat gagatcttct  27660
agatttggct tgacttccag gccaccgttg tctcccagac atgcatttag ctgagctgat  27720
tctttcttcc actcttccag aaaatttgtt cctttaaccc cgaaaggttt tcggctgagg  27780
gcgtctgcta ctacgttggc ctttccgggg tggtagtgga tttcgaggtc ataatccttg  27840
atcaattcga gccaccttct ttgacggagg ttgaggtccg gttgcgtgaa gatgtacttt  27900
agactctttt gatcagtgaa tatgtggcat ttgttcccaa tcagataatg cctccatatt  27960
tttagggcgt gcactatggc tgccaattcc agatcgtggg tggggtagtt ctgttcgtgc  28020
ggcttgagta agcgagatgc ataagcaatg actttctcat tttgcattaa gacacaccct  28080
aagccttgct tggaagcatc acagaagatg acaaaatcct ggtgtatgtc tggcagagtc  28140
aggactggtg cggttgtaag cttctccttg atgatttgga aacttccttc acatttggga  28200
gtccacacaa acttattgtc ctttttgaga agttcggtca tgggctttgc tatgctggag  28260
aatcccttga taaagcggcg ataataccct gccattccca gaaagcttcg tacttcactg  28320
acgttggatg gttgcttcca atttgaaaca gcttctacct tagatgggtc cacttctatc  28380
ccttctgcag tcaagatatg ccccaggaaa gctatcttct ctaaccagaa ctcacacttg  28440
ctaagtttag cataaagttg atgtgctctg agtcttccga ggacgattcg aaggtgatgc  28500
tcatggtcct tgcgactctt ggaatatatg aggatgtcgt cgataaagac catgacaaac  28560
ttatctaact cttccataaa taccttattc atgaggttca tgaaaaaggc gggtgcgttc  28620
gttagcccaa atggcatcac tgtgaattca tattgcccat atctggtgac gaatgcagtt  28680
ttctgaatgt ctgcttcctt aatccttagt tggtgatacc ctgacctgag gtctatcttg  28740
gagaagtatt tggctccttg tagttggtcg aagaggtcat cgattcgagg gagagggtac  28800
ttattcttga ttgtaacttc gttcaaggat cgataatcaa tacacatcct catacttcca  28860
tcctttttgg taacgaaaag aacgggtgct ccccagggag acgaactggg tcggatgtac  28920
```

```
ccttttgtt gtagttctga aatctgaagt ttcaattctg ccaattcagt gggggccatg  28980
cggtatggtc tctttgcgat gggcgcagtg ctaggaatga gatctatata gaactccact  29040
cctctttctg gtggcattcc gggcaactct tccggaaata catcttcaaa ctccttgatt  29100
acagacatgc tctctgctgt tagattaaac atcattggat cgtttgcggg cagttgggct  29160
tgacaggaaa ctgcctttcc ttggtgatcg gtgaggagaa caatcttgct tgcacagctg  29220
atgataccct tatgcttagc tagccagtcc atccctagga tcacatcaat tccttgggat  29280
ggcaagatgg ttaagtctgc caggaacact accccactta aaagaattct gacttgggag  29340
cacctgagtt tgcacaggag gtctgatccc ggggttcggg tgaccaaagg gatagctagg  29400
ggtgcagagg ggatgccatg cttttccaca aacttagtgg ctataaaaga atgggatgct  29460
cccgaatcaa aaagcacagt agcgggagta aattcaacaa ggaactcacc gagcactact  29520
cccggggctt gctgagcttc ttgagcgtcg atgtggttga cccgggctct gccctgatac  29580
tgagtcctgc tctactggct gtttgaagga agtgccttgg aggtaggtgc cgatgtaatc  29640
ttagggccat tcaccgagtt ggagtaagtt ggttcgggtg ccttcaactg agggcagttg  29700
ttcttgaagt gactggggtc tccgcagtgc caacaggcgt ttgctggcgg ctggttgctt  29760
gcaacagagg gtgcctgaag ggagctctga ctctgctgac tgtagcgtga tggagtgggt  29820
ccagattgtt tattgaagct tggacccctg ggtggaagcc caaatggtcg agctctctgg  29880
tgacgttctt gctgttgcgc tcggaggact tggaatttcc tcttgatgtg cccttttct  29940
tcctcttttg ccctttccac ttgaatagct ttgttggaga ggtgagagaa gctgtggaag  30000
tcttggctgg cgaggatggt cttaagctcg ggtcttaacc ctttcagaaa acgggccatt  30060
tttctggcct cggtgctgac atcctcgggc gcgtagcggg ccagttctgt gaacttgtgc  30120
acatactcac tgactgacct ttcgccttga gttaactccc ggaattcatc ctccttgagt  30180
tgaactatcc cttggggtac gtggtgctca cggaaagctg cttcgaattc tgcccatgta  30240
gcatctctga cggcttcact gaaagtgtcc caccaagcta atgccattcc tgaaagctga  30300
tgagatgcca gctgaacacg ctgattctcg ggacaagcga tggcttccaa cttcctcttg  30360
atcgtgcgaa gccagtcatc tgcatcgagg ggattgctgg accccgcgaa cgtgggaggc  30420
ttgagtctta aaaattctcc catcctgtcc tgtggccttc caccgcctgg gcgctggttt  30480
tccagacttc gagtgaggac ttcaatgagt cgggtttgat tggccagaac ttgggctagg  30540
tctaatggta gttccggagg tgcggggagg tgggtctcac ccccttctcc gccagcctct  30600
ccttcagctc ctagaggaag tcttgctcca atcccggagg cggtaggcat ggttctatcc  30660
gaagccatct gccatgggaa gagagtcact attatgcaca tgccattttt tttaactagt  30720
tattttattc attacatcaa gccattacat aacacaacac cctgctacta caagcccatc  30780
acacacgagt gctatctagg gtactcccga actccttctc taaagtgtcc ccaaattcct  30840
tgagaaggtc atcaaggctg gccagggaca tctcttcggt gtcggatggg ttccttggag  30900
ggttttcttc cttctgctca gtctgacatc cttggctttt ggtcttcttg cgaatttttc  30960
ttgcgggggc gagcttcttc agtttcttgt cgtagtccat ttttagggtg cggtaagctt  31020
cgcgggtatt ggtctcttcc ccttcggcca ttgagaggct ctcttgaagg gacgcctttt  31080
cttctgaaag ttccctgact ttttgctcca ggctttccac ccgggaggtt agggaggtgc  31140
agtggagggc gaggtcatca tattggttgt caagggtgtg aaggtatccg accatgtaga  31200
caatggtggg atcattctca ataggatctc ctcctgatag ggcctggagt cttttcctcc  31260
```

```
aggtgggggt attcttgttg ctgggtggaa agtagcgaag gggggtttcg aagatcactt  31320
tgttgtagtt ctgacacagt tgtcggaggg cttttcgggc aacattttgg caagtatcgg  31380
ggaaacggta tccggtaaca gtgacttgga aggaaggatg gtttggatag tttcggcttt  31440
ctcctaggta gactgccata gagcatttct ctattccgcc ttcgatatgc tccgtccaga  31500
tgtattccgg cttcttgcgg attcccatgc gaagcgcaca gcttcgcagg agatgcggga  31560
acccttccac ctctgagcag taggatgtcc taatggccag agagtcttcc atctggaata  31620
ggaaaagaag ggccttgtta aaatcgggga gaagagaaaa cttttcttgg ggtaagagat  31680
attttctttt tagggcaagt ttttaaggtc agggttgcgt cctacggcca gtcctatggc  31740
tctgatacca cctgaagcgt cccgatcctt tgggactcaa atgtgaaaca attactagtc  31800
ccaggaggct agtaaacaca ttccttcctt caaatagtac agagtttaga taaaattatt  31860
acaataccgg ggtacaagct cgagagagcc aaattaggaa acgtagtagg aaaatacact  31920
agcccaagcc acaggcagaa ctgggtgcag acacagccct cttaataaag catagcagaa  31980
aagaagtcct cggcggctga aaaacataaa taaatctggg tgaatacact aggtattccg  32040
caagcccacc ccgctcccgt agagagaaag agacctatga tatacatgct caatttggtg  32100
gagttgtggt cactcaacat ttttcttaga gaaaggcaga tacttgaagg tttttcccat  32160
agtcttatac taaccaaaaa ctcaaccgcc actgagcttc ccgctcccgt ggccttagtt  32220
tctttcctaa cacctactta ttcacacatt cccctttttct tgaaactcat agagaaagtt  32280
ctaattgcca taccataccg gactcatcca taccagtgga cacggactat tcgaataggt  32340
ttcaaactct gcgcagaggt gtacacttta cccactagcc cggtttctgc gatctcaccg  32400
tcgcgagacc cgaatgccgg atctctttcc ttacccgtac gtcctaacct taatggttat  32460
ccggaaggag tcaggccacc accatgtcca aaccggacaa atctttcccc ctccttatcc  32520
tcccggtgct ccccagcctt cttaaccctg ggttggacc gcacgagttc ggattgagtg  32580
actgcccaca cagtctcgag tggttgtacg ataaaggagt acaggtagtg aaaatgacaa  32640
gccggtcctt atatgagggg ataatccttc tgctcacgcc taaaccagct gagccaacac  32700
cttaggtcct cccctaaacc agggagtccc tgatcatccc actcccaggg tgatgagggt  32760
gagtaccctt catcgcaaaa cttttcaaga ggagacttta tttgaagaaa tcacatttcc  32820
tttcttccca aaccacattt cgtatccaga atgaatatgt taatgcgggc catctctcac  32880
tcacaatgca atattccccc atagttcccg gcctaggcag tggtagagag aatgggtaat  32940
ttatgcatca agggaaggat ggacttgcct ttgttgaagc tctcttggca cagaagatct  33000
acttccggaa gttcgggctc cgacccttct tccggagctg cgggatccgg atctgcggtc  33060
cccgcttctt ctaggaaaca ggcagtaaaa caatacatca atagtgattt atcaatcata  33120
gtgtgtcatt ttctaacaac attattgtat gtaaccttgg aaatcctttt tgataatttt  33180
tggtgcataa aatattgaga aaactattta agtgggaaaa ctggtggaaa aagaaaaaga  33240
aaagagaaat cctcatcctg ggctgggggc acggcttttg gcccaccccg ggcgcgagcg  33300
cgtgcgctga agcgctttcg gcccaggggc ggcccaagag cgagggggag acggcgcgac  33360
tgcgagggtg acggcgcttc tgtgggccca cttgccagcg agaggggggg aggaaacggc  33420
atcgcggcca gacggcgggg cgaaccggcc gagcgaggga gaaaaggcca gccgccgggg  33480
aagcttgacg gcggcttgcc gccggtggcc cggttcttcg accaagggag ggtggtttgg  33540
cacgggcgga ggctggcgat tccaacggta ggctcaattt ggccggagag ggttgggagg  33600
gggctgccca cggggagggg gcggagttcc acggcgggga tcgccgccgg tgggctctgg  33660
```

-continued gtgggggacg ggggttggaa ggtggtgctt cgggttcgtg gctacgtgag ggagctgctc 33720
ggcccactta atttcttgcc ggaccaacgg agaaggagag ggaggaggag aaagggactc 33780
accggagagg agaacgacgc cggcgcttcg cgaattgtgc tcgggggagg ggaggagagg 33840
gatggccgag gctggtgcga ggaaggaggg gctcggggcg agccttttat aggcacgcga 33900
gggaaggggg ggcggtggag cttctgggct ccggcgagct tcacagtgcc gccattaatg 33960
ctgcacagcg ccgccgaggg gacactacgg cggggcggta ccggcgagga cgctggtcaa 34020 ggggggacg gagcggtgcc aaacttccct gtgcggcgag atggcagagg ggaggacgaa 34080
ggcgatgacc agaggtgact tcggtgaggg gacggcggaa ggacgacgaa gcaactgacc 34140
agcggggcca ttctgccaga gggagcgagc gcgcgagaga gagggcggct gacgggtggg 34200
gacgccttgc cagcgagagg gatgcggggt gtggagcggg ctggcgcgcg cgcgcggagg 34260
caggccgaag atgggccgag agaggaggag cgcgggcgcg tgggaagggg gaggtcgcgg 34320
gtttgggccg ggattcggtc cagcagggag aggagaaagc ttttctcttt ttctttttac 34380
tttctaattc ctatttccca ttttccccct ttccttttga acaaattatt ttgtggatac 34440
tctaagtgtt tagaaaatag aatctaagtg aggtgctttg tgatcaaaca aaatgtatgc 34500
atatgaagaa agaaaaacta gtggaggtct tggaattaga ggatgaaagg aggggaaaag 34560
ggtagattag ggttccaaac ctgggttagg atttttggga tgttacattt gggttgccta 34620
gttacaagag aattaattga caaactagga gtgggattgt taccaatggg acaatccttg 34680
cattgatgtc ccttctttcg gcatatgtag cataggcgat cctcaagtct tgacgatttc 34740
ttctttcctt gtttctttct tgctacatgg ttagtgaata ttttcttttc taacactatg 34800
cctttttgtt ttaaatgggg gcaagaccta aacaagtgcc ccttcttgga gcatttaaaa 34860
caaagtttat catccttgtt aataatcaag tcatttttaa tatagggaca tgacctaata 34920
gagtgcccct tttcaaagca ttcactacac ttcttacttc tcttagtgtg aagtgtgact 34980
tgattattat cttggatgtt accttttatg gaggcttggt tgaggctttt ggaagaggta 35040
ttgattttct tcttttgttc cttcctcttg acaattctca agtccttgac attttcttca 35100
agggatttag tgcatgccac ggttgttccc atctcaagct tcttcaccat gtgatcacgg 35160
ttatcttgag aaggttgagc aatgcacttc ccttttagtt gtgtcaagct cacttttagc 35220
ctctcatttt cttctttgag cttttgatat gtatcatcgt ttgttcctgc aaattttagc 35280
tcaaaggaag atttgcttgt tgatggacaa caagcattag cacatggtaa tgtagtttca 35340
atttgaatac atgtgcatga gtgaggttgt tgggatttta agttttctat tacaacctta 35400
tgagcaatat ttaatatgat atgatcatcc ataagatttt catgagaaca taggagcata 35460
tcatattttt cttgaaaagc tagattttca tattttagct tttctacttg gtccttaagc 35520
aaggcattcc tatttactaa ttgagcgata caatgtaaag cgttatcttg ctcaattgaa 35580
atagtttcat acctttggac caaatcaaca tgagagaact ttagctcctc atgttcttta 35640
gtcaacccat caaagtatag cattttcatt gagagaacat tttctagcct ttgacgagct 35700
tcgctttgct ctctcgctct ttctagaagt ttgagcatga ccgccttatc ttcttggctt 35760
aggcgagcgt agagttgcat gaagcttttt tcttcctcct catcctcgtt tgtgcttccg 35820
ctatcatttt cattagccac acaacatatg tgggaatcga aatgggaaga caaacctctt 35880
ggagaggtgg attcattgtt tggtctccat cggtcatttt attcttcttc cttgcaaggg 35940
ttagtatcac aaagaccaaa ggaagtagaa gcacaaaatg aactatcatg tttgaactca 36000

```
tcaaatttac ttttgatcct agtccaaata tcatgcgcat caggaatatg ttcattataa  36060
tttgtaatga aggcatgata atcttcttcg ctaagagaat tacctaagat gtcaagagct  36120
agatggttta agcgtataca tctttgatct tcctctgaag catcataatc agagggtatg  36180
atactcttgt ctataatttg ttctaatcgt ggatctatag ttctaaaagc atttagtaca  36240
ctagtagacc atgaatcata gttagaacaa tcggaaaata atatctcaag agttacctcc  36300
ttccgagttg tgttcttgtt cttttgggat cttctttgag ccatcacttt gatttgttag  36360
actcaatatg aagtgcctag ctctgatacc aattgaaagt cgcctagagg ggggggtgga  36420
taggcgaaac ctgaaaatta taactttaca ccccaactag atcccttgat tagtggttag  36480
aacaagatac acatttgtcg gagtataaaa actaagtcct ttgcttgtaa ggagtattgc  36540
tttcaaataa tatggaattg ataaatcaat actactaata attctatgag aataaatcaa  36600
gagggcttag ataagaagag caataacaca agttctttct tgcaaggtgt tgcttcacta  36660
aatgagaatt taacttaaag caacaccaaa tattattagc aaagaatagt gcaagaaaaa  36720
cttataaagg gaaagaacaa acaaatcaca agcaataagc acacgagaca cgagtgattt  36780
gttttaccga ggttcgaccc tcgaaggtct agtccccgtt gaggagtcca ctaaggacgg  36840
gtctctttca atcctttccc tctctccacc gatcacacaa gatcggcgag ctcttcttct  36900
tctcaaggat cacttaagac cccgcaagga tcaccacact ctttggtgtc tcttgctagc  36960
tttacaaccc tccaaaactt tggaggaagt tcaatgggag tcaaaactcc acgcgcaaat  37020
gaacacaaag atgtagcaca cactatctct caatgaatct cacaaggcac acactatctc  37080
tcaatgagta gctctctctt gcttgctctc tttttgtgg cacttgtgtt ggttgtagtg  37140
gtctaaatct tgtgtatagg atggatcaat gaatagaggt ggttgggagg gcttgagtat  37200
gtcaactata tgacttggaa tgttgcttgg gctccctcac cttgaagtgg ccggttgggg  37260
tggtatttat agtcaccaac caaattgtag ccgttagaga aggctgctgg cgatgggcgc  37320
accggacaat gttcggtgcg ccgccacgtc atcctcccgt tagggcttgg agcttggtcg  37380
accgttggag gctttgtcct catgcgtcac cggacagtcc ggtgcccctc tgaccatctg  37440
ctctgacatt tgaattgcac tgttcacttt gcagagtcga ccgttgcgcg caggtagccg  37500
ttgcctcgct ggtgcaccgg acagtccggt ggcacaccgg acagtctggt gaattatagc  37560
ggagctgcgc ctggagaacc cgaagctaag gagtttgagc tgattcaccc tggtgcaccg  37620
gacagtccgg tgagccagac cagggcacac ttcggtttcc tttttgctcc tttcttttga  37680
agcctaactt gttcttttga ttggtttgtg ttgaaccttt ggcacctgta gaatgtatga  37740
tctagagcaa actagttagt ccaattattt gtgttggaca attcaaccac caaaatcatt  37800
taggaaaagg tttgacccta tttccctttc actcacccct cttcatggcg aacctcccca  37860
gctcgccttc aatcaacacc atttttgtga ttattgaggc gtcatttccc tcatgcgcga  37920
ttttgagggt gtccctatat ttctgtggca ttgtccaagc cactaacctt gttatattca  37980
tccctacata gagatgctaa aagaacagta gtagcctgga cattcttata aatttgttca  38040
tgaatgaata taacattatc attactatca aagtgcattc cattttctac tacttcccaa  38100
atgctaggat gaagagaaaa tagatgccta cacattttat gactccgaaa agaataatca  38160
tccccatcaa agtgagaggg tttgccaaga gtaatagata ataaatgagc attggagttg  38220
tacggaatac gagaataata aaaagagtaa ttttggttaa ctatcttttt ctttaacgta  38280
aaaatcatca ttggaatgca tacatagtgt aaatagaagg ataaaacata atcttcgata  38340
gcataaacat ggatcggata gtttgtcacc ggggatgatc tcgaggccgc tagatcaaag  38400
```

gacgtcgccg aagccaccgg atcagaggag ttagtcattg aaggacgcca gagccaccca 38460
gagaatttgt ttgccgctca cgtatgcaga ggggggtccc actccatatc ttttttttcct 38520 tttttgtttg ccgcaatgtc cgcatgcgtg cttgcatggt ttttttttct tttttgctac 38580
acatattttg atattttgag atgtaaatat gatagcacat ttattcattt tttgtgtatg 38640
catgttgtat ttgtcctttt tgtgcgttaa gtaatatatg tacttagtaa tatagcaagc 38700
atcagacaat aattttatag aattcactca gtactaataa cagtagtgaa taaatgttgt 38760
gtaattacta acaaaacact cggtaattac tgatgaaacg ttcggttatt actgacgaga 38820
cgttcggtta tttacagacg aaacactcgg taattactga taaacattcg gttattaccg 38880
acgaaacgtc cgattgttac tggagaaaag ttttgttgtt ctacgaaacg tttgattatt 38940
actgacccaa tgttcgatta tttactgata aaacgtttgg ttcttactaa cgaaacattc 39000
gattattacc gatgaaaagt tcggttgtta ctgacgaaac gtttgattat tattgacaca 39060
atattcggtt atttactgat gaaagtttag ttcttactga caaaacgttc ggttgttact 39120
gatgaaacgt tcgattatta ctgacaaaac gtttgattat taccggcgga acgttcggtt 39180
attactaaag aaacgttcac ttattatcga cgaaatgttc gtttattact gacaaaatat 39240
tcataatgac gaaacatttg attattactt gatgaaatat ttagttatta ttgacgaagt 39300
gtttggttat tattgacgaa cgtttggtta ttactgagtg gatgtatgca aaaaaaagaa 39360
aaaatatgca tggagttatt ggatcccaaa aaaagaaaaa acctaaatgc acatgcgagt 39420
tgtgcagcac caaaaaaaag aaaaaaaaag gggtgcgtca catggacggg atgggagcaa 39480
gactgtgcga ggtctggaga aagctatgtt taagcgtctt ccccacataa tatgcagaga 39540
ggctatgact caaatctggg accttctagt tgcagaaaaa taattataat agtagcctcc 39600
cgaataagtg aataataata atagttttta aaaattgaat tatgctagta atccaaataa 39660
ctcgaaatat atattgcacc agagcctcta cagatagctt attcatataa tagaatctct 39720 actataggggg ctagctgtag taaaatactg agaaacattc gttgtttggg tataaaacaa 39780
ttcgttgaac atggaagtaa gttccgtatt ggcagcggag ctcgaagaga tagatagctg 39840
atagcatcat cgacggggag agccgggtga ttgttgctta agcgccaatc gtcgcctccg 39900
tctcgccggg tgcgcgcacc gaggcaaagc cgtcccctcc ggcggcagtg gcgaggggga 39960
tgaggccctt ctcctggcaa gtccggatgg cggcgtcgaa catgtcctcc agcgtcttgt 40020
acctgaaggt gaacccgagg tcctggagct tcttggacga gaagcgcacc ggctggaggt 40080
cgtcctggat cccggggaac ctctgcggga cgtcgtactc ggggtaccta tccctgagca 40140
tggcggcgag gccgtggatg gtgacgtcgt gcgaggagca gacgtagcgc ccggccgcgg 40200
ccgggttctc gaagaggaag atctcggcgt cgcagaggtc gtcgaggtgg atgagctgca 40260
cctgcttgag gatcgagtag tggggcgcgt tccccgtgat gagcgccagc gcggtgatga 40320
gcaatgtatt aaatcgcggg ctaagaggtt tagcggctgg gttccagaac agctaagtcc 40380
agctataacc ggctatagcg gaagctaaac cttttagcgg atttgcaaaa aaaaaagagt 40440
ataaacatga acatctattg aagaatacat gcctgtttgc ttctcttgct gagatatggt 40500
gccggttgaa ctggacagca attggaggtt ggagagtgga gagaatacta ttggagtact 40560
gccttgatta ttgctacttg cttcattgct tgccgccagc agtgagctag ggacagggag 40620
tagtggccga gatcctacag gagcagcaac ggcatctcct gcttcatccc catcgccgcc 40680
aacgtgttga acttgaaccg ttgaagccag ccgccgccat caggttgaaa atgagagtct 40740

-continued

```
gagctagggt ttgcagtttt gcacaagaaa aggcagagag agatacgtac gccacctgct  40800
gaaattgagc acgataatgg gctgggtcgg acgcgcgcaa gaaaatggcc caggtttgct  40860
ttagctgccg ctagaagatg gcccatttaa cggatttcgc cggctaatag cggctaatag  40920
cggtcaccaa gcaatagcgg caaaattgta atctcctagc ggcattattt gccagaggcg  40980
atctccggct atagcggcag cgatctccgg tgatttaaaa cactggtgat gaggctgggc  41040
ggcatggacg cgctgatgaa cgggccgacc acgagcgtcg ggatgatggt gaccaggtcc  41100
aggccgtgct ccgccgcgta cgccagggcc gccttctccg ccagggtttt agacacgaag  41160
tacatctgca ggggggtgg acataaataa aacgtgtgcc gcagccgcag gcagggctga  41220
tggtgatggt gaccaaacac cgtcgtcgtc gtcgaagttc agttgaattg atgaggcgca  41280
gcgcagggct gacaagtggc tgcgtacgta cccatcctgt catcttgacg cgacggcaga  41340
agtcgacgtc ggtccagctt tcctcgtcgt agacgggcct ctgccgctcc tccaggttga  41400
ccgtcccggc ggaggaagtg aagacgatgc gccgcacggt gccggcctcc ttgcatgccc  41460
gcatgatgct tatcatccct tccaccgtcg gcttgattac ctcattctgc aatggaaacc  41520
atacgtatgt agtatacgtg tgcagtctgc agtgcatgtg cagtgaagac gtagagatga  41580
tcgagagact aattgtgcag ccagagctag agactgatct acctcagggt ctttggacag  41640
gaagtccatg ggcgtggcga cgtggaagac gccggtgcag cccctgatgg cgtcgtggaa  41700
gctgccttcc tccgccaggt cggctttcca tatggacagg cgctccgttg ctccgggaag  41760
gtccatcaat ggcttcgtct tcccaacgtt cgctgcagga ggatcaggac acggcatata  41820
tacacggagc gaatcagagt ttggctgcag gaggaggacg tacgcaggac gatcgagaca  41880
aactcaccgg gatcgcgcac ggtcgcccgg acggtgtagc cggcctggag gagcttcatg  41940
acgagccagg agccgacgaa gcccgacgcc cccgtgacca gcaccttccc tttctcgctc  42000
gcaccggcac ctccctccat tatcgcctcc cgcgtttttt tctccgagag cgagctcttg  42060
cgcaggactg agtgagcaga cacttgcttt gcttctttag ctgctgctcc agttccgatc  42120
gacgacggtg tgatatataa tgccgcaaca gcgcgagtgt ttaaggttgg taggtacact  42180
gacccgcgcg attgagcgca tcctccattc aacaccacac gctgcaccta ccggcatatc  42240
tctgcgcgcg tttttttttt ttttttgaca aaccaagctg ggcccgggcc gtagagcccg  42300
tttggacaca tctagctgga gctcctccta tactcctctc caactccaaa ctcccactcg  42360
aacagccagc agtactcagt gctctcaagg tacgcaggca gaaaaaccag acatagagtt  42420
ctattattat actaaccaca tagaaattaa agaaaaatga caccaacacc aaaccccttca  42480
acctgtcttc ccacgttcag aaacgtattg tctcgagcag cagacatgga cagccatcaa  42540
agccgatctt gccatttgtg attcaataaa ttgacacgcc tagctagagc cataactttg  42600
gccaaggact gtacaagcag gcagcccatg aggctatcca ccagcctttt tatcccgctt  42660
catattctac tcagggccgt ctcatgattt tagaaagccc taggccgatc taaatttatt  42720
ggcccttata tatacttctg tatcgttaag aacaacacta taaataaaaa acaagtttat  42780
ataaacatca ttacgaatat attaaactag taaaaatttg gtacattatt tgacactata  42840
caatgtttct caaaataaac aattgagtcg agcatttctt gaagcaaaat cattaaggac  42900
aatatttagg tcaacatttg tcaatacatc cttctcgata gagcaagtag ctaagccatt  42960
taacctttcc tgtgtcatag ttgaccttag aaaatttttc aacaacttca attttgagaa  43020
acttctttcg tctgaggcta tagtgacatg tatggtcaat aaaatccgat atgcaataga  43080
gacatctgga taacaatctg caattgtaat gcactgaaga atcccagatg ctatcatcaa  43140
```

accatctggt aaagttactt gcaagacttg taattcacta atacaatcat tgagatcaac 43200
gtcagataag tcatcatgag taaaagtttt tgcaaaagta gtacaacact ttctcatatc 43260
ttgatcatct aaagacttca acctttctga gtttaataag aaactaaaat atgttttcaa 43320
atatctccat atgctcaaat cgactattca atgaagcaat ttccatatca atcatgacaa 43380
gaaagtaatt aactctgaat gactctatag ctgacagtgc ttcttcttca ttctggtcat 43440
tttgttcatc aaaatgtttc tttcttttag cttgacggtt tctaggaaat gctggctcta 43500
catccatctc ttctaccatt tcttttgcaa tatcgatgat gcgattgaag ccttcagctc 43560
tatacttctt aaaatatgaa atgacccttt aatttgttca agtgcagcat ccatgcacac 43620
actcttagat tgcagtttcg tactcaccat atttatagaa aatataatat catgccaaat 43680
aaccatacca cataaaaatt caaaattctc aagtgcaatt actaaacctt gagcattact 43740
taatcctttt gggtcatttg tagaacatct ccccacttcc atcaaagcat cccttatctg 43800
gggagtttaa aacctgacag cttgtacact ttttattcga ctctcccaac gagtagtgga 43860
caaagctttg accgttagtt taggaacatt gtcaagcaaa atcttccacc ttttagtaga 43920
acttgagaat aatacatata tctgttgtta acaccaaaga atgaaatagc tttggtacaa 43980
gactgtgcca tatcacaaag ggttaaattt agactatgac atgcatatgg catgtataaa 44040
gctcttggat tgatctcaag caaaggcttt tgaacaccct gatgttttcc cttcatatta 44100
gagccattgt cataaccttg acctctcaca tcttcaacat tcaattcaag aagttccgaa 44160
tgatccaaca attctataaa aagaccaaat cctgatgtgt catctactct gctggcaaga 44220
agcataaaaa gaactccact cttggagtgc tacttgatat attaactcaa cgtacaatta 44280
aagtcatatg ttcttcatga cttttatatg gattacaatc caagataata gagaaatatt 44340
tggcaccctt aatgatacta aagatatatc ttctcacagt gtcagcaata agtagaatga 44400
gctcattcta aatattatga ccaagataat gatgatgaat ttcataattt tgaatgcgcc 44460
taatgtgttc ttgcatcaca gtatcaaatt catcaatcat ctcaattgag cctagaaaaa 44520
taccattact atcttgataa attttctcat ttgttcctcg aaggggcaaa ttatttttag 44580
cgcaaaactg aacagcagca acaattctaa ccaacacttg tctccatcgc tctttttctt 44640
ttgcaatttc acgttgcaaa tcatcatcaa ttgtcttgtt tttgtttaac ctcaacctga 44700
gttcattcca tgtattcatg ttcctcatat gctcggtact attttcatgt tgttttagcc 44760
tcccactcag atgcttctag tcactcaatc tagcatgtgc cagtaaactc ttggtcacat 44820
ttgatttgaa caatcgacaa caaaaacaat aaactttatc cacatgctta gaataaacta 44880
accactttct atcaacaatc tcagaattac ttaactttct ctggtagaaa gtatagaaaa 44940
aaatgcctac cgagattgtc tttagggaac tgcagattca attctctcat aggtcccttt 45000
tcaattaaga tatctcttct tttattgtct agattatccc atattttagg accaaagatt 45060
tcaggaaaag attcttctcc atcaccatga cctgattatc ctcatcgtcc tggttgattt 45120
gaacttcatc taaattttgt tcctgttctt gatcatgtgt atcctggcca tcttcctcta 45180
aatccttagg aggaacatta gtgctagcta agcaaaatct atgaatagca cctttctgtg 45240
attcaattaa ttgattttct cgctttcttt tgttcctctt ttgagcacca gacaaatgtt 45300
ctgtaggaaa cattttaaca ccccgctaac acctaaattt ataaataatg atatgtcaat 45360
taaaacaata actaacatgt attcaaaatt ctagagcgaa gaacatgtat ctaacttaat 45420
tataaagata aatacacaat ttaaattaat caaccttgag tttgacgtct tgctggatga 45480
cgttgatcta gggcatccaa tcctcttccg gcttctttag attgatcttg atcctcttga 45540
atcatcgacc tccggcacgg cggcacctac accccaccca cagatccaat tcatcagcag 45600
ggacacgttc tgcttggaga gcagatcaga gtcgtatacg cacttgtacg catgtacgac 45660
catacctttt tttgaagggc aagatggatg cttatgcttc cttgcttctg gatgtggcct 45720
gcggatgctt gctttttttct atcgtataca cggtaaacag tacagtatat gcatatttct 45780
gctaggtacg gcataaggag tgcagctcgc cttcatcgac cgtcacttca actattgacc 45840
atagtatcaa ccgtgctacc aactatggtt ggctcccaac tatcatatcg ttccggtctt 45900
tactatcact cggtgtcata tcaacttttc tttatagatt tttagttaat atgaacatgt 45960
cttgctaaaa caaaaataga atcgactaca taattgagta aataaaattt acataattca 46020
taaaatacag atgaaaaata cataattcat aaactacata atttataaaa cataaataaa 46080
aactacatat tttctcaagc tgaaaattac ataattcata aatatatttt ttagaatttt 46140
ccaatatttt agaattttg ggtttcaaac tacttttcta gctgagaaat tatataattc 46200
ataaatattt tttttagaa ttttggggtt tcaaactatt tttagaaaaa aataactcaa 46260
atgacgcacg tgaggatcaa cgctaacacg ataagtctct atccatatcg accgatatat 46320
ttcattaccg gtcgatattc ggtatgttcg tttggtttta atgtataccg gttttactat 46380
ttacagctgc accaatctaa atagccgatt ttaatctaaa atgaatatca taataaggac 46440
taaggtactt tggtaacctc atttcttaa gtaattttta ttttcccaat aaaaattagt 46500
aatattttc ttgaaaataa aaatctttta aaaaaataag ttctcaaact agttctaatt 46560
agatcgatcg acaaacccac caatggacag actgaaccga tcaacgtagt aaccggttgg 46620
tacaggctgc ggtgggaacc agcctgaagt tctgaaccgc tgcaatcatc agtgactgcg 46680
aaacagttac cgagatagtt agcgtaaaag agagcacggc ttcagcacga aacatcgtct 46740
tcgatcgatg aaagcatctt cagtgaaact agctgctaaa gttggcaaac ttggtacaag 46800
attcagtaaa ctgtaaatcc atctgattgt tcatgtgacc gtttaggtat tgttttatat 46860
ttacatgagc tagaaagttt aactcctctg ctctggcagt ggcagaggtg cgggagccag 46920
agcacctgta agctatgatg cacccatgtt tcacagagct cacgaaaaaa atactttgtg 46980
tgaacttacc tatcggtgtc gaataccgta tcggatacaa atactccttg atacttccgg 47040
atacatatcc ggagcgtatc gggaatttat gtgaatttga ataaataaaa aatgacggat 47100
actcctagga cacctctcca atagctgcgg aataccttat atggtctctg gtctgttaga 47160
attagaactt agaacttgtg tggtgaacta gtgattattt gcgagtctgc tgatgtagtg 47220
tatccctatt attaagtaag tcattatcat tatcctgaca tttactaagt ccaattttag 47280
aatacttttg tctttgttag tcccacatag acacaagtcc gtaccctagt aggatgatac 47340
acaagaaatg gtcaggatag cagaggacta aaaatcctcg tgtcaccagt tcaaatctgg 47400
ttcctggcac agaaaaaagg atctactaaa taggtattga tacaaattac tcgagatgga 47460
ttacacatgt tttggcatgc tgatttcatt gatttgagtc cagataaatt ttggaagagg 47520
aagtagatat ttactttagt caaaattatt gaacattaac ttctaatacc cttaaattga 47580
actgatgggc aatggtctat ctcagacatt tcagcattta attttattta taatatatat 47640
tttatatcac cgtatcagag tattttctga gaaatagcgt atcagagtat tttttgataa 47700
atagcgtatc agagtatcga cgtatcccgt atccatatcc ctcctatcag ggcaacatag 47760
ccggtaagta ccatgtacat cttcctcact gcaacaaact aaagcctccc tgcattccag 47820
ttttgtctga aactagttct gaaacatctg cccgttctca acgcggcagc cagcctgctc 47880
gagcgcagcc gagaagaacg tggccccgtc aatcctcgag tccatgcacg gcggggagaa 47940
cacggagatg atgtcccttg tggtcaccac tccttggacg cgcccgtgct cgtcgacgat 48000
gaagctgcag ctgctcctta aagctgtcag cttctccatc gcttgcttta gggtgtcgga 48060
ttccaggttg gtggctggta ggcccaccat gcctgactgc ctgctcctga gcgcgaggat 48120
gtttcggcca ggcgcagatg aattttcagc ggtgctgcat ttcctgtcgg tcttgttatt 48180
caggctgatt aattcttcca gagtagttgt cctgtatgga tcaggaaata cgaggggaat 48240
tcttaattat ttcggaaaac ttggcaaaag gagatggcag tactcacgtt cgcttgctga 48300
aaagggtgct gtcatctaga aacaggtaga gatcactgca ctgtaatgat ccgattagac 48360
ggctggtttt cctgtcaatg actgcaaccc ccgttttttc ctttgagaga atatgcagcc 48420
catcagctag agtttgatct gagtacacca aaacaggctt cctcacattt gcaaacctgt 48480
cgacaagtca aatgcagcat tttagacttg cagaagttat gttcgcggtg gtatcatgca 48540
tgttgagcac atgcaggtac gggctttgac aagcttgcat ttatagctga ctgcttttca 48600
ggatatttcc ccacaagata cttcttttat aagcatatcc ccttgtcacg gctagtttaa 48660
aaactcaaat ctcctccaag attggagggg attggggcct caatcccctc gaatccaatc 48720
ctgaagatga tttgagtttc caattagccc tcaaggctat accttcccaa gaccccaccc 48780
taggtcttat tcggccgcgc agagatcgga ggaaattgag gaggattaaa catcttttat 48840
tcaattttga ttatgaaggg atttattccc ctccaattcc tttcaattca cttctaattg 48900
aacaagctct tatgcgggag tcaatctgct ccttttttatg ctctagaaaa aagaaattaa 48960
tgaaacctaa gaagcatttg acctgttcgc actacaaagc atacctcata cacacagttc 49020
acttccttac atttgtttcc tattcatgac gcatacaagg tattctaaat agtagttagg 49080
catacaactg aatcatggta agcattttca cctaactgta ctgaagcact tcttattcag 49140
gctcagggct tacctaaatt ccgaaagctg cttgtctgca attttatcaa gccactcaag 49200
gccacttgac tggagaagca gctccatcac tgcatcctag tgcaatacat cggccggccg 49260
tcagcatcac gattgagttc tgtatccata atcaccgagc ataaaaagag caccgacaga 49320
gcatcaagca aggcaccagt tacctgtgtg acaaatccaa tagcactcga gttcattgac 49380
tcgacaaccg gtgccacgtt gagcctgtgg tgtttcgaga agagaagcat tgcgtggaac 49440
agcgtgtcat gggtccgaac agggaagaat ggctcccaca ggaacaactt cgctaaccag 49500
gcgatctgtt ttgtttcatc agagtaacag ccgcatgtta aaaatagaag aagaaaaatc 49560
accattttta tccccaccat tcgtcctatt tcgctaacgg ggcgtttaga tcccttcatt 49620
ttagagaaat tgaaattcac tcaataaaat aacttattta gtttgaaatt tggcattcca 49680
ccacattcca aagttcagat ataaacatat gtcaaattta ttgggtggag gatggaaaat 49740
gattttattc attagtagaa tttgtttcga ctatgtaact tatacaacac tcttcgtctc 49800
actcctttat agtaaaaatg taacacataa atatcttcga catcttgcta ataataatat 49860
acaaatatat tttgtataaa accaaattat cttaattgat atatggctaa ttactattat 49920
tagaatggaa ttcgattcta atgatccaaa cggagcgtaa gagaaaggta ttcagaatac 49980
attacatata tgtcccatcc attccagtgt acaaacataa gtgaagggtg acattcgata 50040
tgtggagtac cttcgtttct gcaatctgat gatgctgttt cagagtagag aggaaatcag 50100
tactgtctgt tgattcactt tccactttgc caagttccta tgaatggcca acacaacaga 50160
tgaatttgtc aagatcggat ggcaaccaaa agtaatgatc gttcactctt cacacaaaaa 50220
aaggccacat gaactgtcta taagacgaat ttcagagcaa cgtttcgatc tccgccggca 50280
aaccgaaaaa tttagtgact tgaaaaaaca tgtactccta gatcgtcagg ttacctcaag 50340
tgcccacagg actaggctcg agaactcgac gaagccaata tcgcgatcga cgtacttgcc 50400
tagactgctg tgcaccacgt cgatgatcac cgcgcccgcg gcgttgctgc tgtacatggc 50460
gtcgagggcg cccaggacgg agccgtggag cttgacctcc accgctgcgt gcggaacaaa 50520
cacgaacgcg agatggttag tggtcgggta tatggaatgg aatggatcgt cctcgtccga 50580
cccaacgcct acctacacat acaggaagcg agaggaagca actctgtgcc tcgtgtcgtg 50640
atacctgggg aggcagtggg ttggagcgcg cccgggacgg aggagacggg gatgtggtcc 50700
aggaacgact tgagcgcttc gctccagcac tcccctgccg cctccgcccc gctttcgcgg 50760
cttgcggtgg cttcgctcgc tgcttctctc gccatctccc cagcgatctc tgcgctcccg 50820
gactctggct gcggtgcaag tgcaacggac aggtctctga gcttttcgcc ctgctccttc 50880
agcgactcag cgtccttctg cagtttcgcg agaggttgcc gggacacgtc tgcgggtgcg 50940
ccgggacaga tggcgcatac caggatacgt gttgcgtttg gatttgtcca gtagttgtac 51000
tacggtttcg gttttggctc catatatcaa gcagtagttt gaaggtaacg gcgtgtgccg 51060
atgttcgaat tttctcgggg ctctacaatt tagaagtaga ttttaaataa ataggttaat 51120
tttttaagtt ttagtcttca tatatttaaa ttttagatct tataaggaag tttaaagtat 51180
ttttaaaaca attagagctc taaaatttag ataagaaata ttctttagat actatgggac 51240
gagggaattt ggccgttggt tgtacaagcc gcaaccgctg cagcagtgca actatttacc 51300
gtgcgttggc gtcggttgtc aaagtacaat ataacttaga ccggtctttt attgtcagaa 51360
cttggaccag tcttgcaacc gcagcggctt aaattcagtg acgattgtag gatttcaatt 51420
tagtttggtc caatattata ataaataaaa taaataaatg tgtttttgtt ttgaattcta 51480
taacatctga gaatcaaaag aaacaaataa atcaaaaaca tctatatact ttaacagaat 51540
caaaatcata atggaccgga cccatcctat tcatcctcta gatcggttac tgctttaatt 51600
tacagcaaat aggtctcaac cattagggct agcttagaaa tcatattttt ctaagagatt 51660
ttttcattta aaaaataatt tatttttttct taagaaaata tgaatttctt tagaaaaata 51720
gagttcttaa actagtcgtt aaaaacattt ttctaagaga ttttcatttt tttaaaaaaa 51780
taatttattt ttttcttaaga aaatatgaat ttctttagaa aaatagattt cttaaactaa 51840
tccttacagt tgggtgttta acggcagggg cgggcctgga atttccctat gacaggcaaa 51900
aaaaaaaagc ataaaaagtt tgtaaacttg gtcacccgtc aacggatagc aaagaaaaaa 51960
atcgactgat acaagactga aactccgtaa atccatgcag atgatataag acagcaagca 52020
cacaacgtca atttcctgtg catcttcatt tgtagtcctc aaggatctaa ctttatggga 52080
gctttacaaa atggcatcat gaattcaaca tgtatatatg acggaaacaa gccctcgctc 52140
ttattcgtgc gctatccgtc tcccccatgc ttccgcatga acaggtcagg acttcctcca 52200
gcacgctatt gtctgcagta ccaaccatga acaaacattc tcaccacagc atcataaaag 52260
tgcagagtat cacaagggcc caagcatgct ttattatgag tctgcatgtt ccaccgcaac 52320
tttgtaggca cagccgtaca gagcaaggta gcacgcggcc aaggccaact acaacacacg 52380
gttcaagaac aagaacgaac tacttgatac aaaggtggca caaggataac gccataatgg 52440
cgttcgagtc cactgatgct gacactgcaa taggagtgcc agcttatatc caacaaggaa 52500
cagatcgaca gggctgtatc gccctgttga ttttatcacg aattaatact actgtttcca 52560
ggttactagc tctcgaactc atggctttcg gaccaggtgg tgggaaaaaa agccaagagc 52620

```
attgggtggc cgagagctta tcgcttcctc ctgtttgttc gccactgtct caggacaaac  52680
tggacagctt ccttcagagt caccttccgg ttttctttga agttccatag ctcccccaca  52740
gggtagctgc cttttgattt gtactcgttg gtttcaagca gcgcctttgt caccattgca  52800
tagatttctt ctccatgttc ttctttgagt gctcgaagct ttgcatcatc ctcgattatt  52860
gcctacatca cagcagcatg caccacttaa aggtagtatg acacaatgca tgttacaaaa  52920
tgcaaggtat ctataaaatt ggatagatcg agggtttagg gttcactagg ccatgtttga  52980
atgcaccaga actaatagtt agctgctaaa actaactaaa gacatccaaa cagtctagct  53040
aatagctaag ctattagcta tttttagcaa attagctaat agctagctag ctaattctac  53100
tagcattttt tagccaacta actattaact ctagtgcatt caaacacccc ctaaattaaa  53160
caggaaacga aggatacaaa atagtactcc cataatgagc ttacaggtca gcatccatac  53220
cattgcctgt acatgactat aagtagttac aactgaaaca gaaggtatcc cccttctttt  53280
cctttttttt tgagaaagag agggagggag ggcgagataa agtacaggat gtagcaccaa  53340
actatatcca tacaagatat tagatatggg atctgatgat tcaggaagga acttaacagc  53400
ttctactaga caggatagga ttattcagca actcaattat actccatccc acaatactta  53460
tgtccctaga aaaaatatat ggctggaatg gcatatatgc cgtgccccaa taaaaagtgt  53520
cccagcatga agtgattgtt ctttggaaac taattctagt gtcccaacat ggcagcaatt  53580
gagccttcta gtgcttcgca ggggcggacc tacgttgaca ttcatggggg cataggctcc  53640
cgctcatttg tctactgtaa gtagtagtgt ctagattttc attatgaggt tccctgctca  53700
gactaactta gagacccctg ctttagtatt ttggcgctca tccttgcaag tgtgccctca  53760
gtcccatttt tttctgggtc tgcccctggt gcttcgtggc ccacaagcta gaaagacact  53820
ttgttcagac aaattttgaa aactagaatt gcacttattg tggaatagaa ggagaaggct  53880
attaagctaa ggacatgaca tggaagtagt tcaagtgaag actcatacca tctcctttcc  53940
atcaattgtg acgaccctaa aagggtgcca gtcaggattt tttatttcag cctcccactt  54000
tgaacaaaga aaggcagcag taacttctgc attttctgta cgctcctttt ggcatgcctt  54060
tgaaaatgct tttagatcaa gctctcccat tctcttgatt cctatatgtg tctgcccacc  54120
tgaaagatca agcaggccct gtggagcatg ccatagaaca aaagatggat aacaatgaaa  54180
tctgatggac aatattagtc acatagatct tattggtaaa atagcataca ttttctagct  54240
ctttgcgagc ttcttgcagt tcaatgttgc ttttgctttc tttgataacc agagtttggt  54300
taagtgactc cattccatcc agttcatcta tcttttcttg caatgcctca ctcagctcat  54360
taattttatt ctttgacgct gaatcttcat cacctggcat atgctccatc acttttagtt  54420
tgcccttcaa ctgctgtatt tctaattcaa gcttttgttt tgcatccaat tgttgttcca  54480
acatcagaat cttctttaac gcagcatgtt tctccctctg tagtttccat acagtaagac  54540
taccatagga cacattgttt gaaacctaaa gcatcatatc acaggagcca aggtacatac  54600
tttttgttct tccacaagct tcagcacatt ctcatcagct ttctgctgct ctaatgttgc  54660
caatttaaga tgactcgatt tgatagcatt ctgagttaaa gcaaaaaacga aacacataat  54720
tgcatggata tttctaaatg atccaacttt atcgaaattg gaatatgaag aagttactaa  54780
taaaaaataa atgtcatcta acatgtctca aactaatatg acactaagga aatcaactct  54840
ttccattctt ttatagaggc aaaggatgag atggatgaaa tcacacacct tttgcttctc  54900
ctgctcaagg ctccttctgt cataatcgct ttttgctgca atctcatcga gttgcttgga  54960
```

```
tctcacatca agatcattca tttttgcctc aaggtcagaa cgcagctttt gattctcatc  55020
aatgatcttc tgagaatgcc tgcgagctag ctgctgcatc ttgctaattt ctggtaatgg  55080
ttatgcttat taatttatct ttcaaatgaa acttcacagc tgctgatgat agaaaactgg  55140
aaatataact aaacccatgc ggaaaaaatc aacaaaaaga ataacataaa ccttcattgt  55200
atgactggag aagttgttcc ctttgcccca tcatcttctc aagtgatgca gttgtctcac  55260
tgtatttgca ttctagttcc tgtaaatacc tatttttcac ctcaatttgg ttagctaaat  55320
tagcaacaag cctgtcattt ttacgcgctc cttcctttgc aagatcattg acagatttca  55380
agtcgccatt ttttctcaag tggtccgcta ttattcctgg agaattgtaa tcttcagccc  55440
gcgcaagcca tccatagagc tcggatcctt gattcttttt tccaatccag tccttcttac  55500
cgaatcctcc tgccgcaaag tgactttcaa aggtacgcgc atttctgaaa ccattccagt  55560
cctttccaaa ctcaacaata gcatttcctg tatgacctct aaaagtccat aacgggatga  55620
ccctcagtgg gaaaaagtgt gatagttgct ccttcagacg atttccactt tctccaattt  55680
ggcgcccatc cttccattca gtaggcacat taactaggac acccatccag ggccacacaa  55740
acttctcgtc tcggttctga agaggttgtg gctccacagg agttgcatgt gaccctggtt  55800
caggtgattt agcaagacca ttcttcaaat atttgaagag ggcgcgatgg actgcttttt  55860
cttttgcctc gcgattaggt gctgcactga ctcctgaggc atgttgaacc aggctacttt  55920
tactgtaatt cttcttcttg ctgctacaga agggacaaat gtaattttct ccattcttat  55980
ttaattttaa atctcctgac atcagtcttg cataaatttt tccttcataa tcatcaatct  56040
cagaatcact gatttctgta tcttcgtcag aactatgatc cattttcaag aaggggaaga  56100
aaatataggc aacctagcaa ggcaaaacaa ataacactga gaacacaaca ataaagtttg  56160
ttttttgaac taatttttca ttatgaagta ggaatgagca cttgggaaag agaacagcaa  56220
gcatggaaca ctgaaatact atcatgcaag gggaacaggt ttgcccattc agaacacatt  56280
gctcctagat tgagcccaca gttcggagca ggctgacctt aacaggaaga gggttcaaag  56340
ggtaggaacc attttgacac cctagggccg ccccgctcat gagtggtgcc atccactcac  56400
ctctgcctca cttgtgacct ctgagaaaga gatgcagtac cgatgcccat gcagatgctg  56460
gcactagtgg tgaccctaaa cacaggaatc accaccgaac atgtccaaag ggtgcctatt  56520
tccaccctct catacctga gaccctgaag atctaaaaca tgcttcgttt tgtttctaga  56580
tgccggttga ttccgattag aggattagta gagatgctag gttttcattt ctagatttct  56640
tggtggattt taccagcttt ctttgaaggg gatccaccag cttcaccatt gtcagggaaa  56700
aacaaaattc tctacaagta atatcttgct tggaatcatc taacaacaat gtgtgtcatg  56760
tctggttgga ttattcttga tttcagtttt ggtaagtcat gtttgtataa aggcatgtta  56820
gcaagctgcc atgaattttt attttggtaa cgctctcagc tattagcaga ctgtaacttc  56880
gggggggggg gggggggggg acaaacaaaa cttctaatag gttacattaa gcatatgtac  56940
tgaatatctg aagcgcctgc acctatgttg acctgatacg gggatacgga tacgcgatac  57000
gccatttctc aaaaaatacg gatacggcga tacgcaatat atattataaa taaaattaaa  57060
tgctgaaatg tctgaaatgg accacagccg atcagttcaa tttaaggacg ttagaagtta  57120
atgttcaaca actttgacta aagtaaacat ctacttcctc ttccagaatt tatctggact  57180
caaatcaatg aatccagcat gccaaaagcc caaaaacatg tgtaacgata cgctacacca  57240
gcagactcgc aaaataatca ctagttcacc aaatcaccac acaagttcta agttttaatt  57300
cgaacagacc acagaccaca gaccagacat gagacaacaa cagatgggag atacactaca  57360
```

```
ccagcagact cgcaaaataa tcactagttc accaaatcag tagatgcact cgttgccatg  57420
ggatattggg atctaacaag aacagagaat ggacaaccgc agcgtcagac agggcagatg  57480
ggagatggca gcagaatagc agatcacgta cctcagtacc tcacgacggc agatgggttg  57540
gctgacggcg cgaccacaga gctggcggcg gtggacgcgg ccacggaagc gcggctgtcg  57600
gctggagtgg cggtgcgcag ggaagcgcgg ctgcgcgcgt ctccaagcgg tgaagggctg  57660
gcggcgcgca gggaagcgcg gggctagcag cgcgcaggga agcgcggggc tagcggcgcg  57720
caggaaggtg cgcggggatg gcggcgcgcg gtggggagaa gcggggctgg cggcgcgcag  57780
ggaagcgcgg ggctggcggc gagcaggaag gtgcgcgggg atggcggcgc gccgtgggga  57840
gaagcggggc tggcggcgcg cagagaagtt gcgcgtgtgc gccgtgggga gaagcggtgc  57900
gcaggaaatt agggatataa ggtaccccac atgtgttcaa gaggtgtcct agaactatcc  57960
gtcttttttt atttatttaa attcacagaa atttccaata cgtctcagat atgtatccag  58020
aagtatccgc gaagtatccg tatctaatac ggtatccgac accggtacgt gaattttgag  58080
aagtatccgc gcatcatagg catgcacttg gttggtttca tgaaggattt gtagcatgta  58140
tgaattattg tttctactag ttggcatgca agtctgtttc tcctggaaag aactctgaaa  58200
aaatatgcac gcgtcaacag atcagagcct cgatgatcag aaaaaaacaa agagcatgtg  58260
tttctgtagt atgtactgca catcgtcatg cattatagca ggctatgttt gagtaacctt  58320
tgtgtttacc aataccgcct atctagctat tattaatcat attcaacccg acttccctag  58380
gctggttgcc cttttcttag actaaatatg cagggtgtca aacaagtggc caaattgatc  58440
aagtgcatat aatgacaccc attgtaagtg tagatcaggt ctcataaacc aggaacatag  58500
aacttgtcca cgttcctcgt tccgagaacg ttcgttccgt cccaggaacg cggaaacaat  58560
ctcgtccctg tagtgttaaa atcgtctttt aagtatcata ccatgaacca tgttcccgtt  58620
cctcgacctt atcaatatga gaacctggtt actgaggatc aggtttcctt tctgttatga  58680
acctttgttc atttggggtg accattgcca ggaggacagc caagcaaagt cagtttggtt  58740
acttcccgtc aatgctacac tttcttgttc gtttttatgc aatttctaga tgaactatca  58800
actaggcatc cattgatgtt agcacagttt agctcctgta atgtgtatcc atctatggat  58860
tgttcaatca tgtgattaat taattgataa aagtacgaat agaaaataca gtagtaacat  58920
atccttgttc ctcttgctgt ggcaactggc atctgtttgt tgttagttga tacttacttg  58980
gcaggcatag tgctggcatt gtcataaatt tggagactac ttcacagtat atgcatatgt  59040
gtgtttttgc aattttggtg atagggtgga taactatcct ggaaccaaat ccttgcttaa  59100
ggtgtacttg tcggtttcag ctgatggtat ccaggcaaca aaaagagtct gttatttctt  59160
gtttttata gctatgtaat gttgtcttgt attcagccag tggcacaaga tggataaaaa  59220
atgtgtaaaa aatcggagaa aattggagaa acatctcacg cccttaatgg ggcagagggt  59280
gtgacctttc atatatagaa ccgagtaggc ttaggttaca aaaatacgac aagacctatt  59340
caaatacaat ggcgcgacta tatgcatttc taataaaata agcttccaga tacttgatta  59400
atgctaattg tatcagaata atgtgagctt tctgatgttg tcaatgtgaa aacccttcag  59460
cttggacagt atcttccttt cctaactgat tttttagaga acaaaattct tggtccagct  59520
tttattgaaa gccgatgaaa cggttctttc tttcctaact gattgatatt ggtaacttgt  59580
tttctgagct ttaatcctcg gatatctcag gtgcgctctt actagagaag gatgttgtca  59640
agttggactc cattgctcag aaagtcaata cccattgtct aagctcaggt tgttggaaaa  59700
```

```
tcattaggaa ttattgcatg aaaataatct aagagcggac ttcattagcc ttcctgagga  59760
tagtggtcac tgaccaaatc ttccatgttt atgcaaggaa acataacatt tactgactat  59820
gagtgttcaa aatttgttca cttgcttttg aagatagctt ctggttccaa gagacaggtg  59880
ttgttgtagg agatctgcta acattttgat caaatccagt tggtgttata cagcactggc  59940
ttactaacat tactataaaa tccttgttga agaatctgta agttgttaat ctttgttgaa  60000
tactaacttc tttataattt tatttattat cttctatatt tagtcactga gtgtgcagtg  60060
cgctttgcat gcatagagaa gttgaaagca acacaatcga gactgcagca atctctattt  60120
gctagttcag tagttctcgt ctattctctg tttgcgaact tcagcgtgaa gaaagtcctt  60180
aaagaaaagg tgaggacgat caaaccaagg ggcggaccca gtaaagggca tggatataca  60240
cccaataatt tttgcaaagc aaacaaagtt agtagacatg atacattcat atacacttgt  60300
aattagattc agatccgatc acgaagagta tgttagtgtt tgggcgcacg gcttcgcaca  60360
gcaggaaggg aagaaagggg agggagcacc tggtgtccta gtgatgctcg tcgcctccca  60420
aggtggcgag gaagggggcg agctcggacg cgggtaggaa gaggaggcag ccgccaccct  60480
ctgctgatgg gtcggggtag gtagaggggg aaagaaaatg gaaaaagtta ctctcttcgt  60540
tcttcagcca aactctctat ctcactctat gttacaaact tcactctaca aacaaacagt  60600
acaatttact gtgcaaaaga gtattttgca cgacctttta tattaaatat aaccttagag  60660
cgttttcaaa actatcttca tttttctct ctattcgatt ctctatttac ctttccataa  60720
aaattacact ctatatatag catttcactc caacaaatta tttatctact ttgactagtc  60780
agattggcta gctaagttga ctagtgagag catctctaaa agactagcaa atggtttatc  60840
aagccaaatt tcggctactc aacaataaaa taactctcca acggactagc catccaactc  60900
gccaaggtat tcgactcttt aaattggtct cctctctagt caaatttata ggtgtacgtt  60960
cgggccgccc ggcccggccc aagcccgaaa aggcccgtaa tatttgaatt tcgggccgat  61020
ccggcccgtt tgaatttcgg gacgtgtcgg gccagcccac gggcctagcc ctcggcccac  61080
ggccggtccg taattggtta aacatgcctg gctcatttcg ggcggcccga aattataaaa  61140
gcctgaaatt cacattaaga cccgaaattc attttttggc ccgaaattca catcagggcc  61200
cgaaattcaa aacaaattta ataaaacaaa taaaagataa gacaaataaa tttgaccaaa  61260
agcaaactta atatttgtat taagttacta gagctataca atgactacct cgtttacaaa  61320
tcattttgtt agaaagaaaa agagtataat cagctctata taaagttcgt aagttcagtt  61380
cattatctaa tattcataac aaaaataaaa ttacatcaca tactctaatt caaagataca  61440
aaaaacatct aactaacatt atctctagct ttgtgttctt tatcaagtac atgaaagtgt  61500
ggaataaagt gtgattttaa taaatatatg agccttttc tgcttctata tgagtcattt  61560
cgtgtctgcc ttaaacgggt cgtgctcgtg cccgcccatg ggccgcgacc tcggcccaaa  61620
cccggcccaa cactaaaata tttcgtgtcg tgtcgtgcct gggccgtgct tttttccgt  61680
gctttgggcc ggcccatcag gcccggctca aatgtacacc tatagccaaa tttgactagc  61740
cactctggct agacaaacta aataaatagt ctgttagagt gagatgctac atatggagtg  61800
taatcttatg gagaggtaaa tagagtgtca aatagagagt taaaaatgga gtccctggag  61860
atgctctgag gaagctaatt tggagaatcg aatagcttgg cgagttagat ggctagtcta  61920
ttgaagagtt tttttctgtt gagtaactaa aatttggctt gacgaactct ttggctagtc  61980
tcttggagat actagactct ctcccgctat tccccatggc cccatataat ctctctattt  62040
atatttatta gagtaaaata tactagtggt ctttaaactt atattgttgt attattctag  62100
```

```
tcactaaacc cctaaagtgc aaatataagg tccttaaact tgtgaatttg tatcgttctg  62160
gtccctaact ctgaacatgc acatttcagt ctttatactt gtaggattgt gtgtcgtctg  62220
ggcctctaaa cttatttttg gtgtcatcaa gggtctaaac tatttataca tataatgaca  62280
ccaaaaataa gtttatggat ccaagtgaca caaccataga agtataggac caaaaatatg  62340
tatcttgaga ttttagggac caagatgata caacttaaca agtttaggga ccttagatgt  62400
gcacttttag agtttaggga ccaggatgaa acaacgctaa aaatgtaggg accgctaatg  62460
cattttactc tatttttatt atattttact atataagata cttctcttat ataccatctc  62520
ctctatagaa ctcttcatat acgctataac tcaattattt aatattttat caactttaaa  62580
aatctaaaaa atgatataat attttactat tataatacac attatcatta ggttacatga  62640
cttaaacatg attaatatca taaacaaatg atctaattaa attatagggg tagtatatgt  62700
ccaccctatg agagggtttt atctctccct cccatatgag agttagttgg agaagaattt  62760
ccctccaaaa ccccttatgc tctgtttcga tgtcgatatt taagaagatg gaattgaatt  62820
gagtcgaata ccaaatcaga catggtattg aaatgagatg taatttcaat tctactgttt  62880
ggatgccact aaattgagtt tggaattgtg cggtctaatt ccacgcaaca tcaaggggtg  62940
aggctttgta ttgggagagg ggtttctagt tatagtccaa tttcaggaaa tttagtctct  63000
gatttcaaat ctcaattcca tgtgcaacca aacaacagaa tttagaaaag ttggtttcat  63060
tttctaatta tgtgctctaa tatctatatc taaacagggg tattacatat ggtgaggtga  63120
gagatagagg cactgtctta tagtctgata gatgaacata tgtgttatct ccttttttta  63180
atagaccaaa tagaaaagaa tagaaaaaag ttaaacctat cccccgctat atctcataac  63240
cacacatatc tacaatattt tttaaaaaat caaagacact aatagtagaa gttactatga  63300
caaagtttag tctgtgttac atcgaatgtt tgaatgttgg ttataattat atatagtata  63360
attataaaaa ataatcatat agatgaagac tatatgattt aaccccttgag agagtcttcc  63420
ccgagcccgc gggcttgtcg tcggtcacgt tctccctctt ggcgtgatct ccagacatca  63480
ctttgagttg attagactct taatgaagca ctaactttga taccaattga aagtcgccta  63540
gagggggtga ataggcgaaa cctaaaattt acaaacataa acacacacta aggccggggt  63600
tagcgttgga attaaattca agtctgaaag attgtttctt ttgctaagag ttgttcaaag  63660
gatgcggatg acgtatggga gcaaactcaa atcaatatta gcaaggaaac gttagagaga  63720
ggaaagaggg caaacaaatc aagcgagtag acatagtgat ttgttttacc gaggttcggt  63780
tctaaagaac ctaatccccg ttgaggaggc cacaaaggcc gggtctattt caaccctttc  63840
cctctctctc aaatggtcac ttagaccgat tgagccttct ccttaatcaa acgggtcact  63900
aaggtgtctc ttgcaaactt tacaagcact tagaaaaaga atgaggaagg aagaaaggca  63960
atccaagcga caagagcaac aaaagaacac aaatgaccct ctcacaatcc cttaagcact  64020
agcgttgatt ttgggaagtt ttgagtggat tgattgtttt gattgtgtct tggagtgttg  64080
gactttgctc ttgcaatgaa tgagaaactc aaaatgcttg gatggctttg aatgaggtgg  64140
ttgaggggta tttatagccc ccaaccactt cctagccgtt ggtaaaggct gctggcgatg  64200
ggcgcaccgg acagtcactg ttcattgtcc ggtgcacgcc acgttagcgc gcccgttagg  64260
gtttggagca gttgaccgtt gaagccgttt gtctttttgc tgcaccggac agtccggtga  64320
cttctgcacg gcactgtttg gcactgttcc tctgcgcagt cgaccgttgg cgcgtaggga  64380
gccgttgctc cgctggctca ccggatagtc cggtgaatta tagtggagcg cacgcggcac  64440
```

```
aaccaccaaa gtggccgttg ggaggggctg ctatcgatgg gcgcaccgga ccgtccggtg  64500
cgccagacca gggcagcctt cgggtttctt tgctcctttc tttttgaacc ctatcttgga  64560
ctttttattg gtttgtgttg aacctttggc acctatagaa cttataatct agagcaaact  64620
agttagtcca attatttgtg ttgggcaatt caaccaccaa aatcatttag gaaaaggttt  64680
gaccctattt ccctttcagt ctcccccttt ttggtgattg atgccaacac aaaccaaagc  64740
aaatatataa gtgcagaatt gaactagttt gcataaggta agtgcaaagg ttgcttggaa  64800
ttaacccaat ttatactttc ataagatatg catggattgc tttcttctta tttaacattt  64860
tggaccacgc ttgcaccact tgttttgttt ttgcaaaatc ttttggaaat tcttttcaaa  64920
gtctttttgc aaatagtcaa aggtaaatga ataagatttc gagaagcatt ttcaagattt  64980
gaaattttct ccccctgttt caaatgcttt tcctttgact aaacaaaact ccccctcaat  65040
gaaattctcc tcttagtgtt caagagggtt ttagacatta attttgaaag aggtcatacc  65100
aacttgaaat tatataaaaa ataagatacc aattgaaaaa cttctttgat acaaattgaa  65160
agactgcatt taaacacttt ttgaaattgg tggtgatgcg gtccttttgc tttgggttaa  65220
tactttctcc ccctttggca tgaatcgcca aaaacagata ctttgtgagt gaaatatgag  65280
ccctatgttt aaattctctc cccctttggc aaacaatata tgagtgaagg attataccaa  65340
ggtggagagc gatgcggagt gacggcgaag ggcaaataat acgatggagt ggagtggaag  65400
ccttgtcttc gccgaagact ccatttccct ttcaatctat gacttagcat gagatacact  65460
tgaaaaacac attagtaata gcaaataaaa gagatatgat caaaggtaca taaatgaacg  65520
atgtgtgcaa agtatcaatc aaaattccta gaatcaagaa tgtttagctc attcctaagt  65580
ttggtaaagg ttttctcatc taatggtttg gtaaagatat cggctaattg ttctttggtg  65640
ctaacatagg caatctcgat atcccccctt tgttggtgat ccctcaaaaa gtgataccga  65700
atggctatgt gcttagtgcg gctatggtca acgggattat ccgcattgca ctctcattat  65760
cacacagaag agggactttg gttaatttgt aaccataatc cctaagggtt tgcctcatcc  65820
aaagcaattg tgcgcaataa tggcctgcga caatgtactc ggcttcggtg gtagaaagag  65880
ctaccgaatt ttgtttcttt gaagcccaag acaccaggga tcttcccaag aactgacaag  65940
tccctgatgt gctatttcta tcaattttac acccatccca atcagcatct gagtatccta  66000
ttaaatcaaa ggtggatccc ttggggtacc aaagaccaaa cttaggtgta tgaactaaat  66060
atctcaagat tcgtttcatg gccctaaggt gaacttcctt aggattggct tggaatcttg  66120
cacacatgca tacggaaagc ataatatccg gtcgagaagc acataaatag agtaaagatc  66180
ctatcatcga tcggtatacc ttttgatcta cagatttacc tctcgtgtcg aggtcgagat  66240
gcccatggtt cccatgggtg tcttgatggg cttggcatcc ttcattccaa acttggtgag  66300
tatatcttga gtatactttg tttggctgat gaaggtgccc tcttggagtt gcttgacttg  66360
aaatcctaag aaatacttca actcccccat catagacatc tcgaattttt gaatcatgat  66420
cctactaaac tcttcacaag tagatttgtt agtagaccca aatatgatat catcaacata  66480
aatttggcat acaaacaaat catttgcaat ggttttagta aagagtgtag gatcgacttt  66540
tccgactttg aagccattag tgataagaaa gtctcttagg cattcatacc atgctcttgg  66600
ggcttgctta agcccacaaa gtgcctttga gagtttatag acatgattag ggtactcact  66660
atcttcaaag ccggaaggtt gctcaatata gacctcttcc ttgattggtc cattgaggaa  66720
ggcactcttc acgtccattt gataaagctt gaagccatgg taagtagcat aggcaagtaa  66780
tatacgaatt gactcaagcc tagctattgg tgcataggtt tcaccgaaat ccaaaccttc  66840
```

aacttgtgaa tatcccttgg ccacatgtcg ggctttgttc cttgtcacca caccatgctc 66900
atcttgcttg ttgccgaaga cccacttggt ttctacaaca ttttggttag gacgtggaac 66960
aagatgccat acctcgtgaa gttgttgagt tcctcttgca ttgccaacac ccaatccgaa 67020
tcccttaatg tgtcttccac cctgtatggc tcaatagaag acacaaaaga gtaattgtcg 67080
gtaccctgaa ccaggggtac cccctactac agtataagga agcattgccc gtacgacgtt 67140
ccctagccac acggtgagca gcacccgacc ccaccatgtg ggtggctcaa ggggtaccac 67200
gtggcgagaa aagatgacac atcccaggat atatcagttg aaccggacca ccacgaagga 67260
gcaccggacc cctgtatgca caacccggac ccccgattac ggctcgagac tcccaagtaa 67320
gcatgccgag ccccttggat ggggtccaga tccctttgag taaggtccgt accacaacga 67380
ggtcccgaga catgggagac cctggcataa gcaagggtcc ggtattgaca cgtgttaggg 67440
ccttatcatg tgcgcttgcg ctccctgctt aggcggagac ccgctactgc cacgtggctt 67500
gttgcctgtg acataagcca acgggcagag cctgatgtaa ggcctctagg ccgtgcggtc 67560
tctgcattta ttgcggagga gacgcgtcgc ctgcccacct tgctgacagg cgatgtgccc 67620
cctttgcatt taatgcgtcc tgtccactcc accggcaggc gcaccaggcc atcctgcagt 67680
cggcgcacct gtccagtcca ttgtcaaata gtgcacccgt gctacagggc gcactgtgct 67740
catcatccct tatacgataa gcttcctctg cacgccgatg ctaggcagat ctcagacgtc 67800
agggcataag gagattgccc cagcagcaaa catgagtagc gccaaatact acatctgtta 67860
tgttcctggg cccacatgtc ggggctcagt atccttgtgc atgtcccccct tgactataaa 67920
aggggaggca tgcaacgtta caagacaggc tctctaagac ctaaggcaga cttcgaacgc 67980
tcaagcttcc acagcaatcc aacacataat ggagtatggt attacgctct gacggcccga 68040
accactctaa actctcgtgt gttcatgtgc tcggtgatcg cttagctaga caggcaaaat 68100
gcttaagccc cttcctcatc ttaggattaa gggcgggtgc actccgccac ccgaccggag 68160
aattccctct ccaacatttg gtgcgccagg tagggggcta ggcattaggt ttttgtttgt 68220
ttcctcgctc agcatgatgg tgcaaatcgt ggagcaccgc gccgatacat caacgaattt 68280
cctggtggag gaagaagttg tttcttccac gccactggtt cccaaccgcc cagtgtcggg 68340
cactgctgct gtgcacgctg cacaatagca tacagctgcg tagacatctt gtactccgtc 68400
gagggtggct ctgggagcat tgtcggcggc cagggagttg ctgtgccacc ctccaagctc 68460
catggactca ccgggggcca tgaagcagtg gcgggacgac gtcgaccgac tgctcggtat 68520
ggcacattct acctcaacca ggtcgaggcc acggtcatcc cggcgccaac atgaggcgtc 68580
ggcgtctatg cgcgcgccct cagtaagggg cgcatagacc aacgacctcc gggccgagct 68640
caaccgcagg cgtgcgggag aggacgcccg actctcttta gagagggtgc acgagcgccg 68700
acaaaacgtt gagggtcgca acctcgacca agactttgct gcggtagcac cgcaggcccc 68760
aatgggcacc cggtctcgag cgggtgtccc cttggtcggc gtgggctgcg ccgctttcgc 68820
ggatcatctc cgcgcaacat catggccatc caaattctgg ccgcacttgc cggaaaaata 68880
tgacggtacg tcaaacccgt cggagttcct acaggtgtat gtcaccgcta tcacagcagc 68940
aggtggaaac accactacga tgcgtgacat attttcatgt cgccttgtct gggcctaccc 69000
ggtcttggct catgaacctc gccccagggt caatctactc ctgggaagag ctctgcgcat 69060
ggttcgttgc gaacttcgcc agcgcttacc agcagcacgg tgtggaggcc caccttcacg 69120
cggtaaggca ggagcccggg gagactctcc ggacgttcat ctctcgcttc accaaggtgc 69180

```
gaggtactat accttgcatt tttgatgctt ccatcatcac ggctttccga cagggagtac  69240
gtgatgagaa aatgttggag aagttggcca cacacgatgt ggagattgtc cccacactct  69300
tcgctctggc cgacaagtgc gctagagccg ccgaggtccg tgcatggcac tcggccccac  69360
aagccggggc tacccagtcg ggtggctcag gtgtcgtctc ccgggacggt aagaagaaaa  69420
agaagaagga ctacgactac tagaagtcgc ggtccaccgc tctagtcgtt gcagcggtga  69480
ccgagggccg gggcaaccgc aacaaacgcc cacggccgca gaggggtaac agcgactcat  69540
gccctgtgca ccccaacggt cgccacagct ctgcggagtg tcgcgagatc attgacctcg  69600
cgaaacgcgt cagcgagcgg cgtgagcagt cttccaagga tggctctcca cctcgtcgcc  69660
aacccggcaa agaaaaggtc gacgacgctg taagggataa cactgaacat ccaacgttga  69720
ttactctatt atagtattat acagactgta cttttcgaat ttatcttagt tttctacaat  69780
atttagtgga ttcttctcat tttcaagata cacaattgaa ccataatcga agtggtatgt  69840
aagacagtga gttaaaagat tatatttttt gggagacttc cagtcaaatt ttcttagaag  69900
tttttttggt ccagatgttc ataaagtcgc cgctttcata cttttttaa tttttaatt  69960
ggtgcactat taggtacctg ttggaggatg ttacaggctt attgatatcc ctatgagtaa  70020
ctgcttcaac agtggtataa ataagatatt tgtgatgagt cagttcaatt ctacttcgct  70080
taaccgccat attcatcgta catacettga aggcgggatc aactttgctg atggatctgt  70140
acaggtgatt tacctcatct tgttgatgtg taatactgta attaggagta gatttgtgtg  70200
gagagaataa taaacagatg ccgagattct tctctaaaag tctagatcca aaggcattgt  70260
ggttcaaaac actatggact tctaccattt atgttattac tttgccttaa tgttccattg  70320
aatggggcaa attattgatt ctacaagtgt ttaattaaaa actaattgtt catcctgcag  70380
gtattagcgg ctacacaaat gcctgaagag ccagctggat ggttccaggg tacagcagac  70440
tctatcagaa aatttatctg ggtactcgag gtagttgata ttttctcgtt tatgaatgtc  70500
cattcactca ttcctgtagc attgtttctt tgtaattttg agttctcctg tatttcttta  70560
ggattattac agtcacaaat ccattgacaa cattgtaatc ttgagtggcg atcagcttta  70620
tcggatgaat tacatggaac ttgtgcaggt atggtgttct cttgttcctc atgtttcacg  70680
taatgtcctg attttggatt aaccaactac ttttggcatg cattatttcc agaaacatgt  70740
cgaggacgat gctgatatca ctatatcatg tgctcctgtt gatgagaggt aatcagttgt  70800
ttatatcatc ctaatatgaa tatgtcatct tgttatccaa cacaggatgc atatggtcta  70860
atctgctttc ctttttttccc ttcggaagcc gagcttctaa aaatgggcta gtgaagattg  70920
atcatactgg acgtgtactt caattctttg aaaaaccaaa gggtgctgat ttgaattcta  70980
tggttagaaa ttccttgtgt aatccaattc ttttgttttc ctttctttct tgagatgaac  71040
ccctctttta gttatttcca tggataacct gtacttgact tattcagaaa tgattttcta  71100
ttttgctgta gaatctgaca ctaaagctaa tagctactga tgttgcagag agttgagacc  71160
aacttcctga gctatgctat agatgatgca cagaaatatc catacettgc atcaatgggc  71220
atttatgtct tcaagaaaga tgcactttta gaccttctca agtaatcact ttcctgtgac  71280
ttatttctat ccaactccta gtttaccttc taacagtgtc aattcttagg tcaaaatata  71340
ctcaattaca tgactttgga tctgaaatcc tcccaagagc tgtactagat catagtgtgc  71400
aggtaagtct gatctgtctg gagtatgtgt tctgtaaact gtaaattctt catgtcaaaa  71460
agttgttttt gtttccagtt tccactagtt tttatttacc aatgcgcgat ttatgtattt  71520
tcgcttccat gcatcataca tactaacaat acattttacg tattgtgtta ggcatgcatt  71580
```

```
tttacgggct attgggagga tgttggaaca atcaaatcat tctttgatgc aaacttggcc  71640
ctcactgagc aggtactctg tcatgtattc tgtactgcat atatattacc tggaattcaa  71700
tgcatagaat gtgttagacc atcttagttc catcctgttt tcttcaatta gcttatcatt  71760
taatagttgt tggctagaat ttaaacacaa atttacctaa tatgtttctc tcttcagcct  71820
tccaagtttg atttttacga tccaaaaaca cctttcttca ctgcaccccg atgcttgcct  71880
ccgacgcaat tggacaagtg caaggtatat gtcttactga gcacaattgt tacctgagca  71940
agattttgtg tacttgactt gttctcctcc acagatgaaa tatgcattta tctcagatgg  72000
ttgcttactg agagaatgca acatcgagca ttctgtgatt ggagtctgct cacgtgtcag  72060
ctctggatgt gaactcaagg tacatactct gccaatgtat atgctgatgt tttatacatt  72120
ctcttgcata atttgattcg agtcaccaca attagtgtaa ctgcaatcta ctcttgagta  72180
taccatttca acaccaagca tcaccaaatc acacagaaca atagcaacaa agccttttag  72240
ttccaagcaa tttagggtag cctagagttg aaatctaacc aaacaaaagt caaagctcta  72300
tcacgtggat agttgtttc catgcactct tatttaagct aatttttggg tatactacat  72360
ccatttaatt attgttttat tgcttcttcc ctttgccttt cccccattac tatcgcgtct  72420
taagatcata ctacgcacta gtgtctttag aggtctctgg tggacatgtt caaaccatct  72480
caatcggtgt tggacaagtt tttcttgaat ttgtgctaca cctaacctat catgtatgtc  72540
atcgtttcaa actcgatcct tcctgtatca tcataaatcc aatgcaacat acgcatttat  72600
gcaacattta tctgttgaac atgtcatctt tttgtaggtt aacattatac accatacaat  72660
gtagcatgtc taatcatcat cctataaaat ttacatttta gcttatgtgg tatcctcttg  72720
ccacttagaa catcatatgc ttgatgccat ttcatccacc ctgctttgat tctatggcta  72780
acatcttcat taatatcctt gcctctctgt atcattggtc ctaaatatgg aaatacattc  72840
tttctgggca ctacttgacc ttccaaacta acgtctcctt tgatcctttc ttgtgtgtag  72900
tagtaccgaa gtcacatctc atatattcgg ttttagttct actaagtccc gggttcgatc  72960
cccctcaggg gtaaatttcg ggcttggtaa aaaaaatccc ctcgctgtgt cccgccctct  73020
ctcggggatc gatatcctgc gcgccaccct ccggctgggc attgcagagt gggcagttga  73080
tcgactcgtt agtgatgggg agcggggttc aagggttttc tcggccggga ccatgtttcg  73140
gtctcttaat ataataccgg gagggcagtc tttccctccc cggtcgagtt ttagttctac  73200
tgagtctaaa acctttggac tctagagtcc cctgtcacaa ctcacaactc tatttttcta  73260
tttacttcta cctagcgttt attaatgatc actatatcgt ctgtaaaaag catacaccaa  73320
ggtaatcccc ttgtatgtcc cttgtaatat tatccatcac aagaaaaaaa ggtaaggctc  73380
aaagttgact tttgatataa tcctattcta atcgagaagt catctgtatc ttcgtctctt  73440
gttcgaacac tagtcacaaa ttttttgta catgttctta atgagtccaa cgtaatattc  73500
cttgatattt tgtcataagc cctcatcaag tcaatgaaaa tcacgtgtag gtccttcatt  73560
tgttccttat actgctccat cacttgtctc attaagaaaa tatctctcat agttaacctt  73620
ttggcatgaa acaaaatcac acagaatttg tttccttttt ttaagatccc acacaaaaga  73680
ggtttgatct aaggaatctg gatccctgac aggtttatca aaatcctttg tgtttttctt  73740
aaaactgaat attcctccag cttctagtat tgatgtaata ttcaatctgt ttagcaagtg  73800
aacaccttgg ttcttgttgt tactgtacat cccacccacc cccgaggccc agattaccac  73860
aacatgaata caagaatatt gaacccagat ctagagtttg tttgtactgt tgaaaatcgg  73920
```

tgacaattca ttttgttatt gcgctttctg ataacgacag gactccgtga tgatgggagc 73980
ggacatctat gaaactgaag aagaagcttc aaagctactg ttagctggga aggtcccagt 74040
tggaatagga aggaacacaa agataaggtg agtatggatg tggaaccacc ggttagttcc 74100
caaaaatatc actcactgat acctgatggt atcctctgat tattttcagg aactgtatca 74160
ttgacatgaa tgctaggatt gggaagaacg tggtgatcac aaacagtaag gtgagcgagc 74220
gcacctacat gggtgcagaa tcttgtgtgc tcatctatcc taattcggta attcctatcc 74280
agcgctagtc ttgtgaccat ggggcatggg ttcgactctg tgacagggca tccaagaggc 74340
tgatcacccg gaagaagggt actacataag gtctggaatc gtggtgatct tgaagaatgc 74400

<210> SEQ ID NO 33
<211> LENGTH: 19429
<212> TYPE: DNA
<213> ORGANISM: Zea mays

<400> SEQUENCE: 33
acgcagcttt tgattctcat caatgatctt ctgagaatgc ctgcgagcta gctgctgcat 60
cttgctaatt tctggtaatg gttatgctta ttaatttatc tttcaaatga aacttcacag 120
ctgctgatga tagaaaactg gaaatataac taaacccatg cggaaaaaat caacaaaaag 180
aataacataa accttcattg tatgactgga gaagttgttc cctttgcccc atcatcttct 240
caagtgatgc agttgtctca ctgtatttgc attctagttc ctgtaaatac ctatttttca 300
cctcaatttg gttagctaaa ttagcaacaa gcctgtcatt tttacgcgct ccttcctttg 360
caagatcatt gacagatttc aagtcgccat tttttctcaa gtggtccgct attattcctg 420
gagaattgta atcttcagcc cgcgcaagcc atccatagag ctcggatcct tgattctttt 480
ttccaatcca gtccttctta ccgaatcctc ctgccgcaaa gtgactttca aaggtacgcg 540
catttctgaa accattccag tcctttccaa actcaacaat agcatttcct gtatgacctc 600
taaaagtcca taacgggatg accctcagtg ggaaaaagtg tgatagttgc tccttcagac 660
gatttccact ttctccaatt tggcgcccat ccttccattc agtaggcaca ttaactagga 720
cacccatcca gggccacaca aacttctcgt ctcggttctg aagaggttgt ggctccacag 780
gagttgcatg tgaccctggt tcaggtgatt tagcaagacc attcttcaaa tatttgaaga 840
gggcgcgatg gactgctttt tcttttgcct cgcgattagg tgctgcactg actcctgagg 900
catgttgaac caggctactt ttactgtaat tcttcttctt gctgctacag aagggacaaa 960
tgtaattttc tccattctta tttaatttta aatctcctga catcagtctt gcataaattt 1020
ttccttcata atcatcaatc tcagaatcac tgatttctgt atcttcgtca gaactatgat 1080
ccattttcaa gaaggggaag aaaatatagg caacctagca aggcaaaaca aataacactg 1140
agaacacaac aataaagttt gttttttgaa ctaatttttc attatgaagt aggaatgagc 1200
acttgggaaa gagaacagca agcatggaac actgaaatac tatcatgcaa ggggaacagg 1260
tttgcccatt cagaacacat tgctcctaga ttgagcccac agttcggagc aggctgacct 1320
taacaggaag agggttcaaa gggtaggaac cattttgaca ccctagggcc gccccgctca 1380
tgagtggtgc catccactca cctctgcctc acttgtgacc tctgagaaag agatgcagta 1440
ccgatgccca tgcagatgct ggcactagtg gtgaccctaa acacaggaat caccaccgaa 1500
catgtccaaa gggtgcctat ttccaccctc tcataccctg agaccctgaa gatctaaaac 1560
atgcttcgtt ttgtttctag atgccggttg attccgatta gaggattagt agagatgcta 1620
ggttttcatt tctagatttc ttggtggatt ttaccagctt tctttgaagg ggatccacca 1680

```
gcttcaccat tgtcagggaa aaacaaaatt ctctacaagt aatatcttgc ttggaatcat   1740
ctaacaacaa tgtgtgtcat gtctggttgg attattcttg atttcagttt tggtaagtca   1800
tgtttgtata aaggcatgtt agcaagctgc catgaatttt tattttggta acgctctcag   1860
ctattagcag actgtaactt cggggggggg gggggggggg gacaaacaaa acttctaata   1920
ggttacatta agcatatgta ctgaatatct gaagcgcctg cacctatgtt gacctgatac   1980
ggggatacgg atacgcgata cgccatttct caaaaaatac ggatacggcg atacgcaata   2040
tatattataa ataaaattaa atgctgaaat gtctgaaatg gaccacagcc gatcagttca   2100
atttaaggac gttagaagtt aatgttcaac aactttgact aaagtaaaca tctacttcct   2160
cttccagaat ttatctggac tcaaatcaat gaatccagca tgccaaaagc ccaaaaacat   2220
gtgtaacgat acgctacacc agcagactcg caaaataatc actagttcac caaatcacca   2280
cacaagttct aagttttaat tcgaacagac cacagaccac agaccagaca tgagacaaca   2340
acagatggga gatacactac accagcagac tcgcaaaata atcactagtt caccaaatca   2400
gtagatgcac tcgttgccat gggatattgg gatctaacaa gaacagagaa tggacaaccg   2460
cagcgtcaga cagggcagat gggagatggc agcagaatag cagatcacgt acctcagtac   2520
ctcacgacgg cagatgggtt ggctgacggc gcgaccacag agctggcggc ggtggacgcg   2580
gccacggaag cgcggctgtc ggctggagtg gcggtgcgca gggaagcgcg gctgcgcgcg   2640
tctccaagcg gtgaagggct ggcggcgcgc agggaagcgc ggggctagca gcgcgcaggg   2700
aagcgcgggg ctagcggcgc gcaggaaggt gcgcggggat ggcggcgcgc ggtggggaga   2760
agcggggctg gcggcgcgca gggaagcgcg gggctggcgg cgagcaggaa ggtgcgcggg   2820
gatggcggcg cgccgtgggg agaagcgggg ctggcggcgc gcagagaagt tgcgcgtgtg   2880
cgccgtgggg agaagcggtg cgcaggaaat tagggatata aggtacccca catgtgttca   2940
agaggtgtcc tagaactatc cgtctttttt tatttattta aattcacaga aatttccaat   3000
acgtctcaga tatgtatcca gaagtatccg cgaagtatcc gtatctaata cggtatccga   3060
caccggtacg tgaattttga gaagtatccg cgcatcatag gcatgcactt ggttggtttc   3120
atgaaggatt tgtagcatgt atgaattatt gtttctacta gttggcatgc aagtctgttt   3180
ctcctggaaa gaactctgaa aaaatatgca cgcgtcaaca gatcagagcc tcgatgatca   3240
gaaaaaaaca aagagcatgt gtttctgtag tatgtactgc acatcgtcat gcattatagc   3300
aggctatgtt tgagtaacct ttgtgtttac caataccgcc tatctagcta ttattaatca   3360
tattcaaccc gacttcccta ggctggttgc ccttttctta gactaaatat gcagggtgtc   3420
aaacaagtgg ccaaattgat caagtgcata taatgacacc cattgtaagt gtagatcagg   3480
tctcataaac caggaacata gaacttgtcc acgttcctcg ttccgagaac gttcgttccg   3540
tcccaggaac gcggaaacaa tctcgtccct gtagtgttaa aatcgtcttt taagtatcat   3600
accatgaacc atgttcccgt tcctcgacct tatcaatatg agaacctggt tactgaggat   3660
caggtttcct ttctgttatg aacctttgtt catttggggt gaccattgcc aggaggacag   3720
ccaagcaaag tcagtttggt tacttcccgt caatgctaca ctttcttgtt cgtttttatg   3780
caatttctag atgaactatc aactaggcat ccattgatgt tagcacagtt tagctcctgt   3840
aatgtgtatc catctatgga ttgttcaatc atgtgattaa ttaattgata aaagtacgaa   3900
tagaaaatac agtagtaaca tatccttgtt cctcttgctg tggcaactgg catctgtttg   3960
ttgttagttg atacttactt ggcaggcata gtgctggcat tgtcataaat ttggagacta   4020
```

-continued

```
cttcacagta tatgcatatg tgtgtttttg caattttggt gatagggtgg ataactatcc   4080
tggaaccaaa tccttgctta aggtgtactt gtcggtttca gctgatggta tccaggcaac   4140
aaaaagagtc tgttatttct tgttttttat agctatgtaa tgttgtcttg tattcagcca   4200
gtggcacaag atggataaaa aatgtgtaaa aaatcggaga aaattggaga aacatctcac   4260
gcccttaatg gggcagaggg tgtgaccttt catatataga accgagtagg cttaggttac   4320
aaaaatacga caagacctat tcaaatacaa tggcgcgact atatgcattt ctaataaaat   4380
aagcttccag atacttgatt aatgctaatt gtatcagaat aatgtgagct ttctgatgtt   4440
gtcaatgtga aaacccttca gcttggacag tatcttcctt tcctaactga ttttttagag   4500
aacaaaattc ttggtccagc ttttattgaa agccgatgaa acggttcttt ctttcctaac   4560
tgattgatat tggtaacttg ttttctgagc tttaatcctc ggatatctca ggtgcgctct   4620
tactagagaa ggatgttgtc aagttggact ccattgctca gaaagtcaat acccattgtc   4680
taagctcagg ttgttggaaa atcattagga attattgcat gaaaataatc taagagcgga   4740
cttcattagc cttcctgagg atagtggtca ctgaccaaat cttccatgtt tatgcaagga   4800
aacataacat ttactgacta tgagtgttca aaatttgttc acttgctttt gaagatagct   4860
tctggttcca agagacaggt gttgttgtag gagatctgct aacattttga tcaaatccag   4920
ttggtgttat acagcactgg cttactaaca ttactataaa atccttgttg aagaatctgt   4980
aagttgttaa tctttgttga atactaactt ctttataatt ttatttatta tcttctatat   5040
ttagtcactg agtgtgcagt gcgctttgca tgcatagaga agttgaaagc aacacaatcg   5100
agactgcagc aatctctatt tgctagttca gtagttctcg tctattctct gtttgcgaac   5160
ttcagcgtga agaaagtcct taaagaaaag gtgaggacga tcaaaccaag gggcggaccc   5220
agtaaagggc atggatatac acccaataat ttttgcaaag caaacaaagt tagtagacat   5280
gatacattca tatacacttg taattagatt cagatccgat cacgaagagt atgttagtgt   5340
ttgggcgcac ggcttcgcac agcaggaagg gaagaaaggg gagggagcac ctggtgtcct   5400
agtgatgctc gtcgcctccc aaggtggcga ggaagggggc gagctcggac gcgggtagga   5460
agaggaggca gccgccaccc tctgctgatg ggtcggggta ggtagagggg gaaagaaaat   5520
ggaaaaagtt actctcttcg ttcttcagcc aaactctcta tctcactcta tgttacaaac   5580
ttcactctac aaacaaacag tacaatttac tgtgcaaaag agtattttgc acgacctttt   5640
atattaaata taaccttaga gcgttttcaa aactatcttc attttttctc tctattcgat   5700
tctctattta cctttccata aaaattacac tctatatata gcatttcact ccaacaaatt   5760
atttatctac tttgactagt cagattggct agctaagttg actagtgaga gcatctctaa   5820
aagactagca aatggtttat caagccaaat ttcggctact caacaataaa ataactctcc   5880
aacggactag ccatccaact cgccaaggta ttcgactctt taaattggtc tcctctctag   5940
tcaaatttat aggtgtacgt tcgggccgcc cggcccggcc caagcccgaa aaggcccgta   6000
atatttgaat ttcgggccga tccggcccgt ttgaatttcg ggacgtgtcg ggccagccca   6060
cgggcctagc cctcggccca cggccggtcc gtaattggtt aaacatgcct ggctcatttc   6120
gggcggcccg aaattataaa agcctgaaat tcacattaag acccgaaatt catttttttgg   6180
cccgaaattc acatcagggc ccgaaattca aaacaaattt aataaaacaa ataaaagata   6240
agacaaataa atttgaccaa aagcaaactt aatatttgta ttaagttact agagctatac   6300
aatgactacc tcgtttacaa atcattttgt tagaaagaaa aagagtataa tcagctctat   6360
ataaagttcg taagttcagt tcattatcta atattcataa caaaaataaa attacatcac   6420
```

atactctaat tcaaagatac aaaaaacatc taactaacat tatctctagc tttgtgttct 6480
ttatcaagta catgaaagtg tggaataaag tgtgatttta ataaatatat gagccttttt 6540
ctgcttctat atgagtcatt tcgtgtctgc cttaaacggg tcgtgctcgt gcccgcccat 6600
gggccgcgac ctcggcccaa acccggccca acactaaaat atttcgtgtc gtgtcgtgcc 6660
tgggccgtgc tttttttccg tgctttgggc cggcccatca ggcccggctc aaatgtacac 6720
ctatagccaa atttgactag ccactctggc tagacaaact aaataaatag tctgttagag 6780
tgagatgcta catatggagt gtaatcttat ggagaggtaa atagagtgtc aaatagagag 6840
ttaaaaatgg agtccctgga gatgctctga ggaagctaat ttggagaatc gaatagcttg 6900
gcgagttaga tggctagtct attgaagagt ttttttctgt tgagtaacta aaatttggct 6960
tgacgaactc tttggctagt ctcttggaga tactagactc tctcccgcta ttccccatgg 7020
ccccatataa tctctctatt tatatttatt agagtaaaat atactagtgg tctttaaact 7080
tatattgttg tattattcta gtcactaaac ccctaaagtg caaatataag gtccttaaac 7140
ttgtgaattt gtatcgttct ggtccctaac tctgaacatg cacatttcag tctttatact 7200
tgtaggattg tgtgtcgtct gggcctctaa acttattttt ggtgtcatca agggtctaaa 7260
ctatttatac atataatgac accaaaaata agtttatgga tccaagtgac acaaccatag 7320
aagtatagga ccaaaaatat gtatcttgag attttaggga ccaagatgat acaacttaac 7380
aagtttaggg accttagatg tgcactttta gagtttaggg accaggatga aacaacgcta 7440
aaaatgtagg gaccgctaat gcattttact ctatttttat tatattttac tatataagat 7500
acttctctta tataccatct cctctataga actcttcata tacgctataa ctcaattatt 7560
taatatttta tcaactttaa aaatctaaaa aatgatataa tattttacta ttataataca 7620
cattatcatt aggttacatg acttaaacat gattaatatc ataaacaaat gatctaatta 7680
aattataggg gtagtatatg tccaccctat gagagggttt tatctctccc tcccatatga 7740
gagttagttg gagaagaatt tccctccaaa accccttatg ctctgtttcg atgtcgatat 7800
ttaagaagat ggaattgaat tgagtcgaat accaaatcag acatggtatt gaaatgagat 7860
gtaatttcaa ttctactgtt tggatgccac taaattgagt ttggaattgt gcggtctaat 7920
tccacgcaac atcaaggggt gaggctttgt attgggagag ggtttctag ttatagtcca 7980
atttcaggaa atttagtctc tgatttcaaa tctcaattcc atgtgcaacc aaacaacaga 8040
atttagaaaa gttggtttca ttttctaatt atgtgctcta atatctatat ctaaacaggg 8100
gtattacata tggtgaggtg agagatagag gcactgtctt atagtctgat agatgaacat 8160
atgtgttatc tccttttttt aatagaccaa atagaaaaga atagaaaaaa gttaaaccta 8220
tcccccgcta tatctcataa ccacacatat ctacaatatt ttttaaaaaa tcaaagacac 8280
taatagtaga agttactatg acaaagttta gtctgtgtta catcgaatgt ttgaatgttg 8340
gttataatta tatatagtat aattataaaa aataatcata tagatgaaga ctatatgatt 8400
taacccttga gagagtcttc cccgagcccg cgggcttgtc gtcggtcacg ttctccctct 8460
tggcgtgatc tccagacatc actttgagtt gattagactc ttaatgaagc actaactttg 8520
ataccaattg aaagtcgcct agagggggtg aataggcgaa acctaaaatt tacaaacata 8580
aacacacact aaggccgggg ttagcgttgg aattaaattc aagtctgaaa gattgtttct 8640
tttgctaaga gttgttcaaa ggatgcggat gacgtatggg agcaaactca aatcaatatt 8700
agcaaggaaa cgttagagag aggaaagagg gcaaacaaat caagcgagta gacatagtga 8760

-continued

```
tttgttttac cgaggttcgg ttctaaagaa cctaatcccc gttgaggagg ccacaaaggc   8820
cgggtctatt tcaacccttt ccctctctct caaatggtca cttagaccga ttgagccttc   8880
tccttaatca aacgggtcac taaggtgtct cttgcaaact ttacaagcac ttagaaaaag   8940
aatgaggaag gaagaaaggc aatccaagcg acaagagcaa caaaagaaca caaatgaccc   9000
tctcacaatc ccttaagcac tagcgttgat tttgggaagt tttgagtgga ttgattgttt   9060
tgattgtgtc ttggagtgtt ggactttgct cttgcaatga atgagaaact caaaatgctt   9120
ggatggcttt gaatgaggtg gttgaggggt atttatagcc cccaaccact tcctagccgt   9180
tggtaaaggc tgctggcgat gggcgcaccg gacagtcact gttcattgtc cggtgcacgc   9240
cacgttagcg cgcccgttag ggtttggagc agttgaccgt tgaagccgtt tgtctttttg   9300
ctgcaccgga cagtccggtg acttctgcac ggcactgttt ggcactgttc ctctgcgcag   9360
tcgaccgttg gcgcgtaggg agccgttgct ccgctggctc accggatagt ccggtgaatt   9420
atagtggagc gcacgcggca caaccaccaa agtggccgtt gggaggggct gctatcgatg   9480
ggcgcaccgg accgtccggt gcgccagacc agggcagcct tcgggtttct ttgctccttt   9540
ctttttgaac cctatcttgg actttttatt ggtttgtgtt gaacctttgg cacctataga   9600
acttataatc tagagcaaac tagttagtcc aattatttgt gttgggcaat tcaaccacca   9660
aaatcattta ggaaaaggtt tgaccctatt tccctttcag tctcccctt tttggtgatt   9720
gatgccaaca caaaccaaag caaatatata agtgcagaat tgaactagtt tgcataaggt   9780
aagtgcaaag gttgcttgga attaacccaa tttatacttt cataagatat gcatggattg   9840
ctttcttctt atttaacatt ttggaccacg cttgcaccac ttgttttgtt tttgcaaaat   9900
cttttggaaa ttcttttcaa agtctttttg caaatagtca aaggtaaatg aataagattt   9960
cgagaagcat tttcaagatt tgaaattttc tccccctgtt tcaaatgctt ttcctttgac  10020
taaacaaaac tccccctcaa tgaaattctc ctcttagtgt tcaagagggt tttagacatt  10080
aattttgaaa gaggtcatac caacttgaaa ttatataaaa aataagatac caattgaaaa  10140
acttctttga tacaaattga aagactgcat ttaaacactt tttgaaattg gtggtgatgc  10200
ggtccttttg ctttgggtta atactttctc cccctttggc atgaatcgcc aaaaacagat  10260
actttgtgag tgaaatatga gccctatgtt taaattctct cccccttttgg caaacaatat  10320
atgagtgaag gattatacca aggtggagag cgatgcggag tgacggcgaa gggcaaataa  10380
tacgatggag tggagtggaa gccttgtctt cgccgaagac tccatttccc tttcaatcta  10440
tgacttagca tgagatacac ttgaaaaaca cattagtaat agcaaataaa agagatatga  10500
tcaaaggtac ataaatgaac gatgtgtgca aagtatcaat caaaattcct agaatcaaga  10560
atgtttagct cattcctaag tttggtaaag gttttctcat ctaatggttt ggtaaagata  10620
tcggctaatt gttctttggt gctaacatag gcaatctcga tatccccccct ttgttggtga  10680
tccctcaaaa agtgataccg aatggctatg tgcttagtgc ggctatggtc aacgggatta  10740
tccgcattgc actctcatta tcacacagaa gagggacttt ggttaatttg taaccataat  10800
ccctaagggt ttgcctcatc caaagcaatt gtgcgcaata atggcctgcg acaatgtact  10860
cggcttcggt ggtagaaaga gctaccgaat tttgtttctt tgaagcccaa gacaccaggg  10920
atcttcccaa gaactgacaa gtccctgatg tgctatttct atcaatttta cacccatccc  10980
aatcagcatc tgagtatcct attaaatcaa aggtggatcc cttggggtac caaagaccaa  11040
acttaggtgt atgaactaaa tatctcaaga ttcgtttcat ggccctaagg tgaacttcct  11100
taggattggc ttggaatctt gcacacatgc atacggaaag cataatatcc ggtcgagaag  11160
```

```
cacataaata gagtaaagat cctatcatcg atcggtatac cttttgatct acagatttac  11220
ctctcgtgtc gaggtcgaga tgcccatggt tcccatgggt gtcttgatgg gcttggcatc  11280
cttcattcca aacttggtga gtatatcttg agtatacttt gtttggctga tgaaggtgcc  11340
ctcttggagt tgcttgactt gaaatcctaa gaaatacttc aactccccca tcatagacat  11400
ctcgaatttt tgaatcatga tcctactaaa ctcttcacaa gtagatttgt tagtagaccc  11460
aaatatgata tcatcaacat aaatttggca tacaaacaaa tcatttgcaa tggttttagt  11520
aaagagtgta ggatcgactt ttccgacttt gaagccatta gtgataagaa agtctcttag  11580
gcattcatac catgctcttg gggcttgctt aagcccacaa agtgcctttg agagtttata  11640
gacatgatta gggtactcac tatcttcaaa gccggaaggt tgctcaatat agacctcttc  11700
cttgattggt ccattgagga aggcactctt cacgtccatt tgataaagct tgaagccatg  11760
gtaagtagca taggcaagta atatacgaat tgactcaagc ctagctattg gtgcataggt  11820
ttcaccgaaa tccaaacctt caacttgtga atatcccttg gccacatgtc gggctttgtt  11880
ccttgtcacc acaccatgct catcttgctt gttgccgaag acccacttgg tttctacaac  11940
attttggtta ggacgtggaa caagatgcca tacctcgtga agttgttgag ttcctcttgc  12000
attgccaaca cccaatccga atcccttaat gtgtcttcca ccctgtatgg ctcaatagaa  12060
gacacaaaag agtaattgtc ggtaccctga accaggggta cccccctacta cagtataagg  12120
aagcattgcc cgtacgacgt tccctagcca cacggtgagc agcacccgac cccaccatgt  12180
gggtggctca aggggtacca cgtggcgaga aaagatgaca catcccagga tatatcagtt  12240
gaaccggacc accacgaagg agcaccggac ccctgtatgc acaacccgga cccccgatta  12300
cggctcgaga ctcccaagta agcatgccga gccccttgga tggggtccag atccctttga  12360
gtaaggtccg taccacaacg aggtcccgag acatgggaga ccctggcata agcaagggtc  12420
cggtattgac acgtgttagg gccttatcat gtgcgcttgc gctccctgct taggcggaga  12480
cccgctactg ccacgtggct tgttgcctgt gacataagcc aacgggcaga gcctgatgta  12540
aggcctctag gccgtgcggt ctctgcattt attgcggagg agacgcgtcg cctgcccacc  12600
ttgctgacag gcgatgtgcc ccctttgcat ttaatgcgtc ctgtccactc caccggcagg  12660
cgcaccaggc catcctgcag tcggcgcacc tgtccagtcc attgtcaaat agtgcacccg  12720
tgctacaggg cgcactgtgc tcatcatccc ttatacgata agcttcctct gcacgccgat  12780
gctaggcaga tctcagacgt cagggcataa ggagattgcc ccagcagcaa acatgagtag  12840
cgccaaatac tacatctgtt atgttcctgg gcccacatgt cggggctcag tatccttgtg  12900
catgtccccc ttgactataa aaggggaggc atgcaacgtt acaagacagg ctctctaaga  12960
cctaaggcag acttcgaacg ctcaagcttc cacagcaatc caacacataa tggagtatgg  13020
tattacgctc tgacggcccg aaccactcta aactctcgtg tgttcatgtg ctcggtgatc  13080
gcttagctag acaggcaaaa tgcttaagcc ccttcctcat cttaggatta agggcgggtg  13140
cactccgcca cccgaccgga gaattccctc tccaacattt ggtgcgccag gtagggggct  13200
aggcattagg tttttgtttg tttcctcgct cagcatgatg gtgcaaatcg tggagcaccg  13260
cgccgataca tcaacgaatt tcctggtgga ggaagaagtt gtttcttcca cgccactggt  13320
tcccaaccgc ccagtgtcgg gcactgctgc tgtgcacgct gcacaatagc atacagctgc  13380
gtagacatct tgtactccgt cgagggtggc tctgggagca ttgtcggcgg ccagggagtt  13440
gctgtgccac cctccaagct ccatggactc accgggggcc atgaagcagt ggcgggacga  13500
```

-continued

```
cgtcgaccga ctgctcggta tggcacattc tacctcaacc aggtcgaggc cacggtcatc  13560
ccggcgccaa catgaggcgt cggcgtctat gcgcgcgccc tcagtaaggg gcgcatagac  13620
caacgacctc cgggccgagc tcaaccgcag gcgtgcggga gaggacgccc gactctcttt  13680
agagagggtg cacgagcgcc gacaaaacgt tgagggtcgc aacctcgacc aagactttgc  13740
tgcggtagca ccgcaggccc caatgggcac ccggtctcga gcgggtgtcc ccttggtcgg  13800
cgtgggctgc gccgctttcg cggatcatct ccgcgcaaca tcatggccat ccaaattctg  13860
gccgcacttg ccggaaaaat atgacggtac gtcaaacccg tcggagttcc tacaggtgta  13920
tgtcaccgct atcacagcag caggtggaaa caccactacg atgcgtgaca tattttcatg  13980
tcgccttgtc tgggcctacc cggtcttggc tcatgaacct cgccccaggg tcaatctact  14040
cctgggaaga gctctgcgca tggttcgttg cgaacttcgc cagcgcttac cagcagcacg  14100
gtgtggaggc ccaccttcac gcggtaaggc aggagcccgg ggagactctc cggacgttca  14160
tctctcgctt caccaaggtg cgaggtacta taccttgcat tttgatgct tccatcatca  14220
cggctttccg acagggagta cgtgatgaga aaatgttgga gaagttggcc acacacgatg  14280
tggagattgt ccccacactc ttcgctctgg ccgacaagtg cgctagagcc gccgaggtcc  14340
gtgcatggca ctcggcccca caagccgggg ctacccagtc gggtggctca ggtgtcgtct  14400
cccgggacgg taagaagaaa aagaagaagg actacgacta ctagaagtcg cggtccaccg  14460
ctctagtcgt tgcagcggtg accgagggcc ggggcaaccg caacaaacgc ccacggccgc  14520
agaggggtaa cagcgactca tgccctgtgc accccaacgg tcgccacagc tctgcggagt  14580
gtcgcgagat cattgacctc gcgaaacgcg tcagcgagcg gcgtgagcag tcttccaagg  14640
atggctctcc acctcgtcgc caacccggca aagaaaaggt cgacgacgct gtaagggata  14700
acactgaaca tccaacgttg attactctat tatagtatta tacagactgt acttttcgaa  14760
tttatcttag ttttctacaa tatttagtgg attcttctca ttttcaagat acacaattga  14820
accataatcg aagtggtatg taagacagtg agttaaaaga ttatattttt tgggagactt  14880
ccagtcaaat tttcttagaa gtttttttgg tccagatgtt cataaagtcg ccgctttcat  14940
actttttta atttttaat tggtgcacta ttaggtacct gttggaggat gttacaggct  15000
tattgatatc cctatgagta actgcttcaa cagtggtata aataagatat ttgtgatgag  15060
tcagttcaat tctacttcgc ttaaccgcca tattcatcgt acataccttg aaggcgggat  15120
caactttgct gatggatctg tacaggtgat ttacctcatc ttgttgatgt gtaatactgt  15180
aattaggagt agatttgtgt ggagagaata ataaacagat gccgagattc ttctctaaaa  15240
gtctagatcc aaaggcattg tggttcaaaa cactatggac ttctaccatt tatgttatta  15300
ctttgcctta atgttccatt gaatggggca aattattgat tctacaagtg tttaattaaa  15360
aactaattgt tcatcctgca ggtattagcg gctacacaaa tgcctgaaga gccagctgga  15420
tggttccagg gtacagcaga ctctatcaga aaatttatct gggtactcga ggtagttgat  15480
attttctcgt ttatgaatgt ccattcactc attcctgtag cattgtttct ttgtaatttt  15540
gagttctcct gtatttcttt aggattatta cagtcacaaa tccattgaca acattgtaat  15600
cttgagtggc gatcagcttt atcggatgaa ttacatggaa cttgtgcagg tatggtgttc  15660
tcttgttcct catgtttcac gtaatgtcct gattttggat taaccaacta cttttggcat  15720
gcattatttc cagaaacatg tcgaggacga tgctgatatc actatatcat gtgctcctgt  15780
tgatgagagg taatcagttg tttatatcat cctaatatga atatgtcatc ttgttatcca  15840
acacaggatg catatggtct aatctgcttt cctttttcc cttcggaagc cgagcttcta  15900
```

-continued aaaatgggct agtgaagatt gatcatactg gacgtgtact tcaattcttt gaaaaaccaa 15960
agggtgctga tttgaattct atggttagaa attccttgtg taatccaatt cttttgtttt 16020
cctttctttc ttgagatgaa cccctctttt agttatttcc atggataacc tgtacttgac 16080
ttattcagaa atgattttct attttgctgt agaatctgac actaaagcta atagctactg 16140
atgttgcaga gagttgagac caacttcctg agctatgcta tagatgatgc acagaaatat 16200
ccataccttg catcaatggg catttatgtc ttcaagaaag atgcactttt agaccttctc 16260
aagtaatcac tttcctgtga cttatttcta tccaactcct agtttacctt ctaacagtgt 16320
caattcttag gtcaaaatat actcaattac atgactttgg atctgaaatc ctcccaagag 16380
ctgtactaga tcatagtgtg caggtaagtc tgatctgtct ggagtatgtg ttctgtaaac 16440
tgtaaattct tcatgtcaaa aagttgtttt tgtttccagt ttccactagt ttttatttac 16500
caatgcgcga tttatgtatt ttcgcttcca tgcatcatac atactaacaa tacattttac 16560
gtattgtgtt aggcatgcat ttttacgggc tattgggagg atgttggaac aatcaaatca 16620
ttctttgatg caaacttggc cctcactgag caggtactct gtcatgtatt ctgtactgca 16680
tatatattac ctggaattca atgcatagaa tgtgttagac catcttagtt ccatcctgtt 16740
ttcttcaatt agcttatcat ttaatagttg ttggctagaa tttaaacaca aatttaccta 16800
atatgtttct ctcttcagcc ttccaagttt gatttttacg atccaaaaac acctttcttc 16860
actgcacccc gatgcttgcc tccgacgcaa ttggacaagt gcaaggtata tgtcttactg 16920
agcacaattg ttacctgagc aagattttgt gtacttgact tgttctcctc cacagatgaa 16980
atatgcattt atctcagatg gttgcttact gagagaatgc aacatcgagc attctgtgat 17040
tggagtctgc tcacgtgtca gctctggatg tgaactcaag gtacatactc tgccaatgta 17100
tatgctgatg ttttatacat tctcttgcat aatttgattc gagtcaccac aattagtgta 17160
actgcaatct actcttgagt ataccatttc aacaccaagc atcaccaaat cacacagaac 17220
aatagcaaca aagcctttta gttccaagca atttagggta gcctagagtt gaaatctaac 17280
caaacaaaag tcaaagctct atcacgtgga tagttgtttt ccatgcactc ttatttaagc 17340
taatttttgg gtatactaca tccatttaat tattgtttta ttgcttcttc cctttgcctt 17400
tcccccatta ctatcgcgtc ttaagatcat actacgcact agtgtcttta gaggtctctg 17460
gtggacatgt tcaaaccatc tcaatcggtg ttggacaagt ttttcttgaa tttgtgctac 17520
acctaaccta tcatgtatgt catcgtttca aactcgatcc ttcctgtatc atcataaatc 17580
caatgcaaca tacgcattta tgcaacattt atctgttgaa catgtcatct ttttgtaggt 17640
taacattata caccatacaa tgtagcatgt ctaatcatca tcctataaaa tttacatttt 17700
agcttatgtg gtatcctctt gccacttaga acatcatatg cttgatgcca tttcatccac 17760
cctgctttga ttctatggct aacatcttca ttaatatcct tgcctctctg tatcattggt 17820
cctaaatatg gaaatacatt ctttctgggc actacttgac cttccaaact aacgtctcct 17880
ttgatccttt cttgtgtgta gtagtaccga agtcacatct catatattcg gttttagttc 17940
tactaagtcc cgggttcgat ccccctcagg ggtaaatttc gggcttggta aaaaaaatcc 18000
cctcgctgtg tcccgccctc tctcggggat cgatatcctg cgcgccaccc tccggctggg 18060
cattgcagag tgggcagttg atcgactcgt tagtgatggg gagcggggtt caagggtttt 18120
ctcggccggg accatgtttc ggtctcttaa tataataccg ggagggcagt ctttccctcc 18180
ccggtcgagt tttagttcta ctgagtctaa aacctttgga ctctagagtc ccctgtcaca 18240
actcacaact ctatttttct atttacttct acctagcgtt tattaatgat cactatatcg 18300
tctgtaaaaa gcatacacca aggtaatccc cttgtatgtc ccttgtaata ttatccatca 18360
caagaaaaaa aggtaaggct caaagttgac ttttgatata atcctattct aatcgagaag 18420
tcatctgtat cttcgtctct tgttcgaaca ctagtcacaa attttttgt acatgttctt 18480 aatgagtcca acgtaatatt ccttgatatt ttgtcataag ccctcatcaa gtcaatgaaa 18540
atcacgtgta ggtccttcat ttgttcctta tactgctcca tcacttgtct cattaagaaa 18600
atatctctca tagttaacct tttggcatga aacaaaatca cacagaattt gtttcctttt 18660
tttaagatcc cacacaaaag aggtttgatc taaggaatct ggatccctga caggtttatc 18720
aaaatccttt gtgtttttct taaaactgaa tattcctcca gcttctagta ttgatgtaat 18780
attcaatctg tttagcaagt gaacaccttg gttcttgttg ttactgtaca tcccacccac 18840
ccccgaggcc cagattacca caacatgaat acaagaatat tgaacccaga tctagagttt 18900
gtttgtactg ttgaaaatcg gtgacaattc attttgttat tgcgctttct gataacgaca 18960
ggactccgtg atgatgggag cggacatcta tgaaactgaa gaagaagctt caaagctact 19020
gttagctggg aaggtcccag ttggaatagg aaggaacaca aagataaggt gagtatggat 19080
gtggaaccac cggttagttc ccaaaaatat cactcactga tacctgatgg tatcctctga 19140
ttattttcag gaactgtatc attgacatga atgctaggat tgggaagaac gtggtgatca 19200
caaacagtaa ggtgagcgag cgcacctaca tgggtgcaga atcttgtgtg ctcatctatc 19260
ctaattcggt aattcctatc cagcgctagt cttgtgacca tggggcatgg gttcgactct 19320
gtgacagggc atccaagagg ctgatcaccc ggaagaaggg tactacataa ggtctggaat 19380
cgtggtgatc ttgaagaatg caaccatcaa cgatgggtct gtcatatag 19429

<210> SEQ ID NO 34
<211> LENGTH: 15401
<212> TYPE: DNA
<213> ORGANISM: Zea mays

<400> SEQUENCE: 34
cgccatttct caaaaaatac ggatacggcg atacgcaata tatattataa ataaaattaa 60
atgctgaaat gtctgaaatg gaccacagcc gatcagttca atttaaggac gttagaagtt 120
aatgttcaac aactttgact aaagtaaaca tctacttcct cttccagaat ttatctggac 180
tcaaatcaat gaatccagca tgccaaaagc ccaaaaacat gtgtaacgat acgctacacc 240
agcagactcg caaaataatc actagttcac caaatcacca cacaagttct aagttttaat 300
tcgaacagac cacagaccac agaccagaca tgagacaaca acagatggga gatacactac 360
accagcagac tcgcaaaata atcactagtt caccaaatca gtagatgcac tcgttgccat 420
gggatattgg gatctaacaa gaacagagaa tggacaaccg cagcgtcaga cagggcagat 480
gggagatggc agcagaatag cagatcacgt acctcagtac ctcacgacgg cagatgggtt 540
ggctgacggc gcgaccacag agctggcggc ggtggacgcg gccacggaag cgcggctgtc 600
ggctggagtg gcggtgcgca gggaagcgcg gctgcgcgcg tctccaagcg gtgaagggct 660
ggcggcgcgc agggaagcgc ggggctagca gcgcgcaggg aagcgcgggg ctagcggcgc 720
gcaggaaggt gcgcggggat ggcggcgcgc ggtggggaga agcggggctg gcggcgcgca 780
gggaagcgcg gggctggcgg cgagcaggaa ggtgcgcggg gatggcggcg cgccgtgggg 840
agaagcgggg ctggcggcgc gcagagaagt tgcgcgtgtg cgccgtgggg agaagcggtg 900
cgcaggaaat tagggatata aggtacccca catgtgttca agaggtgtcc tagaactatc 960
cgtctttttt tatttattta aattcacaga aatttccaat acgtctcaga tatgtatcca 1020
gaagtatccg cgaagtatcc gtatctaata cggtatccga caccggtacg tgaattttga 1080
gaagtatccg cgcatcatag gcatgcactt ggttggtttc atgaaggatt tgtagcatgt 1140
atgaattatt gtttctacta gttggcatgc aagtctgttt ctcctggaaa gaactctgaa 1200
aaaatatgca cgcgtcaaca gatcagagcc tcgatgatca gaaaaaaaca aagagcatgt 1260
gtttctgtag tatgtactgc acatcgtcat gcattatagc aggctatgtt tgagtaacct 1320
ttgtgtttac caataccgcc tatctagcta ttattaatca tattcaaccc gacttcccta 1380
ggctggttgc ccttttctta gactaaatat gcagggtgtc aaacaagtgg ccaaattgat 1440
caagtgcata taatgacacc cattgtaagt gtagatcagg tctcataaac caggaacata 1500
gaacttgtcc acgttcctcg ttccgagaac gttcgttccg tcccaggaac gcggaaacaa 1560
tctcgtccct gtagtgttaa aatcgtcttt taagtatcat accatgaacc atgttcccgt 1620
tcctcgacct tatcaatatg agaacctggt tactgaggat caggtttcct ttctgttatg 1680
aacctttgtt catttggggt gaccattgcc aggaggacag ccaagcaaag tcagtttggt 1740
tacttcccgt caatgctaca ctttcttgtt cgtttttatg caatttctag atgaactatc 1800
aactaggcat ccattgatgt tagcacagtt tagctcctgt aatgtgtatc catctatgga 1860
ttgttcaatc atgtgattaa ttaattgata aaagtacgaa tagaaaatac agtagtaaca 1920
tatccttgtt cctcttgctg tggcaactgg catctgtttg ttgttagttg atacttactt 1980
ggcaggcata gtgctggcat tgtcataaat ttggagacta cttcacagta tatgcatatg 2040
tgtgtttttg caattttggt gatagggtgg ataactatcc tggaaccaaa tccttgctta 2100
aggtgtactt gtcggtttca gctgatggta tccaggcaac aaaaagagtc tgttatttct 2160
tgttttttat agctatgtaa tgttgtcttg tattcagcca gtggcacaag atggataaaa 2220
aatgtgtaaa aaatcggaga aaattggaga aacatctcac gcccttaatg gggcagaggg 2280
tgtgaccttt catatataga accgagtagg cttaggttac aaaaatacga caagacctat 2340
tcaaatacaa tggcgcgact atatgcattt ctaataaaat aagcttccag atacttgatt 2400
aatgctaatt gtatcagaat aatgtgagct ttctgatgtt gtcaatgtga aaacccttca 2460
gcttggacag tatcttcctt tcctaactga ttttttagag aacaaaattc ttggtccagc 2520
ttttattgaa agccgatgaa acggttcttt ctttcctaac tgattgatat tggtaacttg 2580
ttttctgagc tttaatcctc ggatatctca ggtgcgctct tactagagaa ggatgttgtc 2640
aagttggact ccattgctca gaaagtcaat acccattgtc taagctcagg ttgttggaaa 2700
atcattagga attattgcat gaaaataatc taagagcgga cttcattagc cttcctgagg 2760
atagtggtca ctgaccaaat cttccatgtt tatgcaagga aacataacat ttactgacta 2820
tgagtgttca aaatttgttc acttgctttt gaagatagct tctggttcca agagacaggt 2880
gttgttgtag gagatctgct aacattttga tcaaatccag ttggtgttat acagcactgg 2940
cttactaaca ttactataaa atccttgttg aagaatctgt aagttgttaa tctttgttga 3000
atactaactt ctttataatt ttatttatta tcttctatat ttagtcactg agtgtgcagt 3060
gcgctttgca tgcatagaga agttgaaagc aacacaatcg agactgcagc aatctctatt 3120
tgctagttca gtagttctcg tctattctct gtttgcgaac ttcagcgtga agaaagtcct 3180
taaagaaaag gtgaggacga tcaaaccaag gggcggaccc agtaaagggc atggatatac 3240
acccaataat ttttgcaaag caaacaaagt tagtagacat gatacattca tatacacttg 3300

-continued

```
taattagatt cagatccgat cacgaagagt atgttagtgt ttgggcgcac ggcttcgcac   3360
agcaggaagg gaagaaaggg gagggagcac ctggtgtcct agtgatgctc gtcgcctccc   3420
aaggtggcga ggaagggggc gagctcggac gcgggtagga agaggaggca gccgccaccc   3480
tctgctgatg ggtcggggta ggtagagggg gaaagaaaat ggaaaaagtt actctcttcg   3540
ttcttcagcc aaactctcta tctcactcta tgttacaaac ttcactctac aaacaaacag   3600
tacaatttac tgtgcaaaag agtattttgc acgacctttt atattaaata taaccttaga   3660
gcgttttcaa aactatcttc attttttctc tctattcgat tctctattta cctttccata   3720
aaaattacac tctatatata gcatttcact ccaacaaatt atttatctac tttgactagt   3780
cagattggct agctaagttg actagtgaga gcatctctaa aagactagca aatggtttat   3840
caagccaaat ttcggctact caacaataaa ataactctcc aacggactag ccatccaact   3900
cgccaaggta ttcgactctt taaattggtc tcctctctag tcaaatttat aggtgtacgt   3960
tcgggccgcc cggcccggcc caagcccgaa aaggcccgta atatttgaat ttcgggccga   4020
tccggcccgt ttgaatttcg ggacgtgtcg ggccagccca cgggcctagc cctcggccca   4080
cggccggtcc gtaattggtt aaacatgcct ggctcatttc gggcggcccg aaattataaa   4140
agcctgaaat tcacattaag acccgaaatt catttttttgg cccgaaattc acatcagggc   4200
ccgaaattca aaacaaattt aataaaacaa ataaaagata agacaaataa atttgaccaa   4260
aagcaaactt aatatttgta ttaagttact agagctatac aatgactacc tcgtttacaa   4320
atcattttgt tagaaagaaa aagagtataa tcagctctat ataaagttcg taagttcagt   4380
tcattatcta atattcataa caaaaataaa attacatcac atactctaat tcaaagatac   4440
aaaaaacatc taactaacat tatctctagc tttgtgttct ttatcaagta catgaaagtg   4500
tggaataaag tgtgatttta ataaatatat gagccttttt ctgcttctat atgagtcatt   4560
tcgtgtctgc cttaaacggg tcgtgctcgt gcccgcccat gggccgcgac ctcggcccaa   4620
acccggccca acactaaaat atttcgtgtc gtgtcgtgcc tgggccgtgc tttttttccg   4680
tgctttgggc cggcccatca ggcccggctc aaatgtacac ctatagccaa atttgactag   4740
ccactctggc tagacaaact aaataaatag tctgttagag tgagatgcta catatggagt   4800
gtaatcttat ggagaggtaa atagagtgtc aaatagagag ttaaaaatgg agtccctgga   4860
gatgctctga ggaagctaat ttggagaatc gaatagcttg gcgagttaga tggctagtct   4920
attgaagagt tttttctgt tgagtaacta aaatttggct tgacgaactc tttggctagt   4980
ctcttggaga tactagactc tctcccgcta ttccccatgg ccccatataa tctctctatt   5040
tatatttatt agagtaaaat atactagtgg tctttaaact tatattgttg tattattcta   5100
gtcactaaac ccctaaagtg caaatataag gtccttaaac ttgtgaattt gtatcgttct   5160
ggtccctaac tctgaacatg cacatttcag tctttatact tgtaggattg tgtgtcgtct   5220
gggcctctaa acttattttt ggtgtcatca agggtctaaa ctatttatac atataatgac   5280
accaaaaata agtttatgga tccaagtgac acaaccatag aagtatagga ccaaaaatat   5340
gtatcttgag attttaggga ccaagatgat acaacttaac aagtttaggg accttagatg   5400
tgcactttta gagtttaggg accaggatga aacaacgcta aaaatgtagg gaccgctaat   5460
gcattttact ctatttttat tatattttac tatataagat acttctctta tataccatct   5520
cctctataga actcttcata tacgctataa ctcaattatt taatatttta tcaactttaa   5580
aaatctaaaa aatgatataa tattttacta ttataataca cattatcatt aggttacatg   5640
acttaaacat gattaatatc ataaacaaat gatctaatta aattataggg gtagtatatg   5700
```

```
tccaccctat gagagggttt tatctctccc tcccatatga gagttagttg gagaagaatt   5760
tccctccaaa accccttatg ctctgtttcg atgtcgatat ttaagaagat ggaattgaat   5820
tgagtcgaat accaaatcag acatggtatt gaaatgagat gtaatttcaa ttctactgtt   5880
tggatgccac taaattgagt ttggaattgt gcggtctaat tccacgcaac atcaaggggt   5940
gaggctttgt attgggagag gggtttctag ttatagtcca atttcaggaa atttagtctc   6000
tgatttcaaa tctcaattcc atgtgcaacc aaacaacaga atttagaaaa gttggtttca   6060
ttttctaatt atgtgctcta atatctatat ctaaacaggg gtattacata tggtgaggtg   6120
agagatagag gcactgtctt atagtctgat agatgaacat atgtgttatc tccttttttt   6180
aatagaccaa atagaaaaga atagaaaaaa gttaaaccta tcccccgcta tatctcataa   6240
ccacacatat ctacaatatt ttttaaaaaa tcaaagacac taatagtaga agttactatg   6300
acaaagttta gtctgtgtta catcgaatgt ttgaatgttg gttataatta tatatagtat   6360
aattataaaa aataatcata tagatgaaga ctatatgatt taaccttga gagagtcttc   6420
cccgagcccg cgggcttgtc gtcggtcacg ttctccctct tggcgtgatc tccagacatc   6480
actttgagtt gattagactc ttaatgaagc actaactttg ataccaattg aaagtcgcct   6540
agagggggtg aataggcgaa acctaaaatt tacaaacata aacacacact aaggccgggg   6600
ttagcgttgg aattaaattc aagtctgaaa gattgtttct tttgctaaga gttgttcaaa   6660
ggatgcggat gacgtatggg agcaaactca aatcaatatt agcaaggaaa cgttagagag   6720
aggaaagagg gcaaacaaat caagcgagta gacatagtga tttgttttac cgaggttcgg   6780
ttctaaagaa cctaatcccc gttgaggagg ccacaaaggc cgggtctatt tcaacccttt   6840
ccctctctct caaatggtca cttagaccga ttgagccttc tccttaatca aacgggtcac   6900
taaggtgtct cttgcaaact ttacaagcac ttagaaaaag aatgaggaag gaagaaaggc   6960
aatccaagcg acaagagcaa caaaagaaca caaatgaccc tctcacaatc ccttaagcac   7020
tagcgttgat tttgggaagt tttgagtgga ttgattgttt tgattgtgtc ttggagtgtt   7080
ggactttgct cttgcaatga atgagaaact caaaatgctt ggatggcttt gaatgaggtg   7140
gttgaggggt atttatagcc cccaaccact tcctagccgt tggtaaaggc tgctggcgat   7200
gggcgcaccg gacagtcact gttcattgtc cggtgcacgc cacgttagcg cgcccgttag   7260
ggtttggagc agttgaccgt tgaagccgtt tgtctttttg ctgcaccgga cagtccggtg   7320
acttctgcac ggcactgttt ggcactgttc ctctgcgcag tcgaccgttg gcgcgtaggg   7380
agccgttgct ccgctggctc accggatagt ccggtgaatt atagtggagc gcacgcggca   7440
caaccaccaa agtggccgtt gggaggggct gctatcgatg ggcgcaccgg accgtccggt   7500
gcgccagacc agggcagcct tcgggtttct ttgctccttt ctttttgaac cctatcttgg   7560
actttttatt ggtttgtgtt gaacctttgg cacctataga acttataatc tagagcaaac   7620
tagttagtcc aattatttgt gttgggcaat tcaaccacca aaatcattta ggaaaaggtt   7680
tgaccctatt tccctttcag tctccccctt tttggtgatt gatgccaaca caaaccaaag   7740
caaatatata agtgcagaat tgaactagtt tgcataaggt aagtgcaaag gttgcttgga   7800
attaacccaa tttatacttt cataagatat gcatggattg ctttcttctt atttaacatt   7860
ttggaccacg cttgcaccac ttgttttgtt tttgcaaaat cttttggaaa ttcttttcaa   7920
agtctttttg caaatagtca aaggtaaatg aataagattt cgagaagcat tttcaagatt   7980
tgaaatttc tccccctgtt tcaaatgctt ttcctttgac taaacaaaac tccccctcaa   8040
```

```
tgaaattctc ctcttagtgt tcaagagggt tttagacatt aattttgaaa gaggtcatac   8100
caacttgaaa ttatataaaa aataagatac caattgaaaa acttctttga tacaaattga   8160
aagactgcat ttaaacactt tttgaaattg gtggtgatgc ggtccttttg ctttgggtta   8220
atactttctc cccctttggc atgaatcgcc aaaaacagat actttgtgag tgaaatatga   8280
gccctatgtt taaattctct ccccctttgg caaacaatat atgagtgaag gattatacca   8340
aggtggagag cgatgcggag tgacggcgaa gggcaaataa tacgatggag tggagtggaa   8400
gccttgtctt cgccgaagac tccatttccc tttcaatcta tgacttagca tgagatacac   8460
ttgaaaaaca cattagtaat agcaaataaa agagatatga tcaaaggtac ataaatgaac   8520
gatgtgtgca aagtatcaat caaaattcct agaatcaaga atgtttagct cattcctaag   8580
tttggtaaag gttttctcat ctaatggttt ggtaaagata tcggctaatt gttctttggt   8640
gctaacatag gcaatctcga tatccccccct ttgttggtga tccctcaaaa agtgataccg   8700
aatggctatg tgcttagtgc ggctatggtc aacgggatta tccgcattgc actctcatta   8760
tcacacagaa gagggacttt ggttaatttg taaccataat ccctaagggt ttgcctcatc   8820
caaagcaatt gtgcgcaata atggcctgcg acaatgtact cggcttcggt ggtagaaaga   8880
gctaccgaat tttgtttctt tgaagcccaa gacaccaggg atcttcccaa gaactgacaa   8940
gtccctgatg tgctatttct atcaatttta cacccatccc aatcagcatc tgagtatcct   9000
attaaatcaa aggtggatcc cttggggtac caaagaccaa acttaggtgt atgaactaaa   9060
tatctcaaga ttcgtttcat ggccctaagg tgaacttcct taggattggc ttggaatctt   9120
gcacacatgc atacggaaag cataatatcc ggtcgagaag cacataaata gagtaaagat   9180
cctatcatcg atcggtatac cttttgatct acagatttac ctctcgtgtc gaggtcgaga   9240
tgcccatggt tcccatgggt gtcttgatgg gcttggcatc cttcattcca aacttggtga   9300
gtatatcttg agtatacttt gtttggctga tgaaggtgcc ctcttggagt tgcttgactt   9360
gaaatcctaa gaaatacttc aactccccca tcatagacat ctcgaatttt tgaatcatga   9420
tcctactaaa ctcttcacaa gtagatttgt tagtagaccc aaatatgata tcatcaacat   9480
aaatttggca tacaaacaaa tcatttgcaa tggttttagt aaagagtgta ggatcgactt   9540
ttccgacttt gaagccatta gtgataagaa agtctcttag gcattcatac catgctcttg   9600
gggcttgctt aagcccacaa agtgcctttg agagtttata gacatgatta gggtactcac   9660
tatcttcaaa gccggaaggt tgctcaatat agacctcttc cttgattggt ccattgagga   9720
aggcactctt cacgtccatt tgataaagct tgaagccatg gtaagtagca taggcaagta   9780
atatacgaat tgactcaagc ctagctattg gtgcataggt ttcaccgaaa tccaaacctt   9840
caacttgtga atatcccttg gccacatgtc gggctttgtt ccttgtcacc acaccatgct   9900
catcttgctt gttgccgaag acccacttgg tttctacaac attttggtta ggacgtggaa   9960
caagatgcca tacctcgtga agttgttgag ttcctcttgc attgccaaca cccaatccga  10020
atcccttaat gtgtcttcca ccctgtatgg ctcaatagaa gacacaaaag agtaattgtc  10080
ggtaccctga accaggggta ccccctacta cagtataagg aagcattgcc cgtacgacgt  10140
tccctagcca cacggtgagc agcacccgac cccaccatgt gggtggctca aggggtacca  10200
cgtggcgaga aaagatgaca catcccagga tatatcagtt gaaccggacc accacgaagg  10260
agcaccggac ccctgtatgc acaacccgga cccccgatta cggctcgaga ctcccaagta  10320
agcatgccga gccccttgga tggggtccag atccctttga gtaaggtccg taccacaacg  10380
aggtcccgag acatgggaga ccctggcata agcaagggtc cggtattgac acgtgttagg  10440
```

gccttatcat gtgcgcttgc gctccctgct taggcggaga cccgctactg ccacgtggct 10500
tgttgcctgt gacataagcc aacgggcaga gcctgatgta aggcctctag gccgtgcggt 10560
ctctgcattt attgcggagg agacgcgtcg cctgcccacc ttgctgacag gcgatgtgcc 10620
ccctttgcat ttaatgcgtc ctgtccactc caccggcagg cgcaccaggc catcctgcag 10680
tcggcgcacc tgtccagtcc attgtcaaat agtgcacccg tgctacaggg cgcactgtgc 10740
tcatcatccc ttatacgata agcttcctct gcacgccgat gctaggcaga tctcagacgt 10800
cagggcataa ggagattgcc ccagcagcaa acatgagtag cgccaaatac tacatctgtt 10860
atgttcctgg gcccacatgt cggggctcag tatccttgtg catgtccccc ttgactataa 10920
aaggggaggc atgcaacgtt acaagacagg ctctctaaga cctaaggcag acttcgaacg 10980
ctcaagcttc cacagcaatc caacacataa tggagtatgg tattacgctc tgacggcccg 11040
aaccactcta aactctcgtg tgttcatgtg ctcggtgatc gcttagctag acaggcaaaa 11100
tgcttaagcc ccttcctcat cttaggatta agggcgggtg cactccgcca cccgaccgga 11160
gaattccctc tccaacattt ggtgcgccag gtagggggct aggcattagg tttttgtttg 11220
tttcctcgct cagcatgatg gtgcaaatcg tggagcaccg cgccgataca tcaacgaatt 11280
tcctggtgga ggaagaagtt gtttcttcca cgccactggt tcccaaccgc ccagtgtcgg 11340
gcactgctgc tgtgcacgct gcacaatagc atacagctgc gtagacatct tgtactccgt 11400
cgagggtggc tctgggagca ttgtcggcgg ccagggagtt gctgtgccac cctccaagct 11460
ccatggactc accgggggcc atgaagcagt ggcgggacga cgtcgaccga ctgctcggta 11520
tggcacattc tacctcaacc aggtcgaggc cacggtcatc ccggcgccaa catgaggcgt 11580
cggcgtctat gcgcgcgccc tcagtaaggg gcgcatagac caacgacctc cgggccgagc 11640
tcaaccgcag gcgtgcggga gaggacgccc gactctcttt agagagggtg cacgagcgcc 11700
gacaaaacgt tgagggtcgc aacctcgacc aagactttgc tgcggtagca ccgcaggccc 11760
caatgggcac ccggtctcga gcgggtgtcc ccttggtcgg cgtgggctgc gccgctttcg 11820
cggatcatct ccgcgcaaca tcatggccat ccaaattctg gccgcacttg ccggaaaaat 11880
atgacggtac gtcaaacccg tcggagttcc tacaggtgta tgtcaccgct atcacagcag 11940
caggtggaaa caccactacg atgcgtgaca tattttcatg tcgccttgtc tgggcctacc 12000
cggtcttggc tcatgaacct cgccccaggg tcaatctact cctgggaaga gctctgcgca 12060
tggttcgttg cgaacttcgc cagcgcttac cagcagcacg gtgtggaggc ccaccttcac 12120
gcggtaaggc aggagcccgg ggagactctc cggacgttca tctctcgctt caccaaggtg 12180
cgaggtacta taccttgcat ttttgatgct tccatcatca cggctttccg acagggagta 12240
cgtgatgaga aaatgttgga gaagttggcc acacacgatg tggagattgt ccccacactc 12300
ttcgctctgg ccgacaagtg cgctagagcc gccgaggtcc gtgcatggca ctcggcccca 12360
caagccgggg ctacccagtc gggtggctca ggtgtcgtct cccgggacgg taagaagaaa 12420
aagaagaagg actacgacta ctagaagtcg cggtccaccg ctctagtcgt tgcagcggtg 12480
accgagggcc ggggcaaccg caacaaacgc ccacggccgc agaggggtaa cagcgactca 12540
tgccctgtgc accccaacgg tcgccacagc tctgcggagt gtcgcgagat cattgacctc 12600
gcgaaacgcg tcagcgagcg gcgtgagcag tcttccaagg atggctctcc acctcgtcgc 12660
caacccggca aagaaaaggt cgacgacgct gtaagggata acactgaaca tccaacgttg 12720
attactctat tatagtatta tacagactgt acttttcgaa tttatcttag ttttctacaa 12780

-continued

```
tatttagtgg attcttctca ttttcaagat acacaattga accataatcg aagtggtatg  12840
taagacagtg agttaaaaga ttatattttt tgggagactt ccagtcaaat tttcttagaa  12900
gttttttttgg tccagatgtt cataaagtcg ccgctttcat acttttttta atttttttaat  12960
tggtgcacta ttaggtacct gttggaggat gttacaggct tattgatatc cctatgagta  13020
actgcttcaa cagtggtata aataagatat ttgtgatgag tcagttcaat tctacttcgc  13080
ttaaccgcca tattcatcgt acataccttg aaggcgggat caactttgct gatggatctg  13140
tacaggtgat ttacctcatc ttgttgatgt gtaatactgt aattaggagt agatttgtgt  13200
ggagagaata ataaacagat gccgagattc ttctctaaaa gtctagatcc aaaggcattg  13260
tggttcaaaa cactatggac ttctaccatt tatgttatta ctttgcctta atgttccatt  13320
gaatggggca aattattgat tctacaagtg tttaattaaa aactaattgt tcatcctgca  13380
ggtattagcg gctacacaaa tgcctgaaga gccagctgga tggttccagg gtacagcaga  13440
ctctatcaga aaatttatct gggtactcga ggtagttgat attttctcgt ttatgaatgt  13500
ccattcactc attcctgtag cattgtttct ttgtaatttt gagttctcct gtatttcttt  13560
aggattatta cagtcacaaa tccattgaca acattgtaat cttgagtggc gatcagcttt  13620
atcggatgaa ttacatggaa cttgtgcagg tatggtgttc tcttgttcct catgtttcac  13680
gtaatgtcct gattttggat taaccaacta cttttggcat gcattatttc cagaaacatg  13740
tcgaggacga tgctgatatc actatatcat gtgctcctgt tgatgagagg taatcagttg  13800
tttatatcat cctaatatga atatgtcatc ttgttatcca acacaggatg catatggtct  13860
aatctgcttt cctttttcc cttcggaagc cgagcttcta aaaatgggct agtgaagatt  13920
gatcatactg gacgtgtact tcaattcttt gaaaaaccaa agggtgctga tttgaattct  13980
atggttagaa attccttgtg taatccaatt cttttgtttt cctttctttc ttgagatgaa  14040
cccctctttt agttatttcc atggataacc tgtacttgac ttattcagaa atgattttct  14100
attttgctgt agaatctgac actaaagcta atagctactg atgttgcaga gagttgagac  14160
caacttcctg agctatgcta tagatgatgc acagaaatat ccataccttg catcaatggg  14220
catttatgtc ttcaagaaag atgcactttt agaccttctc aagtaatcac tttcctgtga  14280
cttatttcta tccaactcct agtttacctt ctaacagtgt caattcttag gtcaaaatat  14340
actcaattac atgactttgg atctgaaatc ctcccaagag ctgtactaga tcatagtgtg  14400
caggtaagtc tgatctgtct ggagtatgtg ttctgtaaac tgtaaattct tcatgtcaaa  14460
aagttgtttt tgtttccagt ttccactagt ttttatttac caatgcgcga tttatgtatt  14520
ttcgcttcca tgcatcatac atactaacaa tacattttac gtattgtgtt aggcatgcat  14580
ttttacgggc tattgggagg atgttggaac aatcaaatca ttctttgatg caaacttggc  14640
cctcactgag caggtactct gtcatgtatt ctgtactgca tatatattac ctggaattca  14700
atgcatagaa tgtgttagac catcttagtt ccatcctgtt ttcttcaatt agcttatcat  14760
ttaatagttg ttggctagaa tttaaacaca aatttaccta atatgtttct ctcttcagcc  14820
ttccaagttt gatttttacg atccaaaaac acctttcttc actgcacccc gatgcttgcc  14880
tccgacgcaa ttggacaagt gcaaggtata tgtcttactg agcacaattg ttacctgagc  14940
aagattttgt gtacttgact tgttctcctc cacagatgaa atatgcattt atctcagatg  15000
gttgcttact gagagaatgc aacatcgagc attctgtgat tggagtctgc tcacgtgtca  15060
gctctggatg tgaactcaag gtacatactc tgccaatgta tatgctgatg ttttatacat  15120
tctcttgcat aatttgattc gagtcaccac aattagtgta actgcaatct actcttgagt  15180
```

ataccatttc aacaccaagc atcaccaaat cacacagaac aatagcaaca aagcctttta 15240
gttccaagca atttagggta gcctagagtt gaaatctaac caaacaaaag tcaaagctct 15300
atcacgtgga tagttgtttt ccatgcactc ttatttaagc taatttttgg gtatactaca 15360
tccatttaat tattgtttta ttgcttcttc cctttgcctt t 15401

<210> SEQ ID NO 35
<211> LENGTH: 13001
<212> TYPE: DNA
<213> ORGANISM: Zea mays

<400> SEQUENCE: 35
tgtcataaat ttggagacta cttcacagta tatgcatatg tgtgtttttg caattttggt 60
gatagggtgg ataactatcc tggaaccaaa tccttgctta aggtgtactt gtcggtttca 120
gctgatggta tccaggcaac aaaaagagtc tgttatttct tgttttttat agctatgtaa 180
tgttgtcttg tattcagcca gtggcacaag atggataaaa aatgtgtaaa aaatcggaga 240
aaattggaga aacatctcac gcccttaatg gggcagaggg tgtgaccttt catatataga 300
accgagtagg cttaggttac aaaaatacga caagacctat tcaaatacaa tggcgcgact 360
atatgcattt ctaataaaat aagcttccag atacttgatt aatgctaatt gtatcagaat 420
aatgtgagct ttctgatgtt gtcaatgtga aaacccttca gcttggacag tatcttcctt 480
tcctaactga tttttagag aacaaaattc ttggtccagc ttttattgaa agccgatgaa 540
acggttcttt ctttcctaac tgattgatat tggtaacttg ttttctgagc tttaatcctc 600
ggatatctca ggtgcgctct tactagagaa ggatgttgtc aagttggact ccattgctca 660
gaaagtcaat acccattgtc taagctcagg ttgttggaaa atcattagga attattgcat 720
gaaaataatc taagagcgga cttcattagc cttcctgagg atagtggtca ctgaccaaat 780
cttccatgtt tatgcaagga aacataacat ttactgacta tgagtgttca aaatttgttc 840
acttgctttt gaagatagct tctggttcca agagacaggt gttgttgtag gagatctgct 900
aacattttga tcaaatccag ttggtgttat acagcactgg cttactaaca ttactataaa 960
atccttgttg aagaatctgt aagttgttaa tctttgttga atactaactt ctttataatt 1020
ttatttatta tcttctatat ttagtcactg agtgtgcagt gcgctttgca tgcatagaga 1080
agttgaaagc aacacaatcg agactgcagc aatctctatt tgctagttca gtagttctcg 1140
tctattctct gtttgcgaac ttcagcgtga agaaagtcct taaagaaaag gtgaggacga 1200
tcaaaccaag gggcggaccc agtaaagggc atggatatac acccaataat ttttgcaaag 1260
caaacaaagt tagtagacat gatacattca tatacacttg taattagatt cagatccgat 1320
cacgaagagt atgttagtgt ttgggcgcac ggcttcgcac agcaggaagg gaagaaaggg 1380
gagggagcac ctggtgtcct agtgatgctc gtcgcctccc aaggtggcga ggaagggggc 1440
gagctcggac gcgggtagga agaggaggca gccgccaccc tctgctgatg ggtcggggta 1500
ggtagagggg gaaagaaaat ggaaaaagtt actctcttcg ttcttcagcc aaactctcta 1560
tctcactcta tgttacaaac ttcactctac aaacaaacag tacaatttac tgtgcaaaag 1620
agtattttgc acgacctttt atattaaata taaccttaga gcgttttcaa aactatcttc 1680
attttttctc tctattcgat tctctattta cctttccata aaaattacac tctatatata 1740
gcatttcact ccaacaaatt atttatctac tttgactagt cagattggct agctaagttg 1800
actagtgaga gcatctctaa aagactagca aatggtttat caagccaaat ttcggctact 1860

-continued

```
caacaataaa ataactctcc aacggactag ccatccaact cgccaaggta ttcgactctt   1920
taaattggtc tcctctctag tcaaatttat aggtgtacgt tcgggccgcc cggcccggcc   1980
caagcccgaa aaggcccgta atatttgaat ttcgggccga tccggcccgt ttgaatttcg   2040
ggacgtgtcg ggccagccca cgggcctagc cctcggccca cggccggtcc gtaattggtt   2100
aaacatgcct ggctcatttc gggcggcccg aaattataaa agcctgaaat tcacattaag   2160
acccgaaatt catttttttgg cccgaaattc acatcagggc ccgaaattca aaacaaattt   2220
aataaaacaa ataaaagata agacaaataa atttgaccaa aagcaaactt aatatttgta   2280
ttaagttact agagctatac aatgactacc tcgtttacaa atcattttgt tagaaagaaa   2340
aagagtataa tcagctctat ataaagttcg taagttcagt tcattatcta atattcataa   2400
caaaaataaa attacatcac atactctaat tcaaagatac aaaaaacatc taactaacat   2460
tatctctagc tttgtgttct ttatcaagta catgaaagtg tggaataaag tgtgatttta   2520
ataaatatat gagccttttt ctgcttctat atgagtcatt tcgtgtctgc cttaaacggg   2580
tcgtgctcgt gcccgcccat gggccgcgac ctcggcccaa acccggccca acactaaaat   2640
atttcgtgtc gtgtcgtgcc tgggccgtgc tttttttccg tgctttgggc cggcccatca   2700
ggcccggctc aaatgtacac ctatagccaa atttgactag ccactctggc tagacaaact   2760
aaataaatag tctgttagag tgagatgcta catatggagt gtaatcttat ggagaggtaa   2820
atagagtgtc aaatagagag ttaaaaatgg agtccctgga gatgctctga ggaagctaat   2880
ttggagaatc gaatagcttg gcgagttaga tggctagtct attgaagagt tttttctgt   2940
tgagtaacta aaatttggct tgacgaactc tttggctagt ctcttggaga tactagactc   3000
tctcccgcta ttccccatgg ccccatataa tctctctatt tatatttatt agagtaaaat   3060
atactagtgg tctttaaact tatattgttg tattattcta gtcactaaac ccctaaagtg   3120
caaatataag gtccttaaac ttgtgaattt gtatcgttct ggtccctaac tctgaacatg   3180
cacatttcag tctttatact tgtaggattg tgtgtcgtct gggcctctaa acttattttt   3240
ggtgtcatca agggtctaaa ctatttatac atataatgac accaaaaata agtttatgga   3300
tccaagtgac acaaccatag aagtatagga ccaaaaatat gtatcttgag attttaggga   3360
ccaagatgat acaacttaac aagtttaggg accttagatg tgcactttta gagtttaggg   3420
accaggatga aacaacgcta aaaatgtagg gaccgctaat gcattttact ctatttttat   3480
tatattttac tatataagat acttctctta tataccatct cctctataga actcttcata   3540
tacgctataa ctcaattatt taatatttta tcaactttaa aaatctaaaa aatgatataa   3600
tattttacta ttataataca cattatcatt aggttacatg acttaaacat gattaatatc   3660
ataaacaaat gatctaatta aattataggg gtagtatatg tccaccctat gagagggttt   3720
tatctctccc tcccatatga gagttagttg gagaagaatt tccctccaaa accccttatg   3780
ctctgtttcg atgtcgatat ttaagaagat ggaattgaat tgagtcgaat accaaatcag   3840
acatggtatt gaaatgagat gtaatttcaa ttctactgtt tggatgccac taaattgagt   3900
ttggaattgt gcggtctaat tccacgcaac atcaaggggt gaggctttgt attgggagag   3960
gggtttctag ttatagtcca atttcaggaa atttagtctc tgatttcaaa tctcaattcc   4020
atgtgcaacc aaacaacaga atttagaaaa gttggtttca ttttctaatt atgtgctcta   4080
atatctatat ctaaacaggg gtattacata tggtgaggtg agagatagag gcactgtctt   4140
atagtctgat agatgaacat atgtgttatc tcctttttttt aatagaccaa atagaaaaga   4200
atagaaaaaa gttaaaccta tcccccgcta tatctcataa ccacacatat ctacaatatt   4260
```

```
ttttaaaaaa tcaaagacac taatagtaga agttactatg acaaagttta gtctgtgtta   4320
catcgaatgt ttgaatgttg gttataatta tatatagtat aattataaaa aataatcata   4380
tagatgaaga ctatatgatt taacccttga gagagtcttc cccgagcccg cgggcttgtc   4440
gtcggtcacg ttctccctct tggcgtgatc tccagacatc actttgagtt gattagactc   4500
ttaatgaagc actaactttg ataccaattg aaagtcgcct agaggggggtg aataggcgaa   4560
acctaaaatt tacaaacata aacacacact aaggccgggg ttagcgttgg aattaaattc   4620
aagtctgaaa gattgtttct tttgctaaga gttgttcaaa ggatgcggat gacgtatggg   4680
agcaaactca aatcaatatt agcaaggaaa cgttagagag aggaaagagg gcaaacaaat   4740
caagcgagta gacatagtga tttgttttac cgaggttcgg ttctaaagaa cctaatcccc   4800
gttgaggagg ccacaaaggc cgggtctatt tcaacccttt ccctctctct caaatggtca   4860
cttagaccga ttgagccttc tccttaatca aacgggtcac taaggtgtct cttgcaaact   4920
ttacaagcac ttagaaaaag aatgaggaag gaagaaaggc aatccaagcg acaagagcaa   4980
caaaagaaca caaatgaccc tctcacaatc ccttaagcac tagcgttgat tttgggaagt   5040
tttgagtgga ttgattgttt tgattgtgtc ttggagtgtt ggactttgct cttgcaatga   5100
atgagaaact caaaatgctt ggatggcttt gaatgaggtg gttgaggggt atttatagcc   5160
cccaaccact tcctagccgt tggtaaaggc tgctggcgat gggcgcaccg gacagtcact   5220
gttcattgtc cggtgcacgc cacgttagcg cgcccgttag ggtttggagc agttgaccgt   5280
tgaagccgtt tgtctttttg ctgcaccgga cagtccggtg acttctgcac ggcactgttt   5340
ggcactgttc ctctgcgcag tcgaccgttg gcgcgtaggg agccgttgct ccgctggctc   5400
accggatagt ccggtgaatt atagtggagc gcacgcggca caaccaccaa agtggccgtt   5460
gggaggggct gctatcgatg ggcgcaccgg accgtccggt gcgccagacc agggcagcct   5520
tcgggtttct ttgctccttt ctttttgaac cctatcttgg actttttatt ggtttgtgtt   5580
gaacctttgg cacctataga acttataatc tagagcaaac tagttagtcc aattatttgt   5640
gttgggcaat tcaaccacca aaatcattta ggaaaaggtt tgaccctatt tccctttcag   5700
tctccccctt tttggtgatt gatgccaaca caaaccaaag caaatatata agtgcagaat   5760
tgaactagtt tgcataaggt aagtgcaaag gttgcttgga attaacccaa tttatacttt   5820
cataagatat gcatggattg ctttcttctt atttaacatt ttggaccacg cttgcaccac   5880
ttgttttgtt tttgcaaaat cttttggaaa ttcttttcaa agtctttttg caaatagtca   5940
aaggtaaatg aataagattt cgagaagcat tttcaagatt tgaaattttc tccccctgtt   6000
tcaaatgctt ttcctttgac taaacaaaac tccccctcaa tgaaattctc ctcttagtgt   6060
tcaagagggt tttagacatt aattttgaaa gaggtcatac caacttgaaa ttatataaaa   6120
aataagatac caattgaaaa acttctttga tacaaattga aagactgcat ttaaacactt   6180
tttgaaattg gtggtgatgc ggtccttttg ctttgggtta atactttctc cccctttggc   6240
atgaatcgcc aaaaacagat actttgtgag tgaaatatga gccctatgtt taaattctct   6300
ccccctttgg caaacaatat atgagtgaag gattatacca aggtggagag cgatgcggag   6360
tgacggcgaa gggcaaataa tacgatggag tggagtggaa gccttgtctt cgccgaagac   6420
tccatttccc tttcaatcta tgacttagca tgagatacac ttgaaaaaca cattagtaat   6480
agcaaataaa agagatatga tcaaaggtac ataaatgaac gatgtgtgca aagtatcaat   6540
caaaattcct agaatcaaga atgtttagct cattcctaag tttggtaaag gtttctcat    6600
```

ctaatggttt ggtaaagata tcggctaatt gttctttggt gctaacatag gcaatctcga 6660
tatcccccct ttgttggtga tccctcaaaa agtgataccg aatggctatg tgcttagtgc 6720
ggctatggtc aacgggatta tccgcattgc actctcatta tcacacagaa gagggacttt 6780
ggttaatttg taaccataat ccctaagggt ttgcctcatc caaagcaatt gtgcgcaata 6840
atggcctgcg acaatgtact cggcttcggt ggtagaaaga gctaccgaat tttgtttctt 6900
tgaagcccaa gacaccaggg atcttcccaa gaactgacaa gtccctgatg tgctatttct 6960
atcaatttta cacccatccc aatcagcatc tgagtatcct attaaatcaa aggtggatcc 7020
cttggggtac caaagaccaa acttaggtgt atgaactaaa tatctcaaga ttcgtttcat 7080
ggccctaagg tgaacttcct taggattggc ttggaatctt gcacacatgc atacggaaag 7140
cataatatcc ggtcgagaag cacataaata gagtaaagat cctatcatcg atcggtatac 7200
cttttgatct acagatttac ctctcgtgtc gaggtcgaga tgcccatggt tcccatgggt 7260
gtcttgatgg gcttggcatc cttcattcca aacttggtga gtatatcttg agtatacttt 7320
gtttggctga tgaaggtgcc ctcttggagt tgcttgactt gaaatcctaa gaaatacttc 7380
aactccccca tcatagacat ctcgaatttt tgaatcatga tcctactaaa ctcttcacaa 7440
gtagatttgt tagtagaccc aaatatgata tcatcaacat aaatttggca tacaaacaaa 7500
tcatttgcaa tggttttagt aaagagtgta ggatcgactt ttccgacttt gaagccatta 7560
gtgataagaa agtctcttag gcattcatac catgctcttg gggcttgctt aagcccacaa 7620
agtgcctttg agagtttata gacatgatta gggtactcac tatcttcaaa gccggaaggt 7680
tgctcaatat agacctcttc cttgattggt ccattgagga aggcactctt cacgtccatt 7740
tgataaagct tgaagccatg gtaagtagca taggcaagta atatacgaat tgactcaagc 7800
ctagctattg gtgcataggt ttcaccgaaa tccaaacctt caacttgtga atatcccttg 7860
gccacatgtc gggctttgtt ccttgtcacc acaccatgct catcttgctt gttgccgaag 7920
acccacttgg tttctacaac attttggtta ggacgtggaa caagatgcca tacctcgtga 7980
agttgttgag ttcctcttgc attgccaaca cccaatccga atcccttaat gtgtcttcca 8040
ccctgtatgg ctcaatagaa gacacaaaag agtaattgtc ggtaccctga accaggggta 8100
ccccctacta cagtataagg aagcattgcc cgtacgacgt tccctagcca cacggtgagc 8160
agcacccgac cccaccatgt gggtggctca aggggtacca cgtggcgaga aaagatgaca 8220
catcccagga tatatcagtt gaaccggacc accacgaagg agcaccggac ccctgtatgc 8280
acaacccgga cccccgatta cggctcgaga ctcccaagta agcatgccga gccccttgga 8340
tggggtccag atccctttga gtaaggtccg taccacaacg aggtcccgag acatgggaga 8400
ccctggcata agcaagggtc cggtattgac acgtgttagg gccttatcat gtgcgcttgc 8460
gctccctgct taggcggaga cccgctactg ccacgtggct tgttgcctgt gacataagcc 8520
aacgggcaga gcctgatgta aggcctctag gccgtgcggt ctctgcattt attgcggagg 8580
agacgcgtcg cctgcccacc ttgctgacag gcgatgtgcc ccctttgcat ttaatgcgtc 8640
ctgtccactc caccggcagg cgcaccaggc catcctgcag tcggcgcacc tgtccagtcc 8700
attgtcaaat agtgcacccg tgctacaggg cgcactgtgc tcatcatccc ttatacgata 8760
agcttcctct gcacgccgat gctaggcaga tctcagacgt cagggcataa ggagattgcc 8820
ccagcagcaa acatgagtag cgccaaatac tacatctgtt atgttcctgg gcccacatgt 8880
cggggctcag tatccttgtg catgtccccc ttgactataa aaggggaggc atgcaacgtt 8940
acaagacagg ctctctaaga cctaaggcag acttcgaacg ctcaagcttc cacagcaatc 9000

```
caacacataa tggagtatgg tattacgctc tgacggcccg aaccactcta aactctcgtg   9060
tgttcatgtg ctcggtgatc gcttagctag acaggcaaaa tgcttaagcc ccttcctcat   9120
cttaggatta agggcgggtg cactccgcca cccgaccgga gaattccctc tccaacattt   9180
ggtgcgccag gtagggggct aggcattagg tttttgtttg tttcctcgct cagcatgatg   9240
gtgcaaatcg tggagcaccg cgccgataca tcaacgaatt tcctggtgga ggaagaagtt   9300
gtttcttcca cgccactggt tcccaaccgc ccagtgtcgg gcactgctgc tgtgcacgct   9360
gcacaatagc atacagctgc gtagacatct tgtactccgt cgagggtggc tctgggagca   9420
ttgtcggcgg ccagggagtt gctgtgccac cctccaagct ccatggactc accgggggcc   9480
atgaagcagt ggcgggacga cgtcgaccga ctgctcggta tggcacattc tacctcaacc   9540
aggtcgaggc cacggtcatc ccggcgccaa catgaggcgt cggcgtctat gcgcgcgccc   9600
tcagtaaggg gcgcatagac caacgacctc cgggccgagc tcaaccgcag gcgtgcggga   9660
gaggacgccc gactctcttt agagagggtg cacgagcgcc gacaaaacgt tgagggtcgc   9720
aacctcgacc aagactttgc tgcggtagca ccgcaggccc caatgggcac ccggtctcga   9780
gcgggtgtcc ccttggtcgg cgtgggctgc gccgctttcg cggatcatct ccgcgcaaca   9840
tcatggccat ccaaattctg gccgcacttg ccggaaaaat atgacggtac gtcaaacccg   9900
tcggagttcc tacaggtgta tgtcaccgct atcacagcag caggtggaaa caccactacg   9960
atgcgtgaca tattttcatg tcgccttgtc tgggcctacc cggtcttggc tcatgaacct  10020
cgccccaggg tcaatctact cctgggaaga gctctgcgca tggttcgttg cgaacttcgc  10080
cagcgcttac cagcagcacg gtgtggaggc ccaccttcac gcggtaaggc aggagcccgg  10140
ggagactctc cggacgttca tctctcgctt caccaaggtg cgaggtacta taccttgcat  10200
ttttgatgct tccatcatca cggctttccg acagggagta cgtgatgaga aaatgttgga  10260
gaagttggcc acacacgatg tggagattgt ccccacactc ttcgctctgg ccgacaagtg  10320
cgctagagcc gccgaggtcc gtgcatggca ctcggcccca caagccgggg ctacccagtc  10380
gggtggctca ggtgtcgtct cccgggacgg taagaagaaa aagaagaagg actacgacta  10440
ctagaagtcg cggtccaccg ctctagtcgt tgcagcggtg accgagggcc ggggcaaccg  10500
caacaaacgc ccacggccgc agaggggtaa cagcgactca tgccctgtgc accccaacgg  10560
tcgccacagc tctgcggagt gtcgcgagat cattgacctc gcgaaacgcg tcagcgagcg  10620
gcgtgagcag tcttccaagg atggctctcc acctcgtcgc caacccggca aagaaaaggt  10680
cgacgacgct gtaagggata acactgaaca tccaacgttg attactctat tatagtatta  10740
tacagactgt acttttcgaa tttatcttag ttttctacaa tatttagtgg attcttctca  10800
ttttcaagat acacaattga accataatcg aagtggtatg taagacagtg agttaaaaga  10860
ttatattttt tgggagactt ccagtcaaat tttcttagaa gttttttggg tccagatgtt  10920
cataaagtcg ccgctttcat acttttttta attttttaat tggtgcacta ttaggtacct  10980
gttggaggat gttacaggct tattgatatc cctatgagta actgcttcaa cagtggtata  11040
aataagatat ttgtgatgag tcagttcaat tctacttcgc ttaaccgcca tattcatcgt  11100
acataccttg aaggcgggat caactttgct gatggatctg tacaggtgat ttacctcatc  11160
ttgttgatgt gtaatactgt aattaggagt agatttgtgt ggagagaata ataaacagat  11220
gccgagattc ttctctaaaa gtctagatcc aaaggcattg tggttcaaaa cactatggac  11280
ttctaccatt tatgttatta ctttgcctta atgttccatt gaatggggca aattattgat  11340
```

-continued

```
tctacaagtg tttaattaaa aactaattgt tcatcctgca ggtattagcg gctacacaaa  11400

tgcctgaaga gccagctgga tggttccagg gtacagcaga ctctatcaga aaatttatct  11460

gggtactcga ggtagttgat attttctcgt ttatgaatgt ccattcactc attcctgtag  11520

cattgtttct ttgtaatttt gagttctcct gtatttcttt aggattatta cagtcacaaa  11580

tccattgaca acattgtaat cttgagtggc gatcagcttt atcggatgaa ttacatggaa  11640

cttgtgcagg tatggtgttc tcttgttcct catgtttcac gtaatgtcct gatttggat  11700

taaccaacta cttttggcat gcattatttc cagaaacatg tcgaggacga tgctgatatc  11760

actatatcat gtgctcctgt tgatgagagg taatcagttg tttatatcat cctaatatga  11820

atatgtcatc ttgttatcca acacaggatg catatggtct aatctgcttt cctttttcc  11880

cttcggaagc cgagcttcta aaaatgggct agtgaagatt gatcatactg gacgtgtact  11940

tcaattcttt gaaaaaccaa agggtgctga tttgaattct atggttagaa attccttgtg  12000

taatccaatt cttttgtttt cctttctttc ttgagatgaa cccctctttt agttatttcc  12060

atggataacc tgtacttgac ttattcagaa atgatttct attttgctgt agaatctgac  12120

actaaagcta atagctactg atgttgcaga gagttgagac caacttcctg agctatgcta  12180

tagatgatgc acagaaatat ccataccttg catcaatggg catttatgtc ttcaagaaag  12240

atgcactttt agaccttctc aagtaatcac tttcctgtga cttatttcta tccaactcct  12300

agtttacctt ctaacagtgt caattcttag gtcaaaatat actcaattac atgactttgg  12360

atctgaaatc ctcccaagag ctgtactaga tcatagtgtg caggtaagtc tgatctgtct  12420

ggagtatgtg ttctgtaaac tgtaaattct tcatgtcaaa aagttgtttt tgtttccagt  12480

ttccactagt ttttatttac caatgcgcga tttatgtatt ttcgcttcca tgcatcatac  12540

atactaacaa tacattttac gtattgtgtt aggcatgcat ttttacgggc tattgggagg  12600

atgttggaac aatcaaatca ttctttgatg caaacttggc cctcactgag caggtactct  12660

gtcatgtatt ctgtactgca tatatattac ctggaattca atgcatagaa tgtgttagac  12720

catcttagtt ccatcctgtt ttcttcaatt agcttatcat ttaatagttg ttggctagaa  12780

tttaaacaca aatttaccta atatgtttct ctcttcagcc ttccaagttt gatttttacg  12840

atccaaaaac acctttcttc actgcacccc gatgcttgcc tccgacgcaa ttggacaagt  12900

gcaaggtata tgtcttactg agcacaattg ttacctgagc aagattttgt gtacttgact  12960

tgttctcctc cacagatgaa atatgcattt atctcagatg g                      13001
```

```
<210> SEQ ID NO 36
<211> LENGTH: 10001
<212> TYPE: DNA
<213> ORGANISM: Zea mays

<400> SEQUENCE: 36

atatttgaat ttcgggccga tccggcccgt ttgaatttcg ggacgtgtcg ggccagccca     60

cgggcctagc cctcggccca cggccggtcc gtaattggtt aaacatgcct ggctcatttc    120

gggcggcccg aaattataaa agcctgaaat tcacattaag acccgaaatt catttttttgg    180

cccgaaattc acatcagggc ccgaaattca aaacaaattt aataaaacaa ataaaagata    240

agacaaataa atttgaccaa aagcaaactt aatatttgta ttaagttact agagctatac    300

aatgactacc tcgtttacaa atcattttgt tagaaagaaa aagagtataa tcagctctat    360

ataaagttcg taagttcagt tcattatcta atattcataa caaaaataaa attacatcac    420

atactctaat tcaaagatac aaaaaacatc taactaacat tatctctagc tttgtgttct    480
```

```
ttatcaagta catgaaagtg tggaataaag tgtgatttta ataaatatat gagccttttt    540
ctgcttctat atgagtcatt tcgtgtctgc cttaaacggg tcgtgctcgt gcccgcccat    600
gggccgcgac ctcggcccaa acccggccca acactaaaat atttcgtgtc gtgtcgtgcc    660
tgggccgtgc ttttttttccg tgctttgggc cggcccatca ggcccggctc aaatgtacac    720
ctatagccaa atttgactag ccactctggc tagacaaact aaataaatag tctgttagag    780
tgagatgcta catatggagt gtaatcttat ggagaggtaa atagagtgtc aaatagagag    840
ttaaaaatgg agtccctgga gatgctctga ggaagctaat ttggagaatc gaatagcttg    900
gcgagttaga tggctagtct attgaagagt ttttttctgt tgagtaacta aaatttggct    960
tgacgaactc tttggctagt ctcttggaga tactagactc tctcccgcta ttccccatgg   1020
ccccatataa tctctctatt tatatttatt agagtaaaat atactagtgg tctttaaact   1080
tatattgttg tattattcta gtcactaaac ccctaaagtg caaatataag gtccttaaac   1140
ttgtgaattt gtatcgttct ggtccctaac tctgaacatg cacatttcag tctttatact   1200
tgtaggattg tgtgtcgtct gggcctctaa acttattttt ggtgtcatca agggtctaaa   1260
ctatttatac atataatgac accaaaaata agtttatgga tccaagtgac acaaccatag   1320
aagtatagga ccaaaaatat gtatcttgag attttaggga ccaagatgat acaacttaac   1380
aagtttaggg accttagatg tgcactttta gagtttaggg accaggatga aacaacgcta   1440
aaaatgtagg gaccgctaat gcatttttact ctatttttat tatattttac tatataagat   1500
acttctctta tataccatct cctctataga actcttcata tacgctataa ctcaattatt   1560
taatatttta tcaactttaa aaatctaaaa aatgatataa tattttacta ttataataca   1620
cattatcatt aggttacatg acttaaacat gattaatatc ataaacaaat gatctaatta   1680
aattataggg gtagtatatg tccaccctat gagagggttt tatctctccc tcccatatga   1740
gagttagttg gagaagaatt tccctccaaa accccttatg ctctgtttcg atgtcgatat   1800
ttaagaagat ggaattgaat tgagtcgaat accaaatcag acatggtatt gaaatgagat   1860
gtaatttcaa ttctactgtt tggatgccac taaattgagt ttggaattgt gcggtctaat   1920
tccacgcaac atcaaggggt gaggctttgt attgggagag ggtttctag ttatagtcca    1980
atttcaggaa atttagtctc tgatttcaaa tctcaattcc atgtgcaacc aaacaacaga   2040
atttagaaaa gttggtttca ttttctaatt atgtgctcta atatctatat ctaaacaggg   2100
gtattacata tggtgaggtg agagatagag gcactgtctt atagtctgat agatgaacat   2160
atgtgttatc tccttttttt aatagaccaa atagaaaaga atagaaaaaa gttaaaccta   2220
tcccccgcta tatctcataa ccacacatat ctacaatatt ttttaaaaaa tcaaagacac   2280
taatagtaga agttactatg acaaagttta gtctgtgtta catcgaatgt ttgaatgttg   2340
gttataatta tatatagtat aattataaaa aataatcata tagatgaaga ctatatgatt   2400
taacccttga gagagtcttc cccgagcccg cgggcttgtc gtcggtcacg ttctccctct   2460
tggcgtgatc tccagacatc actttgagtt gattagactc ttaatgaagc actaactttg   2520
ataccaattg aaagtcgcct agagggggtg aataggcgaa acctaaaatt tacaaacata   2580
aacacacact aaggccgggg ttagcgttgg aattaaattc aagtctgaaa gattgtttct   2640
tttgctaaga gttgttcaaa ggatgcggat gacgtatggg agcaaactca aatcaatatt   2700
agcaaggaaa cgttagagag aggaaagagg gcaaacaaat caagcgagta gacatagtga   2760
tttgttttac cgaggttcgg ttctaaagaa cctaatcccc gttgaggagg ccacaaaggc   2820
```

-continued cggtctatt tcaaccttt ccctctctct caaatggtca cttagaccga ttgagccttc 2880
tccttaatca aacgggtcac taaggtgtct cttgcaaact ttacaagcac ttagaaaaag 2940
aatgaggaag gaagaaaggc aatccaagcg acaagagcaa caaaagaaca caaatgaccc 3000
tctcacaatc ccttaagcac tagcgttgat tttgggaagt tttgagtgga ttgattgttt 3060
tgattgtgtc ttggagtgtt ggactttgct cttgcaatga atgagaaact caaaatgctt 3120
ggatggcttt gaatgaggtg gttgaggggt atttatagcc cccaaccact tcctagccgt 3180
tggtaaaggc tgctggcgat gggcgcaccg gacagtcact gttcattgtc cggtgcacgc 3240
cacgttagcg cgcccgttag ggtttggagc agttgaccgt tgaagccgtt tgtctttttg 3300
ctgcaccgga cagtccggtg acttctgcac ggcactgttt ggcactgttc ctctgcgcag 3360
tcgaccgttg gcgcgtaggg agccgttgct ccgctggctc accggatagt ccggtgaatt 3420
atagtggagc gcacgcggca caaccaccaa agtggccgtt gggaggggct gctatcgatg 3480
ggcgcaccgg accgtccggt gcgccagacc agggcagcct tcgggtttct ttgctccttt 3540
ctttttgaac cctatcttgg actttttatt ggtttgtgtt gaacctttgg cacctataga 3600
acttataatc tagagcaaac tagttagtcc aattatttgt gttgggcaat tcaaccacca 3660
aaatcattta ggaaaaggtt tgaccctatt tccctttcag tctccccctt tttggtgatt 3720
gatgccaaca caaaccaaag caaatatata agtgcagaat tgaactagtt tgcataaggt 3780
aagtgcaaag gttgcttgga attaacccaa tttatacttt cataagatat gcatggattg 3840
ctttcttctt atttaacatt ttggaccacg cttgcaccac ttgtttttgtt tttgcaaaat 3900 cttttggaaa ttcttttcaa agtctttttg caaatagtca aaggtaaatg aataagattt 3960
cgagaagcat tttcaagatt tgaaattttc tccccctgtt tcaaatgctt ttcctttgac 4020
taaacaaaac tccccctcaa tgaaattctc ctcttagtgt tcaagagggt tttagacatt 4080
aattttgaaa gaggtcatac caacttgaaa ttatataaaa aataagatac caattgaaaa 4140
acttctttga tacaaattga aagactgcat ttaaacactt tttgaaattg gtggtgatgc 4200
ggtccttttg ctttgggtta atactttctc cccctttggc atgaatcgcc aaaaacagat 4260
actttgtgag tgaaatatga gccctatgtt taaattctct cccccctttgg caaacaatat 4320 atgagtgaag gattatacca aggtggagag cgatgcggag tgacggcgaa gggcaaataa 4380
tacgatggag tggagtggaa gccttgtctt cgccgaagac tccatttccc tttcaatcta 4440
tgacttagca tgagatacac ttgaaaaaca cattagtaat agcaaataaa agagatatga 4500
tcaaaggtac ataaatgaac gatgtgtgca aagtatcaat caaaattcct agaatcaaga 4560
atgtttagct cattcctaag tttggtaaag gttttctcat ctaatggttt ggtaaagata 4620
tcggctaatt gttctttggt gctaacatag gcaatctcga tatccccccct ttgttggtga 4680 tccctcaaaa agtgataccg aatggctatg tgcttagtgc ggctatggtc aacgggatta 4740
tccgcattgc actctcatta tcacacagaa gagggacttt ggttaatttg taaccataat 4800
ccctaagggt ttgcctcatc caaagcaatt gtgcgcaata atggcctgcg acaatgtact 4860
cggcttcggt ggtagaaaga gctaccgaat tttgtttctt tgaagcccaa gacaccaggg 4920
atcttcccaa gaactgacaa gtccctgatg tgctatttct atcaatttta cacccatccc 4980
aatcagcatc tgagtatcct attaaatcaa aggtggatcc cttggggtac caaagaccaa 5040
acttaggtgt atgaactaaa tatctcaaga ttcgtttcat ggccctaagg tgaacttcct 5100
taggattggc ttggaatctt gcacacatgc atacggaaag cataatatcc ggtcgagaag 5160
cacataaata gagtaaagat cctatcatcg atcggtatac cttttgatct acagatttac 5220

```
ctctcgtgtc gaggtcgaga tgcccatggt tcccatgggt gtcttgatgg gcttggcatc   5280
cttcattcca aacttggtga gtatatcttg agtatacttt gtttggctga tgaaggtgcc   5340
ctcttggagt tgcttgactt gaaatcctaa gaaatacttc aactccccca tcatagacat   5400
ctcgaatttt tgaatcatga tcctactaaa ctcttcacaa gtagatttgt tagtagaccc   5460
aaatatgata tcatcaacat aaatttggca tacaaacaaa tcatttgcaa tggttttagt   5520
aaagagtgta ggatcgactt ttccgacttt gaagccatta gtgataagaa agtctcttag   5580
gcattcatac catgctcttg gggcttgctt aagcccacaa agtgcctttg agagtttata   5640
gacatgatta gggtactcac tatcttcaaa gccggaaggt tgctcaatat agacctcttc   5700
cttgattggt ccattgagga aggcactctt cacgtccatt tgataaagct tgaagccatg   5760
gtaagtagca taggcaagta atatacgaat tgactcaagc ctagctattg gtgcataggt   5820
ttcaccgaaa tccaaacctt caacttgtga atatcccttg gccacatgtc gggctttgtt   5880
ccttgtcacc acaccatgct catcttgctt gttgccgaag acccacttgg tttctacaac   5940
attttggtta ggacgtggaa caagatgcca tacctcgtga agttgttgag ttcctcttgc   6000
attgccaaca cccaatccga atcccttaat gtgtcttcca ccctgtatgg ctcaatagaa   6060
gacacaaaag agtaattgtc ggtaccctga accaggggta cccccctacta cagtataagg   6120
aagcattgcc cgtacgacgt tccctagcca cacggtgagc agcacccgac cccaccatgt   6180
gggtggctca aggggtacca cgtggcgaga aaagatgaca catcccagga tatatcagtt   6240
gaaccggacc accacgaagg agcaccggac ccctgtatgc acaacccgga cccccgatta   6300
cggctcgaga ctcccaagta agcatgccga gccccttgga tggggtccag atccctttga   6360
gtaaggtccg taccacaacg aggtcccgag acatgggaga ccctggcata agcaagggtc   6420
cggtattgac acgtgttagg gccttatcat gtgcgcttgc gctccctgct taggcggaga   6480
cccgctactg ccacgtggct tgttgcctgt gacataagcc aacgggcaga gcctgatgta   6540
aggcctctag gccgtgcggt ctctgcattt attgcggagg agacgcgtcg cctgccccacc   6600
ttgctgacag gcgatgtgcc ccctttgcat ttaatgcgtc ctgtccactc caccggcagg   6660
cgcaccaggc catcctgcag tcggcgcacc tgtccagtcc attgtcaaat agtgcacccg   6720
tgctacaggg cgcactgtgc tcatcatccc ttatacgata agcttcctct gcacgccgat   6780
gctaggcaga tctcagacgt cagggcataa ggagattgcc ccagcagcaa acatgagtag   6840
cgccaaatac tacatctgtt atgttcctgg gcccacatgt cggggctcag tatccttgtg   6900
catgtccccc ttgactataa aaggggaggc atgcaacgtt acaagacagg ctctctaaga   6960
cctaaggcag acttcgaacg ctcaagcttc cacagcaatc caacacataa tggagtatgg   7020
tattacgctc tgacggcccg aaccactcta aactctcgtg tgttcatgtg ctcggtgatc   7080
gcttagctag acaggcaaaa tgcttaagcc ccttcctcat cttaggatta agggcgggtg   7140
cactccgcca cccgaccgga gaattccctc tccaacattt ggtgcgccag gtagggggct   7200
aggcattagg tttttgtttg tttcctcgct cagcatgatg gtgcaaatcg tggagcaccg   7260
cgccgataca tcaacgaatt tcctggtgga ggaagaagtt gtttcttcca cgccactggt   7320
tcccaaccgc ccagtgtcgg gcactgctgc tgtgcacgct gcacaatagc atacagctgc   7380
gtagacatct tgtactccgt cgagggtggc tctgggagca ttgtcggcgg ccagggagtt   7440
gctgtgccac cctccaagct ccatggactc accgggggcc atgaagcagt ggcgggacga   7500
cgtcgaccga ctgctcggta tggcacattc tacctcaacc aggtcgaggc cacggtcatc   7560
```

-continued

```
ccggcgccaa catgaggcgt cggcgtctat gcgcgcgccc tcagtaaggg gcgcatagac   7620
caacgacctc cgggccgagc tcaaccgcag gcgtgcggga gaggacgccc gactctcttt   7680
agagagggtg cacgagcgcc gacaaaacgt tgagggtcgc aacctcgacc aagactttgc   7740
tgcggtagca ccgcaggccc caatgggcac ccggtctcga gcgggtgtcc ccttggtcgg   7800
cgtgggctgc gccgctttcg cggatcatct ccgcgcaaca tcatggccat ccaaattctg   7860
gccgcacttg ccggaaaaat atgacggtac gtcaaacccg tcggagttcc tacaggtgta   7920
tgtcaccgct atcacagcag caggtggaaa caccactacg atgcgtgaca tattttcatg   7980
tcgccttgtc tgggcctacc cggtcttggc tcatgaacct cgccccaggg tcaatctact   8040
cctgggaaga gctctgcgca tggttcgttg cgaacttcgc cagcgcttac cagcagcacg   8100
gtgtggaggc ccaccttcac gcggtaaggc aggagcccgg ggagactctc cggacgttca   8160
tctctcgctt caccaaggtg cgaggtacta taccttgcat tttgatgct tccatcatca   8220
cggctttccg acagggagta cgtgatgaga aaatgttgga gaagttggcc acacacgatg   8280
tggagattgt ccccacactc ttcgctctgg ccgacaagtg cgctagagcc gccgaggtcc   8340
gtgcatggca ctcggcccca caagccgggg ctacccagtc gggtggctca ggtgtcgtct   8400
cccgggacgg taagaagaaa aagaagaagg actacgacta ctagaagtcg cggtccaccg   8460
ctctagtcgt tgcagcggtg accgagggcc ggggcaaccg caacaaacgc ccacggccgc   8520
agaggggtaa cagcgactca tgccctgtgc accccaacgg tcgccacagc tctgcggagt   8580
gtcgcgagat cattgacctc gcgaaacgcg tcagcgagcg gcgtgagcag tcttccaagg   8640
atggctctcc acctcgtcgc caacccggca aagaaaaggt cgacgacgct gtaagggata   8700
acactgaaca tccaacgttg attactctat tatagtatta tacagactgt acttttcgaa   8760
tttatcttag ttttctacaa tatttagtgg attcttctca ttttcaagat acacaattga   8820
accataatcg aagtggtatg taagacagtg agttaaaaga ttatattttt tgggagactt   8880
ccagtcaaat tttcttagaa gttttttgg tccagatgtt cataaagtcg ccgctttcat   8940
acttttttta attttttaat tggtgcacta ttaggtacct gttggaggat gttacaggct   9000
tattgatatc cctatgagta actgcttcaa cagtggtata aataagatat ttgtgatgag   9060
tcagttcaat tctacttcgc ttaaccgcca tattcatcgt acataccttg aaggcgggat   9120
caactttgct gatggatctg tacaggtgat ttacctcatc ttgttgatgt gtaatactgt   9180
aattaggagt agatttgtgt ggagagaata ataaacagat gccgagattc ttctctaaaa   9240
gtctagatcc aaaggcattg tggttcaaaa cactatggac ttctaccatt tatgttatta   9300
ctttgcctta atgttccatt gaatggggca aattattgat tctacaagtg tttaattaaa   9360
aactaattgt tcatcctgca ggtattagcg gctacacaaa tgcctgaaga gccagctgga   9420
tggttccagg gtacagcaga ctctatcaga aaatttatct gggtactcga ggtagttgat   9480
attttctcgt ttatgaatgt ccattcactc attcctgtag cattgtttct ttgtaatttt   9540
gagttctcct gtatttcttt aggattatta cagtcacaaa tccattgaca acattgtaat   9600
cttgagtggc gatcagcttt atcggatgaa ttacatggaa cttgtgcagg tatggtgttc   9660
tcttgttcct catgtttcac gtaatgtcct gattttggat taaccaacta cttttggcat   9720
gcattatttc cagaaacatg tcgaggacga tgctgatatc actatatcat gtgctcctgt   9780
tgatgagagg taatcagttg tttatatcat cctaatatga atatgtcatc ttgttatcca   9840
acacaggatg catatggtct aatctgcttt ccttttttcc cttcggaagc cgagcttcta   9900
aaaatgggct agtgaagatt gatcatactg gacgtgtact tcaattcttt gaaaaaccaa   9960
```

agggtgctga tttgaattct atggttagaa attccttgtg t 10001

<210> SEQ ID NO 37
<211> LENGTH: 9001
<212> TYPE: DNA
<213> ORGANISM: Zea mays

<400> SEQUENCE: 37
tctcccgcta ttccccatgg ccccatataa tctctctatt tatatttatt agagtaaaat 60
atactagtgg tctttaaact tatattgttg tattattcta gtcactaaac ccctaaagtg 120
caaatataag gtccttaaac ttgtgaattt gtatcgttct ggtccctaac tctgaacatg 180
cacatttcag tctttatact tgtaggattg tgtgtcgtct gggcctctaa acttattttt 240
ggtgtcatca agggtctaaa ctatttatac atataatgac accaaaaata agtttatgga 300
tccaagtgac acaaccatag aagtatagga ccaaaaatat gtatcttgag attttaggga 360
ccaagatgat acaacttaac aagtttaggg accttagatg tgcactttta gagtttaggg 420
accaggatga aacaacgcta aaaatgtagg gaccgctaat gcattttact ctatttttat 480
tatattttac tatataagat acttctctta tataccatct cctctataga actcttcata 540
tacgctataa ctcaattatt taatatttta tcaactttaa aaatctaaaa aatgatataa 600
tattttacta ttataataca cattatcatt aggttacatg acttaaacat gattaatatc 660
ataaacaaat gatctaatta aattataggg gtagtatatg tccaccctat gagagggttt 720
tatctctccc tcccatatga gagttagttg gagaagaatt tccctccaaa accccttatg 780
ctctgtttcg atgtcgatat ttaagaagat ggaattgaat tgagtcgaat accaaatcag 840
acatggtatt gaaatgagat gtaatttcaa ttctactgtt tggatgccac taaattgagt 900
ttggaattgt gcggtctaat tccacgcaac atcaaggggt gaggctttgt attgggagag 960
gggtttctag ttatagtcca atttcaggaa atttagtctc tgatttcaaa tctcaattcc 1020
atgtgcaacc aaacaacaga atttagaaaa gttggtttca ttttctaatt atgtgctcta 1080
atatctatat ctaaacaggg gtattacata tggtgaggtg agagatagag gcactgtctt 1140
atagtctgat agatgaacat atgtgttatc tccttttttt aatagaccaa atagaaaaga 1200
atagaaaaaa gttaaaccta tcccccgcta tatctcataa ccacacatat ctacaatatt 1260
ttttaaaaaa tcaaagacac taatagtaga agttactatg acaaagttta gtctgtgtta 1320
catcgaatgt ttgaatgttg gttataatta tatatagtat aattataaaa aataatcata 1380
tagatgaaga ctatatgatt taacccttga gagagtcttc cccgagcccg cgggcttgtc 1440
gtcggtcacg ttctccctct tggcgtgatc tccagacatc actttgagtt gattagactc 1500
ttaatgaagc actaactttg ataccaattg aaagtcgcct agagggggtg aataggcgaa 1560
acctaaaatt tacaaacata aacacacact aaggccgggg ttagcgttgg aattaaattc 1620
aagtctgaaa gattgtttct tttgctaaga gttgttcaaa ggatgcggat gacgtatggg 1680
agcaaactca aatcaatatt agcaaggaaa cgttagagag aggaaagagg gcaaacaaat 1740
caagcgagta gacatagtga tttgttttac cgaggttcgg ttctaaagaa cctaatcccc 1800
gttgaggagg ccacaaaggc cggtctatt tcaacccttt ccctctctct caaatggtca 1860
cttagaccga ttgagccttc tccttaatca aacgggtcac taaggtgtct cttgcaaact 1920
ttacaagcac ttagaaaaag aatgaggaag gaagaaaggc aatccaagcg acaagagcaa 1980
caaaagaaca caaatgaccc tctcacaatc ccttaagcac tagcgttgat tttgggaagt 2040

```
tttgagtgga ttgattgttt tgattgtgtc ttggagtgtt ggactttgct cttgcaatga   2100
atgagaaact caaaatgctt ggatggcttt gaatgaggtg gttgaggggt atttatagcc   2160
cccaaccact tcctagccgt tggtaaaggc tgctggcgat gggcgcaccg gacagtcact   2220
gttcattgtc cggtgcacgc cacgttagcg cgcccgttag ggtttggagc agttgaccgt   2280
tgaagccgtt tgtctttttg ctgcaccgga cagtccggtg acttctgcac ggcactgttt   2340
ggcactgttc ctctgcgcag tcgaccgttg gcgcgtaggg agccgttgct ccgctggctc   2400
accggatagt ccggtgaatt atagtggagc gcacgcggca caaccaccaa agtggccgtt   2460
gggaggggct gctatcgatg ggcgcaccgg accgtccggt gcgccagacc agggcagcct   2520
tcgggtttct ttgctccttt ctttttgaac cctatcttgg actttttatt ggtttgtgtt   2580
gaacctttgg cacctataga acttataatc tagagcaaac tagttagtcc aattatttgt   2640
gttgggcaat tcaaccacca aaatcattta ggaaaaggtt tgaccctatt tccctttcag   2700
tctcccctt tttggtgatt gatgccaaca caaaccaaag caaatatata agtgcagaat   2760
tgaactagtt tgcataaggt aagtgcaaag gttgcttgga attaacccaa tttatacttt   2820
cataagatat gcatggattg ctttcttctt atttaacatt ttggaccacg cttgcaccac   2880
ttgttttgtt tttgcaaaat cttttggaaa ttcttttcaa agtcttttttg caaatagtca   2940
aaggtaaatg aataagattt cgagaagcat tttcaagatt tgaaattttc tcccccctgtt   3000
tcaaatgctt ttcctttgac taaacaaaac tcccccctcaa tgaaattctc ctcttagtgt   3060
tcaagagggt tttagacatt aattttgaaa gaggtcatac caacttgaaa ttatataaaa   3120
aataagatac caattgaaaa acttctttga tacaaattga aagactgcat ttaaacactt   3180
tttgaaattg gtggtgatgc ggtccttttg ctttgggtta atactttctc cccctttggc   3240
atgaatcgcc aaaaacagat actttgtgag tgaaatatga gccctatgtt taaattctct   3300
ccccctttgg caaacaatat atgagtgaag gattatacca aggtggagag cgatgcggag   3360
tgacggcgaa gggcaaataa tacgatggag tggagtggaa gccttgtctt cgccgaagac   3420
tccatttccc tttcaatcta tgacttagca tgagatacac ttgaaaaaca cattagtaat   3480
agcaaataaa agagatatga tcaaaggtac ataaatgaac gatgtgtgca aagtatcaat   3540
caaaattcct agaatcaaga atgtttagct cattcctaag tttggtaaag gttttctcat   3600
ctaatggttt ggtaaagata tcggctaatt gttctttggt gctaacatag gcaatctcga   3660
tatccccccct ttgttggtga tccctcaaaa agtgataccg aatggctatg tgcttagtgc   3720
ggctatggtc aacgggatta tccgcattgc actctcatta tcacacagaa gagggacttt   3780
ggttaatttg taaccataat ccctaagggt ttgcctcatc caaagcaatt gtgcgcaata   3840
atggcctgcg acaatgtact cggcttcggt ggtagaaaga gctaccgaat tttgtttctt   3900
tgaagcccaa gacaccaggg atcttcccaa gaactgacaa gtccctgatg tgctatttct   3960
atcaatttta cacccatccc aatcagcatc tgagtatcct attaaatcaa aggtggatcc   4020
cttggggtac caaagaccaa acttaggtgt atgaactaaa tatctcaaga ttcgtttcat   4080
ggccctaagg tgaacttcct taggattggc ttggaatctt gcacacatgc atacggaaag   4140
cataatatcc ggtcgagaag cacataaata gagtaaagat cctatcatcg atcggtatac   4200
cttttgatct acagatttac ctctcgtgtc gaggtcgaga tgcccatggt tcccatgggt   4260
gtcttgatgg gcttggcatc cttcattcca aacttggtga gtatatcttg agtatacttt   4320
gtttggctga tgaaggtgcc ctcttggagt tgcttgactt gaaatcctaa gaaatacttc   4380
aactccccca tcatagacat ctcgaatttt tgaatcatga tcctactaaa ctcttcacaa   4440
```

```
gtagatttgt tagtagaccc aaatatgata tcatcaacat aaatttggca tacaaacaaa   4500
tcatttgcaa tggttttagt aaagagtgta ggatcgactt ttccgacttt gaagccatta   4560
gtgataagaa agtctcttag gcattcatac catgctcttg ggcttgcttt aagcccacaa   4620
agtgcctttg agagtttata gacatgatta gggtactcac tatcttcaaa gccggaaggt   4680
tgctcaatat agacctcttc cttgattggt ccattgagga aggcactctt cacgtccatt   4740
tgataaagct tgaagccatg gtaagtagca taggcaagta atatacgaat tgactcaagc   4800
ctagctattg gtgcataggt ttcaccgaaa tccaaacctt caacttgtga atatcccttg   4860
gccacatgtc gggctttgtt ccttgtcacc acaccatgct catcttgctt gttgccgaag   4920
acccacttgg tttctacaac attttggtta ggacgtggaa caagatgcca tacctcgtga   4980
agttgttgag ttcctcttgc attgccaaca cccaatccga atcccttaat gtgtcttcca   5040
ccctgtatgg ctcaatagaa gacacaaaag agtaattgtc ggtaccctga accaggggta   5100
ccccctacta cagtataagg aagcattgcc cgtacgacgt tccctagcca cacggtgagc   5160
agcacccgac cccaccatgt gggtggctca aggggtacca cgtggcgaga aaagatgaca   5220
catcccagga tatatcagtt gaaccggacc accacgaagg agcaccggac ccctgtatgc   5280
acaacccgga cccccgatta cggctcgaga ctcccaagta agcatgccga gccccttgga   5340
tggggtccag atccctttga gtaaggtccg taccacaacg aggtcccgag acatgggaga   5400
ccctggcata agcaagggtc cggtattgac acgtgttagg gccttatcat gtgcgcttgc   5460
gctccctgct taggcggaga cccgctactg ccacgtggct tgttgcctgt gacataagcc   5520
aacgggcaga gcctgatgta aggcctctag gccgtgcggt ctctgcattt attgcggagg   5580
agacgcgtcg cctgcccacc ttgctgacag gcgatgtgcc ccctttgcat ttaatgcgtc   5640
ctgtccactc caccggcagg cgcaccaggc catcctgcag tcggcgcacc tgtccagtcc   5700
attgtcaaat agtgcacccg tgctacaggg cgcactgtgc tcatcatccc ttatacgata   5760
agcttcctct gcacgccgat gctaggcaga tctcagacgt cagggcataa ggagattgcc   5820
ccagcagcaa acatgagtag cgccaaatac tacatctgtt atgttcctgg gcccacatgt   5880
cggggctcag tatccttgtg catgtccccc ttgactataa aaggggaggc atgcaacgtt   5940
acaagacagg ctctctaaga cctaaggcag acttcgaacg ctcaagcttc cacagcaatc   6000
caacacataa tggagtatgg tattacgctc tgacggcccg aaccactcta aactctcgtg   6060
tgttcatgtg ctcggtgatc gcttagctag acaggcaaaa tgcttaagcc ccttcctcat   6120
cttaggatta agggcgggtg cactccgcca cccgaccgga gaattccctc tccaacattt   6180
ggtgcgccag gtagggggct aggcattagg tttttgtttg tttcctcgct cagcatgatg   6240
gtgcaaatcg tggagcaccg cgccgataca tcaacgaatt tcctggtgga ggaagaagtt   6300
gtttcttcca cgccactggt tcccaaccgc ccagtgtcgg gcactgctgc tgtgcacgct   6360
gcacaatagc atacagctgc gtagacatct tgtactccgt cgagggtggc tctgggagca   6420
ttgtcggcgg ccagggagtt gctgtgccac cctccaagct ccatggactc accgggggcc   6480
atgaagcagt ggcgggacga cgtcgaccga ctgctcggta tggcacattc tacctcaacc   6540
aggtcgaggc cacggtcatc ccggcgccaa catgaggcgt cggcgtctat gcgcgcgccc   6600
tcagtaaggg gcgcatagac caacgacctc cgggccgagc tcaaccgcag gcgtgcggga   6660
gaggacgccc gactctcttt agagagggtg cacgagcgcc gacaaaacgt tgagggtcgc   6720
aacctcgacc aagactttgc tgcggtagca ccgcaggccc caatgggcac ccggtctcga   6780
```

```
gcgggtgtcc ccttggtcgg cgtgggctgc gccgctttcg cggatcatct ccgcgcaaca   6840
tcatggccat ccaaattctg gccgcacttg ccggaaaaat atgacggtac gtcaaacccg   6900
tcggagttcc tacaggtgta tgtcaccgct atcacagcag caggtggaaa caccactacg   6960
atgcgtgaca tattttcatg tcgccttgtc tgggcctacc cggtcttggc tcatgaacct   7020
cgccccaggg tcaatctact cctgggaaga gctctgcgca tggttcgttg cgaacttcgc   7080
cagcgcttac cagcagcacg gtgtggaggc ccaccttcac gcggtaaggc aggagcccgg   7140
ggagactctc cggacgttca tctctcgctt caccaaggtg cgaggtacta taccttgcat   7200
ttttgatgct tccatcatca cggctttccg acagggagta cgtgatgaga aaatgttgga   7260
gaagttggcc acacacgatg tggagattgt ccccacactc ttcgctctgg ccgacaagtg   7320
cgctagagcc gccgaggtcc gtgcatggca ctcggcccca caagccgggg ctacccagtc   7380
gggtggctca ggtgtcgtct cccgggacgg taagaagaaa aagaagaagg actacgacta   7440
ctagaagtcg cggtccaccg ctctagtcgt tgcagcggtg accgagggcc ggggcaaccg   7500
caacaaacgc ccacggccgc agaggggtaa cagcgactca tgccctgtgc accccaacgg   7560
tcgccacagc tctgcggagt gtcgcgagat cattgacctc gcgaaacgcg tcagcgagcg   7620
gcgtgagcag tcttccaagg atggctctcc acctcgtcgc caacccggca aagaaaaggt   7680
cgacgacgct gtaagggata acactgaaca tccaacgttg attactctat tatagtatta   7740
tacagactgt acttttcgaa tttatcttag ttttctacaa tatttagtgg attcttctca   7800
ttttcaagat acacaattga accataatcg aagtggtatg taagacagtg agttaaaaga   7860
ttatattttt tgggagactt ccagtcaaat tttcttagaa gttttttgg tccagatgtt    7920
cataaagtcg ccgctttcat acttttttta atttttaat tggtgcacta ttaggtacct    7980
gttggaggat gttacaggct tattgatatc cctatgagta actgcttcaa cagtggtata   8040
aataagatat ttgtgatgag tcagttcaat tctacttcgc ttaaccgcca tattcatcgt   8100
acataccttg aaggcgggat caactttgct gatggatctg tacaggtgat ttacctcatc   8160
ttgttgatgt gtaatactgt aattaggagt agatttgtgt ggagagaata ataaacagat   8220
gccgagattc ttctctaaaa gtctagatcc aaaggcattg tggttcaaaa cactatggac   8280
ttctaccatt tatgttatta ctttgcctta atgttccatt gaatggggca aattattgat   8340
tctacaagtg tttaattaaa aactaattgt tcatcctgca ggtattagcg gctacacaaa   8400
tgcctgaaga gccagctgga tggttccagg gtacagcaga ctctatcaga aaatttatct   8460
gggtactcga ggtagttgat attttctcgt ttatgaatgt ccattcactc attcctgtag   8520
cattgtttct ttgtaatttt gagttctcct gtatttcttt aggattatta cagtcacaaa   8580
tccattgaca acattgtaat cttgagtggc gatcagcttt atcggatgaa ttacatggaa   8640
cttgtgcagg tatggtgttc tcttgttcct catgtttcac gtaatgtcct gattttggat   8700
taaccaacta cttttggcat gcattatttc cagaaacatg tcgaggacga tgctgatatc   8760
actatatcat gtgctcctgt tgatgagagg taatcagttg tttatatcat cctaatatga   8820
atatgtcatc ttgttatcca acacaggatg catatggtct aatctgcttt cctttttcc    8880
cttcggaagc cgagcttcta aaaatgggct agtgaagatt gatcatactg gacgtgtact   8940
tcaattcttt gaaaaaccaa agggtgctga tttgaattct atggttagaa attccttgtg   9000
t                                                                   9001
```

<210> SEQ ID NO 38
<211> LENGTH: 8001

<212> TYPE: DNA
<213> ORGANISM: Zea mays

<400> SEQUENCE: 38
tgatttcaaa tctcaattcc atgtgcaacc aaacaacaga atttagaaaa gttggtttca 60
ttttctaatt atgtgctcta atatctatat ctaaacaggg gtattacata tggtgaggtg 120
agagatagag gcactgtctt atagtctgat agatgaacat atgtgttatc tccttttttt 180
aatagaccaa atagaaaaga atagaaaaaa gttaaaccta tcccccgcta tatctcataa 240
ccacacatat ctacaatatt ttttaaaaaa tcaaagacac taatagtaga agttactatg 300
acaaagttta gtctgtgtta catcgaatgt ttgaatgttg gttataatta tatatagtat 360
aattataaaa aataatcata tagatgaaga ctatatgatt taacccttga gagagtcttc 420
cccgagcccg cgggcttgtc gtcggtcacg ttctccctct tggcgtgatc tccagacatc 480
actttgagtt gattagactc ttaatgaagc actaactttg ataccaattg aaagtcgcct 540 agaggggggtg aataggcgaa acctaaaatt tacaaacata aacacacact aaggccgggg 600
ttagcgttgg aattaaattc aagtctgaaa gattgtttct tttgctaaga gttgttcaaa 660
ggatgcggat gacgtatggg agcaaactca aatcaatatt agcaaggaaa cgttagagag 720
aggaaagagg gcaaacaaat caagcgagta gacatagtga tttgttttac cgaggttcgg 780
ttctaaagaa cctaatcccc gttgaggagg ccacaaaggc cgggtctatt tcaacccttt 840
ccctctctct caaatggtca cttagaccga ttgagccttc tccttaatca aacgggtcac 900
taaggtgtct cttgcaaact ttacaagcac ttagaaaaag aatgaggaag gaagaaaggc 960
aatccaagcg acaagagcaa caaaagaaca caaatgaccc tctcacaatc ccttaagcac 1020
tagcgttgat tttgggaagt tttgagtgga ttgattgttt tgattgtgtc ttggagtgtt 1080
ggactttgct cttgcaatga atgagaaact caaaatgctt ggatggcttt gaatgaggtg 1140
gttgaggggt atttatagcc cccaaccact tcctagccgt tggtaaaggc tgctggcgat 1200
gggcgcaccg gacagtcact gttcattgtc cggtgcacgc cacgttagcg cgcccgttag 1260
ggtttggagc agttgaccgt tgaagccgtt tgtctttttg ctgcaccgga cagtccggtg 1320
acttctgcac ggcactgttt ggcactgttc ctctgcgcag tcgaccgttg gcgcgtaggg 1380
agccgttgct ccgctggctc accggatagt ccggtgaatt atagtggagc gcacgcggca 1440
caaccaccaa agtggccgtt gggaggggct gctatcgatg ggcgcaccgg accgtccggt 1500
gcgccagacc agggcagcct tcgggtttct ttgctccttt ctttttgaac cctatcttgg 1560
actttttatt ggtttgtgtt gaacctttgg cacctataga acttataatc tagagcaaac 1620
tagttagtcc aattatttgt gttgggcaat tcaaccacca aaatcattta ggaaaaggtt 1680
tgaccctatt tccctttcag tctccccctt tttggtgatt gatgccaaca caaaccaaag 1740
caaatatata agtgcagaat tgaactagtt tgcataaggt aagtgcaaag gttgcttgga 1800
attaacccaa tttatacttt cataagatat gcatggattg ctttcttctt atttaacatt 1860
ttggaccacg cttgcaccac ttgttttgtt tttgcaaaat cttttggaaa ttcttttcaa 1920 agtcttttttg caaatagtca aaggtaaatg aataagattt cgagaagcat tttcaagatt 1980
tgaaattttc tccccctgtt tcaaatgctt ttcctttgac taaacaaaac tccccctcaa 2040
tgaaattctc ctcttagtgt tcaagagggt tttagacatt aattttgaaa gaggtcatac 2100
caacttgaaa ttatataaaa aataagatac caattgaaaa acttctttga tacaaattga 2160
aagactgcat ttaaacactt tttgaaattg gtggtgatgc ggtccttttg ctttgggtta 2220

-continued

```
atactttctc cccctttggc atgaatcgcc aaaaacagat actttgtgag tgaaatatga   2280
gccctatgtt taaattctct ccccctttgg caaacaatat atgagtgaag gattatacca   2340
aggtggagag cgatgcggag tgacggcgaa gggcaaataa tacgatggag tggagtggaa   2400
gccttgtctt cgccgaagac tccatttccc tttcaatcta tgacttagca tgagatacac   2460
ttgaaaaaca cattagtaat agcaaataaa agagatatga tcaaaggtac ataaatgaac   2520
gatgtgtgca aagtatcaat caaaattcct agaatcaaga atgtttagct cattcctaag   2580
tttggtaaag gttttctcat ctaatggttt ggtaaagata tcggctaatt gttctttggt   2640
gctaacatag gcaatctcga tatccccccct ttgttggtga tccctcaaaa agtgataccg   2700
aatggctatg tgcttagtgc ggctatggtc aacgggatta tccgcattgc actctcatta   2760
tcacacagaa gagggacttt ggttaatttg taaccataat ccctaagggt ttgcctcatc   2820
caaagcaatt gtgcgcaata atggcctgcg acaatgtact cggcttcggt ggtagaaaga   2880
gctaccgaat tttgtttctt tgaagcccaa gacaccaggg atcttcccaa gaactgacaa   2940
gtccctgatg tgctatttct atcaatttta cacccatccc aatcagcatc tgagtatcct   3000
attaaatcaa aggtggatcc cttggggtac caaagaccaa acttaggtgt atgaactaaa   3060
tatctcaaga ttcgtttcat ggccctaagg tgaacttcct taggattggc ttggaatctt   3120
gcacacatgc atacggaaag cataatatcc ggtcgagaag cacataaata gagtaaagat   3180
cctatcatcg atcggtatac cttttgatct acagatttac ctctcgtgtc gaggtcgaga   3240
tgcccatggt tcccatgggt gtcttgatgg gcttggcatc cttcattcca aacttggtga   3300
gtatatcttg agtatacttt gtttggctga tgaaggtgcc ctcttggagt tgcttgactt   3360
gaaatcctaa gaaatacttc aactccccca tcatagacat ctcgaatttt tgaatcatga   3420
tcctactaaa ctcttcacaa gtagatttgt tagtagaccc aaatatgata tcatcaacat   3480
aaatttggca tacaaacaaa tcatttgcaa tggttttagt aaagagtgta ggatcgactt   3540
ttccgacttt gaagccatta gtgataagaa agtctcttag gcattcatac catgctcttg   3600
gggcttgctt aagcccacaa agtgcctttg agagtttata gacatgatta gggtactcac   3660
tatcttcaaa gccggaaggt tgctcaatat agacctcttc cttgattggt ccattgagga   3720
aggcactctt cacgtccatt tgataaagct tgaagccatg gtaagtagca taggcaagta   3780
atatacgaat tgactcaagc ctagctattg gtgcataggt ttcaccgaaa tccaaacctt   3840
caacttgtga atatcccttg gccacatgtc gggctttgtt ccttgtcacc acaccatgct   3900
catcttgctt gttgccgaag acccacttgg tttctacaac attttggtta ggacgtggaa   3960
caagatgcca tacctcgtga agttgttgag ttcctcttgc attgccaaca cccaatccga   4020
atcccttaat gtgtcttcca ccctgtatgg ctcaatagaa gacacaaaag agtaattgtc   4080
ggtaccctga accaggggta cccccctacta cagtataagg aagcattgcc cgtacgacgt   4140
tccctagcca cacggtgagc agcacccgac cccaccatgt gggtggctca aggggtacca   4200
cgtggcgaga aaagatgaca catcccagga tatatcagtt gaaccggacc accacgaagg   4260
agcaccggac ccctgtatgc acaacccgga cccccgatta cggctcgaga ctcccaagta   4320
agcatgccga gccccttgga tggggtccag atccctttga gtaaggtccg taccacaacg   4380
aggtcccgag acatgggaga ccctggcata agcaagggtc cggtattgac acgtgttagg   4440
gccttatcat gtgcgcttgc gctccctgct taggcggaga cccgctactg ccacgtggct   4500
tgttgcctgt gacataagcc aacgggcaga gcctgatgta aggcctctag gccgtgcggt   4560
ctctgcattt attgcggagg agacgcgtcg cctgcccacc ttgctgacag gcgatgtgcc   4620
```

```
ccctttgcat ttaatgcgtc ctgtccactc caccggcagg cgcaccaggc catcctgcag   4680
tcggcgcacc tgtccagtcc attgtcaaat agtgcacccg tgctacaggg cgcactgtgc   4740
tcatcatccc ttatacgata agcttcctct gcacgccgat gctaggcaga tctcagacgt   4800
cagggcataa ggagattgcc ccagcagcaa acatgagtag cgccaaatac tacatctgtt   4860
atgttcctgg gcccacatgt cggggctcag tatccttgtg catgtccccc ttgactataa   4920
aaggggaggc atgcaacgtt acaagacagg ctctctaaga cctaaggcag acttcgaacg   4980
ctcaagcttc cacagcaatc caacacataa tggagtatgg tattacgctc tgacggcccg   5040
aaccactcta aactctcgtg tgttcatgtg ctcggtgatc gcttagctag acaggcaaaa   5100
tgcttaagcc ccttcctcat cttaggatta agggcgggtg cactccgcca cccgaccgga   5160
gaattccctc tccaacattt ggtgcgccag gtagggggct aggcattagg tttttgtttg   5220
tttcctcgct cagcatgatg gtgcaaatcg tggagcaccg cgccgataca tcaacgaatt   5280
tcctggtgga ggaagaagtt gtttcttcca cgccactggt tcccaaccgc ccagtgtcgg   5340
gcactgctgc tgtgcacgct gcacaatagc atacagctgc gtagacatct tgtactccgt   5400
cgagggtggc tctgggagca ttgtcggcgg ccagggagtt gctgtgccac cctccaagct   5460
ccatggactc accgggggcc atgaagcagt ggcgggacga cgtcgaccga ctgctcggta   5520
tggcacattc tacctcaacc aggtcgaggc cacggtcatc ccggcgccaa catgaggcgt   5580
cggcgtctat gcgcgcgccc tcagtaaggg gcgcatagac caacgacctc cgggccgagc   5640
tcaaccgcag gcgtgcggga gaggacgccc gactctcttt agagagggtg cacgagcgcc   5700
gacaaaacgt tgagggtcgc aacctcgacc aagactttgc tgcggtagca ccgcaggccc   5760
caatgggcac ccggtctcga gcgggtgtcc ccttggtcgg cgtgggctgc gccgctttcg   5820
cggatcatct ccgcgcaaca tcatggccat ccaaattctg gccgcacttg ccggaaaaat   5880
atgacggtac gtcaaacccg tcggagttcc tacaggtgta tgtcaccgct atcacagcag   5940
caggtggaaa caccactacg atgcgtgaca tattttcatg tcgccttgtc tgggcctacc   6000
cggtcttggc tcatgaacct cgccccaggg tcaatctact cctgggaaga gctctgcgca   6060
tggttcgttg cgaacttcgc cagcgcttac cagcagcacg gtgtggaggc ccaccttcac   6120
gcggtaaggc aggagcccgg ggagactctc cggacgttca tctctcgctt caccaaggtg   6180
cgaggtacta taccttgcat ttttgatgct tccatcatca cggctttccg acagggagta   6240
cgtgatgaga aaatgttgga gaagttggcc acacacgatg tggagattgt ccccacactc   6300
ttcgctctgg ccgacaagtg cgctagagcc gccgaggtcc gtgcatggca ctcggcccca   6360
caagccgggg ctacccagtc gggtggctca ggtgtcgtct cccgggacgg taagaagaaa   6420
aagaagaagg actacgacta ctagaagtcg cggtccaccg ctctagtcgt tgcagcggtg   6480
accgagggcc ggggcaaccg caacaaacgc ccacggccgc agaggggtaa cagcgactca   6540
tgccctgtgc accccaacgg tcgccacagc tctgcggagt gtcgcgagat cattgacctc   6600
gcgaaacgcg tcagcgagcg gcgtgagcag tcttccaagg atggctctcc acctcgtcgc   6660
caacccggca aagaaaaggt cgacgacgct gtaagggata acactgaaca tccaacgttg   6720
attactctat tatagtatta tacagactgt acttttcgaa tttatcttag ttttctacaa   6780
tatttagtgg attcttctca ttttcaagat acacaattga accataatcg aagtggtatg   6840
taagacagtg agttaaaaga ttatattttt tgggagactt ccagtcaaat tttcttagaa   6900
gttttttttgg tccagatgtt cataaagtcg ccgctttcat acttttttta attttttaat   6960
```

tggtgcacta ttaggtacct gttggaggat gttacaggct tattgatatc cctatgagta 7020
actgcttcaa cagtggtata aataagatat ttgtgatgag tcagttcaat tctacttcgc 7080
ttaaccgcca tattcatcgt acataccttg aaggcgggat caactttgct gatggatctg 7140
tacaggtgat ttacctcatc ttgttgatgt gtaatactgt aattaggagt agatttgtgt 7200
ggagagaata ataaacagat gccgagattc ttctctaaaa gtctagatcc aaaggcattg 7260
tggttcaaaa cactatggac ttctaccatt tatgttatta ctttgcctta atgttccatt 7320
gaatggggca aattattgat tctacaagtg tttaattaaa aactaattgt tcatcctgca 7380
ggtattagcg gctacacaaa tgcctgaaga gccagctgga tggttccagg gtacagcaga 7440
ctctatcaga aaatttatct gggtactcga ggtagttgat attttctcgt ttatgaatgt 7500
ccattcactc attcctgtag cattgtttct ttgtaatttt gagttctcct gtatttcttt 7560
aggattatta cagtcacaaa tccattgaca acattgtaat cttgagtggc gatcagcttt 7620
atcggatgaa ttacatggaa cttgtgcagg tatggtgttc tcttgttcct catgtttcac 7680
gtaatgtcct gattttggat taaccaacta cttttggcat gcattatttc cagaaacatg 7740
tcgaggacga tgctgatatc actatatcat gtgctcctgt tgatgagagg taatcagttg 7800
tttatatcat cctaatatga atatgtcatc ttgttatcca acacaggatg catatggtct 7860
aatctgcttt cctttttcc cttcggaagc cgagcttcta aaaatgggct agtgaagatt 7920
gatcatactg gacgtgtact tcaattcttt gaaaaaccaa agggtgctga tttgaattct 7980
atggttagaa attccttgtg t 8001

<210> SEQ ID NO 39
<211> LENGTH: 7001
<212> TYPE: DNA
<213> ORGANISM: Zea mays

<400> SEQUENCE: 39
tctcacaatc ccttaagcac tagcgttgat tttgggaagt tttgagtgga ttgattgttt 60
tgattgtgtc ttggagtgtt ggactttgct cttgcaatga atgagaaact caaaatgctt 120
ggatggcttt gaatgaggtg gttgaggggt atttatagcc cccaaccact tcctagccgt 180
tggtaaaggc tgctggcgat gggcgcaccg gacagtcact gttcattgtc cggtgcacgc 240
cacgttagcg cgcccgttag ggtttggagc agttgaccgt tgaagccgtt tgtctttttg 300
ctgcaccgga cagtccggtg acttctgcac ggcactgttt ggcactgttc ctctgcgcag 360
tcgaccgttg gcgcgtaggg agccgttgct ccgctggctc accggatagt ccggtgaatt 420
atagtggagc gcacgcggca caaccaccaa agtggccgtt gggaggggct gctatcgatg 480
ggcgcaccgg accgtccggt gcgccagacc agggcagcct tcgggtttct ttgctccttt 540
ctttttgaac cctatcttgg actttttatt ggtttgtgtt gaacctttgg cacctataga 600
acttataatc tagagcaaac tagttagtcc aattatttgt gttgggcaat tcaaccacca 660
aaatcattta ggaaaaggtt tgaccctatt tccctttcag tctcccccttt tttggtgatt 720 gatgccaaca caaaccaaag caaatatata agtgcagaat tgaactagtt tgcataaggt 780
aagtgcaaag gttgcttgga attaacccaa tttatacttt cataagatat gcatggattg 840
ctttcttctt atttaacatt ttggaccacg cttgcaccac ttgttttgtt tttgcaaaat 900
cttttggaaa ttcttttcaa agtctttttg caaatagtca aaggtaaatg aataagattt 960
cgagaagcat tttcaagatt tgaaattttc tccccctgtt tcaaatgctt ttcctttgac 1020
taaacaaaac tccccctcaa tgaaattctc ctcttagtgt tcaagagggt tttagacatt 1080

-continued aattttgaaa gaggtcatac caacttgaaa ttatataaaa aataagatac caattgaaaa 1140
acttctttga tacaaattga aagactgcat ttaaacactt tttgaaattg gtggtgatgc 1200
ggtccttttg ctttgggtta atactttctc cccctttggc atgaatcgcc aaaaacagat 1260
actttgtgag tgaaatatga gccctatgtt taaattctct ccccctttgg caaacaatat 1320
atgagtgaag gattatacca aggtggagag cgatgcggag tgacggcgaa gggcaaataa 1380
tacgatggag tggagtggaa gccttgtctt cgccgaagac tccatttccc tttcaatcta 1440
tgacttagca tgagatacac ttgaaaaaca cattagtaat agcaaataaa agagatatga 1500
tcaaaggtac ataaatgaac gatgtgtgca aagtatcaat caaaattcct agaatcaaga 1560
atgtttagct cattcctaag tttggtaaag gttttctcat ctaatggttt ggtaaagata 1620
tcggctaatt gttctttggt gctaacatag gcaatctcga tatccccccct ttgttggtga 1680
tccctcaaaa agtgataccg aatggctatg tgcttagtgc ggctatggtc aacgggatta 1740
tccgcattgc actctcatta tcacacagaa gagggacttt ggttaatttg taaccataat 1800
ccctaagggt ttgcctcatc caaagcaatt gtgcgcaata atggcctgcg acaatgtact 1860
cggcttcggt ggtagaaaga gctaccgaat tttgtttctt tgaagcccaa gacaccaggg 1920
atcttcccaa gaactgacaa gtccctgatg tgctatttct atcaatttta cacccatccc 1980
aatcagcatc tgagtatcct attaaatcaa aggtggatcc cttggggtac caaagaccaa 2040
acttaggtgt atgaactaaa tatctcaaga ttcgtttcat ggccctaagg tgaacttcct 2100
taggattggc ttggaatctt gcacacatgc atacggaaag cataatatcc ggtcgagaag 2160
cacataaata gagtaaagat cctatcatcg atcggtatac cttttgatct acagatttac 2220
ctctcgtgtc gaggtcgaga tgcccatggt tcccatgggt gtcttgatgg gcttggcatc 2280
cttcattcca aacttggtga gtatatcttg agtatacttt gtttggctga tgaaggtgcc 2340
ctcttggagt tgcttgactt gaaatcctaa gaaatacttc aactccccca tcatagacat 2400
ctcgaatttt tgaatcatga tcctactaaa ctcttcacaa gtagatttgt tagtagaccc 2460
aaatatgata tcatcaacat aaatttggca tacaaacaaa tcatttgcaa tggttttagt 2520
aaagagtgta ggatcgactt ttccgacttt gaagccatta gtgataagaa agtctcttag 2580
gcattcatac catgctcttg gggcttgctt aagcccacaa agtgcctttg agagtttata 2640
gacatgatta gggtactcac tatcttcaaa gccggaaggt tgctcaatat agacctcttc 2700
cttgattggt ccattgagga aggcactctt cacgtccatt tgataaagct tgaagccatg 2760
gtaagtagca taggcaagta atatacgaat tgactcaagc ctagctattg gtgcataggt 2820
ttcaccgaaa tccaaacctt caacttgtga atatcccttg gccacatgtc gggctttgtt 2880
ccttgtcacc acaccatgct catcttgctt gttgccgaag acccacttgg tttctacaac 2940
attttggtta ggacgtggaa caagatgcca tacctcgtga agttgttgag ttcctcttgc 3000
attgccaaca cccaatccga atcccttaat gtgtcttcca ccctgtatgg ctcaatagaa 3060
gacacaaaag agtaattgtc ggtaccctga accaggggta ccccctacta cagtataagg 3120
aagcattgcc cgtacgacgt tccctagcca cacggtgagc agcacccgac cccaccatgt 3180
gggtggctca aggggtacca cgtggcgaga aaagatgaca catcccagga tatatcagtt 3240
gaaccggacc accacgaagg agcaccggac ccctgtatgc acaacccgga cccccgatta 3300
cggctcgaga ctcccaagta agcatgccga gcccccttgga tggggtccag atccctttga 3360
gtaaggtccg taccacaacg aggtcccgag acatgggaga ccctggcata agcaagggtc 3420

-continued cggtattgac acgtgttagg gccttatcat gtgcgcttgc gctccctgct taggcggaga 3480
cccgctactg ccacgtggct tgttgcctgt gacataagcc aacgggcaga gcctgatgta 3540
aggcctctag gccgtgcggt ctctgcattt attgcggagg agacgcgtcg cctgcccacc 3600
ttgctgacag gcgatgtgcc ccctttgcat ttaatgcgtc ctgtccactc caccggcagg 3660
cgcaccaggc catcctgcag tcggcgcacc tgtccagtcc attgtcaaat agtgcacccg 3720
tgctacaggg cgcactgtgc tcatcatccc ttatacgata agcttcctct gcacgccgat 3780
gctaggcaga tctcagacgt cagggcataa ggagattgcc ccagcagcaa acatgagtag 3840
cgccaaatac tacatctgtt atgttcctgg gcccacatgt cggggctcag tatccttgtg 3900
catgtccccc ttgactataa aaggggaggc atgcaacgtt acaagacagg ctctctaaga 3960
cctaaggcag acttcgaacg ctcaagcttc cacagcaatc caacacataa tggagtatgg 4020
tattacgctc tgacggcccg aaccactcta aactctcgtg tgttcatgtg ctcggtgatc 4080
gcttagctag acaggcaaaa tgcttaagcc ccttcctcat cttaggatta agggcgggtg 4140
cactccgcca cccgaccgga gaattccctc tccaacattt ggtgcgccag gtagggggct 4200
aggcattagg tttttgtttg tttcctcgct cagcatgatg gtgcaaatcg tggagcaccg 4260
cgccgataca tcaacgaatt tcctggtgga ggaagaagtt gtttcttcca cgccactggt 4320
tcccaaccgc ccagtgtcgg gcactgctgc tgtgcacgct gcacaatagc atacagctgc 4380
gtagacatct tgtactccgt cgagggtggc tctgggagca ttgtcggcgg ccagggagtt 4440
gctgtgccac cctccaagct ccatggactc accgggggcc atgaagcagt ggcgggacga 4500
cgtcgaccga ctgctcggta tggcacattc tacctcaacc aggtcgaggc cacggtcatc 4560
ccggcgccaa catgaggcgt cggcgtctat gcgcgcgccc tcagtaaggg gcgcatagac 4620
caacgacctc cgggccgagc tcaaccgcag gcgtgcggga gaggacgccc gactctcttt 4680
agagagggtg cacgagcgcc gacaaaacgt tgagggtcgc aacctcgacc aagactttgc 4740
tgcggtagca ccgcaggccc caatgggcac ccggtctcga gcgggtgtcc ccttggtcgg 4800
cgtgggctgc gccgctttcg cggatcatct ccgcgcaaca tcatggccat ccaaattctg 4860
gccgcacttg ccggaaaaat atgacggtac gtcaaacccg tcggagttcc tacaggtgta 4920
tgtcaccgct atcacagcag caggtggaaa caccactacg atgcgtgaca tattttcatg 4980
tcgccttgtc tgggcctacc cggtcttggc tcatgaacct cgccccaggg tcaatctact 5040
cctgggaaga gctctgcgca tggttcgttg cgaacttcgc cagcgcttac cagcagcacg 5100
gtgtggaggc ccaccttcac gcggtaaggc aggagcccgg ggagactctc cggacgttca 5160
tctctcgctt caccaaggtg cgaggtacta taccttgcat ttttgatgct tccatcatca 5220
cggctttccg acagggagta cgtgatgaga aaatgttgga gaagttggcc acacacgatg 5280
tggagattgt ccccacactc ttcgctctgg ccgacaagtg cgctagagcc gccgaggtcc 5340
gtgcatggca ctcggcccca caagccgggg ctacccagtc gggtggctca ggtgtcgtct 5400
cccgggacgg taagaagaaa aagaagaagg actacgacta ctagaagtcg cggtccaccg 5460
ctctagtcgt tgcagcggtg accgagggcc ggggcaaccg caacaaacgc ccacggccgc 5520
agaggggtaa cagcgactca tgccctgtgc accccaacgg tcgccacagc tctgcggagt 5580
gtcgcgagat cattgacctc gcgaaacgcg tcagcgagcg gcgtgagcag tcttccaagg 5640
atggctctcc acctcgtcgc caacccggca aagaaaaggt cgacgacgct gtaagggata 5700
acactgaaca tccaacgttg attactctat tatagtatta tacagactgt acttttcgaa 5760
tttatcttag ttttctacaa tatttagtgg attcttctca ttttcaagat acacaattga 5820
accataatcg aagtggtatg taagacagtg agttaaaaga ttatattttt tgggagactt 5880
ccagtcaaat tttcttagaa gtttttttgg tccagatgtt cataaagtcg ccgctttcat 5940
acttttttta atttttaat tggtgcacta ttaggtacct gttggaggat gttacaggct 6000
tattgatatc cctatgagta actgcttcaa cagtggtata aataagatat ttgtgatgag 6060
tcagttcaat tctacttcgc ttaaccgcca tattcatcgt acataccttg aaggcgggat 6120
caactttgct gatggatctg tacaggtgat ttacctcatc ttgttgatgt gtaatactgt 6180
aattaggagt agatttgtgt ggagagaata ataaacagat gccgagattc ttctctaaaa 6240
gtctagatcc aaaggcattg tggttcaaaa cactatggac ttctaccatt tatgttatta 6300
ctttgcctta atgttccatt gaatggggca aattattgat tctacaagtg tttaattaaa 6360
aactaattgt tcatcctgca ggtattagcg gctacacaaa tgcctgaaga gccagctgga 6420
tggttccagg gtacagcaga ctctatcaga aaatttatct gggtactcga ggtagttgat 6480
attttctcgt ttatgaatgt ccattcactc attcctgtag cattgtttct ttgtaatttt 6540
gagttctcct gtatttcttt aggattatta cagtcacaaa tccattgaca acattgtaat 6600
cttgagtggc gatcagcttt atcggatgaa ttacatggaa cttgtgcagg tatggtgttc 6660
tcttgttcct catgtttcac gtaatgtcct gattttggat taaccaacta cttttggcat 6720
gcattatttc cagaaacatg tcgaggacga tgctgatatc actatatcat gtgctcctgt 6780
tgatgagagg taatcagttg tttatatcat cctaatatga atatgtcatc ttgttatcca 6840
acacaggatg catatggtct aatctgcttt cctttttcc cttcggaagc cgagcttcta 6900
aaaatgggct agtgaagatt gatcatactg gacgtgtact tcaattcttt gaaaaaccaa 6960
agggtgctga tttgaattct atggttagaa attccttgtg t 7001

<210> SEQ ID NO 40
<211> LENGTH: 6001
<212> TYPE: DNA
<213> ORGANISM: Zea mays

<400> SEQUENCE: 40
tcaaatgctt ttcctttgac taaacaaaac tccccctcaa tgaaattctc ctcttagtgt 60
tcaagagggt tttagacatt aattttgaaa gaggtcatac caacttgaaa ttatataaaa 120
aataagatac caattgaaaa acttctttga tacaaattga aagactgcat ttaaacactt 180
tttgaaattg gtggtgatgc ggtccttttg ctttgggtta atactttctc cccctttggc 240
atgaatcgcc aaaaacagat actttgtgag tgaaatatga gccctatgtt taaattctct 300
ccccctttgg caaacaatat atgagtgaag gattatacca aggtggagag cgatgcggag 360
tgacggcgaa gggcaaataa tacgatggag tggagtggaa gccttgtctt cgccgaagac 420
tccatttccc tttcaatcta tgacttagca tgagatacac ttgaaaaaca cattagtaat 480
agcaaataaa agagatatga tcaaaggtac ataaatgaac gatgtgtgca aagtatcaat 540
caaaattcct agaatcaaga atgtttagct cattcctaag tttggtaaag gttttctcat 600
ctaatggttt ggtaaagata tcggctaatt gttctttggt gctaacatag gcaatctcga 660 tatccccccct ttgttggtga tccctcaaaa agtgataccg aatggctatg tgcttagtgc 720
ggctatggtc aacgggatta tccgcattgc actctcatta tcacacagaa gagggacttt 780
ggttaatttg taaccataat ccctaagggt ttgcctcatc caaagcaatt gtgcgcaata 840
atggcctgcg acaatgtact cggcttcggt ggtagaaaga gctaccgaat tttgtttctt 900

```
tgaagcccaa gacaccaggg atcttcccaa gaactgacaa gtccctgatg tgctatttct    960
atcaatttta cacccatccc aatcagcatc tgagtatcct attaaatcaa aggtggatcc   1020
cttggggtac caaagaccaa acttaggtgt atgaactaaa tatctcaaga ttcgtttcat   1080
ggccctaagg tgaacttcct taggattggc ttggaatctt gcacacatgc atacggaaag   1140
cataatatcc ggtcgagaag cacataaata gagtaaagat cctatcatcg atcggtatac   1200
cttttgatct acagatttac ctctcgtgtc gaggtcgaga tgcccatggt tcccatgggt   1260
gtcttgatgg gcttggcatc cttcattcca aacttggtga gtatatcttg agtatacttt   1320
gtttggctga tgaaggtgcc ctcttggagt tgcttgactt gaaatcctaa gaaatacttc   1380
aactccccca tcatagacat ctcgaatttt tgaatcatga tcctactaaa ctcttcacaa   1440
gtagatttgt tagtagaccc aaatatgata tcatcaacat aaatttggca tacaaacaaa   1500
tcatttgcaa tggttttagt aaagagtgta ggatcgactt ttccgacttt gaagccatta   1560
gtgataagaa agtctcttag gcattcatac catgctcttg ggcttgctt aagcccacaa    1620
agtgcctttg agagtttata gacatgatta gggtactcac tatcttcaaa gccggaaggt   1680
tgctcaatat agacctcttc cttgattggt ccattgagga aggcactctt cacgtccatt   1740
tgataaagct tgaagccatg gtaagtagca taggcaagta atatacgaat tgactcaagc   1800
ctagctattg gtgcataggt ttcaccgaaa tccaaacctt caacttgtga atatcccttg   1860
gccacatgtc gggctttgtt ccttgtcacc acaccatgct catcttgctt gttgccgaag   1920
acccacttgg tttctacaac attttggtta ggacgtggaa caagatgcca tacctcgtga   1980
agttgttgag ttcctcttgc attgccaaca cccaatccga atcccttaat gtgtcttcca   2040
ccctgtatgg ctcaatagaa gacacaaaag agtaattgtc ggtaccctga accaggggta   2100
ccccctacta cagtataagg aagcattgcc cgtacgacgt tccctagcca cacggtgagc   2160
agcacccgac cccaccatgt gggtggctca aggggtacca cgtggcgaga aaagatgaca   2220
catcccagga tatatcagtt gaaccggacc accacgaagg agcaccggac ccctgtatgc   2280
acaacccgga cccccgatta cggctcgaga ctcccaagta agcatgccga gccccttgga   2340
tggggtccag atccctttga gtaaggtccg taccacaacg aggtcccgag acatgggaga   2400
ccctggcata agcaagggtc cggtattgac acgtgttagg gccttatcat gtgcgcttgc   2460
gctccctgct taggcggaga cccgctactg ccacgtggct tgttgcctgt gacataagcc   2520
aacgggcaga gcctgatgta aggcctctag gccgtgcggt ctctgcattt attgcggagg   2580
agacgcgtcg cctgcccacc ttgctgacag gcgatgtgcc ccctttgcat ttaatgcgtc   2640
ctgtccactc caccggcagg cgcaccaggc catcctgcag tcggcgcacc tgtccagtcc   2700
attgtcaaat agtgcacccg tgctacaggg cgcactgtgc tcatcatccc ttatacgata   2760
agcttcctct gcacgccgat gctaggcaga tctcagacgt cagggcataa ggagattgcc   2820
ccagcagcaa acatgagtag cgccaaatac tacatctgtt atgttcctgg gcccacatgt   2880
cggggctcag tatccttgtg catgtccccc ttgactataa aaggggaggc atgcaacgtt   2940
acaagacagg ctctctaaga cctaaggcag acttcgaacg ctcaagcttc cacagcaatc   3000
caacacataa tggagtatgg tattacgctc tgacggcccg aaccactcta aactctcgtg   3060
tgttcatgtg ctcggtgatc gcttagctag acaggcaaaa tgcttaagcc ccttcctcat   3120
cttaggatta agggcgggtg cactccgcca cccgaccgga gaattccctc tccaacattt   3180
ggtgcgccag gtagggggct aggcattagg tttttgtttg tttcctcgct cagcatgatg   3240
gtgcaaatcg tggagcaccg cgccgataca tcaacgaatt tcctggtgga ggaagaagtt   3300
```

gtttcttcca cgccactggt tcccaaccgc ccagtgtcgg gcactgctgc tgtgcacgct 3360
gcacaatagc atacagctgc gtagacatct tgtactccgt cgagggtggc tctgggagca 3420
ttgtcggcgg ccagggagtt gctgtgccac cctccaagct ccatggactc accgggggcc 3480
atgaagcagt ggcgggacga cgtcgaccga ctgctcggta tggcacattc tacctcaacc 3540
aggtcgaggc cacggtcatc ccggcgccaa catgaggcgt cggcgtctat gcgcgcgccc 3600
tcagtaaggg gcgcatagac caacgacctc cgggccgagc tcaaccgcag gcgtgcggga 3660
gaggacgccc gactctcttt agagagggtg cacgagcgcc gacaaaacgt tgagggtcgc 3720
aacctcgacc aagactttgc tgcggtagca ccgcaggccc caatgggcac ccggtctcga 3780
gcgggtgtcc ccttggtcgg cgtgggctgc gccgctttcg cggatcatct ccgcgcaaca 3840
tcatggccat ccaaattctg gccgcacttg ccggaaaaat atgacggtac gtcaaacccg 3900
tcggagttcc tacaggtgta tgtcaccgct atcacagcag caggtggaaa caccactacg 3960
atgcgtgaca tattttcatg tcgccttgtc tgggcctacc cggtcttggc tcatgaacct 4020
cgccccaggg tcaatctact cctgggaaga gctctgcgca tggttcgttg cgaacttcgc 4080
cagcgcttac cagcagcacg gtgtggaggc ccaccttcac gcggtaaggc aggagcccgg 4140
ggagactctc cggacgttca tctctcgctt caccaaggtg cgaggtacta taccttgcat 4200
ttttgatgct tccatcatca cggctttccg acagggagta cgtgatgaga aaatgttgga 4260
gaagttggcc acacacgatg tggagattgt ccccacactc ttcgctctgg ccgacaagtg 4320
cgctagagcc gccgaggtcc gtgcatggca ctcggcccca caagccgggg ctacccagtc 4380
gggtggctca ggtgtcgtct cccgggacgg taagaagaaa aagaagaagg actacgacta 4440
ctagaagtcg cggtccaccg ctctagtcgt tgcagcggtg accgagggcc ggggcaaccg 4500
caacaaacgc ccacggccgc agaggggtaa cagcgactca tgccctgtgc accccaacgg 4560
tcgccacagc tctgcggagt gtcgcgagat cattgacctc gcgaaacgcg tcagcgagcg 4620
gcgtgagcag tcttccaagg atggctctcc acctcgtcgc caacccggca aagaaaaggt 4680
cgacgacgct gtaagggata acactgaaca tccaacgttg attactctat tatagtatta 4740
tacagactgt acttttcgaa tttatcttag ttttctacaa tatttagtgg attcttctca 4800
ttttcaagat acacaattga accataatcg aagtggtatg taagacagtg agttaaaaga 4860
ttatattttt tgggagactt ccagtcaaat tttcttagaa gttttttggg tccagatgtt 4920
cataaagtcg ccgctttcat acttttttta attttttaat tggtgcacta ttaggtacct 4980
gttggaggat gttacaggct tattgatatc cctatgagta actgcttcaa cagtggtata 5040
aataagatat ttgtgatgag tcagttcaat tctacttcgc ttaaccgcca tattcatcgt 5100
acataccttg aaggcgggat caactttgct gatggatctg tacaggtgat ttacctcatc 5160
ttgttgatgt gtaatactgt aattaggagt agatttgtgt ggagagaata ataaacagat 5220
gccgagattc ttctctaaaa gtctagatcc aaaggcattg tggttcaaaa cactatggac 5280
ttctaccatt tatgttatta ctttgcctta atgttccatt gaatggggca aattattgat 5340
tctacaagtg tttaattaaa aactaattgt tcatcctgca ggtattagcg gctacacaaa 5400
tgcctgaaga gccagctgga tggttccagg gtacagcaga ctctatcaga aaatttatct 5460
gggtactcga ggtagttgat attttctcgt ttatgaatgt ccattcactc attcctgtag 5520
cattgtttct ttgtaatttt gagttctcct gtatttcttt aggattatta cagtcacaaa 5580
tccattgaca acattgtaat cttgagtggc gatcagcttt atcggatgaa ttacatggaa 5640

-continued

```
cttgtgcagg tatggtgttc tcttgttcct catgtttcac gtaatgtcct gattttggat   5700
taaccaacta cttttggcat gcattatttc cagaaacatg tcgaggacga tgctgatatc   5760
actatatcat gtgctcctgt tgatgagagg taatcagttg tttatatcat cctaatatga   5820
atatgtcatc ttgttatcca acacaggatg catatggtct aatctgcttt cctttttttcc   5880
cttcggaagc cgagcttcta aaaatgggct agtgaagatt gatcatactg gacgtgtact   5940
tcaattcttt gaaaaaccaa agggtgctga tttgaattct atggttagaa attccttgtg   6000
t                                                                  6001
```

<210> SEQ ID NO 41
<211> LENGTH: 5001
<212> TYPE: DNA
<213> ORGANISM: Zea mays

<400> SEQUENCE: 41

```
attaaatcaa aggtggatcc cttggggtac caaagaccaa acttaggtgt atgaactaaa     60
tatctcaaga ttcgtttcat ggccctaagg tgaacttcct taggattggc ttggaatctt    120
gcacacatgc atacggaaag cataatatcc ggtcgagaag cacataaata gagtaaagat    180
cctatcatcg atcggtatac cttttgatct acagatttac ctctcgtgtc gaggtcgaga    240
tgcccatggt tcccatgggt gtcttgatgg gcttggcatc cttcattcca aacttggtga    300
gtatatcttg agtatacttt gtttggctga tgaaggtgcc ctcttggagt tgcttgactt    360
gaaatcctaa gaaatacttc aactccccca tcatagacat ctcgaatttt tgaatcatga    420
tcctactaaa ctcttcacaa gtagatttgt tagtagaccc aaatatgata tcatcaacat    480
aaatttggca tacaaacaaa tcatttgcaa tggttttagt aaagagtgta ggatcgactt    540
ttccgacttt gaagccatta gtgataagaa agtctcttag gcattcatac catgctcttg    600
gggcttgctt aagcccacaa agtgcctttg agagtttata gacatgatta gggtactcac    660
tatcttcaaa gccggaaggt tgctcaatat agacctcttc cttgattggt ccattgagga    720
aggcactctt cacgtccatt tgataaagct tgaagccatg gtaagtagca taggcaagta    780
atatacgaat tgactcaagc ctagctattg gtgcataggt ttcaccgaaa tccaaacctt    840
caacttgtga atatcccttg gccacatgtc gggctttgtt ccttgtcacc acaccatgct    900
catcttgctt gttgccgaag acccacttgg tttctacaac attttggtta ggacgtggaa    960
caagatgcca tacctcgtga agttgttgag ttcctcttgc attgccaaca cccaatccga   1020
atcccttaat gtgtcttcca ccctgtatgg ctcaatagaa gacacaaaag agtaattgtc   1080
ggtaccctga accaggggta cccccctacta cagtataagg aagcattgcc cgtacgacgt   1140
tccctagcca cacggtgagc agcacccgac cccaccatgt gggtggctca aggggtacca   1200
cgtggcgaga aaagatgaca catcccagga tatatcagtt gaaccggacc accacgaagg   1260
agcaccggac ccctgtatgc acaacccgga cccccgatta cggctcgaga ctcccaagta   1320
agcatgccga gccccttgga tggggtccag atccctttga gtaaggtccg taccacaacg   1380
aggtcccgag acatgggaga ccctggcata agcaagggtc cggtattgac acgtgttagg   1440
gccttatcat gtgcgcttgc gctccctgct taggcggaga cccgctactg ccacgtggct   1500
tgttgcctgt gacataagcc aacgggcaga gcctgatgta aggcctctag gccgtgcggt   1560
ctctgcattt attgcggagg agacgcgtcg cctgcccacc ttgctgacag gcgatgtgcc   1620
ccctttgcat ttaatgcgtc ctgtccactc caccggcagg cgcaccaggc catcctgcag   1680
tcggcgcacc tgtccagtcc attgtcaaat agtgcacccg tgctacaggg cgcactgtgc   1740
```

```
tcatcatccc ttatacgata agcttcctct gcacgccgat gctaggcaga tctcagacgt   1800
cagggcataa ggagattgcc ccagcagcaa acatgagtag cgccaaatac tacatctgtt   1860
atgttcctgg gcccacatgt cggggctcag tatccttgtg catgtccccc ttgactataa   1920
aaggggaggc atgcaacgtt acaagacagg ctctctaaga cctaaggcag acttcgaacg   1980
ctcaagcttc cacagcaatc caacacataa tggagtatgg tattacgctc tgacggcccg   2040
aaccactcta aactctcgtg tgttcatgtg ctcggtgatc gcttagctag acaggcaaaa   2100
tgcttaagcc ccttcctcat cttaggatta agggcgggtg cactccgcca cccgaccgga   2160
gaattccctc tccaacattt ggtgcgccag gtagggggct aggcattagg tttttgtttg   2220
tttcctcgct cagcatgatg gtgcaaatcg tggagcaccg cgccgataca tcaacgaatt   2280
tcctggtgga ggaagaagtt gtttcttcca cgccactggt tcccaaccgc ccagtgtcgg   2340
gcactgctgc tgtgcacgct gcacaatagc atacagctgc gtagacatct tgtactccgt   2400
cgagggtggc tctgggagca ttgtcggcgg ccagggagtt gctgtgccac cctccaagct   2460
ccatggactc accgggggcc atgaagcagt ggcgggacga cgtcgaccga ctgctcggta   2520
tggcacattc tacctcaacc aggtcgaggc cacggtcatc ccggcgccaa catgaggcgt   2580
cggcgtctat gcgcgcgccc tcagtaaggg gcgcatagac caacgacctc cgggccgagc   2640
tcaaccgcag gcgtgcggga gaggacgccc gactctcttt agagagggtg cacgagcgcc   2700
gacaaaacgt tgagggtcgc aacctcgacc aagactttgc tgcggtagca ccgcaggccc   2760
caatgggcac ccggtctcga gcgggtgtcc ccttggtcgg cgtgggctgc gccgctttcg   2820
cggatcatct ccgcgcaaca tcatggccat ccaaattctg gccgcacttg ccggaaaaat   2880
atgacggtac gtcaaacccg tcggagttcc tacaggtgta tgtcaccgct atcacagcag   2940
caggtggaaa caccactacg atgcgtgaca tattttcatg tcgccttgtc tgggcctacc   3000
cggtcttggc tcatgaacct cgccccaggg tcaatctact cctgggaaga gctctgcgca   3060
tggttcgttg cgaacttcgc cagcgcttac cagcagcacg gtgtggaggc ccaccttcac   3120
gcggtaaggc aggagcccgg ggagactctc cggacgttca tctctcgctt caccaaggtg   3180
cgaggtacta taccttgcat ttttgatgct tccatcatca cggctttccg acagggagta   3240
cgtgatgaga aaatgttgga gaagttggcc acacacgatg tggagattgt ccccacactc   3300
ttcgctctgg ccgacaagtg cgctagagcc gccgaggtcc gtgcatggca ctcggcccca   3360
caagccgggg ctacccagtc gggtggctca ggtgtcgtct cccgggacgg taagaagaaa   3420
aagaagaagg actacgacta ctagaagtcg cggtccaccg ctctagtcgt tgcagcggtg   3480
accgagggcc ggggcaaccg caacaaacgc ccacggccgc agaggggtaa cagcgactca   3540
tgccctgtgc accccaacgg tcgccacagc tctgcggagt gtcgcgagat cattgacctc   3600
gcgaaacgcg tcagcgagcg gcgtgagcag tcttccaagg atggctctcc acctcgtcgc   3660
caacccggca aagaaaaggt cgacgacgct gtaagggata acactgaaca tccaacgttg   3720
attactctat tatagtatta tacagactgt acttttcgaa tttatcttag ttttctacaa   3780
tatttagtgg attcttctca ttttcaagat acacaattga accataatcg aagtggtatg   3840
taagacagtg agttaaaaga ttatattttt tgggagactt ccagtcaaat tttcttagaa   3900
gtttttttgg tccagatgtt cataaagtcg ccgctttcat actttttta atttttaat     3960
tggtgcacta ttaggtacct gttggaggat gttacaggct tattgatatc cctatgagta   4020
actgcttcaa cagtggtata aataagatat ttgtgatgag tcagttcaat tctacttcgc   4080
```

```
ttaaccgcca tattcatcgt acataccttg aaggcgggat caactttgct gatggatctg   4140
tacaggtgat ttacctcatc ttgttgatgt gtaatactgt aattaggagt agatttgtgt   4200
ggagagaata ataaacagat gccgagattc ttctctaaaa gtctagatcc aaaggcattg   4260
tggttcaaaa cactatggac ttctaccatt tatgttatta ctttgcctta atgttccatt   4320
gaatggggca aattattgat tctacaagtg tttaattaaa aactaattgt tcatcctgca   4380
ggtattagcg gctacacaaa tgcctgaaga gccagctgga tggttccagg gtacagcaga   4440
ctctatcaga aaatttatct gggtactcga ggtagttgat attttctcgt ttatgaatgt   4500
ccattcactc attcctgtag cattgtttct ttgtaatttt gagttctcct gtatttcttt   4560
aggattatta cagtcacaaa tccattgaca acattgtaat cttgagtggc gatcagcttt   4620
atcggatgaa ttacatggaa cttgtgcagg tatggtgttc tcttgttcct catgtttcac   4680
gtaatgtcct gattttggat taaccaacta cttttggcat gcattatttc cagaaacatg   4740
tcgaggacga tgctgatatc actatatcat gtgctcctgt tgatgagagg taatcagttg   4800
tttatatcat cctaatatga atatgtcatc ttgttatcca acacaggatg catatggtct   4860
aatctgcttt cctttttcc cttcggaagc cgagcttcta aaaatgggct agtgaagatt   4920
gatcatactg gacgtgtact tcaattcttt gaaaaaccaa agggtgctga tttgaattct   4980
atggttagaa attccttgtg t                                             5001
```

<210> SEQ ID NO 42
<211> LENGTH: 3001
<212> TYPE: DNA
<213> ORGANISM: Zea mays

<400> SEQUENCE: 42

```
attgccaaca cccaatccga atcccttaat gtgtcttcca ccctgtatgg ctcaatagaa     60
gacacaaaag agtaattgtc ggtaccctga accaggggta cccccctacta cagtataagg   120
aagcattgcc cgtacgacgt tccctagcca cacggtgagc agcacccgac cccaccatgt   180
gggtggctca aggggtacca cgtggcgaga aaagatgaca catcccagga tatatcagtt   240
gaaccggacc accacgaagg agcaccggac ccctgtatgc acaacccgga cccccgatta   300
cggctcgaga ctcccaagta agcatgccga gccccttgga tggggtccag atccctttga   360
gtaaggtccg taccacaacg aggtcccgag acatgggaga ccctggcata agcaagggtc   420
cggtattgac acgtgttagg gccttatcat gtgcgcttgc gctccctgct taggcggaga   480
cccgctactg ccacgtggct tgttgcctgt gacataagcc aacgggcaga gcctgatgta   540
aggcctctag gccgtgcggt ctctgcattt attgcggagg agacgcgtcg cctgcccacc   600
ttgctgacag gcgatgtgcc ccctttgcat ttaatgcgtc ctgtccactc caccggcagg   660
cgcaccaggc catcctgcag tcggcgcacc tgtccagtcc attgtcaaat agtgcacccg   720
tgctacaggg cgcactgtgc tcatcatccc ttatacgata agcttcctct gcacgccgat   780
gctaggcaga tctcagacgt cagggcataa ggagattgcc ccagcagcaa acatgagtag   840
cgccaaatac tacatctgtt atgttcctgg gcccacatgt cggggctcag tatccttgtg   900
catgtccccc ttgactataa aaggggaggc atgcaacgtt acaagacagg ctctctaaga   960
cctaaggcag acttcgaacg ctcaagcttc cacagcaatc caacacataa tggagtatgg  1020
tattacgctc tgacggcccg aaccactcta aactctcgtg tgttcatgtg ctcggtgatc  1080
gcttagctag acaggcaaaa tgcttaagcc ccttcctcat cttaggatta agggcgggtg  1140
cactccgcca cccgaccgga gaattccctc tccaacattt ggtgcgccag gtagggggct  1200
```

-continued

```
aggcattagg tttttgtttg tttcctcgct cagcatgatg gtgcaaatcg tggagcaccg   1260

cgccgataca tcaacgaatt tcctggtgga ggaagaagtt gtttcttcca cgccactggt   1320

tcccaaccgc ccagtgtcgg gcactgctgc tgtgcacgct gcacaatagc atacagctgc   1380

gtagacatct tgtactccgt cgagggtggc tctgggagca ttgtcggcgg ccagggagtt   1440

gctgtgccac cctccaagct ccatggactc accgggggcc atgaagcagt ggcgggacga   1500

cgtcgaccga ctgctcggta tggcacattc tacctcaacc aggtcgaggc cacggtcatc   1560

ccggcgccaa catgaggcgt cggcgtctat gcgcgcgccc tcagtaaggg gcgcatagac   1620

caacgacctc cgggccgagc tcaaccgcag gcgtgcggga gaggacgccc gactctcttt   1680

agagagggtg cacgagcgcc gacaaaacgt tgagggtcgc aacctcgacc aagactttgc   1740

tgcggtagca ccgcaggccc caatgggcac ccggtctcga gcgggtgtcc ccttggtcgg   1800

cgtgggctgc gccgctttcg cggatcatct ccgcgcaaca tcatggccat ccaaattctg   1860

gccgcacttg ccggaaaaat atgacggtac gtcaaacccg tcggagttcc tacaggtgta   1920

tgtcaccgct atcacagcag caggtggaaa caccactacg atgcgtgaca tattttcatg   1980

tcgccttgtc tgggcctacc cggtcttggc tcatgaacct cgccccaggg tcaatctact   2040

cctgggaaga gctctgcgca tggttcgttg cgaacttcgc cagcgcttac cagcagcacg   2100

gtgtggaggc ccaccttcac gcggtaaggc aggagcccgg ggagactctc cggacgttca   2160

tctctcgctt caccaaggtg cgaggtacta taccttgcat ttttgatgct tccatcatca   2220

cggctttccg acagggagta cgtgatgaga aaatgttgga gaagttggcc acacacgatg   2280

tggagattgt ccccacactc ttcgctctgg ccgacaagtg cgctagagcc gccgaggtcc   2340

gtgcatggca ctcggcccca caagccgggg ctacccagtc gggtggctca ggtgtcgtct   2400

cccgggacgg taagaagaaa aagaagaagg actacgacta ctagaagtcg cggtccaccg   2460

ctctagtcgt tgcagcggtg accgagggcc ggggcaaccg caacaaacgc ccacggccgc   2520

agaggggtaa cagcgactca tgccctgtgc accccaacgg tcgccacagc tctgcggagt   2580

gtcgcgagat cattgacctc gcgaaacgcg tcagcgagcg gcgtgagcag tcttccaagg   2640

atggctctcc acctcgtcgc caacccggca aagaaaaggt cgacgacgct gtaagggata   2700

acactgaaca tccaacgttg attactctat tatagtatta tacagactgt acttttcgaa   2760

tttatcttag ttttctacaa tatttagtgg attcttctca ttttcaagat acacaattga   2820

accataatcg aagtggtatg taagacagtg agttaaaaga ttatattttt tgggagactt   2880

ccagtcaaat tttcttagaa gttttttgg tccagatgtt cataaagtcg ccgctttcat   2940

actttttta atttttaat tggtgcacta ttaggtacct gttggaggat gttacaggct   3000

t                                                                  3001
```

<210> SEQ ID NO 43
<211> LENGTH: 14687
<212> TYPE: DNA
<213> ORGANISM: Zea mays

<400> SEQUENCE: 43

```
acgcagcttt tgattctcat caatgatctt ctgagaatgc ctgcgagcta gctgctgcat     60

cttgctaatt tctggtaatg gttatgctta ttaatttatc tttcaaatga aacttcacag    120

ctgctgatga tagaaaactg gaaatataac taaacccatg cggaaaaaat caacaaaaag    180

aataacataa accttcattg tatgactgga gaagttgttc cctttgcccc atcatcttct    240
```

```
caagtgatgc agttgtctca ctgtatttgc attctagttc ctgtaaatac ctatttttca    300
cctcaatttg gttagctaaa ttagcaacaa gcctgtcatt tttacgcgct ccttcctttg    360
caagatcatt gacagatttc aagtcgccat tttttctcaa gtggtccgct attattcctg    420
gagaattgta atcttcagcc cgcgcaagcc atccatagag ctcggatcct tgattctttt    480
ttccaatcca gtccttctta ccgaatcctc ctgccgcaaa gtgactttca aaggtacgcg    540
catttctgaa accattccag tcctttccaa actcaacaat agcatttcct gtatgacctc    600
taaaagtcca taacgggatg accctcagtg ggaaaaagtg tgatagttgc tccttcagac    660
gatttccact ttctccaatt tggcgcccat ccttccattc agtaggcaca ttaactagga    720
cacccatcca gggccacaca aacttctcgt ctcggttctg aagaggttgt ggctccacag    780
gagttgcatg tgaccctggt tcaggtgatt tagcaagacc attcttcaaa tatttgaaga    840
gggcgcgatg gactgctttt tcttttgcct cgcgattagg tgctgcactg actcctgagg    900
catgttgaac caggctactt ttactgtaat tcttcttctt gctgctacag aagggacaaa    960
tgtaattttc tccattctta tttaatttta aatctcctga catcagtctt gcataaattt   1020
ttccttcata atcatcaatc tcagaatcac tgatttctgt atcttcgtca gaactatgat   1080
ccattttcaa gaaggggaag aaaatatagg caacctagca aggcaaaaca aataacactg   1140
agaacacaac aataaagttt gtttttttgaa ctaatttttc attatgaagt aggaatgagc   1200
acttgggaaa gagaacagca agcatggaac actgaaatac tatcatgcaa ggggaacagg   1260
tttgcccatt cagaacacat tgctcctaga ttgagcccac agttcggagc aggctgacct   1320
taacaggaag agggttcaaa gggtaggaac cattttgaca ccctagggcc gccccgctca   1380
tgagtggtgc catccactca cctctgcctc acttgtgacc tctgagaaag agatgcagta   1440
ccgatgccca tgcagatgct ggcactagtg gtgaccctaa acacaggaat caccaccgaa   1500
catgtccaaa gggtgcctat ttccaccctc tcataccctg agaccctgaa gatctaaaac   1560
atgcttcgtt ttgtttctag atgccggttg attccgatta gaggattagt agagatgcta   1620
ggttttcatt tctagatttc ttggtggatt ttaccagctt tctttgaagg ggatccacca   1680
gcttcaccat tgtcagggaa aaacaaaatt ctctacaagt aatatcttgc ttggaatcat   1740
ctaacaacaa tgtgtgtcat gtctggttgg attattcttg atttcagttt tggtaagtca   1800
tgtttgtata aaggcatgtt agcaagctgc catgaatttt tattttggta acgctctcag   1860
ctattagcag actgtaactt cggggggggg gggggggggg gacaaacaaa acttctaata   1920
ggttacatta agcatatgta ctgaatatct gaagcgcctg cacctatgtt gacctgatac   1980
ggggatacgg atacgcgata cgccatttct caaaaaatac ggatacggcg atacgcaata   2040
tatattataa ataaaattaa atgctgaaat gtctgaaatg gaccacagcc gatcagttca   2100
atttaaggac gttagaagtt aatgttcaac aactttgact aaagtaaaca tctacttcct   2160
cttccagaat ttatctggac tcaaatcaat gaatccagca tgccaaaagc ccaaaaacat   2220
gtgtaacgat acgctacacc agcagactcg caaaataatc actagttcac caaatcacca   2280
cacaagttct aagttttaat tcgaacagac cacagaccac agaccagaca tgagacaaca   2340
acagatggga gatacactac accagcagac tcgcaaaata atcactagtt caccaaatca   2400
gtagatgcac tcgttgccat gggatattgg gatctaacaa gaacagagaa tggacaaccg   2460
cagcgtcaga cagggcagat gggagatggc agcagaatag cagatcacgt acctcagtac   2520
ctcacgacgg cagatgggtt ggctgacggc gcgaccacag agctggcggc ggtggacgcg   2580
gccacggaag cgcggctgtc ggctggagtg gcggtgcgca gggaagcgcg gctgcgcgcg   2640
```

```
tctccaagcg gtgaagggct ggcggcgcgc agggaagcgc ggggctagca gcgcgcaggg   2700
aagcgcgggg ctagcggcgc gcaggaaggt gcgcggggat ggcggcgcgc ggtggggaga   2760
agcggggctg gcggcgcgca gggaagcgcg gggctggcgg cgagcaggaa ggtgcgcggg   2820
gatggcggcg cgccgtgggg agaagcgggg ctggcggcgc gcagagaagt tgcgcgtgtg   2880
cgccgtgggg agaagcggtg cgcaggaaat tagggatata aggtacccca catgtgttca   2940
agaggtgtcc tagaactatc cgtctttttt tatttattta aattcacaga aatttccaat   3000
acgtctcaga tatgtatcca gaagtatccg cgaagtatcc gtatctaata cggtatccga   3060
caccggtacg tgaattttga gaagtatccg cgcatcatag gcatgcactt ggttggtttc   3120
atgaaggatt tgtagcatgt atgaattatt gtttctacta gttggcatgc aagtctgttt   3180
ctcctggaaa gaactctgaa aaaatatgca cgcgtcaaca gatcagagcc tcgatgatca   3240
gaaaaaaaca aagagcatgt gtttctgtag tatgtactgc acatcgtcat gcattatagc   3300
aggctatgtt tgagtaacct ttgtgtttac caataccgcc tatctagcta ttattaatca   3360
tattcaaccc gacttcccta ggctggttgc ccttttctta gactaaatat gcagggtgtc   3420
aaacaagtgg ccaaattgat caagtgcata taatgacacc cattgtaagt gtagatcagg   3480
tctcataaac caggaacata gaacttgtcc acgttcctcg ttccgagaac gttcgttccg   3540
tcccaggaac gcggaaacaa tctcgtccct gtagtgttaa aatcgtcttt taagtatcat   3600
accatgaacc atgttcccgt tcctcgacct tatcaatatg agaacctggt tactgaggat   3660
caggtttcct ttctgttatg aacctttgtt catttggggt gaccattgcc aggaggacag   3720
ccaagcaaag tcagtttggt tacttcccgt caatgctaca ctttcttgtt cgtttttatg   3780
caatttctag atgaactatc aactaggcat ccattgatgt tagcacagtt tagctcctgt   3840
aatgtgtatc catctatgga ttgttcaatc atgtgattaa ttaattgata aaagtacgaa   3900
tagaaaatac agtagtaaca tatccttgtt cctcttgctg tggcaactgg catctgtttg   3960
ttgttagttg atacttactt ggcaggcata gtgctggcat tgtcataaat ttggagacta   4020
cttcacagta tatgcatatg tgtgtttttg caattttggt gatagggtgg ataactatcc   4080
tggaaccaaa tccttgctta aggtgtactt gtcggtttca gctgatggta tccaggcaac   4140
aaaaagagtc tgttatttct tgttttttat agctatgtaa tgttgtcttg tattcagcca   4200
gtggcacaag atggataaaa aatgtgtaaa aaatcggaga aaattggaga aacatctcac   4260
gcccttaatg gggcagaggg tgtgaccttt catatataga accgagtagg cttaggttac   4320
aaaaatacga caagacctat tcaaatacaa tggcgcgact atatgcattt ctaataaaat   4380
aagcttccag atacttgatt aatgctaatt gtatcagaat aatgtgagct ttctgatgtt   4440
gtcaatgtga aaacccttca gcttggacag tatcttcctt tcctaactga ttttttagag   4500
aacaaaattc ttggtccagc ttttattgaa agccgatgaa acggttcttt ctttcctaac   4560
tgattgatat tggtaacttg ttttctgagc tttaatcctc ggatatctca ggtgcgctct   4620
tactagagaa ggatgttgtc aagttggact ccattgctca gaaagtcaat acccattgtc   4680
taagctcagg ttgttggaaa atcattagga attattgcat gaaaataatc taagagcgga   4740
cttcattagc cttcctgagg atagtggtca ctgaccaaat cttccatgtt tatgcaagga   4800
aacataacat ttactgacta tgagtgttca aaatttgttc acttgctttt gaagatagct   4860
tctggttcca agagacaggt gttgttgtag gagatctgct aacattttga tcaaatccag   4920
ttggtgttat acagcactgg cttactaaca ttactataaa atccttgttg aagaatctgt   4980
```

```
aagttgttaa tctttgttga atactaactt ctttataatt ttatttatta tcttctatat   5040
ttagtcactg agtgtgcagt gcgctttgca tgcatagaga agttgaaagc aacacaatcg   5100
agactgcagc aatctctatt tgctagttca gtagttctcg tctattctct gtttgcgaac   5160
ttcagcgtga agaaagtcct taaagaaaag gtgaggacga tcaaaccaag gggcggaccc   5220
agtaaagggc atggatatac acccaataat ttttgcaaag caaacaaagt tagtagacat   5280
gatacattca tatacacttg taattagatt cagatccgat cacgaagagt atgttagtgt   5340
ttgggcgcac ggcttcgcac agcaggaagg gaagaaaggg gagggagcac ctggtgtcct   5400
agtgatgctc gtcgcctccc aaggtggcga ggaagggggc gagctcggac gcgggtagga   5460
agaggaggca gccgccaccc tctgctgatg ggtcggggta ggtagagggg gaaagaaaat   5520
ggaaaaagtt actctcttcg ttcttcagcc aaactctcta tctcactcta tgttacaaac   5580
ttcactctac aaacaaacag tacaatttac tgtgcaaaag agtattttgc acgacctttt   5640
atattaaata taaccttaga gcgttttcaa aactatcttc atttttctc tctattcgat   5700
tctctattta cctttccata aaaattacac tctatatata gcatttcact ccaacaaatt   5760
atttatctac tttgactagt cagattggct agctaagttg actagtgaga gcatctctaa   5820
aagactagca aatggtttat caagccaaat ttcggctact caacaataaa ataactctcc   5880
aacggactag ccatccaact cgccaaggta ttcgactctt taaattggtc tcctctctag   5940
tcaaatttat aggtgtacgt tcgggccgcc cggcccggcc caagcccgaa aaggcccgta   6000
atatttgaat ttcgggccga tccggcccgt ttgaatttcg ggacgtgtcg ggccagccca   6060
cgggcctagc cctcggccca cggccggtcc gtaattggtt aaacatgcct ggctcatttc   6120
gggcggcccg aaattataaa agcctgaaat tcacattaag acccgaaatt catttttgg    6180
cccgaaattc acatcagggc ccgaaattca aaacaaattt aataaaacaa ataaaagata   6240
agacaaataa atttgaccaa aagcaaactt aatatttgta ttaagttact agagctatac   6300
aatgactacc tcgtttacaa atcattttgt tagaaagaaa aagagtataa tcagctctat   6360
ataaagttcg taagttcagt tcattatcta atattcataa caaaaataaa attacatcac   6420
atactctaat tcaaagatac aaaaaacatc taactaacat tatctctagc tttgtgttct   6480
ttatcaagta catgaaagtg tggaataaag tgtgatttta ataaatatat gagccttttt   6540
ctgcttctat atgagtcatt tcgtgtctgc cttaaacggg tcgtgctcgt gcccgcccat   6600
gggccgcgac ctcggcccaa acccggccca acactaaaat atttcgtgtc gtgtcgtgcc   6660
tgggccgtgc ttttttccg tgctttgggc cggcccatca ggcccggctc aaatgtacac   6720
ctatagccaa atttgactag ccactctggc tagacaaact aaataaatag tctgttagag   6780
tgagatgcta catatggagt gtaatcttat ggagaggtaa atagagtgtc aaatagagag   6840
ttaaaaatgg agtccctgga gatgctctga ggaagctaat ttggagaatc gaatagcttg   6900
gcgagttaga tggctagtct attgaagagt tttttctgt tgagtaacta aaatttggct   6960
tgacgaactc tttggctagt ctcttggaga tactagactc tctcccgcta ttccccatgg   7020
ccccatataa tctctctatt tatatttatt agagtaaaat atactagtgg tctttaaact   7080
tatattgttg tattattcta gtcactaaac ccctaaagtg caaatataag gtccttaaac   7140
ttgtgaattt gtatcgttct ggtccctaac tctgaacatg cacatttcag tctttatact   7200
tgtaggattg tgtgtcgtct gggcctctaa acttattttt ggtgtcatca agggtctaaa   7260
ctatttatac atataatgac accaaaaata agtttatgga tccaagtgac acaaccatag   7320
aagtatagga ccaaaaatat gtatcttgag attttaggga ccaagatgat acaacttaac   7380
```

```
aagtttaggg accttagatg tgcactttta gagtttaggg accaggatga aacaacgcta   7440
aaaatgtagg gaccgctaat gcattttact ctatttttat tatattttac tatataagat   7500
acttctctta tataccatct cctctataga actcttcata tacgctataa ctcaattatt   7560
taatatttta tcaactttaa aaatctaaaa aatgatataa tattttacta ttataataca   7620
cattatcatt aggttacatg acttaaacat gattaatatc ataaacaaat gatctaatta   7680
aattataggg gtagtatatg tccaccctat gagagggttt tatctctccc tcccatatga   7740
gagttagttg gagaagaatt tccctccaaa accccttatg ctctgtttcg atgtcgatat   7800
ttaagaagat ggaattgaat tgagtcgaat accaaatcag acatggtatt gaaatgagat   7860
gtaatttcaa ttctactgtt tggatgccac taaattgagt ttggaattgt gcggtctaat   7920
tccacgcaac atcaaggggt gaggctttgt attgggagag ggtttctag ttatagtcca    7980
atttcaggaa atttagtctc tgatttcaaa tctcaattcc atgtgcaacc aaacaacaga   8040
atttagaaaa gttggtttca ttttctaatt atgtgctcta atatctatat ctaaacaggg   8100
gtattacata tggtgaggtg agagatagag gcactgtctt atagtctgat agatgaacat   8160
atgtgttatc tccttttttt aatagaccaa atagaaaaga atagaaaaaa gttaaaccta   8220
tcccccgcta tatctcataa ccacacatat ctacaatatt ttttaaaaaa tcaaagacac   8280
taatagtaga agttactatg acaaagttta gtctgtgtta catcgaatgt ttgaatgttg   8340
gttataatta tatatagtat aattataaaa aataatcata tagatgaaga ctatatgatt   8400
taacccttga gagagtcttc cccgagcccg cgggcttgtc gtcggtcacg ttctccctct   8460
tggcgtgatc tccagacatc actttgagtt gattagactc ttaatgaagc actaactttg   8520
ataccaattg aaagtcgcct agaggggggtg aataggcgaa acctaaaatt tacaaacata  8580
aacacacact aaggccgggg ttagcgttgg aattaaattc aagtctgaaa gattgtttct   8640
tttgctaaga gttgttcaaa ggatgcggat gacgtatggg agcaaactca aatcaatatt   8700
agcaaggaaa cgttagagag aggaaagagg gcaaacaaat caagcgagta gacatagtga   8760
tttgttttac cgaggttcgg ttctaaagaa cctaatcccc gttgaggagg ccacaaaggc   8820
cgggtctatt tcaacccttt ccctctctct caaatggtca cttagaccga ttgagccttc   8880
tccttaatca aacgggtcac taaggtgtct cttgcaaact ttacaagcac ttagaaaaag   8940
aatgaggaag gaagaaaggc aatccaagcg acaagagcaa caaaagaaca caaatgaccc   9000
tctcacaatc ccttaagcac tagcgttgat tttgggaagt tttgagtgga ttgattgttt   9060
tgattgtgtc ttggagtgtt ggactttgct cttgcaatga atgagaaact caaaatgctt   9120
ggatggcttt gaatgaggtg gttgaggggt atttatagcc cccaaccact tcctagccgt   9180
tggtaaaggc tgctggcgat gggcgcaccg gacagtcact gttcattgtc cggtgcacgc   9240
cacgttagcg cgcccgttag ggtttggagc agttgaccgt tgaagccgtt tgtctttttg   9300
ctgcaccgga cagtccggtg acttctgcac ggcactgttt ggcactgttc ctctgcgcag   9360
tcgaccgttg gcgcgtaggg agccgttgct ccgctggctc accggatagt ccggtgaatt   9420
atagtggagc gcacgcggca caaccaccaa agtggccgtt gggaggggct gctatcgatg   9480
ggcgcaccgg accgtccggt gcgccagacc agggcagcct tcgggtttct ttgctccttt   9540
ctttttgaac cctatcttgg actttttatt ggtttgtgtt gaacctttgg cacctataga   9600
acttataatc tagagcaaac tagttagtcc aattatttgt gttgggcaat tcaaccacca   9660
aaatcattta ggaaaaggtt tgaccctatt tccctttcag tctccccctt tttggtgatt   9720
```

-continued

```
gatgccaaca caaaccaaag caaatatata agtgcagaat tgaactagtt tgcataaggt   9780
aagtgcaaag gttgcttgga attaacccaa tttatacttt cataagatat gcatggattg   9840
ctttcttctt atttaacatt ttggaccacg cttgcaccac ttgttttgtt tttgcaaaat   9900
cttttggaaa ttcttttcaa agtctttttg caaatagtca aaggtaaatg aataagattt   9960
cgagaagcat tttcaagatt tgaaattttc tccccctgtt tcaaatgctt ttcctttgac  10020
taaacaaaac tccccctcaa tgaaattctc ctcttagtgt tcaagagggt tttagacatt  10080
aattttgaaa gaggtcatac caacttgaaa ttatataaaa aataagatac caattgaaaa  10140
acttctttga tacaaattga aagactgcat ttaaacactt tttgaaattg gtggtgatgc  10200
ggtccttttg ctttgggtta atactttctc cccctttggc atgaatcgcc aaaaacagat  10260
actttgtgag tgaaatatga gccctatgtt taaattctct ccccctttgg caaacaatat  10320
atgagtgaag gattatacca aggtggagag cgatgcggag tgacggcgaa gggcaaataa  10380
tacgatggag tggagtggaa gccttgtctt cgccgaagac tccatttccc tttcaatcta  10440
tgacttagca tgagatacac ttgaaaaaca cattagtaat agcaaataaa agagatatga  10500
tcaaaggtac ataaatgaac gatgtgtgca aagtatcaat caaaattcct agaatcaaga  10560
atgtttagct cattcctaag tttggtaaag gttttctcat ctaatggttt ggtaaagata  10620
tcggctaatt gttctttggt gctaacatag gcaatctcga tatccccccct ttgttggtga  10680
tccctcaaaa agtgataccg aatggctatg tgcttagtgc ggctatggtc aacgggatta  10740
tccgcattgc actctcatta tcacacagaa gagggacttt ggttaatttg taaccataat  10800
ccctaagggt ttgcctcatc caaagcaatt gtgcgcaata atggcctgcg acaatgtact  10860
cggcttcggt ggtagaaaga gctaccgaat tttgtttctt tgaagcccaa gacaccaggg  10920
atcttcccaa gaactgacaa gtccctgatg tgctatttct atcaatttta cacccatccc  10980
aatcagcatc tgagtatcct attaaatcaa aggtggatcc cttggggtac caaagaccaa  11040
acttaggtgt atgaactaaa tatctcaaga ttcgtttcat ggccctaagg tgaacttcct  11100
taggattggc ttggaatctt gcacacatgc atacggaaag cataatatcc ggtcgagaag  11160
cacataaata gagtaaagat cctatcatcg atcggtatac cttttgatct acagatttac  11220
ctctcgtgtc gaggtcgaga tgcccatggt tcccatgggt gtcttgatgg gcttggcatc  11280
cttcattcca aacttggtga gtatatcttg agtatacttt gtttggctga tgaaggtgcc  11340
ctcttggagt tgcttgactt gaaatcctaa gaaatacttc aactccccca tcatagacat  11400
ctcgaatttt tgaatcatga tcctactaaa ctcttcacaa gtagatttgt tagtagaccc  11460
aaatatgata tcatcaacat aaatttggca tacaaacaaa tcatttgcaa tggttttagt  11520
aaagagtgta ggatcgactt ttccgacttt gaagccatta gtgataagaa agtctcttag  11580
gcattcatac catgctcttg gggcttgctt aagcccacaa agtgcctttg agagtttata  11640
gacatgatta gggtactcac tatcttcaaa gccggaaggt tgctcaatat agacctcttc  11700
cttgattggt ccattgagga aggcactctt cacgtccatt tgataaagct tgaagccatg  11760
gtaagtagca taggcaagta atatacgaat tgactcaagc ctagctattg gtgcataggt  11820
ttcaccgaaa tccaaacctt caacttgtga atatcccttg gccacatgtc gggctttgtt  11880
ccttgtcacc acaccatgct catcttgctt gttgccgaag acccacttgg tttctacaac  11940
attttggtta ggacgtggaa caagatgcca tacctcgtga agttgttgag ttcctcttgc  12000
attgccaaca cccaatccga atcccttaat gtgtcttcca ccctgtatgg ctcaatagaa  12060
gacacaaaag agtaattgtc ggtaccctga accaggggta ccccctacta cagtataagg  12120
```

aagcattgcc cgtacgacgt tccctagcca cacggtgagc agcacccgac cccaccatgt 12180
gggtggctca aggggtacca cgtggcgaga aaagatgaca catcccagga tatatcagtt 12240
gaaccggacc accacgaagg agcaccggac ccctgtatgc acaacccgga cccccgatta 12300
cggctcgaga ctcccaagta agcatgccga gccccttgga tggggtccag atccctttga 12360
gtaaggtccg taccacaacg aggtcccgag acatgggaga ccctggcata agcaagggtc 12420
cggtattgac acgtgttagg gccttatcat gtgcgcttgc gctccctgct taggcggaga 12480
cccgctactg ccacgtggct tgttgcctgt gacataagcc aacgggcaga gcctgatgta 12540
aggcctctag gccgtgcggt ctctgcattt attgcggagg agacgcgtcg cctgcccacc 12600
ttgctgacag gcgatgtgcc ccctttgcat ttaatgcgtc ctgtccactc caccggcagg 12660
cgcaccaggc catcctgcag tcggcgcacc tgtccagtcc attgtcaaat agtgcacccg 12720
tgctacaggg cgcactgtgc tcatcatccc ttatacgata agcttcctct gcacgccgat 12780
gctaggcaga tctcagacgt cagggcataa ggagattgcc ccagcagcaa acatgagtag 12840
cgccaaatac tacatctgtt atgttcctgg gcccacatgt cggggctcag tatccttgtg 12900
catgtccccc ttgactataa aaggggaggc atgcaacgtt acaagacagg ctctctaaga 12960
cctaaggcag acttcgaacg ctcaagcttc cacagcaatc caacacataa tggagtatgg 13020
tattacgctc tgacggcccg aaccactcta aactctcgtg tgttcatgtg ctcggtgatc 13080
gcttagctag acaggcaaaa tgcttaagcc ccttcctcat cttaggatta agggcgggtg 13140
cactccgcca cccgaccgga gaattccctc tccaacattt ggtgcgccag gtagggggct 13200
aggcattagg tttttgtttg tttcctcgct cagcatgatg gtgcaaatcg tggagcaccg 13260
cgccgataca tcaacgaatt tcctggtgga ggaagaagtt gtttcttcca cgccactggt 13320
tcccaaccgc ccagtgtcgg gcactgctgc tgtgcacgct gcacaatagc atacagctgc 13380
gtagacatct tgtactccgt cgagggtggc tctgggagca ttgtcggcgg ccagggagtt 13440
gctgtgccac cctccaagct ccatggactc accgggggcc atgaagcagt ggcgggacga 13500
cgtcgaccga ctgctcggta tggcacattc tacctcaacc aggtcgaggc cacggtcatc 13560
ccggcgccaa catgaggcgt cggcgtctat gcgcgcgccc tcagtaaggg gcgcatagac 13620
caacgacctc cgggccgagc tcaaccgcag gcgtgcggga gaggacgccc gactctcttt 13680
agagagggtg cacgagcgcc gacaaaacgt tgagggtcgc aacctcgacc aagactttgc 13740
tgcggtagca ccgcaggccc caatgggcac ccggtctcga gcgggtgtcc ccttggtcgg 13800
cgtgggctgc gccgctttcg cggatcatct ccgcgcaaca tcatggccat ccaaattctg 13860
gccgcacttg ccggaaaaat atgacggtac gtcaaacccg tcggagttcc tacaggtgta 13920
tgtcaccgct atcacagcag caggtggaaa caccactacg atgcgtgaca tattttcatg 13980
tcgccttgtc tgggcctacc cggtcttggc tcatgaacct cgccccaggg tcaatctact 14040
cctgggaaga gctctgcgca tggttcgttg cgaacttcgc cagcgcttac cagcagcacg 14100
gtgtggaggc ccaccttcac gcggtaaggc aggagcccgg ggagactctc cggacgttca 14160
tctctcgctt caccaaggtg cgaggtacta taccttgcat ttttgatgct tccatcatca 14220
cggctttccg acagggagta cgtgatgaga aaatgttgga gaagttggcc acacacgatg 14280
tggagattgt ccccacactc ttcgctctgg ccgacaagtg cgctagagcc gccgaggtcc 14340
gtgcatggca ctcggcccca caagccgggg ctacccagtc gggtggctca ggtgtcgtct 14400
cccgggacgg taagaagaaa aagaagaagg actacgacta ctagaagtcg cggtccaccg 14460
ctctagtcgt tgcagcggtg accgagggcc ggggcaaccg caacaaacgc ccacggccgc 14520
agaggggtaa cagcgactca tgccctgtgc accccaacgg tcgccacagc tctgcggagt 14580
gtcgcgagat cattgacctc gcgaaacgcg tcagcgagcg gcgtgagcag tcttccaagg 14640
atggctctcc acctcgtcgc caacccggca aagaaaaggt cgacgac 14687

<210> SEQ ID NO 44
<211> LENGTH: 12601
<212> TYPE: DNA
<213> ORGANISM: Zea mays

<400> SEQUENCE: 44
cgccatttct caaaaaatac ggatacggcg atacgcaata tatattataa ataaaattaa 60
atgctgaaat gtctgaaatg gaccacagcc gatcagttca atttaaggac gttagaagtt 120
aatgttcaac aactttgact aaagtaaaca tctacttcct cttccagaat ttatctggac 180
tcaaatcaat gaatccagca tgccaaaagc ccaaaaacat gtgtaacgat acgctacacc 240
agcagactcg caaaataatc actagttcac caaatcacca cacaagttct aagttttaat 300
tcgaacagac cacagaccac agaccagaca tgagacaaca acagatggga gatacactac 360
accagcagac tcgcaaaata atcactagtt caccaaatca gtagatgcac tcgttgccat 420
gggatattgg gatctaacaa gaacagagaa tggacaaccg cagcgtcaga cagggcagat 480
gggagatggc agcagaatag cagatcacgt acctcagtac ctcacgacgg cagatgggtt 540
ggctgacggc gcgaccacag agctggcggc ggtggacgcg gccacggaag cgcggctgtc 600
ggctggagtg gcggtgcgca gggaagcgcg gctgcgcgcg tctccaagcg gtgaagggct 660
ggcggcgcgc agggaagcgc ggggctagca gcgcgcaggg aagcgcgggg ctagcggcgc 720
gcaggaaggt gcgcggggat ggcggcgcgc ggtggggaga agcggggctg gcggcgcgca 780
gggaagcgcg gggctggcgg cgagcaggaa ggtgcgcggg gatggcggcg cgccgtgggg 840
agaagcgggg ctggcggcgc gcagagaagt tgcgcgtgtg cgccgtgggg agaagcggtg 900
cgcaggaaat tagggatata aggtacccca catgtgttca agaggtgtcc tagaactatc 960
cgtctttttt tatttattta aattcacaga aatttccaat acgtctcaga tatgtatcca 1020
gaagtatccg cgaagtatcc gtatctaata cggtatccga caccggtacg tgaattttga 1080
gaagtatccg cgcatcatag gcatgcactt ggttggtttc atgaaggatt tgtagcatgt 1140
atgaattatt gtttctacta gttggcatgc aagtctgttt ctcctggaaa gaactctgaa 1200
aaaatatgca cgcgtcaaca gatcagagcc tcgatgatca gaaaaaaaca aagagcatgt 1260
gtttctgtag tatgtactgc acatcgtcat gcattatagc aggctatgtt tgagtaacct 1320
ttgtgtttac caataccgcc tatctagcta ttattaatca tattcaaccc gacttcccta 1380
ggctggttgc ccttttctta gactaaatat gcagggtgtc aaacaagtgg ccaaattgat 1440
caagtgcata taatgacacc cattgtaagt gtagatcagg tctcataaac caggaacata 1500
gaacttgtcc acgttcctcg ttccgagaac gttcgttccg tcccaggaac gcggaaacaa 1560
tctcgtccct gtagtgttaa aatcgtcttt taagtatcat accatgaacc atgttcccgt 1620
tcctcgacct tatcaatatg agaacctggt tactgaggat caggtttcct ttctgttatg 1680
aacctttgtt catttggggt gaccattgcc aggaggacag ccaagcaaag tcagtttggt 1740
tacttcccgt caatgctaca ctttcttgtt cgtttttatg caatttctag atgaactatc 1800
aactaggcat ccattgatgt tagcacagtt tagctcctgt aatgtgtatc catctatgga 1860
ttgttcaatc atgtgattaa ttaattgata aaagtacgaa tagaaaatac agtagtaaca 1920

-continued

```
tatccttgtt cctcttgctg tggcaactgg catctgtttg ttgttagttg atacttactt   1980
ggcaggcata gtgctggcat tgtcataaat ttggagacta cttcacagta tatgcatatg   2040
tgtgtttttg caattttggt gatagggtgg ataactatcc tggaaccaaa tccttgctta   2100
aggtgtactt gtcggtttca gctgatggta tccaggcaac aaaaagagtc tgttatttct   2160
tgttttttat agctatgtaa tgttgtcttg tattcagcca gtggcacaag atggataaaa   2220
aatgtgtaaa aaatcggaga aaattggaga aacatctcac gcccttaatg gggcagaggg   2280
tgtgaccttt catatataga accgagtagg cttaggttac aaaaatacga caagacctat   2340
tcaaatacaa tggcgcgact atatgcattt ctaataaaat aagcttccag atacttgatt   2400
aatgctaatt gtatcagaat aatgtgagct ttctgatgtt gtcaatgtga aaacccttca   2460
gcttggacag tatcttcctt tcctaactga ttttttagag aacaaaattc ttggtccagc   2520
ttttattgaa agccgatgaa acggttcttt ctttcctaac tgattgatat tggtaacttg   2580
ttttctgagc tttaatcctc ggatatctca ggtgcgctct tactagagaa ggatgttgtc   2640
aagttggact ccattgctca gaaagtcaat acccattgtc taagctcagg ttgttggaaa   2700
atcattagga attattgcat gaaaataatc taagagcgga cttcattagc cttcctgagg   2760
atagtggtca ctgaccaaat cttccatgtt tatgcaagga aacataacat ttactgacta   2820
tgagtgttca aaatttgttc acttgctttt gaagatagct tctggttcca agagacaggt   2880
gttgttgtag gagatctgct aacattttga tcaaatccag ttggtgttat acagcactgg   2940
cttactaaca ttactataaa atccttgttg aagaatctgt aagttgttaa tctttgttga   3000
atactaactt ctttataatt ttatttatta tcttctatat ttagtcactg agtgtgcagt   3060
gcgctttgca tgcatagaga agttgaaagc aacacaatcg agactgcagc aatctctatt   3120
tgctagttca gtagttctcg tctattctct gtttgcgaac ttcagcgtga agaaagtcct   3180
taaagaaaag gtgaggacga tcaaaccaag gggcggaccc agtaaagggc atggatatac   3240
acccaataat ttttgcaaag caaacaaagt tagtagacat gatacattca tatacacttg   3300
taattagatt cagatccgat cacgaagagt atgttagtgt ttgggcgcac ggcttcgcac   3360
agcaggaagg gaagaaaggg gagggagcac ctggtgtcct agtgatgctc gtcgcctccc   3420
aaggtggcga ggaagggggc gagctcggac gcgggtagga agaggaggca gccgccaccc   3480
tctgctgatg ggtcggggta ggtagagggg gaaagaaaat ggaaaaagtt actctcttcg   3540
ttcttcagcc aaactctcta tctcactcta tgttacaaac ttcactctac aaacaaacag   3600
tacaatttac tgtgcaaaag agtattttgc acgacctttt atattaaata taaccttaga   3660
gcgttttcaa aactatcttc atttttctc tctattcgat tctctattta cctttccata   3720
aaaattacac tctatatata gcatttcact ccaacaaatt atttatctac tttgactagt   3780
cagattggct agctaagttg actagtgaga gcatctctaa aagactagca aatggtttat   3840
caagccaaat ttcggctact caacaataaa ataactctcc aacggactag ccatccaact   3900
cgccaaggta ttcgactctt taaattggtc tcctctctag tcaaatttat aggtgtacgt   3960
tcgggccgcc cggcccggcc caagcccgaa aaggcccgta atatttgaat ttcgggccga   4020
tccggcccgt ttgaatttcg ggacgtgtcg ggccagccca cgggcctagc cctcggccca   4080
cggccggtcc gtaattggtt aaacatgcct ggctcatttc gggcggcccg aaattataaa   4140
agcctgaaat tcacattaag acccgaaatt catttttgg cccgaaattc acatcagggc   4200
ccgaaattca aaacaaattt aataaaacaa ataaaagata agacaaataa atttgaccaa   4260
```

aagcaaactt aatatttgta ttaagttact agagctatac aatgactacc tcgtttacaa 4320
atcattttgt tagaaagaaa aagagtataa tcagctctat ataaagttcg taagttcagt 4380
tcattatcta atattcataa caaaaataaa attacatcac atactctaat tcaaagatac 4440
aaaaaacatc taactaacat tatctctagc tttgtgttct ttatcaagta catgaaagtg 4500
tggaataaag tgtgatttta ataaatatat gagccttttt ctgcttctat atgagtcatt 4560
tcgtgtctgc cttaaacggg tcgtgctcgt gcccgcccat gggccgcgac ctcggcccaa 4620
acccggccca acactaaaat atttcgtgtc gtgtcgtgcc tgggccgtgc tttttttccg 4680
tgctttgggc cggcccatca ggcccggctc aaatgtacac ctatagccaa atttgactag 4740
ccactctggc tagacaaact aaataaatag tctgttagag tgagatgcta catatggagt 4800
gtaatcttat ggagaggtaa atagagtgtc aaatagagag ttaaaaatgg agtccctgga 4860
gatgctctga ggaagctaat ttggagaatc gaatagcttg gcgagttaga tggctagtct 4920
attgaagagt ttttttctgt tgagtaacta aaatttggct tgacgaactc tttggctagt 4980
ctcttggaga tactagactc tctcccgcta ttccccatgg ccccatataa tctctctatt 5040
tatatttatt agagtaaaat atactagtgg tctttaaact tatattgttg tattattcta 5100
gtcactaaac ccctaaagtg caaatataag gtccttaaac ttgtgaattt gtatcgttct 5160
ggtccctaac tctgaacatg cacatttcag tctttatact tgtaggattg tgtgtcgtct 5220
gggcctctaa acttattttt ggtgtcatca agggtctaaa ctatttatac atataatgac 5280
accaaaaata agtttatgga tccaagtgac acaaccatag aagtatagga ccaaaaatat 5340
gtatcttgag attttaggga ccaagatgat acaacttaac aagtttaggg accttagatg 5400
tgcactttta gagtttaggg accaggatga aacaacgcta aaaatgtagg gaccgctaat 5460
gcattttact ctatttttat tatattttac tatataagat acttctctta tataccatct 5520
cctctataga actcttcata tacgctataa ctcaattatt taatatttta tcaactttaa 5580
aaatctaaaa aatgatataa tattttacta ttataataca cattatcatt aggttacatg 5640
acttaaacat gattaatatc ataaacaaat gatctaatta aattataggg gtagtatatg 5700
tccaccctat gagagggttt tatctctccc tcccatatga gagttagttg gagaagaatt 5760
tccctccaaa accccttatg ctctgtttcg atgtcgatat ttaagaagat ggaattgaat 5820
tgagtcgaat accaaatcag acatggtatt gaaatgagat gtaatttcaa ttctactgtt 5880
tggatgccac taaattgagt ttggaattgt gcggtctaat tccacgcaac atcaaggggt 5940
gaggctttgt attgggagag ggtttctag ttatagtcca atttcaggaa atttagtctc 6000
tgatttcaaa tctcaattcc atgtgcaacc aaacaacaga atttagaaaa gttggtttca 6060
ttttctaatt atgtgctcta atatctatat ctaaacaggg gtattacata tggtgaggtg 6120
agagatagag gcactgtctt atagtctgat agatgaacat atgtgttatc tccttttttt 6180
aatagaccaa atagaaaaga atagaaaaaa gttaaaccta tcccccgcta tatctcataa 6240
ccacacatat ctacaatatt ttttaaaaaa tcaaagacac taatagtaga agttactatg 6300
acaaagttta gtctgtgtta catcgaatgt ttgaatgttg gttataatta tatatagtat 6360
aattataaaa aataatcata tagatgaaga ctatatgatt taacccttga gagagtcttc 6420
cccgagcccg cgggcttgtc gtcggtcacg ttctccctct tggcgtgatc tccagacatc 6480
actttgagtt gattagactc ttaatgaagc actaactttg ataccaattg aaagtcgcct 6540 agaggggggtg aataggcgaa acctaaaatt tacaaacata aacacacact aaggccgggg 6600
ttagcgttgg aattaaattc aagtctgaaa gattgtttct tttgctaaga gttgttcaaa 6660

```
ggatgcggat gacgtatggg agcaaactca aatcaatatt agcaaggaaa cgttagagag   6720
aggaaagagg gcaaacaaat caagcgagta gacatagtga tttgttttac cgaggttcgg   6780
ttctaaagaa cctaatcccc gttgaggagg ccacaaaggc cgggtctatt tcaacccttt   6840
ccctctctct caaatggtca cttagaccga ttgagccttc tccttaatca aacgggtcac   6900
taaggtgtct cttgcaaact ttacaagcac ttagaaaaag aatgaggaag gaagaaaggc   6960
aatccaagcg acaagagcaa caaaagaaca caaatgaccc tctcacaatc ccttaagcac   7020
tagcgttgat tttgggaagt tttgagtgga ttgattgttt tgattgtgtc ttggagtgtt   7080
ggactttgct cttgcaatga atgagaaact caaaatgctt ggatggcttt gaatgaggtg   7140
gttgaggggt atttatagcc cccaaccact tcctagccgt tggtaaaggc tgctggcgat   7200
gggcgcaccg gacagtcact gttcattgtc cggtgcacgc cacgttagcg cgcccgttag   7260
ggtttggagc agttgaccgt tgaagccgtt tgtctttttg ctgcaccgga cagtccggtg   7320
acttctgcac ggcactgttt ggcactgttc ctctgcgcag tcgaccgttg gcgcgtaggg   7380
agccgttgct ccgctggctc accggatagt ccggtgaatt atagtggagc gcacgcggca   7440
caaccaccaa agtggccgtt gggaggggct gctatcgatg ggcgcaccgg accgtccggt   7500
gcgccagacc agggcagcct tcgggtttct ttgctccttt ctttttgaac cctatcttgg   7560
actttttatt ggtttgtgtt gaacctttgg cacctataga acttataatc tagagcaaac   7620
tagttagtcc aattatttgt gttgggcaat tcaaccacca aaatcattta ggaaaaggtt   7680
tgaccctatt tccctttcag tctccccctt tttggtgatt gatgccaaca caaaccaaag   7740
caaatatata agtgcagaat tgaactagtt tgcataaggt aagtgcaaag gttgcttgga   7800
attaacccaa tttatacttt cataagatat gcatggattg ctttcttctt atttaacatt   7860
ttggaccacg cttgcaccac ttgttttgtt tttgcaaaat cttttggaaa ttcttttcaa   7920
agtctttttg caaatagtca aaggtaaatg aataagattt cgagaagcat tttcaagatt   7980
tgaaattttc tccccctgtt tcaaatgctt ttcctttgac taaacaaaac tccccctcaa   8040
tgaaattctc ctcttagtgt tcaagagggt tttagacatt aattttgaaa gaggtcatac   8100
caacttgaaa ttatataaaa aataagatac caattgaaaa acttctttga tacaaattga   8160
aagactgcat ttaaacactt tttgaaattg gtggtgatgc ggtccttttg ctttgggtta   8220
atactttctc cccctttggc atgaatcgcc aaaaacagat actttgtgag tgaaatatga   8280
gccctatgtt taaattctct ccccctttgg caaacaatat atgagtgaag gattatacca   8340
aggtggagag cgatgcggag tgacggcgaa gggcaaataa tacgatggag tggagtggaa   8400
gccttgtctt cgccgaagac tccatttccc tttcaatcta tgacttagca tgagatacac   8460
ttgaaaaaca cattagtaat agcaaataaa agagatatga tcaaaggtac ataaatgaac   8520
gatgtgtgca aagtatcaat caaaattcct agaatcaaga atgtttagct cattcctaag   8580
tttggtaaag gttttctcat ctaatggttt ggtaaagata tcggctaatt gttctttggt   8640
gctaacatag gcaatctcga tatccccccct ttgttggtga tccctcaaaa agtgataccg   8700
aatggctatg tgcttagtgc ggctatggtc aacgggatta tccgcattgc actctcatta   8760
tcacacagaa gagggacttt ggttaatttg taaccataat ccctaagggt ttgcctcatc   8820
caaagcaatt gtgcgcaata atggcctgcg acaatgtact cggcttcggt ggtagaaaga   8880
gctaccgaat tttgtttctt tgaagcccaa gacaccaggg atcttcccaa gaactgacaa   8940
gtccctgatg tgctatttct atcaatttta cacccatccc aatcagcatc tgagtatcct   9000
```

```
attaaatcaa aggtggatcc cttggggtac caaagaccaa acttaggtgt atgaactaaa   9060
tatctcaaga ttcgtttcat ggccctaagg tgaacttcct taggattggc ttggaatctt   9120
gcacacatgc atacggaaag cataatatcc ggtcgagaag cacataaata gagtaaagat   9180
cctatcatcg atcggtatac cttttgatct acagatttac ctctcgtgtc gaggtcgaga   9240
tgcccatggt tcccatgggt gtcttgatgg gcttggcatc cttcattcca aacttggtga   9300
gtatatcttg agtatacttt gtttggctga tgaaggtgcc ctcttggagt tgcttgactt   9360
gaaatcctaa gaaatacttc aactccccca tcatagacat ctcgaatttt tgaatcatga   9420
tcctactaaa ctcttcacaa gtagatttgt tagtagaccc aaatatgata tcatcaacat   9480
aaatttggca tacaaacaaa tcatttgcaa tggttttagt aaagagtgta ggatcgactt   9540
ttccgacttt gaagccatta gtgataagaa agtctcttag gcattcatac catgctcttg   9600
gggcttgctt aagcccacaa agtgcctttg agagtttata gacatgatta gggtactcac   9660
tatcttcaaa gccggaaggt tgctcaatat agacctcttc cttgattggt ccattgagga   9720
aggcactctt cacgtccatt tgataaagct tgaagccatg gtaagtagca taggcaagta   9780
atatacgaat tgactcaagc ctagctattg gtgcataggt ttcaccgaaa tccaaacctt   9840
caacttgtga atatcccttg gccacatgtc gggctttgtt ccttgtcacc acaccatgct   9900
catcttgctt gttgccgaag acccacttgg tttctacaac attttggtta ggacgtggaa   9960
caagatgcca tacctcgtga agttgttgag ttcctcttgc attgccaaca cccaatccga  10020
atcccttaat gtgtcttcca ccctgtatgg ctcaatagaa gacacaaaag agtaattgtc  10080
ggtaccctga accaggggta ccccctacta cagtataagg aagcattgcc cgtacgacgt  10140
tccctagcca cacggtgagc agcacccgac cccaccatgt gggtggctca aggggtacca  10200
cgtggcgaga aaagatgaca catcccagga tatatcagtt gaaccggacc accacgaagg  10260
agcaccggac ccctgtatgc acaacccgga cccccgatta cggctcgaga ctcccaagta  10320
agcatgccga gccccttgga tggggtccag atccctttga gtaaggtccg taccacaacg  10380
aggtcccgag acatgggaga ccctggcata agcaagggtc cggtattgac acgtgttagg  10440
gccttatcat gtgcgcttgc gctccctgct taggcggaga cccgctactg ccacgtggct  10500
tgttgcctgt gacataagcc aacgggcaga gcctgatgta aggcctctag gccgtgcggt  10560
ctctgcattt attgcggagg agacgcgtcg cctgcccacc ttgctgacag gcgatgtgcc  10620
ccctttgcat ttaatgcgtc ctgtccactc caccggcagg cgcaccaggc catcctgcag  10680
tcggcgcacc tgtccagtcc attgtcaaat agtgcacccg tgctacaggg cgcactgtgc  10740
tcatcatccc ttatacgata agcttcctct gcacgccgat gctaggcaga tctcagacgt  10800
cagggcataa ggagattgcc ccagcagcaa acatgagtag cgccaaatac tacatctgtt  10860
atgttcctgg gcccacatgt cggggctcag tatccttgtg catgtccccc ttgactataa  10920
aaggggaggc atgcaacgtt acaagacagg ctctctaaga cctaaggcag acttcgaacg  10980
ctcaagcttc cacagcaatc caacacataa tggagtatgg tattacgctc tgacggcccg  11040
aaccactcta aactctcgtg tgttcatgtg ctcggtgatc gcttagctag acaggcaaaa  11100
tgcttaagcc ccttcctcat cttaggatta agggcgggtg cactccgcca cccgaccgga  11160
gaattccctc tccaacattt ggtgcgccag gtagggggct aggcattagg tttttgtttg  11220
tttcctcgct cagcatgatg gtgcaaatcg tggagcaccg cgccgataca tcaacgaatt  11280
tcctggtgga ggaagaagtt gtttcttcca cgccactggt tcccaaccgc ccagtgtcgg  11340
gcactgctgc tgtgcacgct gcacaatagc atacagctgc gtagacatct tgtactccgt  11400
```

cgagggtggc tctgggagca ttgtcggcgg ccagggagtt gctgtgccac cctccaagct 11460
ccatggactc accgggggcc atgaagcagt ggcgggacga cgtcgaccga ctgctcggta 11520
tggcacattc tacctcaacc aggtcgaggc cacggtcatc ccggcgccaa catgaggcgt 11580
cggcgtctat gcgcgcgccc tcagtaaggg gcgcatagac caacgacctc cgggccgagc 11640
tcaaccgcag gcgtgcggga gaggacgccc gactctcttt agagagggtg cacgagcgcc 11700
gacaaaacgt tgagggtcgc aacctcgacc aagactttgc tgcggtagca ccgcaggccc 11760
caatgggcac ccggtctcga gcgggtgtcc ccttggtcgg cgtgggctgc gccgctttcg 11820
cggatcatct ccgcgcaaca tcatggccat ccaaattctg gccgcacttg ccggaaaaat 11880
atgacggtac gtcaaacccg tcggagttcc tacaggtgta tgtcaccgct atcacagcag 11940
caggtggaaa caccactacg atgcgtgaca tattttcatg tcgccttgtc tgggcctacc 12000
cggtcttggc tcatgaacct cgccccaggg tcaatctact cctgggaaga gctctgcgca 12060
tggttcgttg cgaacttcgc cagcgcttac cagcagcacg gtgtggaggc ccaccttcac 12120
gcggtaaggc aggagcccgg ggagactctc cggacgttca tctctcgctt caccaaggtg 12180
cgaggtacta taccttgcat ttttgatgct tccatcatca cggctttccg acagggagta 12240
cgtgatgaga aaatgttgga gaagttggcc acacacgatg tggagattgt ccccacactc 12300
ttcgctctgg ccgacaagtg cgctagagcc gccgaggtcc gtgcatggca ctcggcccca 12360
caagccgggg ctacccagtc gggtggctca ggtgtcgtct cccgggacgg taagaagaaa 12420
aagaagaagg actacgacta ctagaagtcg cggtccaccg ctctagtcgt tgcagcggtg 12480
accgagggcc ggggcaaccg caacaaacgc ccacggccgc agaggggtaa cagcgactca 12540
tgccctgtgc accccaacgg tcgccacagc tctgcggagt gtcgcgagat cattgacctc 12600
g 12601

<210> SEQ ID NO 45
<211> LENGTH: 10401
<212> TYPE: DNA
<213> ORGANISM: Zea mays

<400> SEQUENCE: 45
tgtcataaat ttggagacta cttcacagta tatgcatatg tgtgtttttg caattttggt 60
gatagggtgg ataactatcc tggaaccaaa tccttgctta aggtgtactt gtcggtttca 120
gctgatggta tccaggcaac aaaaagagtc tgttatttct tgttttttat agctatgtaa 180
tgttgtcttg tattcagcca gtggcacaag atggataaaa aatgtgtaaa aaatcggaga 240
aaattggaga aacatctcac gcccttaatg gggcagaggg tgtgaccttt catatataga 300
accgagtagg cttaggttac aaaaatacga caagacctat tcaaatacaa tggcgcgact 360
atatgcattt ctaataaaat aagcttccag atacttgatt aatgctaatt gtatcagaat 420
aatgtgagct ttctgatgtt gtcaatgtga aaacccttca gcttggacag tatcttcctt 480
tcctaactga ttttttagag aacaaaattc ttggtccagc ttttattgaa agccgatgaa 540
acggttcttt ctttcctaac tgattgatat tggtaacttg ttttctgagc tttaatcctc 600
ggatatctca ggtgcgctct tactagagaa ggatgttgtc aagttggact ccattgctca 660
gaaagtcaat acccattgtc taagctcagg ttgttggaaa atcattagga attattgcat 720
gaaaataatc taagagcgga cttcattagc cttcctgagg atagtggtca ctgaccaaat 780
cttccatgtt tatgcaagga aacataacat ttactgacta tgagtgttca aaatttgttc 840

```
acttgctttt gaagatagct tctggttcca agagacaggt gttgttgtag gagatctgct    900
aacattttga tcaaatccag ttggtgttat acagcactgg cttactaaca ttactataaa    960
atccttgttg aagaatctgt aagttgttaa tctttgttga atactaactt ctttataatt   1020
ttatttatta tcttctatat ttagtcactg agtgtgcagt gcgctttgca tgcatagaga   1080
agttgaaagc aacacaatcg agactgcagc aatctctatt tgctagttca gtagttctcg   1140
tctattctct gtttgcgaac ttcagcgtga agaaagtcct taaagaaaag gtgaggacga   1200
tcaaaccaag gggcggaccc agtaaagggc atggatatac acccaataat ttttgcaaag   1260
caaacaaagt tagtagacat gatacattca tatacacttg taattagatt cagatccgat   1320
cacgaagagt atgttagtgt ttgggcgcac ggcttcgcac agcaggaagg gaagaaaggg   1380
gagggagcac ctggtgtcct agtgatgctc gtcgcctccc aaggtggcga ggaagggggc   1440
gagctcggac gcgggtagga agaggaggca gccgccaccc tctgctgatg ggtcggggta   1500
ggtagagggg gaaagaaaat ggaaaaagtt actctcttcg ttcttcagcc aaactctcta   1560
tctcactcta tgttacaaac ttcactctac aaacaaacag tacaatttac tgtgcaaaag   1620
agtattttgc acgacctttt atattaaata taaccttaga gcgttttcaa aactatcttc   1680
atttttctc tctattcgat tctctattta cctttccata aaaattacac tctatatata   1740
gcatttcact ccaacaaatt atttatctac tttgactagt cagattggct agctaagttg   1800
actagtgaga gcatctctaa aagactagca aatggtttat caagccaaat ttcggctact   1860
caacaataaa ataactctcc aacggactag ccatccaact cgccaaggta ttcgactctt   1920
taaattggtc tcctctctag tcaaatttat aggtgtacgt tcgggccgcc cggcccggcc   1980
caagcccgaa aaggcccgta atatttgaat ttcgggccga tccggcccgt ttgaatttcg   2040
ggacgtgtcg ggccagccca cgggcctagc cctcggccca cggccggtcc gtaattggtt   2100
aaacatgcct ggctcatttc gggcggcccg aaattataaa agcctgaaat tcacattaag   2160
acccgaaatt catttttttgg cccgaaattc acatcagggc ccgaaattca aaacaaattt   2220
aataaaacaa ataaaagata agacaaataa atttgaccaa aagcaaactt aatatttgta   2280
ttaagttact agagctatac aatgactacc tcgtttacaa atcattttgt tagaaagaaa   2340
aagagtataa tcagctctat ataaagttcg taagttcagt tcattatcta atattcataa   2400
caaaaataaa attacatcac atactctaat tcaaagatac aaaaaacatc taactaacat   2460
tatctctagc tttgtgttct ttatcaagta catgaaagtg tggaataaag tgtgatttta   2520
ataaatatat gagccttttt ctgcttctat atgagtcatt tcgtgtctgc cttaaacggg   2580
tcgtgctcgt gcccgcccat gggccgcgac ctcggcccaa acccggccca acactaaaat   2640
atttcgtgtc gtgtcgtgcc tgggccgtgc tttttttccg tgctttgggc cggcccatca   2700
ggcccggctc aaatgtacac ctatagccaa atttgactag ccactctggc tagacaaact   2760
aaataaatag tctgttagag tgagatgcta catatggagt gtaatcttat ggagaggtaa   2820
atagagtgtc aaatagagag ttaaaaatgg agtccctgga gatgctctga ggaagctaat   2880
ttggagaatc gaatagcttg gcgagttaga tggctagtct attgaagagt ttttttctgt   2940
tgagtaacta aaatttggct tgacgaactc tttggctagt ctcttggaga tactagactc   3000
tctcccgcta ttccccatgg ccccatataa tctctctatt tatatttatt agagtaaaat   3060
atactagtgg tctttaaact tatattgttg tattattcta gtcactaaac ccctaaagtg   3120
caaatataag gtccttaaac ttgtgaattt gtatcgttct ggtccctaac tctgaacatg   3180
cacatttcag tctttatact tgtaggattg tgtgtcgtct gggcctctaa acttattttt   3240
```

ggtgtcatca agggtctaaa ctatttatac atataatgac accaaaaata agtttatgga 3300
tccaagtgac acaaccatag aagtatagga ccaaaaatat gtatcttgag attttaggga 3360
ccaagatgat acaacttaac aagtttaggg accttagatg tgcactttta gagtttaggg 3420
accaggatga aacaacgcta aaaatgtagg gaccgctaat gcattttact ctatttttat 3480
tatattttac tatataagat acttctctta tataccatct cctctataga actcttcata 3540
tacgctataa ctcaattatt taatatttta tcaactttaa aaatctaaaa aatgatataa 3600
tattttacta ttataataca cattatcatt aggttacatg acttaaacat gattaatatc 3660
ataaacaaat gatctaatta aattataggg gtagtatatg tccaccctat gagagggttt 3720
tatctctccc tcccatatga gagttagttg gagaagaatt tccctccaaa accccttatg 3780
ctctgtttcg atgtcgatat ttaagaagat ggaattgaat tgagtcgaat accaaatcag 3840
acatggtatt gaaatgagat gtaatttcaa ttctactgtt tggatgccac taaattgagt 3900
ttggaattgt gcggtctaat tccacgcaac atcaaggggt gaggctttgt attgggagag 3960
gggtttctag ttatagtcca atttcaggaa atttagtctc tgatttcaaa tctcaattcc 4020
atgtgcaacc aaacaacaga atttagaaaa gttggtttca ttttctaatt atgtgctcta 4080
atatctatat ctaaacaggg gtattacata tggtgaggtg agagatagag gcactgtctt 4140
atagtctgat agatgaacat atgtgttatc tcctttttt aatagaccaa atagaaaaga 4200
atagaaaaaa gttaaaccta tcccccgcta tatctcataa ccacacatat ctacaatatt 4260
ttttaaaaaa tcaaagacac taatagtaga agttactatg acaaagttta gtctgtgtta 4320
catcgaatgt ttgaatgttg gttataatta tatatagtat aattataaaa aataatcata 4380
tagatgaaga ctatatgatt taacccttga gagagtcttc cccgagcccg cgggcttgtc 4440
gtcggtcacg ttctccctct tggcgtgatc tccagacatc actttgagtt gattagactc 4500
ttaatgaagc actaactttg ataccaattg aaagtcgcct agaggggggtg aataggcgaa 4560
acctaaaatt tacaaacata aacacacact aaggccgggg ttagcgttgg aattaaattc 4620
aagtctgaaa gattgtttct tttgctaaga gttgttcaaa ggatgcggat gacgtatggg 4680
agcaaactca aatcaatatt agcaaggaaa cgttagagag aggaaagagg gcaaacaaat 4740
caagcgagta gacatagtga tttgttttac cgaggttcgg ttctaaagaa cctaatcccc 4800
gttgaggagg ccacaaaggc cgggtctatt tcaacccttt ccctctctct caaatggtca 4860
cttagaccga ttgagccttc tccttaatca aacgggtcac taaggtgtct cttgcaaact 4920
ttacaagcac ttagaaaaag aatgaggaag gaagaaaggc aatccaagcg acaagagcaa 4980
caaaagaaca caaatgaccc tctcacaatc ccttaagcac tagcgttgat tttgggaagt 5040
tttgagtgga ttgattgttt tgattgtgtc ttggagtgtt ggactttgct cttgcaatga 5100
atgagaaact caaaatgctt ggatggcttt gaatgaggtg gttgaggggt atttatagcc 5160
cccaaccact tcctagccgt tggtaaaggc tgctggcgat gggcgcaccg gacagtcact 5220
gttcattgtc cggtgcacgc cacgttagcg cgcccgttag ggtttggagc agttgaccgt 5280
tgaagccgtt tgtctttttg ctgcaccgga cagtccggtg acttctgcac ggcactgttt 5340
ggcactgttc ctctgcgcag tcgaccgttg gcgcgtaggg agccgttgct ccgctggctc 5400
accggatagt ccggtgaatt atagtggagc gcacgcggca caaccaccaa agtggccgtt 5460
gggaggggct gctatcgatg ggcgcaccgg accgtccggt gcgccagacc agggcagcct 5520
tcgggtttct ttgctccttt ctttttgaac cctatcttgg actttttatt ggtttgtgtt 5580

-continued gaacctttgg cacctataga acttataatc tagagcaaac tagttagtcc aattatttgt 5640
gttgggcaat tcaaccacca aaatcattta ggaaaaggtt tgaccctatt tccctttcag 5700
tctccccctt tttggtgatt gatgccaaca caaaccaaag caaatatata agtgcagaat 5760
tgaactagtt tgcataaggt aagtgcaaag gttgcttgga attaacccaa tttatacttt 5820
cataagatat gcatggattg ctttcttctt atttaacatt ttggaccacg cttgcaccac 5880
ttgttttgtt tttgcaaaat cttttggaaa ttcttttcaa agtctttttg caaatagtca 5940
aaggtaaatg aataagattt cgagaagcat tttcaagatt tgaaattttc tccccctgtt 6000
tcaaatgctt ttcctttgac taaacaaaac tccccctcaa tgaaattctc ctcttagtgt 6060
tcaagagggt tttagacatt aattttgaaa gaggtcatac caacttgaaa ttatataaaa 6120
aataagatac caattgaaaa acttctttga tacaaattga aagactgcat ttaaacactt 6180
tttgaaattg gtggtgatgc ggtccttttg ctttgggtta atactttctc cccctttggc 6240
atgaatcgcc aaaaacagat actttgtgag tgaaatatga gccctatgtt taaattctct 6300
ccccctttgg caaacaatat atgagtgaag gattatacca aggtggagag cgatgcggag 6360
tgacggcgaa gggcaaataa tacgatggag tggagtggaa gccttgtctt cgccgaagac 6420
tccatttccc tttcaatcta tgacttagca tgagatacac ttgaaaaaca cattagtaat 6480
agcaaataaa agagatatga tcaaaggtac ataaatgaac gatgtgtgca aagtatcaat 6540
caaaattcct agaatcaaga atgtttagct cattcctaag tttggtaaag gttttctcat 6600
ctaatggttt ggtaaagata tcggctaatt gttctttggt gctaacatag gcaatctcga 6660 tatccccccct ttgttggtga tccctcaaaa agtgataccg aatggctatg tgcttagtgc 6720
ggctatggtc aacgggatta tccgcattgc actctcatta tcacacagaa gagggacttt 6780
ggttaatttg taaccataat ccctaagggt ttgcctcatc caaagcaatt gtgcgcaata 6840
atggcctgcg acaatgtact cggcttcggt ggtagaaaga gctaccgaat tttgtttctt 6900
tgaagcccaa gacaccaggg atcttcccaa gaactgacaa gtccctgatg tgctatttct 6960
atcaatttta cacccatccc aatcagcatc tgagtatcct attaaatcaa aggtggatcc 7020
cttggggtac caaagaccaa acttaggtgt atgaactaaa tatctcaaga ttcgtttcat 7080
ggccctaagg tgaacttcct taggattggc ttggaatctt gcacacatgc atacggaaag 7140
cataatatcc ggtcgagaag cacataaata gagtaaagat cctatcatcg atcggtatac 7200
cttttgatct acagatttac ctctcgtgtc gaggtcgaga tgcccatggt tcccatgggt 7260
gtcttgatgg gcttggcatc cttcattcca aacttggtga gtatatcttg agtatacttt 7320
gtttggctga tgaaggtgcc ctcttggagt tgcttgactt gaaatcctaa gaaatacttc 7380
aactccccca tcatagacat ctcgaatttt tgaatcatga tcctactaaa ctcttcacaa 7440
gtagatttgt tagtagaccc aaatatgata tcatcaacat aaatttggca tacaaacaaa 7500
tcatttgcaa tggttttagt aaagagtgta ggatcgactt ttccgacttt gaagccatta 7560
gtgataagaa agtctcttag gcattcatac catgctcttg gggcttgctt aagcccacaa 7620
agtgcctttg agagtttata gacatgatta gggtactcac tatcttcaaa gccggaaggt 7680
tgctcaatat agacctcttc cttgattggt ccattgagga aggcactctt cacgtccatt 7740
tgataaagct tgaagccatg gtaagtagca taggcaagta atatacgaat tgactcaagc 7800
ctagctattg gtgcataggt ttcaccgaaa tccaaacctt caacttgtga atatcccttg 7860
gccacatgtc gggctttgtt ccttgtcacc acaccatgct catcttgctt gttgccgaag 7920
acccacttgg tttctacaac attttggtta ggacgtggaa caagatgcca tacctcgtga 7980

```
agttgttgag ttcctcttgc attgccaaca cccaatccga atcccttaat gtgtcttcca   8040
ccctgtatgg ctcaatagaa gacacaaaag agtaattgtc ggtaccctga accaggggta   8100
ccccctacta cagtataagg aagcattgcc cgtacgacgt tccctagcca cacggtgagc   8160
agcacccgac cccaccatgt gggtggctca aggggtacca cgtggcgaga aaagatgaca   8220
catcccagga tatatcagtt gaaccggacc accacgaagg agcaccggac ccctgtatgc   8280
acaacccgga cccccgatta cggctcgaga ctcccaagta agcatgccga gcccccttgga  8340
tggggtccag atccctttga gtaaggtccg taccacaacg aggtcccgag acatgggaga   8400
ccctggcata agcaagggtc cggtattgac acgtgttagg gccttatcat gtgcgcttgc   8460
gctccctgct taggcggaga cccgctactg ccacgtggct tgttgcctgt gacataagcc   8520
aacgggcaga gcctgatgta aggcctctag gccgtgcggt ctctgcattt attgcggagg   8580
agacgcgtcg cctgcccacc ttgctgacag gcgatgtgcc ccctttgcat ttaatgcgtc   8640
ctgtccactc caccggcagg cgcaccaggc catcctgcag tcggcgcacc tgtccagtcc   8700
attgtcaaat agtgcacccg tgctacaggg cgcactgtgc tcatcatccc ttatacgata   8760
agcttcctct gcacgccgat gctaggcaga tctcagacgt cagggcataa ggagattgcc   8820
ccagcagcaa acatgagtag cgccaaatac tacatctgtt atgttcctgg gcccacatgt   8880
cggggctcag tatccttgtg catgtccccc ttgactataa aaggggaggc atgcaacgtt   8940
acaagacagg ctctctaaga cctaaggcag acttcgaacg ctcaagcttc cacagcaatc   9000
caacacataa tggagtatgg tattacgctc tgacggcccg aaccactcta aactctcgtg   9060
tgttcatgtg ctcggtgatc gcttagctag acaggcaaaa tgcttaagcc ccttcctcat   9120
cttaggatta agggcgggtg cactccgcca cccgaccgga gaattccctc tccaacattt   9180
ggtgcgccag gtagggggct aggcattagg tttttgtttg tttcctcgct cagcatgatg   9240
gtgcaaatcg tggagcaccg cgccgataca tcaacgaatt tcctggtgga ggaagaagtt   9300
gtttcttcca cgccactggt tcccaaccgc ccagtgtcgg gcactgctgc tgtgcacgct   9360
gcacaatagc atacagctgc gtagacatct tgtactccgt cgagggtggc tctgggagca   9420
ttgtcggcgg ccagggagtt gctgtgccac cctccaagct ccatggactc accgggggcc   9480
atgaagcagt ggcgggacga cgtcgaccga ctgctcggta tggcacattc tacctcaacc   9540
aggtcgaggc cacggtcatc ccggcgccaa catgaggcgt cggcgtctat gcgcgcgccc   9600
tcagtaaggg gcgcatagac caacgacctc cgggccgagc tcaaccgcag gcgtgcggga   9660
gaggacgccc gactctcttt agagagggtg cacgagcgcc gacaaaacgt tgagggtcgc   9720
aacctcgacc aagactttgc tgcggtagca ccgcaggccc caatgggcac ccggtctcga   9780
gcgggtgtcc ccttggtcgg cgtgggctgc gccgctttcg cggatcatct ccgcgcaaca   9840
tcatggccat ccaaattctg gccgcacttg ccggaaaaat atgacggtac gtcaaacccg   9900
tcggagttcc tacaggtgta tgtcaccgct atcacagcag caggtggaaa caccactacg   9960
atgcgtgaca tattttcatg tcgccttgtc tgggcctacc cggtcttggc tcatgaacct  10020
cgccccaggg tcaatctact cctgggaaga gctctgcgca tggttcgttg cgaacttcgc  10080
cagcgcttac cagcagcacg gtgtggaggc ccaccttcac gcggtaaggc aggagcccgg  10140
ggagactctc cggacgttca tctctcgctt caccaaggtg cgaggtacta taccttgcat  10200
ttttgatgct tccatcatca cggctttccg acagggagta cgtgatgaga aaatgttgga  10260
gaagttggcc acacacgatg tggagattgt ccccacactc ttcgctctgg ccgacaagtg  10320
```

cgctagagcc gccgaggtcc gtgcatggca ctcggcccca caagccgggg ctacccagtc 10380
gggtggctca ggtgtcgtct c 10401

<210> SEQ ID NO 46
<211> LENGTH: 8201
<212> TYPE: DNA
<213> ORGANISM: Zea mays

<400> SEQUENCE: 46
atatttgaat ttcgggccga tccggcccgt ttgaatttcg ggacgtgtcg ggccagccca 60
cgggcctagc cctcggccca cggccggtcc gtaattggtt aaacatgcct ggctcatttc 120
gggcggcccg aaattataaa agcctgaaat tcacattaag acccgaaatt catttttttgg 180 cccgaaattc acatcagggc ccgaaattca aaacaaattt aataaaacaa ataaaagata 240
agacaaataa atttgaccaa aagcaaactt aatatttgta ttaagttact agagctatac 300
aatgactacc tcgtttacaa atcattttgt tagaaagaaa aagagtataa tcagctctat 360
ataaagttcg taagttcagt tcattatcta atattcataa caaaaataaa attacatcac 420
atactctaat tcaaagatac aaaaaacatc taactaacat tatctctagc tttgtgttct 480
ttatcaagta catgaaagtg tggaataaag tgtgatttta ataaatatat gagccttttt 540
ctgcttctat atgagtcatt tcgtgtctgc cttaaacggg tcgtgctcgt gcccgcccat 600
gggccgcgac ctcggcccaa acccggccca acactaaaat atttcgtgtc gtgtcgtgcc 660
tgggccgtgc tttttttccg tgctttgggc cggcccatca ggcccggctc aaatgtacac 720
ctatagccaa atttgactag ccactctggc tagacaaact aaataaatag tctgttagag 780
tgagatgcta catatggagt gtaatcttat ggagaggtaa atagagtgtc aaatagagag 840
ttaaaaatgg agtccctgga gatgctctga ggaagctaat ttggagaatc gaatagcttg 900
gcgagttaga tggctagtct attgaagagt ttttttctgt tgagtaacta aaatttggct 960
tgacgaactc tttggctagt ctcttggaga tactagactc tctcccgcta ttccccatgg 1020
ccccatataa tctctctatt tatatttatt agagtaaaat atactagtgg tctttaaact 1080
tatattgttg tattattcta gtcactaaac ccctaaagtg caaatataag gtccttaaac 1140
ttgtgaattt gtatcgttct ggtccctaac tctgaacatg cacatttcag tctttatact 1200
tgtaggattg tgtgtcgtct gggcctctaa acttattttt ggtgtcatca agggtctaaa 1260
ctatttatac atataatgac accaaaaata agtttatgga tccaagtgac acaaccatag 1320
aagtatagga ccaaaaatat gtatcttgag attttaggga ccaagatgat acaacttaac 1380
aagtttaggg accttagatg tgcactttta gagtttaggg accaggatga aacaacgcta 1440
aaaatgtagg gaccgctaat gcattttact ctatttttat tatattttac tatataagat 1500
acttctctta tataccatct cctctataga actcttcata tacgctataa ctcaattatt 1560
taatatttta tcaactttaa aaatctaaaa aatgatataa tattttacta ttataataca 1620
cattatcatt aggttacatg acttaaacat gattaatatc ataaacaaat gatctaatta 1680
aattataggg gtagtatatg tccaccctat gagagggttt tatctctccc tcccatatga 1740
gagttagttg gagaagaatt tccctccaaa accccttatg ctctgtttcg atgtcgatat 1800
ttaagaagat ggaattgaat tgagtcgaat accaaatcag acatggtatt gaaatgagat 1860
gtaatttcaa ttctactgtt tggatgccac taaattgagt ttggaattgt gcggtctaat 1920
tccacgcaac atcaaggggt gaggctttgt attgggagag gggtttctag ttatagtcca 1980
atttcaggaa atttagtctc tgatttcaaa tctcaattcc atgtgcaacc aaacaacaga 2040
atttagaaaa gttggtttca ttttctaatt atgtgctcta atatctatat ctaaacaggg 2100
gtattacata tggtgaggtg agagatagag gcactgtctt atagtctgat agatgaacat 2160
atgtgttatc tcctttttt aatagaccaa atagaaaaga atagaaaaaa gttaaaccta 2220
tcccccgcta tatctcataa ccacacatat ctacaatatt ttttaaaaaa tcaaagacac 2280
taatagtaga agttactatg acaaagttta gtctgtgtta catcgaatgt ttgaatgttg 2340
gttataatta tatatagtat aattataaaa aataatcata tagatgaaga ctatatgatt 2400
taacccttga gagagtcttc cccgagcccg cgggcttgtc gtcggtcacg ttctccctct 2460
tggcgtgatc tccagacatc actttgagtt gattagactc ttaatgaagc actaactttg 2520
ataccaattg aaagtcgcct agagggggtg aataggcgaa acctaaaatt tacaaacata 2580
aacacacact aaggccgggg ttagcgttgg aattaaattc aagtctgaaa gattgtttct 2640
tttgctaaga gttgttcaaa ggatgcggat gacgtatggg agcaaactca aatcaatatt 2700
agcaaggaaa cgttagagag aggaaagagg gcaaacaaat caagcgagta gacatagtga 2760
tttgttttac cgaggttcgg ttctaaagaa cctaatcccc gttgaggagg ccacaaaggc 2820
cgggtctatt tcaacccttt ccctctctct caaatggtca cttagaccga ttgagccttc 2880
tccttaatca aacgggtcac taaggtgtct cttgcaaact ttacaagcac ttagaaaaag 2940
aatgaggaag gaagaaaggc aatccaagcg acaagagcaa caaaagaaca caaatgaccc 3000
tctcacaatc ccttaagcac tagcgttgat tttgggaagt tttgagtgga ttgattgttt 3060
tgattgtgtc ttggagtgtt ggactttgct cttgcaatga atgagaaact caaaatgctt 3120
ggatggcttt gaatgaggtg gttgaggggt atttatagcc cccaaccact tcctagccgt 3180
tggtaaaggc tgctggcgat gggcgcaccg gacagtcact gttcattgtc cggtgcacgc 3240
cacgttagcg cgcccgttag ggtttggagc agttgaccgt tgaagccgtt tgtctttttg 3300
ctgcaccgga cagtccggtg acttctgcac ggcactgttt ggcactgttc ctctgcgcag 3360
tcgaccgttg gcgcgtaggg agccgttgct ccgctggctc accggatagt ccggtgaatt 3420
atagtggagc gcacgcggca caaccaccaa agtggccgtt gggaggggct gctatcgatg 3480
ggcgcaccgg accgtccggt gcgccagacc agggcagcct tcgggtttct ttgctccttt 3540
ctttttgaac cctatcttgg actttttatt ggtttgtgtt gaacctttgg cacctataga 3600
acttataatc tagagcaaac tagttagtcc aattatttgt gttgggcaat tcaaccacca 3660
aaatcattta ggaaaaggtt tgaccctatt tccctttcag tctccccctt tttggtgatt 3720
gatgccaaca caaaccaaag caaatatata agtgcagaat tgaactagtt tgcataaggt 3780
aagtgcaaag gttgcttgga attaacccaa tttatacttt cataagatat gcatggattg 3840
ctttcttctt atttaacatt ttggaccacg cttgcaccac ttgttttgtt tttgcaaaat 3900
cttttggaaa ttcttttcaa agtctttttg caaatagtca aaggtaaatg aataagattt 3960
cgagaagcat tttcaagatt tgaaattttc tccccctgtt tcaaatgctt ttcctttgac 4020
taaacaaaac tccccctcaa tgaaattctc ctcttagtgt tcaagagggt tttagacatt 4080
aattttgaaa gaggtcatac caacttgaaa ttatataaaa aataagatac caattgaaaa 4140
acttctttga tacaaattga aagactgcat ttaaacactt tttgaaattg gtggtgatgc 4200
ggtccttttg ctttgggtta atactttctc cccctttggc atgaatcgcc aaaaacagat 4260
actttgtgag tgaaatatga gccctatgtt taaattctct ccccctttgg caaacaatat 4320
atgagtgaag gattatacca aggtggagag cgatgcggag tgacggcgaa gggcaaataa 4380
tacgatggag tggagtggaa gccttgtctt cgccgaagac tccatttccc tttcaatcta 4440
tgacttagca tgagatacac ttgaaaaaca cattagtaat agcaaataaa agagatatga 4500
tcaaaggtac ataaatgaac gatgtgtgca aagtatcaat caaaattcct agaatcaaga 4560
atgtttagct cattcctaag tttggtaaag gttttctcat ctaatggttt ggtaaagata 4620
tcggctaatt gttctttggt gctaacatag gcaatctcga tatcccccct ttgttggtga 4680
tccctcaaaa agtgataccg aatggctatg tgcttagtgc ggctatggtc aacgggatta 4740
tccgcattgc actctcatta tcacacagaa gagggacttt ggttaatttg taaccataat 4800
ccctaagggt ttgcctcatc caaagcaatt gtgcgcaata atggcctgcg acaatgtact 4860
cggcttcggt ggtagaaaga gctaccgaat tttgtttctt tgaagcccaa gacaccaggg 4920
atcttcccaa gaactgacaa gtccctgatg tgctatttct atcaatttta cacccatccc 4980
aatcagcatc tgagtatcct attaaatcaa aggtggatcc cttggggtac caaagaccaa 5040
acttaggtgt atgaactaaa tatctcaaga ttcgtttcat ggccctaagg tgaacttcct 5100
taggattggc ttggaatctt gcacacatgc atacggaaag cataatatcc ggtcgagaag 5160
cacataaata gagtaaagat cctatcatcg atcggtatac cttttgatct acagatttac 5220
ctctcgtgtc gaggtcgaga tgcccatggt tcccatgggt gtcttgatgg gcttggcatc 5280
cttcattcca aacttggtga gtatatcttg agtatacttt gtttggctga tgaaggtgcc 5340
ctcttggagt tgcttgactt gaaatcctaa gaaatacttc aactccccca tcatagacat 5400
ctcgaatttt tgaatcatga tcctactaaa ctcttcacaa gtagatttgt tagtagaccc 5460
aaatatgata tcatcaacat aaatttggca tacaaacaaa tcatttgcaa tggttttagt 5520
aaagagtgta ggatcgactt ttccgacttt gaagccatta gtgataagaa agtctcttag 5580
gcattcatac catgctcttg gggcttgctt aagcccacaa agtgcctttg agagtttata 5640
gacatgatta gggtactcac tatcttcaaa gccggaaggt tgctcaatat agacctcttc 5700
cttgattggt ccattgagga aggcactctt cacgtccatt tgataaagct tgaagccatg 5760
gtaagtagca taggcaagta atatacgaat tgactcaagc ctagctattg gtgcataggt 5820
ttcaccgaaa tccaaacctt caacttgtga atatcccttg gccacatgtc gggctttgtt 5880
ccttgtcacc acaccatgct catcttgctt gttgccgaag acccacttgg tttctacaac 5940
attttggtta ggacgtggaa caagatgcca tacctcgtga agttgttgag ttcctcttgc 6000
attgccaaca cccaatccga atcccttaat gtgtcttcca ccctgtatgg ctcaatagaa 6060
gacacaaaag agtaattgtc ggtaccctga accaggggta ccccctacta cagtataagg 6120
aagcattgcc cgtacgacgt tccctagcca cacggtgagc agcacccgac cccaccatgt 6180
gggtggctca aggggtacca cgtggcgaga aaagatgaca catcccagga tatatcagtt 6240
gaaccggacc accacgaagg agcaccggac ccctgtatgc acaacccgga cccccgatta 6300
cggctcgaga ctcccaagta agcatgccga gcccccttgga tggggtccag atccctttga 6360
gtaaggtccg taccacaacg aggtcccgag acatgggaga ccctggcata agcaagggtc 6420
cggtattgac acgtgttagg gccttatcat gtgcgcttgc gctccctgct taggcggaga 6480
cccgctactg ccacgtggct tgttgcctgt gacataagcc aacgggcaga gcctgatgta 6540
aggcctctag gccgtgcggt ctctgcattt attgcggagg agacgcgtcg cctgcccacc 6600
ttgctgacag gcgatgtgcc ccctttgcat ttaatgcgtc ctgtccactc caccggcagg 6660
cgcaccaggc catcctgcag tcggcgcacc tgtccagtcc attgtcaaat agtgcacccg 6720
tgctacaggg cgcactgtgc tcatcatccc ttatacgata agcttcctct gcacgccgat 6780

```
gctaggcaga tctcagacgt cagggcataa ggagattgcc ccagcagcaa acatgagtag   6840
cgccaaatac tacatctgtt atgttcctgg gcccacatgt cggggctcag tatccttgtg   6900
catgtccccc ttgactataa aaggggaggc atgcaacgtt acaagacagg ctctctaaga   6960
cctaaggcag acttcgaacg ctcaagcttc cacagcaatc caacacataa tggagtatgg   7020
tattacgctc tgacggcccg aaccactcta aactctcgtg tgttcatgtg ctcggtgatc   7080
gcttagctag acaggcaaaa tgcttaagcc ccttcctcat cttaggatta agggcgggtg   7140
cactccgcca cccgaccgga gaattccctc tccaacattt ggtgcgccag gtagggggct   7200
aggcattagg tttttgtttg tttcctcgct cagcatgatg gtgcaaatcg tggagcaccg   7260
cgccgataca tcaacgaatt tcctggtgga ggaagaagtt gtttcttcca cgccactggt   7320
tcccaaccgc ccagtgtcgg gcactgctgc tgtgcacgct gcacaatagc atacagctgc   7380
gtagacatct tgtactccgt cgagggtggc tctgggagca ttgtcggcgg ccagggagtt   7440
gctgtgccac cctccaagct ccatggactc accgggggcc atgaagcagt ggcgggacga   7500
cgtcgaccga ctgctcggta tggcacattc tacctcaacc aggtcgaggc cacggtcatc   7560
ccggcgccaa catgaggcgt cggcgtctat gcgcgcgccc tcagtaaggg gcgcatagac   7620
caacgacctc cgggccgagc tcaaccgcag gcgtgcggga gaggacgccc gactctcttt   7680
agagagggtg cacgagcgcc gacaaaacgt tgagggtcgc aacctcgacc aagactttgc   7740
tgcggtagca ccgcaggccc caatgggcac ccggtctcga gcgggtgtcc ccttggtcgg   7800
cgtgggctgc gccgctttcg cggatcatct ccgcgcaaca tcatggccat ccaaattctg   7860
gccgcacttg ccggaaaaat atgacggtac gtcaaacccg tcggagttcc tacaggtgta   7920
tgtcaccgct atcacagcag caggtggaaa caccactacg atgcgtgaca tattttcatg   7980
tcgccttgtc tgggcctacc cggtcttggc tcatgaacct cgccccaggg tcaatctact   8040
cctgggaaga gctctgcgca tggttcgttg cgaacttcgc cagcgcttac cagcagcacg   8100
gtgtggaggc ccaccttcac gcggtaaggc aggagcccgg ggagactctc cggacgttca   8160
tctctcgctt caccaaggtg cgaggtacta taccttgcat t                        8201
```

<210> SEQ ID NO 47
<211> LENGTH: 6001
<212> TYPE: DNA
<213> ORGANISM: Zea mays

<400> SEQUENCE: 47

```
tgatttcaaa tctcaattcc atgtgcaacc aaacaacaga atttagaaaa gttggtttca     60
ttttctaatt atgtgctcta atatctatat ctaaacaggg gtattacata tggtgaggtg    120
agagatagag gcactgtctt atagtctgat agatgaacat atgtgttatc tccttttttt    180
aatagaccaa atagaaaaga atagaaaaaa gttaaaccta tcccccgcta tatctcataa    240
ccacacatat ctacaatatt ttttaaaaaa tcaaagacac taatagtaga agttactatg    300
acaaagttta gtctgtgtta catcgaatgt ttgaatgttg gttataatta tatatagtat    360
aattataaaa aataatcata tagatgaaga ctatatgatt taacccttga gagagtcttc    420
cccgagcccg cgggcttgtc gtcggtcacg ttctccctct tggcgtgatc tccagacatc    480
actttgagtt gattagactc ttaatgaagc actaactttg ataccaattg aaagtcgcct    540
agagggggtg aataggcgaa acctaaaatt tacaaacata aacacacact aaggccgggg    600
ttagcgttgg aattaaattc aagtctgaaa gattgtttct tttgctaaga gttgttcaaa    660
```

-continued

```
ggatgcggat gacgtatggg agcaaactca aatcaatatt agcaaggaaa cgttagagag    720
aggaaagagg gcaaacaaat caagcgagta gacatagtga tttgttttac cgaggttcgg    780
ttctaaagaa cctaatcccc gttgaggagg ccacaaaggc cgggtctatt tcaacccttt    840
ccctctctct caaatggtca cttagaccga ttgagccttc tccttaatca aacgggtcac    900
taaggtgtct cttgcaaact ttacaagcac ttagaaaaag aatgaggaag gaagaaaggc    960
aatccaagcg acaagagcaa caaaagaaca caaatgaccc tctcacaatc ccttaagcac   1020
tagcgttgat tttgggaagt tttgagtgga ttgattgttt tgattgtgtc ttggagtgtt   1080
ggactttgct cttgcaatga atgagaaact caaaatgctt ggatggcttt gaatgaggtg   1140
gttgaggggt atttatagcc cccaaccact tcctagccgt tggtaaaggc tgctggcgat   1200
gggcgcaccg gacagtcact gttcattgtc cggtgcacgc cacgttagcg cgcccgttag   1260
ggtttggagc agttgaccgt tgaagccgtt tgtctttttg ctgcaccgga cagtccggtg   1320
acttctgcac ggcactgttt ggcactgttc ctctgcgcag tcgaccgttg gcgcgtaggg   1380
agccgttgct ccgctggctc accggatagt ccggtgaatt atagtggagc gcacgcggca   1440
caaccaccaa agtggccgtt gggaggggct gctatcgatg ggcgcaccgg accgtccggt   1500
gcgccagacc agggcagcct tcgggtttct ttgctccttt ctttttgaac cctatcttgg   1560
actttttatt ggtttgtgtt gaacctttgg cacctataga acttataatc tagagcaaac   1620
tagttagtcc aattatttgt gttgggcaat tcaaccacca aaatcattta ggaaaaggtt   1680
tgaccctatt tccctttcag tctccccctt tttggtgatt gatgccaaca caaaccaaag   1740
caaatatata agtgcagaat tgaactagtt tgcataaggt aagtgcaaag gttgcttgga   1800
attaacccaa tttatacttt cataagatat gcatggattg ctttcttctt atttaacatt   1860
ttggaccacg cttgcaccac ttgttttgtt tttgcaaaat cttttggaaa ttcttttcaa   1920
agtctttttg caaatagtca aaggtaaatg aataagattt cgagaagcat tttcaagatt   1980
tgaaattttc tccccctgtt tcaaatgctt ttcctttgac taaacaaaac tccccctcaa   2040
tgaaattctc ctcttagtgt tcaagagggt tttagacatt aattttgaaa gaggtcatac   2100
caacttgaaa ttatataaaa aataagatac caattgaaaa acttctttga tacaaattga   2160
aagactgcat ttaaacactt tttgaaattg gtggtgatgc ggtccttttg ctttgggtta   2220
atactttctc cccctttggc atgaatcgcc aaaaacagat actttgtgag tgaaatatga   2280
gccctatgtt taaattctct ccccctttgg caaacaatat atgagtgaag gattatacca   2340
aggtggagag cgatgcggag tgacggcgaa gggcaaataa tacgatggag tggagtggaa   2400
gccttgtctt cgccgaagac tccatttccc tttcaatcta tgacttagca tgagatacac   2460
ttgaaaaaca cattagtaat agcaaataaa agagatatga tcaaaggtac ataaatgaac   2520
gatgtgtgca aagtatcaat caaaattcct agaatcaaga atgtttagct cattcctaag   2580
tttggtaaag gttttctcat ctaatggttt ggtaaagata tcggctaatt gttctttggt   2640
gctaacatag gcaatctcga tatccccccct ttgttggtga tccctcaaaa agtgataccg   2700
aatggctatg tgcttagtgc ggctatggtc aacgggatta tccgcattgc actctcatta   2760
tcacacagaa gagggacttt ggttaatttg taaccataat ccctaagggt ttgcctcatc   2820
caaagcaatt gtgcgcaata atggcctgcg acaatgtact cggcttcggt ggtagaaaga   2880
gctaccgaat tttgtttctt tgaagcccaa gacaccaggg atcttcccaa gaactgacaa   2940
gtccctgatg tgctatttct atcaatttta cacccatccc aatcagcatc tgagtatcct   3000
attaaatcaa aggtggatcc cttggggtac caaagaccaa acttaggtgt atgaactaaa   3060
```

tatctcaaga ttcgtttcat ggccctaagg tgaacttcct taggattggc ttggaatctt 3120
gcacacatgc atacggaaag cataatatcc ggtcgagaag cacataaata gagtaaagat 3180
cctatcatcg atcggtatac cttttgatct acagatttac ctctcgtgtc gaggtcgaga 3240
tgcccatggt tcccatgggt gtcttgatgg gcttggcatc cttcattcca aacttggtga 3300
gtatatcttg agtatacttt gtttggctga tgaaggtgcc ctcttggagt tgcttgactt 3360
gaaatcctaa gaaatacttc aactccccca tcatagacat ctcgaatttt tgaatcatga 3420
tcctactaaa ctcttcacaa gtagatttgt tagtagaccc aaatatgata tcatcaacat 3480
aaatttggca tacaaacaaa tcatttgcaa tggttttagt aaagagtgta ggatcgactt 3540
ttccgacttt gaagccatta gtgataagaa agtctcttag gcattcatac catgctcttg 3600
gggcttgctt aagcccacaa agtgcctttg agagtttata gacatgatta gggtactcac 3660
tatcttcaaa gccggaaggt tgctcaatat agacctcttc cttgattggt ccattgagga 3720
aggcactctt cacgtccatt tgataaagct tgaagccatg gtaagtagca taggcaagta 3780
atatacgaat tgactcaagc ctagctattg gtgcataggt ttcaccgaaa tccaaacctt 3840
caacttgtga atatcccttg gccacatgtc gggctttgtt ccttgtcacc acaccatgct 3900
catcttgctt gttgccgaag acccacttgg tttctacaac attttggtta ggacgtggaa 3960
caagatgcca tacctcgtga agttgttgag ttcctcttgc attgccaaca cccaatccga 4020
atcccttaat gtgtcttcca ccctgtatgg ctcaatagaa gacacaaaag agtaattgtc 4080
ggtaccctga accaggggta ccccctacta cagtataagg aagcattgcc cgtacgacgt 4140
tccctagcca cacggtgagc agcacccgac cccaccatgt gggtggctca aggggtacca 4200
cgtggcgaga aaagatgaca catcccagga tatatcagtt gaaccggacc accacgaagg 4260
agcaccggac ccctgtatgc acaacccgga cccccgatta cggctcgaga ctcccaagta 4320
agcatgccga gccccttgga tggggtccag atccctttga gtaaggtccg taccacaacg 4380
aggtcccgag acatgggaga ccctggcata agcaagggtc cggtattgac acgtgttagg 4440
gccttatcat gtgcgcttgc gctccctgct taggcggaga cccgctactg ccacgtggct 4500
tgttgcctgt gacataagcc aacgggcaga gcctgatgta aggcctctag gccgtgcggt 4560
ctctgcattt attgcggagg agacgcgtcg cctgcccacc ttgctgacag gcgatgtgcc 4620
ccctttgcat ttaatgcgtc ctgtccactc caccggcagg cgcaccaggc catcctgcag 4680
tcggcgcacc tgtccagtcc attgtcaaat agtgcacccg tgctacaggg cgcactgtgc 4740
tcatcatccc ttatacgata agcttcctct gcacgccgat gctaggcaga tctcagacgt 4800
cagggcataa ggagattgcc ccagcagcaa acatgagtag cgccaaatac tacatctgtt 4860
atgttcctgg gcccacatgt cggggctcag tatccttgtg catgtccccc ttgactataa 4920
aaggggaggc atgcaacgtt acaagacagg ctctctaaga cctaaggcag acttcgaacg 4980
ctcaagcttc cacagcaatc caacacataa tggagtatgg tattacgctc tgacggcccg 5040
aaccactcta aactctcgtg tgttcatgtg ctcggtgatc gcttagctag acaggcaaaa 5100
tgcttaagcc ccttcctcat cttaggatta agggcgggtg cactccgcca cccgaccgga 5160
gaattccctc tccaacattt ggtgcgccag gtagggggct aggcattagg tttttgtttg 5220
tttcctcgct cagcatgatg gtgcaaatcg tggagcaccg cgccgataca tcaacgaatt 5280
tcctggtgga ggaagaagtt gtttcttcca cgccactggt tcccaaccgc ccagtgtcgg 5340
gcactgctgc tgtgcacgct gcacaatagc atacagctgc gtagacatct tgtactccgt 5400

```
cgagggtggc tctgggagca ttgtcggcgg ccagggagtt gctgtgccac cctccaagct   5460

ccatggactc accgggggcc atgaagcagt ggcgggacga cgtcgaccga ctgctcggta   5520

tggcacattc tacctcaacc aggtcgaggc cacggtcatc ccggcgccaa catgaggcgt   5580

cggcgtctat gcgcgcgccc tcagtaaggg gcgcatagac caacgacctc cgggccgagc   5640

tcaaccgcag gcgtgcggga gaggacgccc gactctcttt agagagggtg cacgagcgcc   5700

gacaaaacgt tgagggtcgc aacctcgacc aagactttgc tgcggtagca ccgcaggccc   5760

caatgggcac ccggtctcga gcgggtgtcc ccttggtcgg cgtgggctgc gccgctttcg   5820

cggatcatct ccgcgcaaca tcatggccat ccaaattctg gccgcacttg ccggaaaaat   5880

atgacggtac gtcaaacccg tcggagttcc tacaggtgta tgtcaccgct atcacagcag   5940

caggtggaaa caccactacg atgcgtgaca tattttcatg tcgccttgtc tgggcctacc   6000

c                                                                   6001
```

<210> SEQ ID NO 48
<211> LENGTH: 4001
<212> TYPE: DNA
<213> ORGANISM: Zea mays

<400> SEQUENCE: 48

```
tcaaatgctt ttcctttgac taaacaaaac tccccctcaa tgaaattctc ctcttagtgt     60

tcaagagggt tttagacatt aattttgaaa gaggtcatac caacttgaaa ttatataaaa    120

aataagatac caattgaaaa acttctttga tacaaattga aagactgcat ttaaacactt    180

tttgaaattg gtggtgatgc ggtccttttg ctttgggtta atactttctc cccctttggc    240

atgaatcgcc aaaaacagat actttgtgag tgaaatatga gccctatgtt taaattctct    300

ccccctttgg caaacaatat atgagtgaag gattatacca aggtggagag cgatgcggag    360

tgacggcgaa gggcaaataa tacgatggag tggagtggaa gccttgtctt cgccgaagac    420

tccatttccc tttcaatcta tgacttagca tgagatacac ttgaaaaaca cattagtaat    480

agcaaataaa agagatatga tcaaaggtac ataaatgaac gatgtgtgca aagtatcaat    540

caaaattcct agaatcaaga atgtttagct cattcctaag tttggtaaag gttttctcat    600

ctaatggttt ggtaaagata tcggctaatt gttctttggt gctaacatag gcaatctcga    660

tatcccccct ttgttggtga tccctcaaaa agtgataccg aatggctatg tgcttagtgc    720

ggctatggtc aacgggatta tccgcattgc actctcatta tcacacagaa gagggacttt    780

ggttaatttg taaccataat ccctaagggt ttgcctcatc caaagcaatt gtgcgcaata    840

atggcctgcg acaatgtact cggcttcggt ggtagaaaga gctaccgaat tttgtttctt    900

tgaagcccaa gacaccaggg atcttcccaa gaactgacaa gtccctgatg tgctatttct    960

atcaatttta cacccatccc aatcagcatc tgagtatcct attaaatcaa aggtggatcc   1020

cttggggtac caaagaccaa acttaggtgt atgaactaaa tatctcaaga ttcgtttcat   1080

ggccctaagg tgaacttcct taggattggc ttggaatctt gcacacatgc atacggaaag   1140

cataatatcc ggtcgagaag cacataaata gagtaaagat cctatcatcg atcggtatac   1200

cttttgatct acagatttac ctctcgtgtc gaggtcgaga tgcccatggt tcccatgggt   1260

gtcttgatgg gcttggcatc cttcattcca aacttggtga gtatatcttg agtatacttt   1320

gtttggctga tgaaggtgcc ctcttggagt tgcttgactt gaaatcctaa gaaatacttc   1380

aactccccca tcatagacat ctcgaatttt tgaatcatga tcctactaaa ctcttcacaa   1440

gtagatttgt tagtagaccc aaatatgata tcatcaacat aaatttggca tacaaacaaa   1500
```

-continued

```
tcatttgcaa tggttttagt aaagagtgta ggatcgactt ttccgacttt gaagccatta   1560
gtgataagaa agtctcttag gcattcatac catgctcttg gggcttgctt aagcccacaa   1620
agtgcctttg agagtttata gacatgatta gggtactcac tatcttcaaa gccggaaggt   1680
tgctcaatat agacctcttc cttgattggt ccattgagga aggcactctt cacgtccatt   1740
tgataaagct tgaagccatg gtaagtagca taggcaagta atatacgaat tgactcaagc   1800
ctagctattg gtgcataggt ttcaccgaaa tccaaacctt caacttgtga atatcccttg   1860
gccacatgtc gggctttgtt ccttgtcacc acaccatgct catcttgctt gttgccgaag   1920
acccacttgg tttctacaac attttggtta ggacgtggaa caagatgcca tacctcgtga   1980
agttgttgag ttcctcttgc attgccaaca cccaatccga atcccttaat gtgtcttcca   2040
ccctgtatgg ctcaatagaa gacacaaaag agtaattgtc ggtaccctga accaggggta   2100
ccccctacta cagtataagg aagcattgcc cgtacgacgt tccctagcca cacggtgagc   2160
agcacccgac cccaccatgt gggtggctca aggggtacca cgtggcgaga aaagatgaca   2220
catcccagga tatatcagtt gaaccggacc accacgaagg agcaccggac ccctgtatgc   2280
acaacccgga cccccgatta cggctcgaga ctcccaagta agcatgccga gcccccttgga   2340
tggggtccag atccctttga gtaaggtccg taccacaacg aggtcccgag acatgggaga   2400
ccctggcata agcaagggtc cggtattgac acgtgttagg gccttatcat gtgcgcttgc   2460
gctccctgct taggcggaga cccgctactg ccacgtggct tgttgcctgt gacataagcc   2520
aacgggcaga gcctgatgta aggcctctag gccgtgcggt ctctgcattt attgcggagg   2580
agacgcgtcg cctgcccacc ttgctgacag gcgatgtgcc ccctttgcat ttaatgcgtc   2640
ctgtccactc caccggcagg cgcaccaggc catcctgcag tcggcgcacc tgtccagtcc   2700
attgtcaaat agtgcacccg tgctacaggg cgcactgtgc tcatcatccc ttatacgata   2760
agcttcctct gcacgccgat gctaggcaga tctcagacgt cagggcataa ggagattgcc   2820
ccagcagcaa acatgagtag cgccaaatac tacatctgtt atgttcctgg gcccacatgt   2880
cggggctcag tatccttgtg catgtccccc ttgactataa aaggggaggc atgcaacgtt   2940
acaagacagg ctctctaaga cctaaggcag acttcgaacg ctcaagcttc cacagcaatc   3000
caacacataa tggagtatgg tattacgctc tgacggcccg aaccactcta aactctcgtg   3060
tgttcatgtg ctcggtgatc gcttagctag acaggcaaaa tgcttaagcc ccttcctcat   3120
cttaggatta agggcgggtg cactccgcca cccgaccgga gaattccctc tccaacattt   3180
ggtgcgccag gtagggggct aggcattagg tttttgtttg tttcctcgct cagcatgatg   3240
gtgcaaatcg tggagcaccg cgccgataca tcaacgaatt tcctggtgga ggaagaagtt   3300
gtttcttcca cgccactggt tcccaaccgc ccagtgtcgg gcactgctgc tgtgcacgct   3360
gcacaatagc atacagctgc gtagacatct tgtactccgt cgagggtggc tctgggagca   3420
ttgtcggcgg ccagggagtt gctgtgccac cctccaagct ccatggactc accgggggcc   3480
atgaagcagt ggcgggacga cgtcgaccga ctgctcggta tggcacattc tacctcaacc   3540
aggtcgaggc cacggtcatc ccggcgccaa catgaggcgt cggcgtctat gcgcgcgccc   3600
tcagtaaggg gcgcatagac caacgacctc cgggccgagc tcaaccgcag gcgtgcggga   3660
gaggacgccc gactctcttt agagagggtg cacgagcgcc gacaaaacgt tgagggtcgc   3720
aacctcgacc aagactttgc tgcggtagca ccgcaggccc caatgggcac ccggtctcga   3780
gcgggtgtcc ccttggtcgg cgtgggctgc gccgctttcg cggatcatct ccgcgcaaca   3840
```

tcatggccat ccaaattctg gccgcacttg ccggaaaaat atgacggtac gtcaaacccg 3900
tcggagttcc tacaggtgta tgtcaccgct atcacagcag caggtggaaa caccactacg 3960
atgcgtgaca tattttcatg tcgccttgtc tgggcctacc c 4001

<210> SEQ ID NO 49
<211> LENGTH: 3001
<212> TYPE: DNA
<213> ORGANISM: Zea mays

<400> SEQUENCE: 49
attaaatcaa aggtggatcc cttggggtac caaagaccaa acttaggtgt atgaactaaa 60
tatctcaaga ttcgtttcat ggccctaagg tgaacttcct taggattggc ttggaatctt 120
gcacacatgc atacggaaag cataatatcc ggtcgagaag cacataaata gagtaaagat 180
cctatcatcg atcggtatac cttttgatct acagatttac ctctcgtgtc gaggtcgaga 240
tgcccatggt tcccatgggt gtcttgatgg gcttggcatc cttcattcca aacttggtga 300
gtatatcttg agtatacttt gtttggctga tgaaggtgcc ctcttggagt tgcttgactt 360
gaaatcctaa gaaatacttc aactccccca tcatagacat ctcgaatttt tgaatcatga 420
tcctactaaa ctcttcacaa gtagatttgt tagtagaccc aaatatgata tcatcaacat 480
aaatttggca tacaaacaaa tcatttgcaa tggttttagt aaagagtgta ggatcgactt 540
ttccgacttt gaagccatta gtgataagaa agtctcttag gcattcatac catgctcttg 600
gggcttgctt aagcccacaa agtgcctttg agagtttata gacatgatta gggtactcac 660
tatcttcaaa gccggaaggt tgctcaatat agacctcttc cttgattggt ccattgagga 720
aggcactctt cacgtccatt tgataaagct tgaagccatg gtaagtagca taggcaagta 780
atatacgaat tgactcaagc ctagctattg gtgcataggt ttcaccgaaa tccaaacctt 840
caacttgtga atatcccttg gccacatgtc gggctttgtt ccttgtcacc acaccatgct 900
catcttgctt gttgccgaag acccacttgg tttctacaac attttggtta ggacgtggaa 960
caagatgcca tacctcgtga agttgttgag ttcctcttgc attgccaaca cccaatccga 1020
atcccttaat gtgtcttcca ccctgtatgg ctcaatagaa gacacaaaag agtaattgtc 1080
ggtaccctga accaggggta ccccctacta cagtataagg aagcattgcc cgtacgacgt 1140
tccctagcca cacggtgagc agcacccgac cccaccatgt gggtggctca aggggtacca 1200
cgtggcgaga aaagatgaca catcccagga tatatcagtt gaaccggacc accacgaagg 1260
agcaccggac ccctgtatgc acaacccgga cccccgatta cggctcgaga ctcccaagta 1320
agcatgccga gccccttgga tggggtccag atccctttga gtaaggtccg taccacaacg 1380
aggtcccgag acatgggaga ccctggcata agcaagggtc cggtattgac acgtgttagg 1440
gccttatcat gtgcgcttgc gctccctgct taggcggaga cccgctactg ccacgtggct 1500
tgttgcctgt gacataagcc aacgggcaga gcctgatgta aggcctctag gccgtgcggt 1560
ctctgcattt attgcggagg agacgcgtcg cctgcccacc ttgctgacag gcgatgtgcc 1620
ccctttgcat ttaatgcgtc ctgtccactc caccggcagg cgcaccaggc catcctgcag 1680
tcggcgcacc tgtccagtcc attgtcaaat agtgcacccg tgctacaggg cgcactgtgc 1740
tcatcatccc ttatacgata agcttcctct gcacgccgat gctaggcaga tctcagacgt 1800
cagggcataa ggagattgcc ccagcagcaa acatgagtag cgccaaatac tacatctgtt 1860
atgttcctgg gcccacatgt cggggctcag tatccttgtg catgtccccc ttgactataa 1920
aaggggaggc atgcaacgtt acaagacagg ctctctaaga cctaaggcag acttcgaacg 1980

```
ctcaagcttc cacagcaatc caacacataa tggagtatgg tattacgctc tgacggcccg   2040
aaccactcta aactctcgtg tgttcatgtg ctcggtgatc gcttagctag acaggcaaaa   2100
tgcttaagcc ccttcctcat cttaggatta agggcgggtg cactccgcca cccgaccgga   2160
gaattccctc tccaacattt ggtgcgccag gtagggggct aggcattagg tttttgtttg   2220
tttcctcgct cagcatgatg gtgcaaatcg tggagcaccg cgccgataca tcaacgaatt   2280
tcctggtgga ggaagaagtt gtttcttcca cgccactggt tcccaaccgc ccagtgtcgg   2340
gcactgctgc tgtgcacgct gcacaatagc atacagctgc gtagacatct tgtactccgt   2400
cgagggtggc tctgggagca ttgtcggcgg ccagggagtt gctgtgccac cctccaagct   2460
ccatggactc accgggggcc atgaagcagt ggcgggacga cgtcgaccga ctgctcggta   2520
tggcacattc tacctcaacc aggtcgaggc cacggtcatc ccggcgccaa catgaggcgt   2580
cggcgtctat gcgcgcgccc tcagtaaggg gcgcatagac caacgacctc cgggccgagc   2640
tcaaccgcag gcgtgcggga gaggacgccc gactctcttt agagagggtg cacgagcgcc   2700
gacaaaacgt tgagggtcgc aacctcgacc aagactttgc tgcggtagca ccgcaggccc   2760
caatgggcac ccggtctcga gcgggtgtcc ccttggtcgg cgtgggctgc gccgctttcg   2820
cggatcatct ccgcgcaaca tcatggccat ccaaattctg gccgcacttg ccggaaaaat   2880
atgacggtac gtcaaacccg tcggagttcc tacaggtgta tgtcaccgct atcacagcag   2940
caggtggaaa caccactacg atgcgtgaca tattttcatg tcgccttgtc tgggcctacc   3000
c                                                                    3001
```

<210> SEQ ID NO 50
<211> LENGTH: 2001
<212> TYPE: DNA
<213> ORGANISM: Zea mays

<400> SEQUENCE: 50

```
attgccaaca cccaatccga atcccttaat gtgtcttcca ccctgtatgg ctcaatagaa     60
gacacaaaag agtaattgtc ggtaccctga accaggggta cccccctacta cagtataagg    120
aagcattgcc cgtacgacgt tccctagcca cacggtgagc agcacccgac cccaccatgt    180
gggtggctca aggggtacca cgtggcgaga aaagatgaca catcccagga tatatcagtt    240
gaaccggacc accacgaagg agcaccggac ccctgtatgc acaacccgga cccccgatta    300
cggctcgaga ctcccaagta agcatgccga gcccccttgga tggggtccag atccctttga    360
gtaaggtccg taccacaacg aggtcccgag acatgggaga ccctggcata agcaagggtc    420
cggtattgac acgtgttagg gccttatcat gtgcgcttgc gctccctgct taggcggaga    480
cccgctactg ccacgtggct tgttgcctgt gacataagcc aacgggcaga gcctgatgta    540
aggcctctag gccgtgcggt ctctgcattt attgcggagg agacgcgtcg cctgcccacc    600
ttgctgacag gcgatgtgcc cccttttgcat ttaatgcgtc ctgtccactc caccggcagg    660
cgcaccaggc catcctgcag tcggcgcacc tgtccagtcc attgtcaaat agtgcacccg    720
tgctacaggg cgcactgtgc tcatcatccc ttatacgata agcttcctct gcacgccgat    780
gctaggcaga tctcagacgt cagggcataa ggagattgcc ccagcagcaa acatgagtag    840
cgccaaatac tacatctgtt atgttcctgg gcccacatgt cggggctcag tatccttgtg    900
catgtccccc ttgactataa aaggggaggc atgcaacgtt acaagacagg ctctctaaga    960
cctaaggcag acttcgaacg ctcaagcttc cacagcaatc caacacataa tggagtatgg   1020
```

-continued

```
tattacgctc tgacggcccg aaccactcta aactctcgtg tgttcatgtg ctcggtgatc   1080

gcttagctag acaggcaaaa tgcttaagcc ccttcctcat cttaggatta agggcgggtg   1140

cactccgcca cccgaccgga gaattccctc tccaacattt ggtgcgccag gtagggggct   1200

aggcattagg tttttgtttg tttcctcgct cagcatgatg gtgcaaatcg tggagcaccg   1260

cgccgataca tcaacgaatt tcctggtgga ggaagaagtt gtttcttcca cgccactggt   1320

tcccaaccgc ccagtgtcgg gcactgctgc tgtgcacgct gcacaatagc atacagctgc   1380

gtagacatct tgtactccgt cgagggtggc tctgggagca ttgtcggcgg ccagggagtt   1440

gctgtgccac cctccaagct ccatggactc accgggggcc atgaagcagt ggcgggacga   1500

cgtcgaccga ctgctcggta tggcacattc tacctcaacc aggtcgaggc cacggtcatc   1560

ccggcgccaa catgaggcgt cggcgtctat gcgcgcgccc tcagtaaggg gcgcatagac   1620

caacgacctc cgggccgagc tcaaccgcag gcgtgcggga gaggacgccc gactctcttt   1680

agagagggtg cacgagcgcc gacaaaacgt tgagggtcgc aacctcgacc aagactttgc   1740

tgcggtagca ccgcaggccc caatgggcac ccggtctcga gcgggtgtcc ccttggtcgg   1800

cgtgggctgc gccgctttcg cggatcatct ccgcgcaaca tcatggccat ccaaattctg   1860

gccgcacttg ccggaaaaat atgacggtac gtcaaacccg tcggagttcc tacaggtgta   1920

tgtcaccgct atcacagcag caggtggaaa caccactacg atgcgtgaca tattttcatg   1980

tcgccttgtc tgggcctacc c                                             2001
```

<210> SEQ ID NO 51
<211> LENGTH: 4742
<212> TYPE: DNA
<213> ORGANISM: Zea mays

<400> SEQUENCE: 51

```
gctgtaaggg ataacactga acatccaacg ttgattactc tattatagta ttatacagac     60

tgtacttttc gaatttatct tagttttcta caatatttag tggattcttc tcattttcaa    120

gatacacaat tgaaccataa tcgaagtggt atgtaagaca gtgagttaaa agattatatt    180

ttttgggaga cttccagtca aattttctta gaagtttttt tggtccagat gttcataaag    240

tcgccgcttt catacttttt ttaatttttt aattggtgca ctattaggta cctgttggag    300

gatgttacag gcttattgat atccctatga gtaactgctt caacagtggt ataaataaga    360

tatttgtgat gagtcagttc aattctactt cgcttaaccg ccatattcat cgtacatacc    420

ttgaaggcgg gatcaacttt gctgatggat ctgtacaggt gatttacctc atcttgttga    480

tgtgtaatac tgtaattagg agtagatttg tgtggagaga ataataaaca gatgccgaga    540

ttcttctcta aaagtctaga tccaaaggca ttgtggttca aaacactatg gacttctacc    600

atttatgtta ttactttgcc ttaatgttcc attgaatggg gcaaattatt gattctacaa    660

gtgtttaatt aaaaactaat tgttcatcct gcaggtatta gcggctacac aaatgcctga    720

agagccagct ggatggttcc agggtacagc agactctatc agaaaattta tctgggtact    780

cgaggtagtt gatattttct cgtttatgaa tgtccattca ctcattcctg tagcattgtt    840

tctttgtaat tttgagttct cctgtatttc tttaggatta ttacagtcac aaatccattg    900

acaacattgt aatcttgagt ggcgatcagc tttatcggat gaattacatg gaacttgtgc    960

aggtatggtg ttctcttgtt cctcatgttt cacgtaatgt cctgattttg gattaaccaa   1020

ctacttttgg catgcattat ttccagaaac atgtcgagga cgatgctgat atcactatat   1080

catgtgctcc tgttgatgag aggtaatcag ttgtttatat catcctaata tgaatatgtc   1140
```

-continued

```
atcttgttat ccaacacagg atgcatatgg tctaatctgc tttccttttt tcccttcgga   1200
agccgagctt ctaaaaatgg gctagtgaag attgatcata ctggacgtgt acttcaattc   1260
tttgaaaaac caaagggtgc tgatttgaat tctatggtta gaaattcctt gtgtaatcca   1320
attcttttgt tttcctttct ttcttgagat gaacccctct tttagttatt tccatggata   1380
acctgtactt gacttattca gaaatgattt tctattttgc tgtagaatct gacactaaag   1440
ctaatagcta ctgatgttgc agagagttga gaccaacttc ctgagctatg ctatagatga   1500
tgcacagaaa tatccatacc ttgcatcaat gggcatttat gtcttcaaga aagatgcact   1560
tttagacctt ctcaagtaat cactttcctg tgacttattt ctatccaact cctagtttac   1620
cttctaacag tgtcaattct taggtcaaaa tatactcaat tacatgactt tggatctgaa   1680
atcctcccaa gagctgtact agatcatagt gtgcaggtaa gtctgatctg tctggagtat   1740
gtgttctgta aactgtaaat tcttcatgtc aaaaagttgt ttttgtttcc agtttccact   1800
agtttttatt taccaatgcg cgatttatgt attttcgctt ccatgcatca tacatactaa   1860
caatacattt tacgtattgt gttaggcatg catttttacg ggctattggg aggatgttgg   1920
aacaatcaaa tcattctttg atgcaaactt ggccctcact gagcaggtac tctgtcatgt   1980
attctgtact gcatatatat tacctggaat tcaatgcata gaatgtgtta gaccatctta   2040
gttccatcct gttttcttca attagcttat catttaatag ttgttggcta gaatttaaac   2100
acaaatttac ctaatatgtt tctctcttca gccttccaag tttgattttt acgatccaaa   2160
aacacctttc ttcactgcac cccgatgctt gcctccgacg caattggaca agtgcaaggt   2220
atatgtctta ctgagcacaa ttgttacctg agcaagattt tgtgtacttg acttgttctc   2280
ctccacagat gaaatatgca tttatctcag atggttgctt actgagagaa tgcaacatcg   2340
agcattctgt gattggagtc tgctcacgtg tcagctctgg atgtgaactc aaggtacata   2400
ctctgccaat gtatatgctg atgttttata cattctcttg cataatttga ttcgagtcac   2460
cacaattagt gtaactgcaa tctactcttg agtataccat ttcaacacca agcatcacca   2520
aatcacacag aacaatagca acaaagcctt ttagttccaa gcaatttagg gtagcctaga   2580
gttgaaatct aaccaaacaa aagtcaaagc tctatcacgt ggatagttgt tttccatgca   2640
ctcttattta agctaatttt tgggtatact acatccattt aattattgtt ttattgcttc   2700
ttccctttgc ctttccccca ttactatcgc gtcttaagat catactacgc actagtgtct   2760
ttagaggtct ctggtggaca tgttcaaacc atctcaatcg gtgttggaca agtttttctt   2820
gaatttgtgc tacacctaac ctatcatgta tgtcatcgtt tcaaactcga tccttcctgt   2880
atcatcataa atccaatgca acatacgcat ttatgcaaca tttatctgtt gaacatgtca   2940
tctttttgta ggttaacatt atacaccata caatgtagca tgtctaatca tcatcctata   3000
aaatttacat tttagcttat gtggtatcct cttgccactt agaacatcat atgcttgatg   3060
ccatttcatc caccctgctt tgattctatg gctaacatct tcattaatat ccttgcctct   3120
ctgtatcatt ggtcctaaat atggaaatac attctttctg ggcactactt gaccttccaa   3180
actaacgtct cctttgatcc tttcttgtgt gtagtagtac cgaagtcaca tctcatatat   3240
tcggttttag ttctactaag tcccgggttc gatccccctc aggggtaaat ttcgggcttg   3300
gtaaaaaaaa tcccctcgct gtgtcccgcc ctctctcggg gatcgatatc ctgcgcgcca   3360
ccctccggct gggcattgca gagtgggcag ttgatcgact cgttagtgat ggggagcggg   3420
gttcaagggt tttctcggcc gggaccatgt ttcggtctct taatataata ccgggagggc   3480
```

-continued

```
agtctttccc tccccggtcg agttttagtt ctactgagtc taaaaccttt ggactctaga   3540
gtcccctgtc acaactcaca actctatttt tctatttact tctacctagc gtttattaat   3600
gatcactata tcgtctgtaa aaagcataca ccaaggtaat ccccttgtat gtcccttgta   3660
atattatcca tcacaagaaa aaaaggtaag gctcaaagtt gacttttgat ataatcctat   3720
tctaatcgag aagtcatctg tatcttcgtc tcttgttcga acactagtca caaatttttt   3780
tgtacatgtt cttaatgagt ccaacgtaat attccttgat attttgtcat aagccctcat   3840
caagtcaatg aaaatcacgt gtaggtcctt catttgttcc ttatactgct ccatcacttg   3900
tctcattaag aaaatatctc tcatagttaa ccttttggca tgaaacaaaa tcacacagaa   3960
tttgtttcct ttttttaaga tcccacacaa aagaggtttg atctaaggaa tctggatccc   4020
tgacaggttt atcaaaatcc tttgtgtttt tcttaaaact gaatattcct ccagcttcta   4080
gtattgatgt aatattcaat ctgtttagca agtgaacacc ttggttcttg ttgttactgt   4140
acatcccacc cacccccgag gcccagatta ccacaacatg aatacaagaa tattgaaccc   4200
agatctagag tttgtttgta ctgttgaaaa tcggtgacaa ttcattttgt tattgcgctt   4260
tctgataacg acaggactcc gtgatgatgg gagcggacat ctatgaaact gaagaagaag   4320
cttcaaagct actgttagct gggaaggtcc cagttggaat aggaaggaac acaaagataa   4380
ggtgagtatg gatgtggaac caccggttag ttcccaaaaa tatcactcac tgatacctga   4440
tggtatcctc tgattatttt caggaactgt atcattgaca tgaatgctag gattgggaag   4500
aacgtggtga tcacaaacag taaggtgagc gagcgcacct acatgggtgc agaatcttgt   4560
gtgctcatct atcctaattc ggtaattcct atccagcgct agtcttgtga ccatggggca   4620
tgggttcgac tctgtgacag ggcatccaag aggctgatca cccggaagaa gggtactaca   4680
taaggtctgg aatcgtggtg atcttgaaga atgcaaccat caacgatggg tctgtcatat   4740
ag                                                                  4742

<210> SEQ ID NO 52
<211> LENGTH: 4401
<212> TYPE: DNA
<213> ORGANISM: Zea mays

<400> SEQUENCE: 52

acactgaaca tccaacgttg attactctat tatagtatta tacagactgt acttttcgaa     60
tttatcttag ttttctacaa tatttagtgg attcttctca ttttcaagat acacaattga    120
accataatcg aagtggtatg taagacagtg agttaaaaga ttatattttt tgggagactt    180
ccagtcaaat tttcttagaa gttttttggg tccagatgtt cataaagtcg ccgctttcat    240
actttttta attttttaat tggtgcacta ttaggtacct gttggaggat gttacaggct    300
tattgatatc cctatgagta actgcttcaa cagtggtata aataagatat ttgtgatgag    360
tcagttcaat tctacttcgc ttaaccgcca tattcatcgt acataccttg aaggcgggat    420
caactttgct gatggatctg tacaggtgat ttacctcatc ttgttgatgt gtaatactgt    480
aattaggagt agatttgtgt ggagagaata ataaacagat gccgagattc ttctctaaaa    540
gtctagatcc aaaggcattg tggttcaaaa cactatggac ttctaccatt tatgttatta    600
ctttgcctta atgttccatt gaatggggca aattattgat tctacaagtg tttaattaaa    660
aactaattgt tcatcctgca ggtattagcg gctacacaaa tgcctgaaga gccagctgga    720
tggttccagg gtacagcaga ctctatcaga aaatttatct gggtactcga ggtagttgat    780
attttctcgt ttatgaatgt ccattcactc attcctgtag cattgtttct ttgtaatttt    840
```

```
gagttctcct gtatttcttt aggattatta cagtcacaaa tccattgaca acattgtaat    900
cttgagtggc gatcagcttt atcggatgaa ttacatggaa cttgtgcagg tatggtgttc    960
tcttgttcct catgtttcac gtaatgtcct gattttggat taaccaacta cttttggcat   1020
gcattatttc cagaaacatg tcgaggacga tgctgatatc actatatcat gtgctcctgt   1080
tgatgagagg taatcagttg tttatatcat cctaatatga atatgtcatc ttgttatcca   1140
acacaggatg catatggtct aatctgcttt ccttttttcc cttcggaagc cgagcttcta   1200
aaaatgggct agtgaagatt gatcatactg gacgtgtact tcaattcttt gaaaaaccaa   1260
agggtgctga tttgaattct atggttagaa attccttgtg taatccaatt cttttgtttt   1320
cctttctttc ttgagatgaa cccctctttt agttatttcc atggataacc tgtacttgac   1380
ttattcagaa atgattttct attttgctgt agaatctgac actaaagcta atagctactg   1440
atgttgcaga gagttgagac caacttcctg agctatgcta tagatgatgc acagaaatat   1500
ccataccttg catcaatggg catttatgtc ttcaagaaag atgcactttt agaccttctc   1560
aagtaatcac tttcctgtga cttatttcta tccaactcct agtttacctt ctaacagtgt   1620
caattcttag gtcaaaatat actcaattac atgactttgg atctgaaatc ctcccaagag   1680
ctgtactaga tcatagtgtg caggtaagtc tgatctgtct ggagtatgtg ttctgtaaac   1740
tgtaaattct tcatgtcaaa aagttgtttt tgtttccagt ttccactagt ttttatttac   1800
caatgcgcga tttatgtatt ttcgcttcca tgcatcatac atactaacaa tacattttac   1860
gtattgtgtt aggcatgcat ttttacgggc tattgggagg atgttggaac aatcaaatca   1920
ttctttgatg caaacttggc cctcactgag caggtactct gtcatgtatt ctgtactgca   1980
tatatattac ctggaattca atgcatagaa tgtgttagac catcttagtt ccatcctgtt   2040
ttcttcaatt agcttatcat ttaatagttg ttggctagaa tttaaacaca aatttaccta   2100
atatgtttct ctcttcagcc ttccaagttt gatttttacg atccaaaaac acctttcttc   2160
actgcacccc gatgcttgcc tccgacgcaa ttggacaagt gcaaggtata tgtcttactg   2220
agcacaattg ttacctgagc aagattttgt gtacttgact tgttctcctc cacagatgaa   2280
atatgcattt atctcagatg gttgcttact gagagaatgc aacatcgagc attctgtgat   2340
tggagtctgc tcacgtgtca gctctggatg tgaactcaag gtacatactc tgccaatgta   2400
tatgctgatg ttttatacat tctcttgcat aatttgattc gagtcaccac aattagtgta   2460
actgcaatct actcttgagt ataccatttc aacaccaagc atcaccaaat cacacagaac   2520
aatagcaaca aagcctttta gttccaagca atttagggta gcctagagtt gaaatctaac   2580
caaacaaaag tcaaagctct atcacgtgga tagttgtttt ccatgcactc ttatttaagc   2640
taatttttgg gtatactaca tccatttaat tattgtttta ttgcttcttc cctttgcctt   2700
tcccccatta ctatcgcgtc ttaagatcat actacgcact agtgtcttta gaggtctctg   2760
gtggacatgt tcaaaccatc tcaatcggtg ttggacaagt ttttcttgaa tttgtgctac   2820
acctaaccta tcatgtatgt catcgtttca aactcgatcc ttcctgtatc atcataaatc   2880
caatgcaaca tacgcattta tgcaacattt atctgttgaa catgtcatct ttttgtaggt   2940
taacattata caccatacaa tgtagcatgt ctaatcatca tcctataaaa tttacatttt   3000
agcttatgtg gtatcctctt gccacttaga acatcatatg cttgatgcca tttcatccac   3060
cctgctttga ttctatggct aacatcttca ttaatatcct tgcctctctg tatcattggt   3120
cctaaatatg gaaatacatt ctttctgggc actacttgac cttccaaact aacgtctcct   3180
```

ttgatccttt cttgtgtgta gtagtaccga agtcacatct catatattcg gttttagttc 3240
tactaagtcc cgggttcgat ccccctcagg ggtaaatttc gggcttggta aaaaaaatcc 3300
cctcgctgtg tcccgccctc tctcggggat cgatatcctg cgcgccaccc tccggctggg 3360
cattgcagag tgggcagttg atcgactcgt tagtgatggg gagcggggtt caagggtttt 3420
ctcggccggg accatgtttc ggtctcttaa tataataccg ggagggcagt ctttccctcc 3480
ccggtcgagt tttagttcta ctgagtctaa aacctttgga ctctagagtc ccctgtcaca 3540
actcacaact ctatttttct atttacttct acctagcgtt tattaatgat cactatatcg 3600
tctgtaaaaa gcatacacca aggtaatccc cttgtatgtc ccttgtaata ttatccatca 3660
caagaaaaaa aggtaaggct caaagttgac ttttgatata atcctattct aatcgagaag 3720
tcatctgtat cttcgtctct tgttcgaaca ctagtcacaa attttttgt acatgttctt 3780 aatgagtcca acgtaatatt ccttgatatt ttgtcataag ccctcatcaa gtcaatgaaa 3840
atcacgtgta ggtccttcat ttgttcctta tactgctcca tcacttgtct cattaagaaa 3900
atatctctca tagttaacct tttggcatga aacaaaatca cacagaattt gtttcctttt 3960
tttaagatcc cacacaaaag aggtttgatc taaggaatct ggatccctga caggtttatc 4020
aaaatccttt gtgtttttct taaaactgaa tattcctcca gcttctagta ttgatgtaat 4080
attcaatctg tttagcaagt gaacaccttg gttcttgttg ttactgtaca tcccacccac 4140
ccccgaggcc cagattacca caacatgaat acaagaatat tgaacccaga tctagagttt 4200
gtttgtactg ttgaaaatcg gtgacaattc attttgttat tgcgctttct gataacgaca 4260
ggactccgtg atgatgggag cggacatcta tgaaactgaa gaagaagctt caaagctact 4320
gttagctggg aaggtcccag ttggaatagg aaggaacaca aagataaggt gagtatggat 4380
gtggaaccac cggttagttc c 4401

<210> SEQ ID NO 53
<211> LENGTH: 3701
<212> TYPE: DNA
<213> ORGANISM: Zea mays

<400> SEQUENCE: 53
ttttcaagat acacaattga accataatcg aagtggtatg taagacagtg agttaaaaga 60
ttatattttt tgggagactt ccagtcaaat tttcttagaa gtttttttgg tccagatgtt 120
cataaagtcg ccgctttcat acttttttta attttttaat tggtgcacta ttaggtacct 180
gttggaggat gttacaggct tattgatatc cctatgagta actgcttcaa cagtggtata 240
aataagatat ttgtgatgag tcagttcaat tctacttcgc ttaaccgcca tattcatcgt 300
acataccttg aaggcgggat caactttgct gatggatctg tacaggtgat ttacctcatc 360
ttgttgatgt gtaatactgt aattaggagt agatttgtgt ggagagaata ataaacagat 420
gccgagattc ttctctaaaa gtctagatcc aaaggcattg tggttcaaaa cactatggac 480
ttctaccatt tatgttatta ctttgcctta atgttccatt gaatggggca aattattgat 540
tctacaagtg tttaattaaa aactaattgt tcatcctgca ggtattagcg gctacacaaa 600
tgcctgaaga gccagctgga tggttccagg gtacagcaga ctctatcaga aaatttatct 660
gggtactcga ggtagttgat attttctcgt ttatgaatgt ccattcactc attcctgtag 720
cattgtttct ttgtaatttt gagttctcct gtatttcttt aggattatta cagtcacaaa 780
tccattgaca acattgtaat cttgagtggc gatcagcttt atcggatgaa ttacatggaa 840
cttgtgcagg tatggtgttc tcttgttcct catgtttcac gtaatgtcct gattttggat 900

-continued

```
taaccaacta cttttggcat gcattatttc cagaaacatg tcgaggacga tgctgatatc    960
actatatcat gtgctcctgt tgatgagagg taatcagttg tttatatcat cctaatatga   1020
atatgtcatc ttgttatcca acacaggatg catatggtct aatctgcttt cctttttttcc   1080
cttcggaagc cgagcttcta aaaatgggct agtgaagatt gatcatactg gacgtgtact   1140
tcaattcttt gaaaaaccaa agggtgctga tttgaattct atggttagaa attccttgtg   1200
taatccaatt cttttgtttt cctttctttc ttgagatgaa cccctctttt agttatttcc   1260
atggataacc tgtacttgac ttattcagaa atgattttct attttgctgt agaatctgac   1320
actaaagcta atagctactg atgttgcaga gagttgagac caacttcctg agctatgcta   1380
tagatgatgc acagaaatat ccataccttg catcaatggg catttatgtc ttcaagaaag   1440
atgcactttt agaccttctc aagtaatcac tttcctgtga cttatttcta tccaactcct   1500
agtttacctt ctaacagtgt caattcttag gtcaaaatat actcaattac atgactttgg   1560
atctgaaatc ctcccaagag ctgtactaga tcatagtgtg caggtaagtc tgatctgtct   1620
ggagtatgtg ttctgtaaac tgtaaattct tcatgtcaaa aagttgtttt tgtttccagt   1680
ttccactagt ttttatttac caatgcgcga tttatgtatt ttcgcttcca tgcatcatac   1740
atactaacaa tacattttac gtattgtgtt aggcatgcat ttttacgggc tattgggagg   1800
atgttggaac aatcaaatca ttctttgatg caaacttggc cctcactgag caggtactct   1860
gtcatgtatt ctgtactgca tatatattac ctggaattca atgcatagaa tgtgttagac   1920
catcttagtt ccatcctgtt ttcttcaatt agcttatcat ttaatagttg ttggctagaa   1980
tttaaacaca aatttaccta atatgtttct ctcttcagcc ttccaagttt gatttttacg   2040
atccaaaaac acctttcttc actgcacccc gatgcttgcc tccgacgcaa ttggacaagt   2100
gcaaggtata tgtcttactg agcacaattg ttacctgagc aagattttgt gtacttgact   2160
tgttctcctc cacagatgaa atatgcattt atctcagatg gttgcttact gagagaatgc   2220
aacatcgagc attctgtgat tggagtctgc tcacgtgtca gctctggatg tgaactcaag   2280
gtacatactc tgccaatgta tatgctgatg ttttatacat tctcttgcat aatttgattc   2340
gagtcaccac aattagtgta actgcaatct actcttgagt ataccatttc aacaccaagc   2400
atcaccaaat cacacagaac aatagcaaca aagcctttta gttccaagca atttagggta   2460
gcctagagtt gaaatctaac caaacaaaag tcaaagctct atcacgtgga tagttgtttt   2520
ccatgcactc ttatttaagc taatttttgg gtatactaca tccatttaat tattgtttta   2580
ttgcttcttc cctttgcctt tcccccatta ctatcgcgtc ttaagatcat actacgcact   2640
agtgtcttta gaggtctctg gtggacatgt tcaaaccatc tcaatcggtg ttggacaagt   2700
ttttcttgaa tttgtgctac acctaaccta tcatgtatgt catcgtttca aactcgatcc   2760
ttcctgtatc atcataaatc caatgcaaca tacgcattta tgcaacattt atctgttgaa   2820
catgtcatct ttttgtaggt taacattata caccatacaa tgtagcatgt ctaatcatca   2880
tcctataaaa tttacatttt agcttatgtg gtatcctctt gccacttaga acatcatatg   2940
cttgatgcca tttcatccac cctgctttga ttctatggct aacatcttca ttaatatcct   3000
tgcctctctg tatcattggt cctaaatatg gaaatacatt ctttctgggc actacttgac   3060
cttccaaact aacgtctcct ttgatccttt cttgtgtgta gtagtaccga agtcacatct   3120
catatattcg gttttagttc tactaagtcc cgggttcgat ccccctcagg ggtaaatttc   3180
gggcttggta aaaaaaatcc cctcgctgtg tcccgccctc tctcggggat cgatatcctg   3240
```

cgcgccaccc tccggctggg cattgcagag tgggcagttg atcgactcgt tagtgatggg 3300
gagcggggtt caagggtttt ctcggccggg accatgtttc ggtctcttaa tataataccg 3360
ggagggcagt ctttccctcc ccggtcgagt tttagttcta ctgagtctaa aacctttgga 3420
ctctagagtc ccctgtcaca actcacaact ctatttttct atttacttct acctagcgtt 3480
tattaatgat cactatatcg tctgtaaaaa gcatacacca aggtaatccc cttgtatgtc 3540
ccttgtaata ttatccatca caagaaaaaa aggtaaggct caaagttgac ttttgatata 3600
atcctattct aatcgagaag tcatctgtat cttcgtctct tgttcgaaca ctagtcacaa 3660 attttttgt acatgttctt aatgagtcca acgtaatatt c 3701

<210> SEQ ID NO 54
<211> LENGTH: 3101
<212> TYPE: DNA
<213> ORGANISM: Zea mays

<400> SEQUENCE: 54
gtttttttgg tccagatgtt cataaagtcg ccgctttcat acttttttta attttttaat 60
tggtgcacta ttaggtacct gttggaggat gttacaggct tattgatatc cctatgagta 120
actgcttcaa cagtggtata aataagatat ttgtgatgag tcagttcaat tctacttcgc 180
ttaaccgcca tattcatcgt acataccttg aaggcgggat caactttgct gatggatctg 240
tacaggtgat ttacctcatc ttgttgatgt gtaatactgt aattaggagt agatttgtgt 300
ggagagaata ataaacagat gccgagattc ttctctaaaa gtctagatcc aaaggcattg 360
tggttcaaaa cactatggac ttctaccatt tatgttatta ctttgcctta atgttccatt 420
gaatggggca aattattgat tctacaagtg tttaattaaa aactaattgt tcatcctgca 480
ggtattagcg gctacacaaa tgcctgaaga gccagctgga tggttccagg gtacagcaga 540
ctctatcaga aaatttatct gggtactcga ggtagttgat attttctcgt tttatgaatgt 600 ccattcactc attcctgtag cattgtttct ttgtaatttt gagttctcct gtatttcttt 660
aggattatta cagtcacaaa tccattgaca acattgtaat cttgagtggc gatcagcttt 720
atcggatgaa ttacatggaa cttgtgcagg tatggtgttc tcttgttcct catgtttcac 780
gtaatgtcct gattttggat taaccaacta cttttggcat gcattatttc cagaaacatg 840
tcgaggacga tgctgatatc actatatcat gtgctcctgt tgatgagagg taatcagttg 900
tttatatcat cctaatatga atatgtcatc ttgttatcca acacaggatg catatggtct 960
aatctgcttt cctttttttcc cttcggaagc cgagcttcta aaaatgggct agtgaagatt 1020
gatcatactg gacgtgtact tcaattcttt gaaaaaccaa agggtgctga tttgaattct 1080
atggttagaa attccttgtg taatccaatt cttttgtttt cctttctttc ttgagatgaa 1140
cccctctttt agttatttcc atggataacc tgtacttgac ttattcagaa atgattttct 1200
attttgctgt agaatctgac actaaagcta atagctactg atgttgcaga gagttgagac 1260
caacttcctg agctatgcta tagatgatgc acagaaatat ccataccttg catcaatggg 1320
catttatgtc ttcaagaaag atgcactttt agaccttctc aagtaatcac tttcctgtga 1380
cttatttcta tccaactcct agtttacctt ctaacagtgt caattcttag gtcaaaatat 1440
actcaattac atgactttgg atctgaaatc ctcccaagag ctgtactaga tcatagtgtg 1500
caggtaagtc tgatctgtct ggagtatgtg ttctgtaaac tgtaaattct tcatgtcaaa 1560
aagttgtttt tgtttccagt ttccactagt ttttatttac caatgcgcga tttatgtatt 1620
ttcgcttcca tgcatcatac atactaacaa tacattttac gtattgtgtt aggcatgcat 1680

```
ttttacgggc tattgggagg atgttggaac aatcaaatca ttctttgatg caaacttggc   1740
cctcactgag caggtactct gtcatgtatt ctgtactgca tatatattac ctggaattca   1800
atgcatagaa tgtgttagac catcttagtt ccatcctgtt ttcttcaatt agcttatcat   1860
ttaatagttg ttggctagaa tttaaacaca aatttaccta atatgtttct ctcttcagcc   1920
ttccaagttt gatttttacg atccaaaaac acctttcttc actgcacccc gatgcttgcc   1980
tccgacgcaa ttggacaagt gcaaggtata tgtcttactg agcacaattg ttacctgagc   2040
aagattttgt gtacttgact tgttctcctc cacagatgaa atatgcattt atctcagatg   2100
gttgcttact gagagaatgc aacatcgagc attctgtgat tggagtctgc tcacgtgtca   2160
gctctggatg tgaactcaag gtacatactc tgccaatgta tatgctgatg ttttatacat   2220
tctcttgcat aatttgattc gagtcaccac aattagtgta actgcaatct actcttgagt   2280
ataccatttc aacaccaagc atcaccaaat cacacagaac aatagcaaca aagcctttta   2340
gttccaagca atttagggta gcctagagtt gaaatctaac caaacaaaag tcaaagctct   2400
atcacgtgga tagttgtttt ccatgcactc ttatttaagc taatttttgg gtatactaca   2460
tccatttaat tattgtttta ttgcttcttc cctttgcctt tcccccatta ctatcgcgtc   2520
ttaagatcat actacgcact agtgtcttta gaggtctctg gtggacatgt tcaaaccatc   2580
tcaatcggtg ttggacaagt ttttcttgaa tttgtgctac acctaaccta tcatgtatgt   2640
catcgtttca aactcgatcc ttcctgtatc atcataaatc caatgcaaca tacgcattta   2700
tgcaacattt atctgttgaa catgtcatct ttttgtaggt taacattata caccatacaa   2760
tgtagcatgt ctaatcatca tcctataaaa tttacatttt agcttatgtg gtatcctctt   2820
gccacttaga acatcatatg cttgatgcca tttcatccac cctgctttga ttctatggct   2880
aacatcttca ttaatatcct tgcctctctg tatcattggt cctaaatatg gaaatacatt   2940
ctttctgggc actacttgac cttccaaact aacgtctcct ttgatccttt cttgtgtgta   3000
gtagtaccga agtcacatct catatattcg gttttagttc tactaagtcc cgggttcgat   3060
ccccctcagg ggtaaatttc gggcttggta aaaaaaatcc c                       3101
```

<210> SEQ ID NO 55
<211> LENGTH: 2101
<212> TYPE: DNA
<213> ORGANISM: Zea mays

<400> SEQUENCE: 55

```
gttttttggg tccagatgtt cataaagtcg ccgctttcat acttttttta attttttaat     60
tggtgcacta ttaggtacct gttggaggat gttacaggct tattgatatc cctatgagta    120
actgcttcaa cagtggtata aataagatat ttgtgatgag tcagttcaat tctacttcgc    180
ttaaccgcca tattcatcgt acataccttg aaggcgggat caactttgct gatggatctg    240
tacaggtgat ttacctcatc ttgttgatgt gtaatactgt aattaggagt agatttgtgt    300
ggagagaata ataaacagat gccgagattc ttctctaaaa gtctagatcc aaaggcattg    360
tggttcaaaa cactatggac ttctaccatt tatgttatta ctttgcctta atgttccatt    420
gaatggggca aattattgat tctacaagtg tttaattaaa aactaattgt tcatcctgca    480
ggtattagcg gctacacaaa tgcctgaaga gccagctgga tggttccagg gtacagcaga    540
ctctatcaga aaatttatct gggtactcga ggtagttgat attttctcgt ttatgaatgt    600
ccattcactc attcctgtag cattgtttct ttgtaatttt gagttctcct gtatttcttt    660
```

aggattatta cagtcacaaa tccattgaca acattgtaat cttgagtggc gatcagcttt 720
atcggatgaa ttacatggaa cttgtgcagg tatggtgttc tcttgttcct catgtttcac 780
gtaatgtcct gattttggat taaccaacta cttttggcat gcattatttc cagaaacatg 840
tcgaggacga tgctgatatc actatatcat gtgctcctgt tgatgagagg taatcagttg 900
tttatatcat cctaatatga atatgtcatc ttgttatcca acacaggatg catatggtct 960
aatctgcttt cctttttcc cttcggaagc cgagcttcta aaaatgggct agtgaagatt 1020
gatcatactg gacgtgtact tcaattcttt gaaaaaccaa agggtgctga tttgaattct 1080
atggttagaa attccttgtg taatccaatt cttttgtttt cctttctttc ttgagatgaa 1140
cccctctttt agttatttcc atggataacc tgtacttgac ttattcagaa atgattttct 1200
attttgctgt agaatctgac actaaagcta atagctactg atgttgcaga gagttgagac 1260
caacttcctg agctatgcta tagatgatgc acagaaatat ccataccttg catcaatggg 1320
catttatgtc ttcaagaaag atgcactttt agaccttctc aagtaatcac tttcctgtga 1380
cttatttcta tccaactcct agtttacctt ctaacagtgt caattcttag gtcaaaatat 1440
actcaattac atgactttgg atctgaaatc ctcccaagag ctgtactaga tcatagtgtg 1500
caggtaagtc tgatctgtct ggagtatgtg ttctgtaaac tgtaaattct tcatgtcaaa 1560
aagttgtttt tgtttccagt ttccactagt ttttatttac caatgcgcga tttatgtatt 1620
ttcgcttcca tgcatcatac atactaacaa tacattttac gtattgtgtt aggcatgcat 1680
ttttacgggc tattgggagg atgttggaac aatcaaatca ttctttgatg caaacttggc 1740
cctcactgag caggtactct gtcatgtatt ctgtactgca tatatattac ctggaattca 1800
atgcatagaa tgtgttagac catcttagtt ccatcctgtt ttcttcaatt agcttatcat 1860
ttaatagttg ttggctagaa tttaaacaca aatttaccta atatgtttct ctcttcagcc 1920
ttccaagttt gatttttacg atccaaaaac acctttcttc actgcacccc gatgcttgcc 1980
tccgacgcaa ttggacaagt gcaaggtata tgtcttactg agcacaattg ttacctgagc 2040
aagattttgt gtacttgact tgttctcctc cacagatgaa atatgcattt atctcagatg 2100
g 2101

<210> SEQ ID NO 56
<211> LENGTH: 21
<212> TYPE: DNA
<213> ORGANISM: Zea mays

<400> SEQUENCE: 56
gcactgtgct catcatccct t 21

<210> SEQ ID NO 57
<211> LENGTH: 22
<212> TYPE: DNA
<213> ORGANISM: Zea mays

<400> SEQUENCE: 57
agaaaatttg actggaagtc tc 22

<210> SEQ ID NO 58
<211> LENGTH: 24
<212> TYPE: DNA
<213> ORGANISM: Zea mays

<400> SEQUENCE: 58
gattatcaca aatcattgct acga 24

-continued

```
<210> SEQ ID NO 59
<211> LENGTH: 20
<212> TYPE: DNA
<213> ORGANISM: Zea mays
<220> FEATURE:
<221> NAME/KEY: SNP
<222> LOCATION: (7)..(7)
<223> OTHER INFORMATION: where r is a or g

<400> SEQUENCE: 59

cccacargac ttatagctcc                                                   20
```